(12) United States Patent
Yamamoto et al.

(10) Patent No.: US 7,618,425 B2
(45) Date of Patent: Nov. 17, 2009

(54) ENDOSCOPIC SUTURING SYSTEM

(75) Inventors: Tetsuya Yamamoto, Hidaka (JP); Sydney Sheung Chee Chung, Hong Kong (CN); Koichi Kawashima, Hachioji (JP)

(73) Assignee: Olympus Corporation, Tokyo (JP)

( * ) Notice: Subject to any disclaimer, the term of this patent is extended or adjusted under 35 U.S.C. 154(b) by 548 days.

(21) Appl. No.: 10/353,866

(22) Filed: Jan. 29, 2003

(65) Prior Publication Data

US 2003/0181924 A1 Sep. 25, 2003

Related U.S. Application Data

(60) Provisional application No. 60/352,728, filed on Jan. 30, 2002, provisional application No. 60/430,259, filed on Dec. 2, 2002.

(51) Int. Cl.
*A61B 17/10* (2006.01)
(52) U.S. Cl. ...................................... 606/139
(58) Field of Classification Search ................. 606/139, 606/144, 147, 148
See application file for complete search history.

(56) References Cited

U.S. PATENT DOCUMENTS

| | | | |
|---|---|---|---|
| 3,842,840 A | * | 10/1974 | Schweizer .................. 606/145 |
| 4,807,593 A | * | 2/1989 | Ito .............................. 600/114 |
| 5,171,258 A | | 12/1992 | Bales et al. |
| 5,527,321 A | * | 6/1996 | Hinchliffe .................... 606/144 |
| 5,674,230 A | * | 10/1997 | Tovey et al. ................. 606/139 |
| 5,814,054 A | * | 9/1998 | Kortenbach et al. ......... 606/139 |
| 6,071,233 A | * | 6/2000 | Ishikawa et al. ............ 600/104 |
| 7,131,978 B2 | * | 11/2006 | Sancoff et al. .............. 606/145 |

FOREIGN PATENT DOCUMENTS

| | | |
|---|---|---|
| JP | 07-155332 | 6/1995 |
| JP | 08-033635 | 2/1996 |
| JP | 11-004834 | 1/1999 |

\* cited by examiner

*Primary Examiner*—Anhtuan T Nguyen
*Assistant Examiner*—Tuan V Nguyen
(74) *Attorney, Agent, or Firm*—Scully, Scott, Murphy & Presser, P.C.

(57) ABSTRACT

An endoscopic treatment device is used with an endoscope. This treatment device includes a transmission member with a flexible structure having a distal end portion to be inserted into a body and can be operated outside the body, a push rod coupled to the distal end portion, and first and second connecting members rotatably coupled to the push rod. The treatment device further includes first and second arm members rotatably coupled to the distal end portion of the connecting member, a holding member rotatably holding the respective arm at a predetermined interval therebetween, and first and second actuating members integrally formed with the arm members and can open/close when the transmission member actuates the first and second connecting members and the first and second arm members through the push rod. This device also includes a needle mounted on at least one of the first and second actuating members.

17 Claims, 108 Drawing Sheets

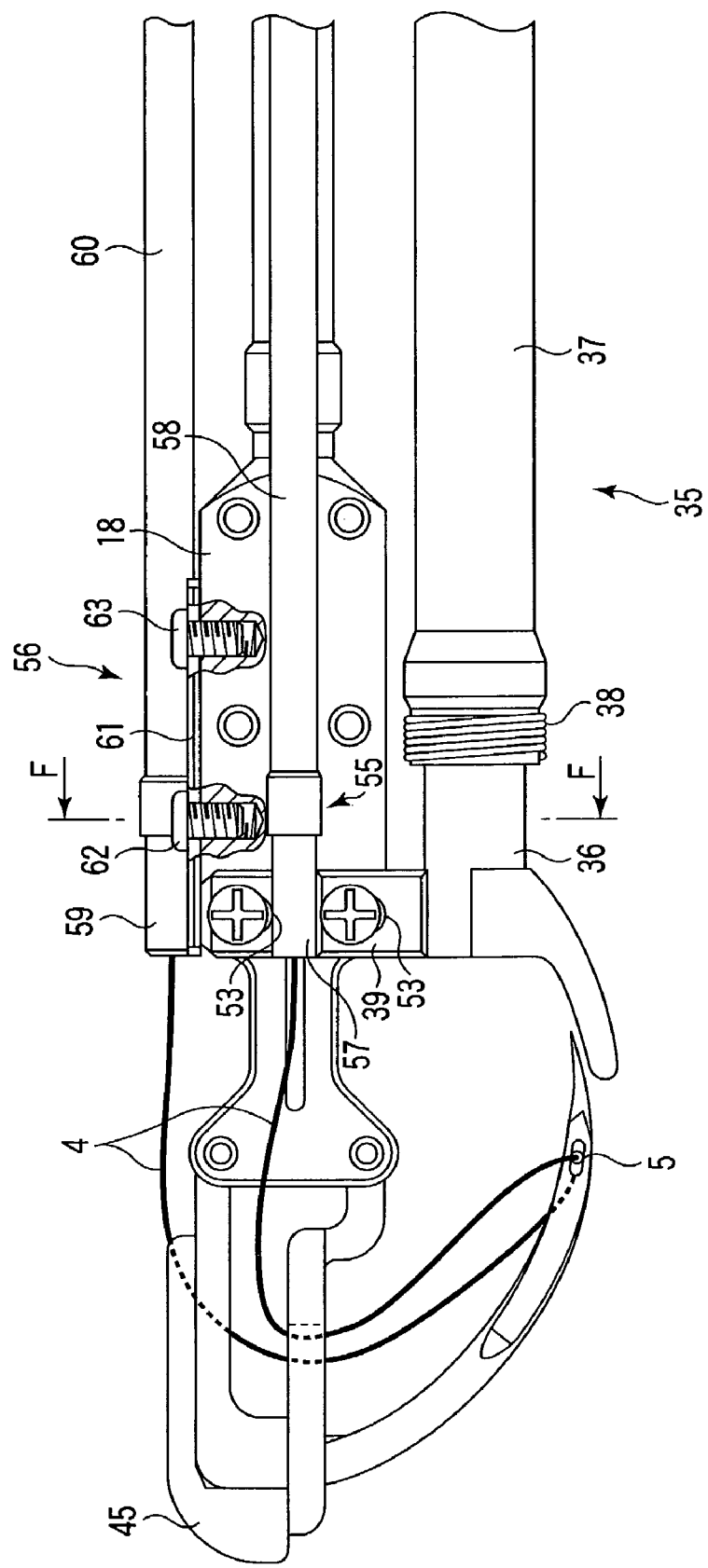
F I G. 13

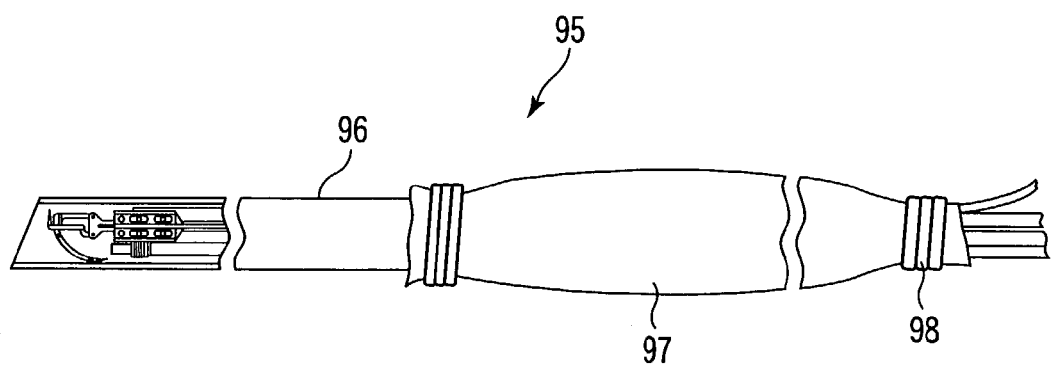
F I G. 20
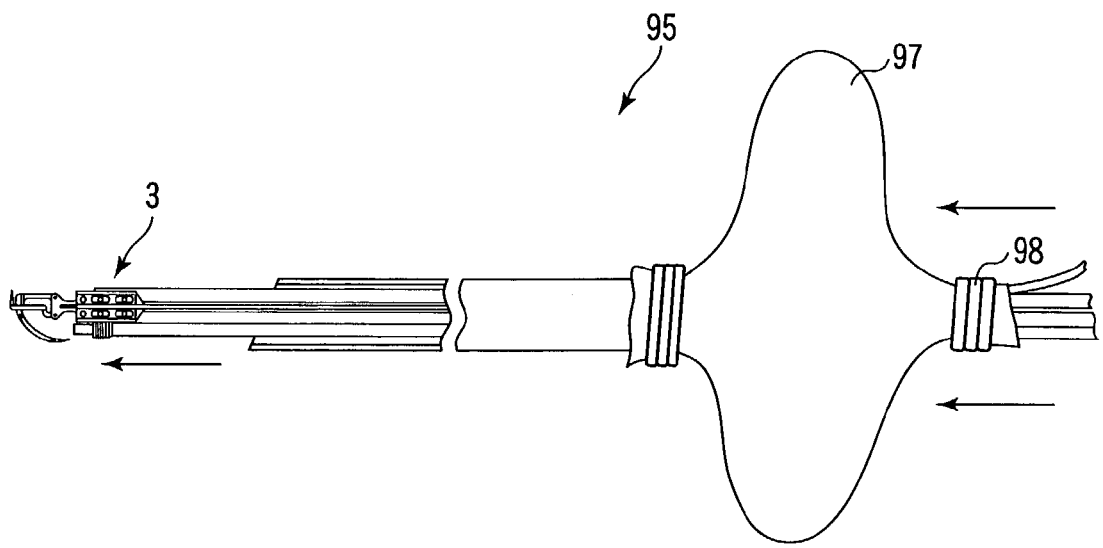
F I G. 21

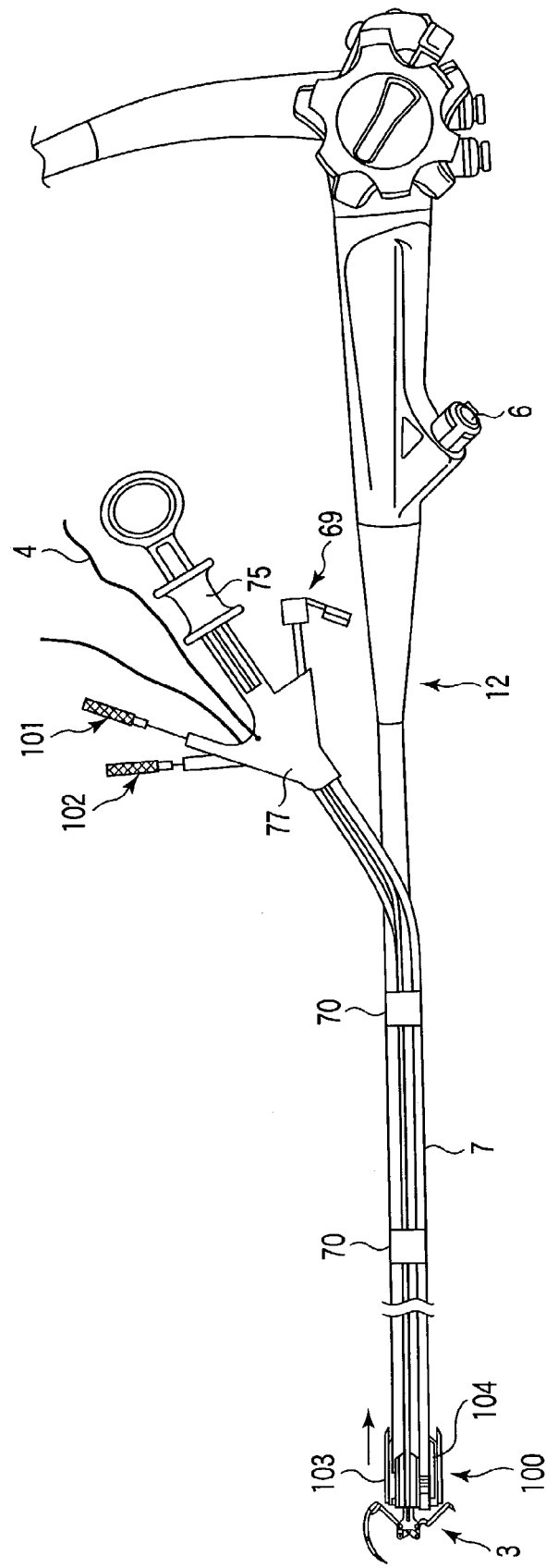
F I G. 31

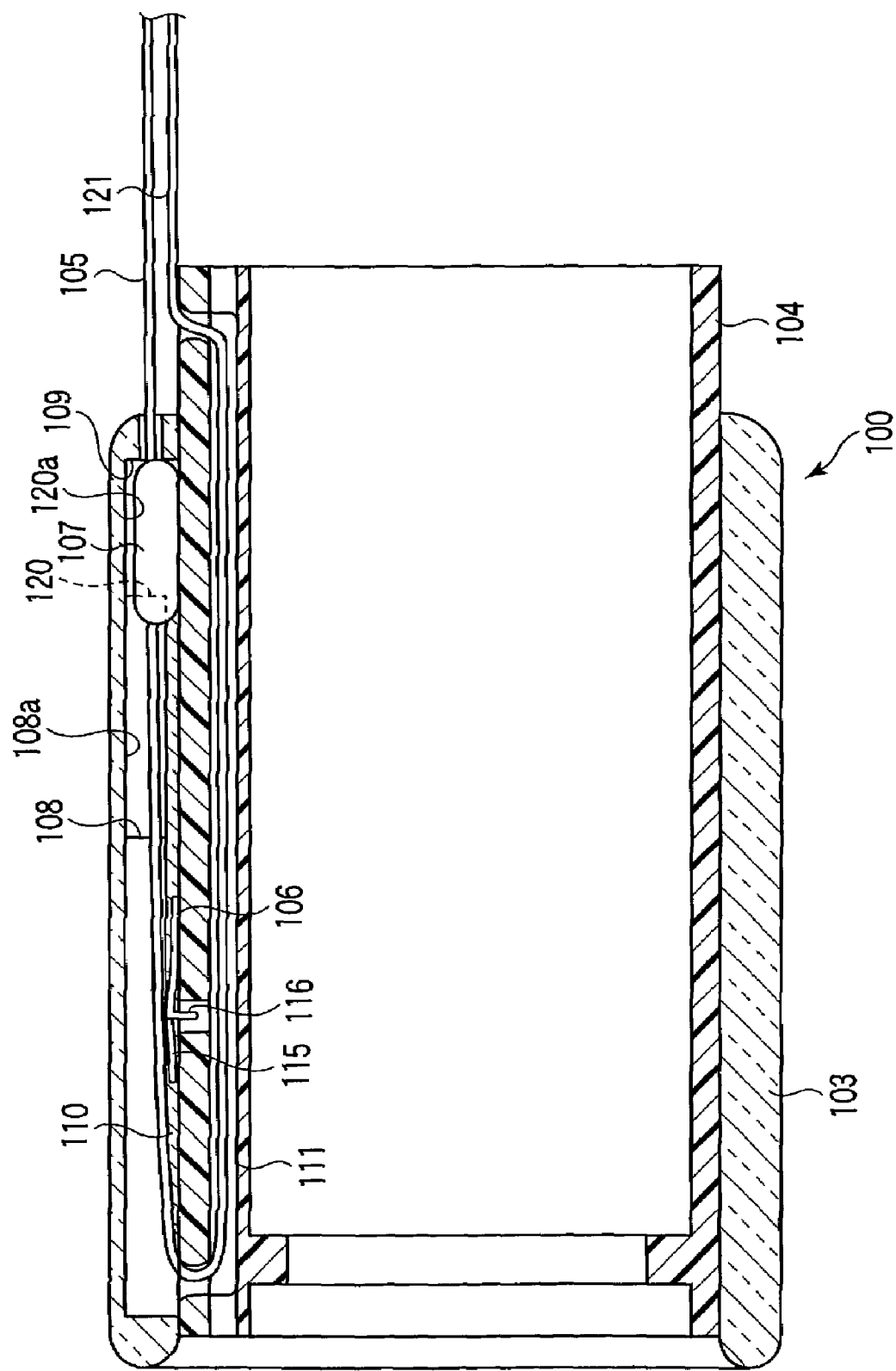
F I G. 34

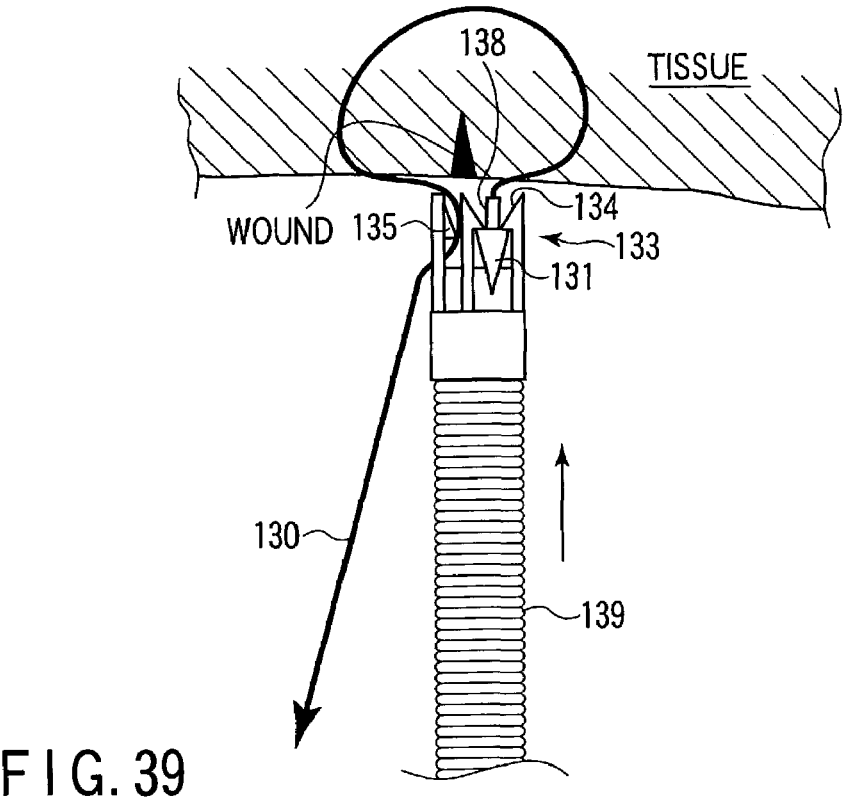
F I G. 39
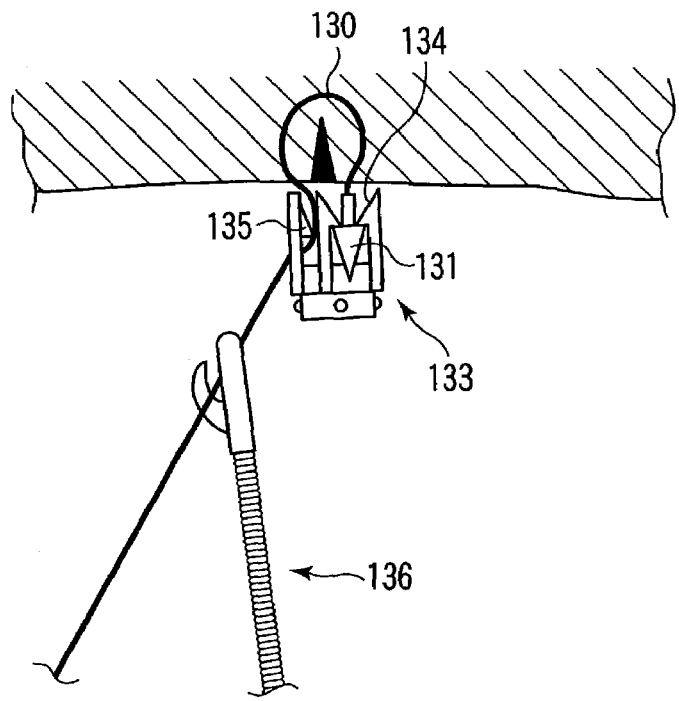
F I G. 40

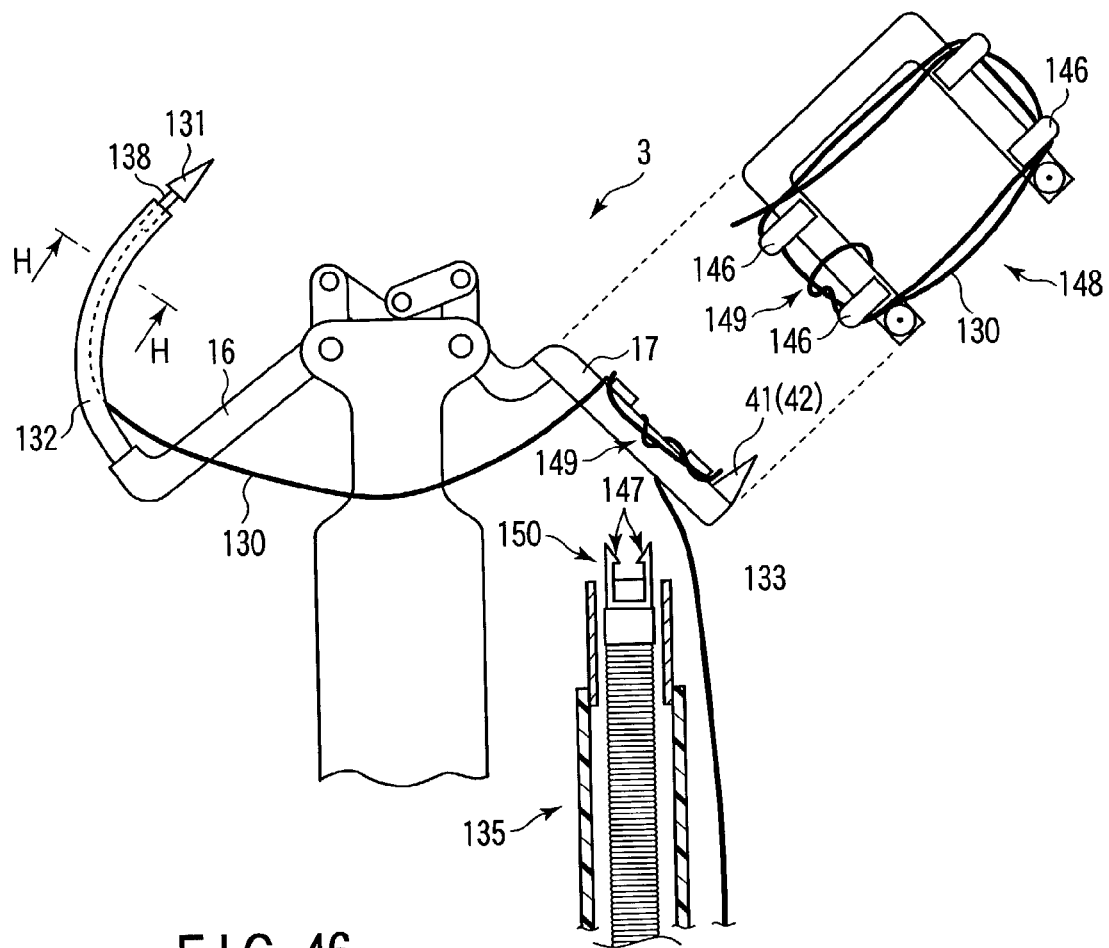
F I G. 46
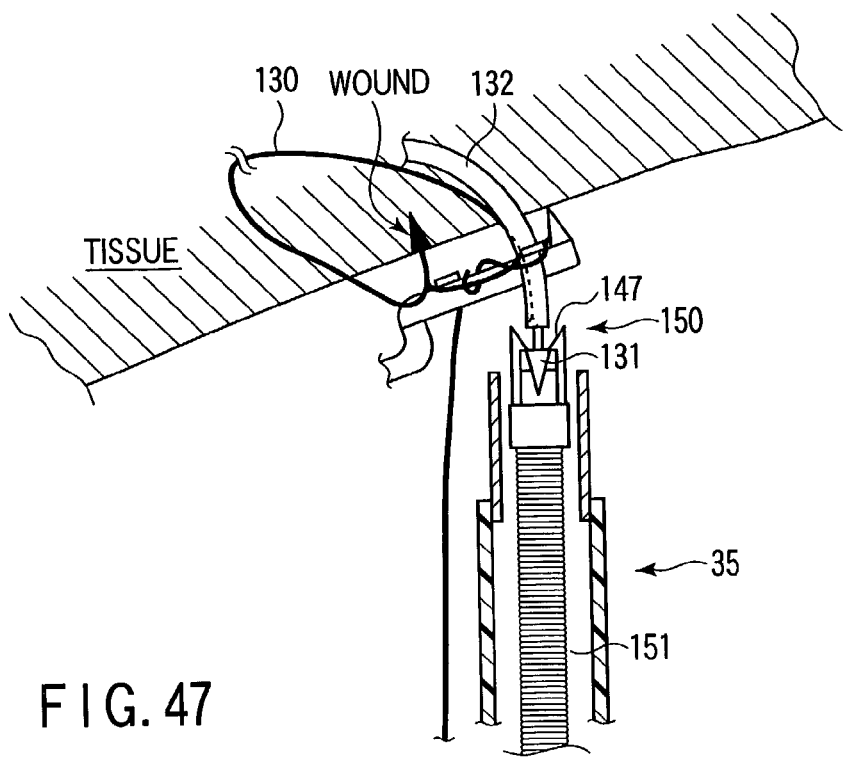
F I G. 47

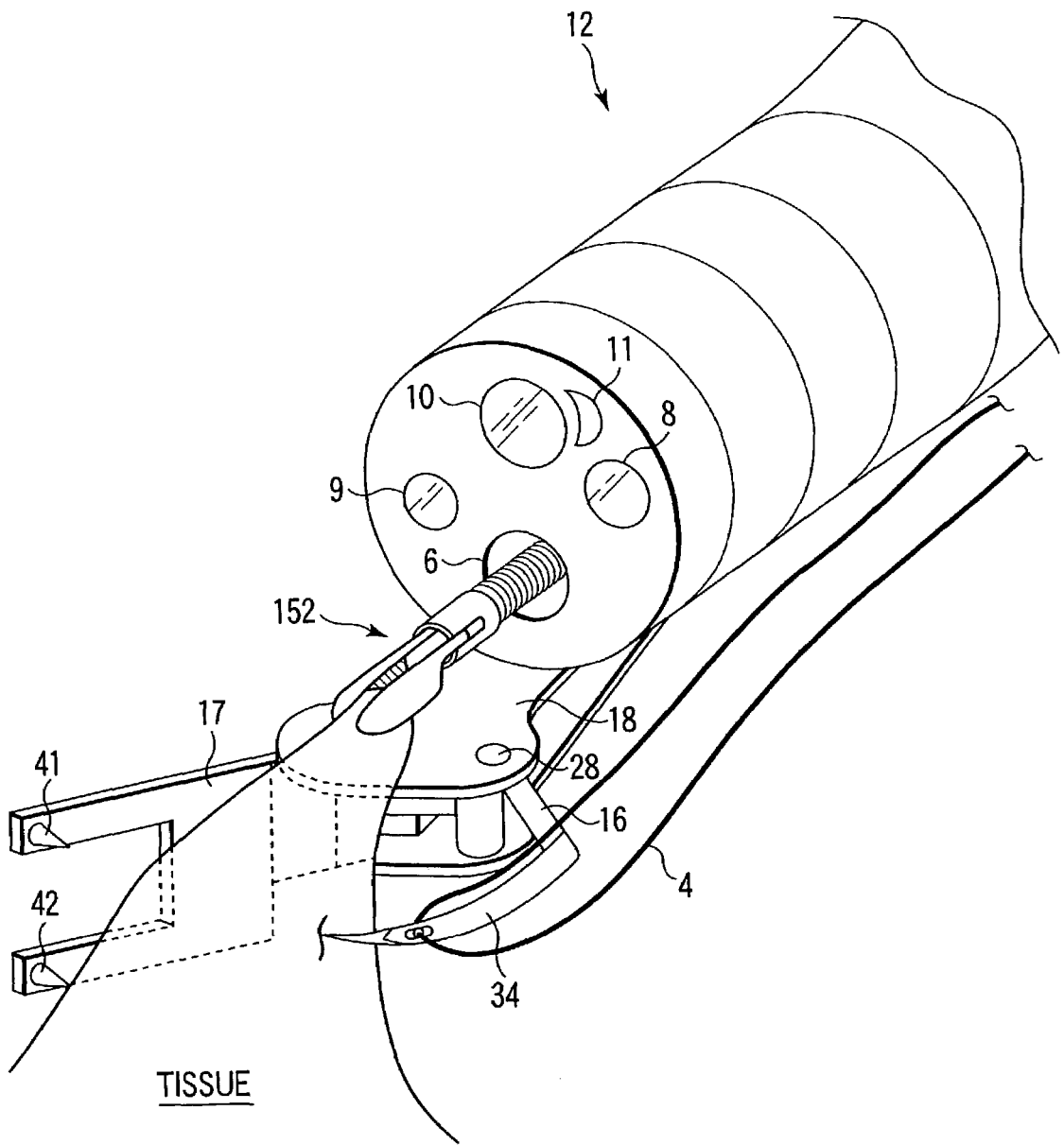
F I G. 50

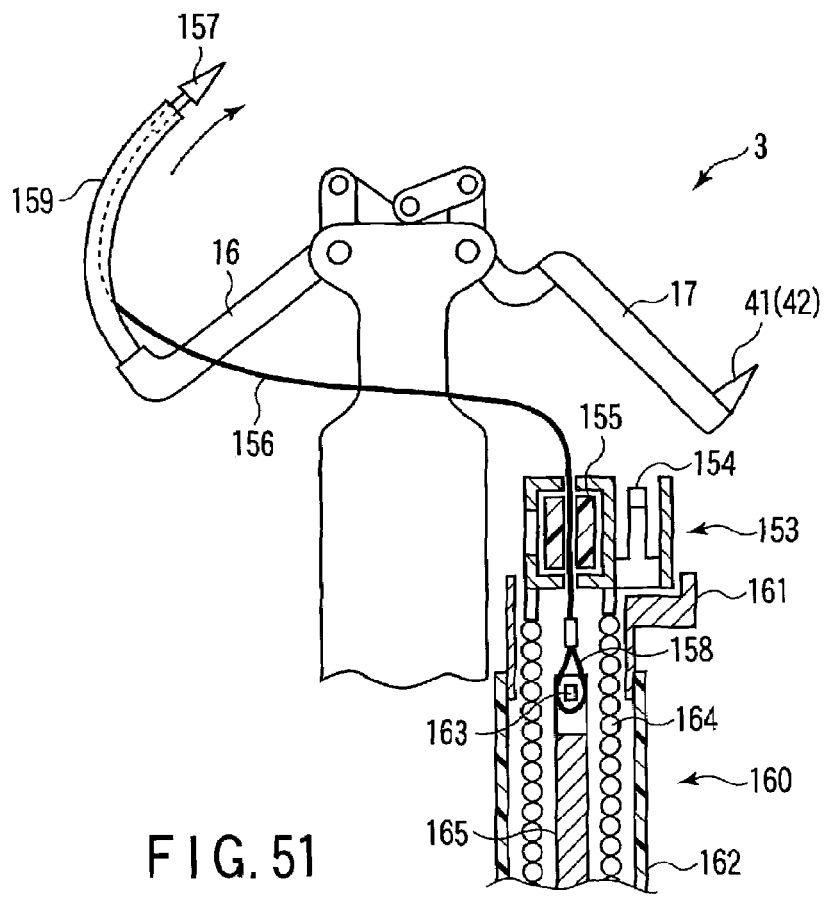
F I G. 51
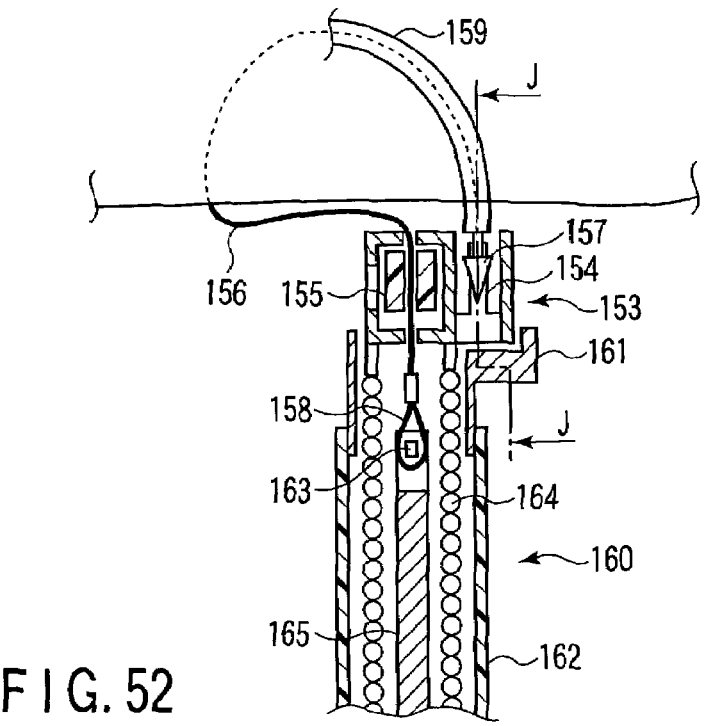
F I G. 52

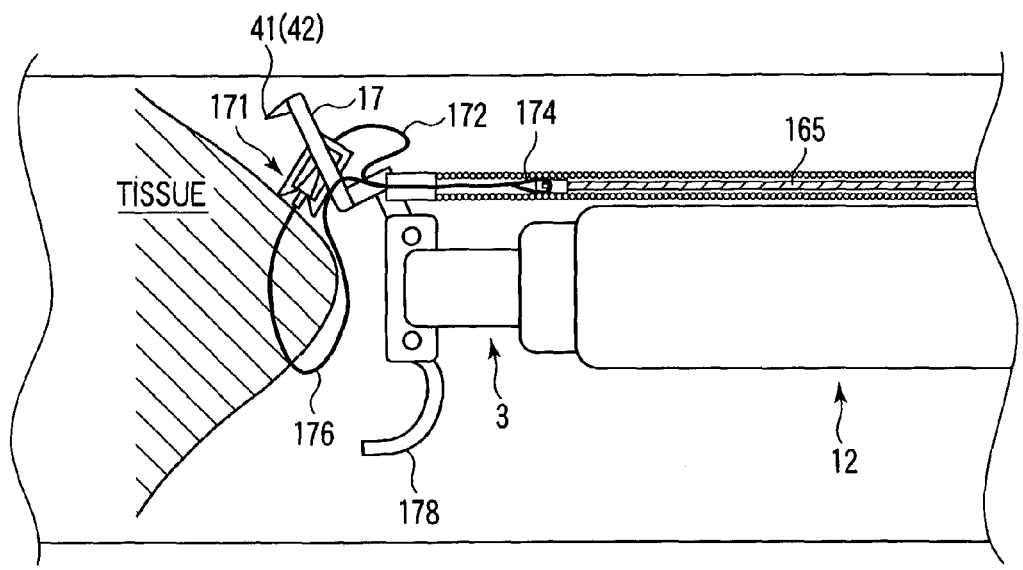
F I G. 59
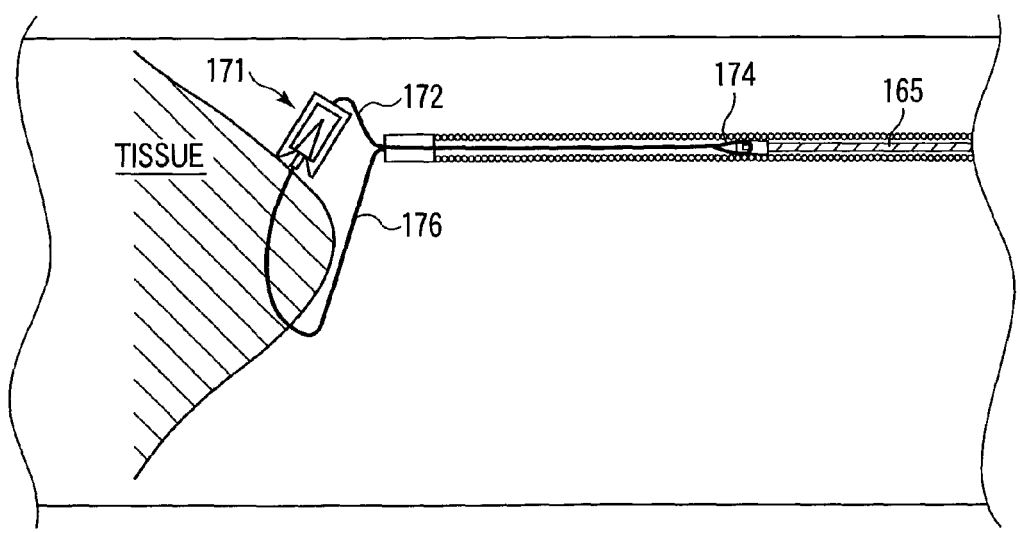
F I G. 60

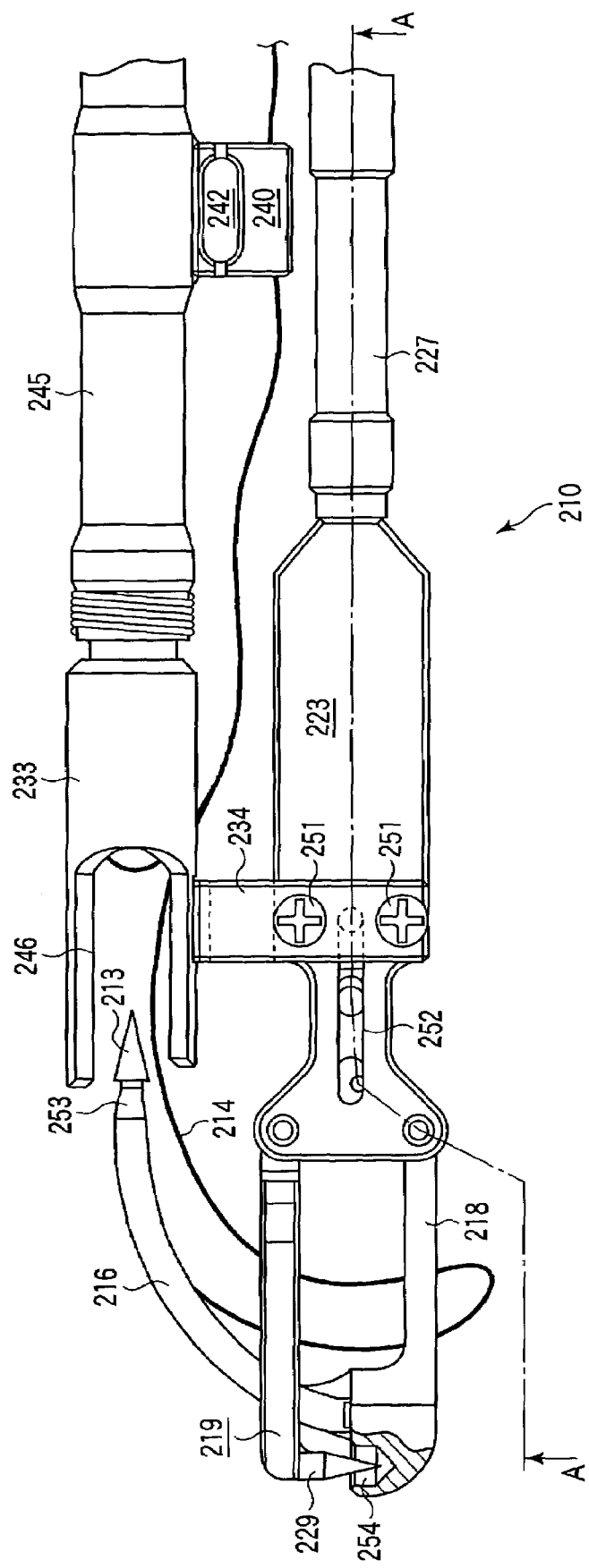
F I G. 68

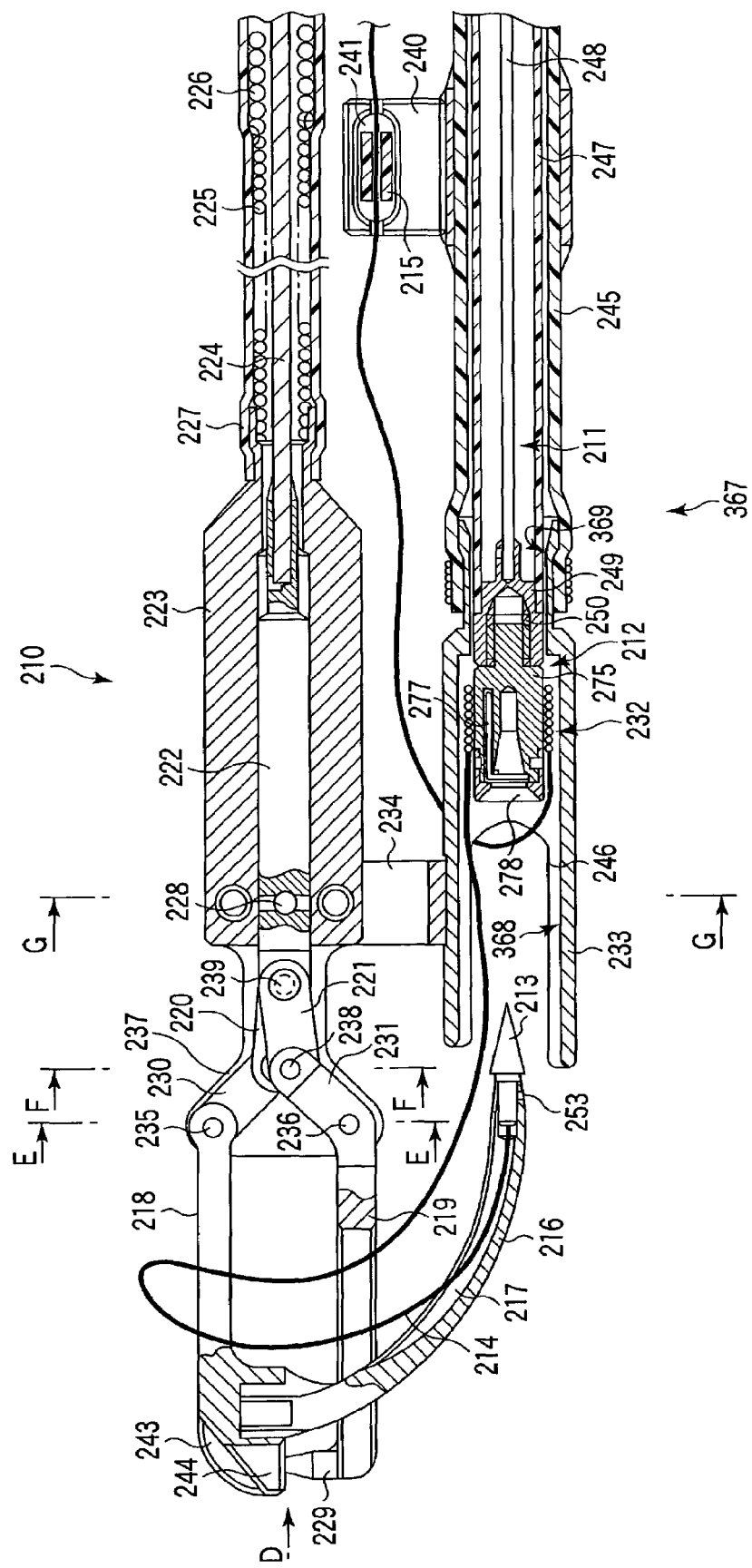

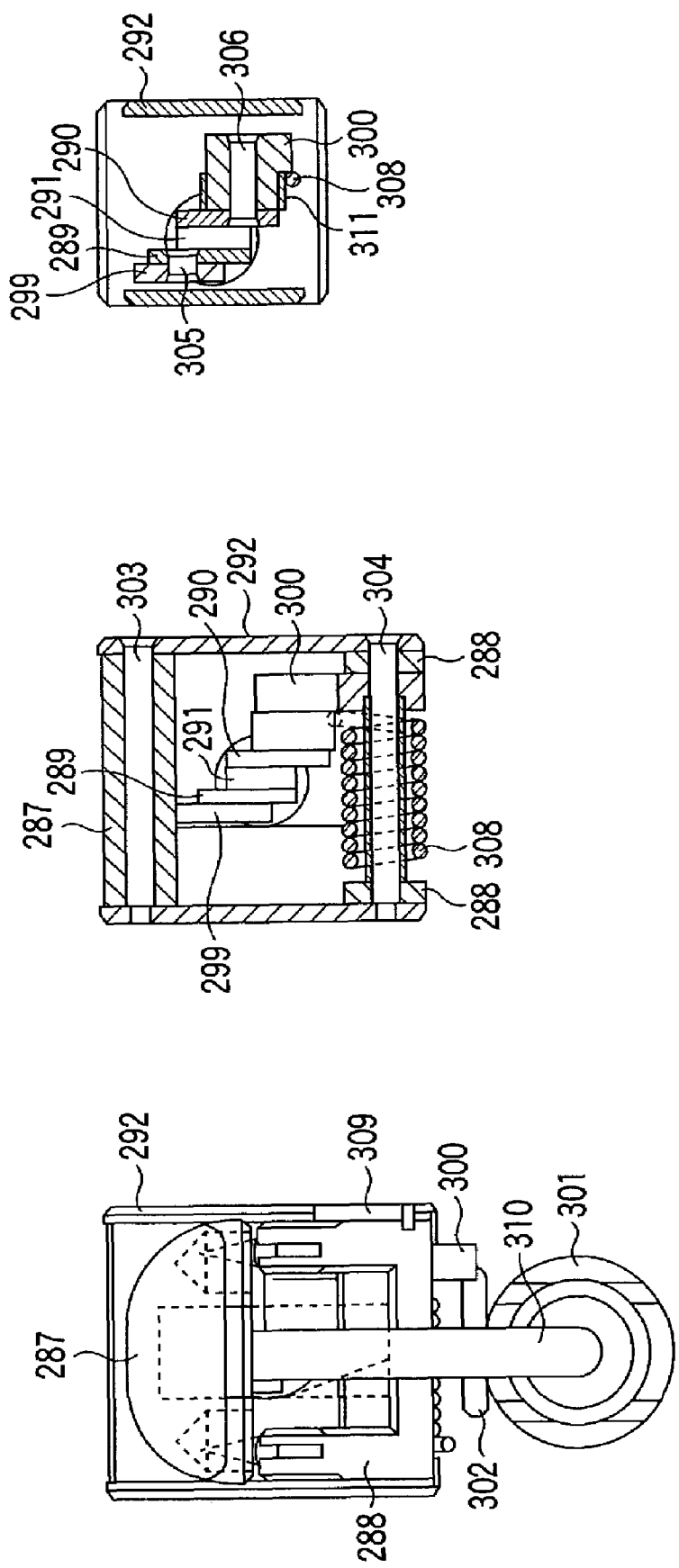

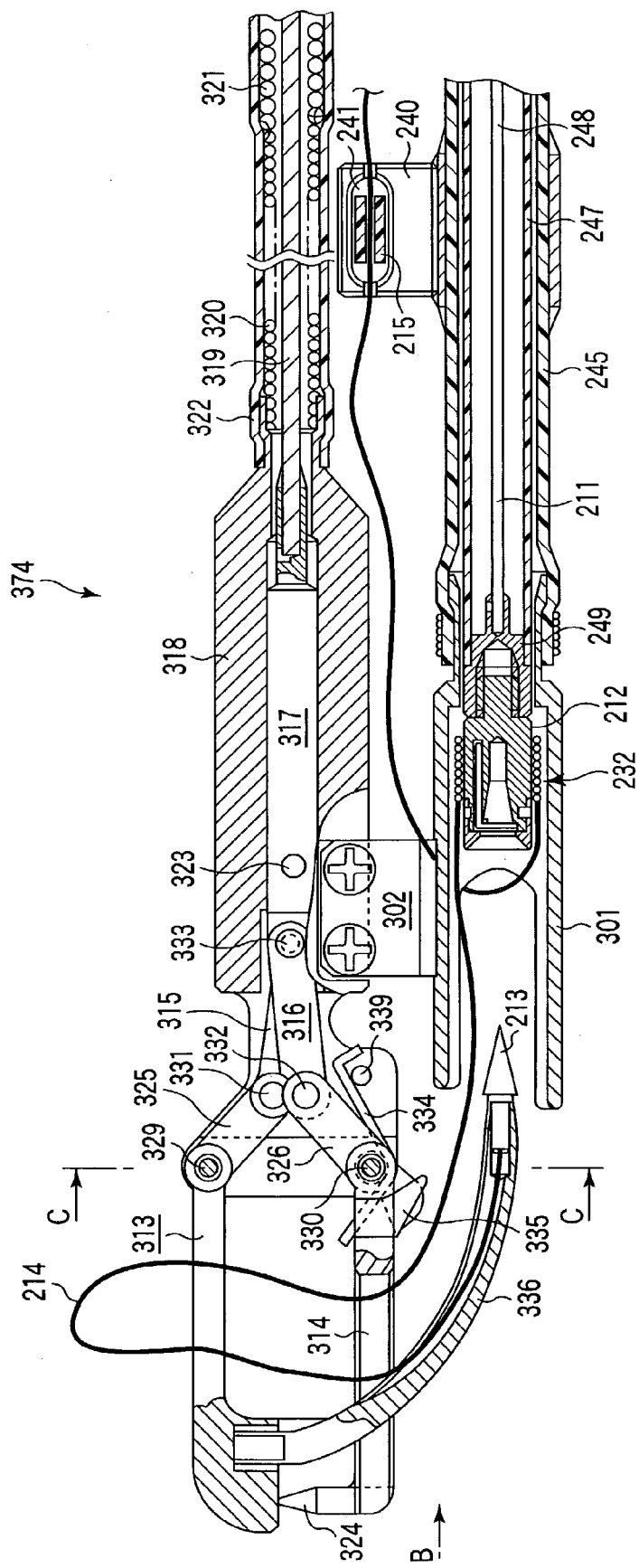
F I G. 113

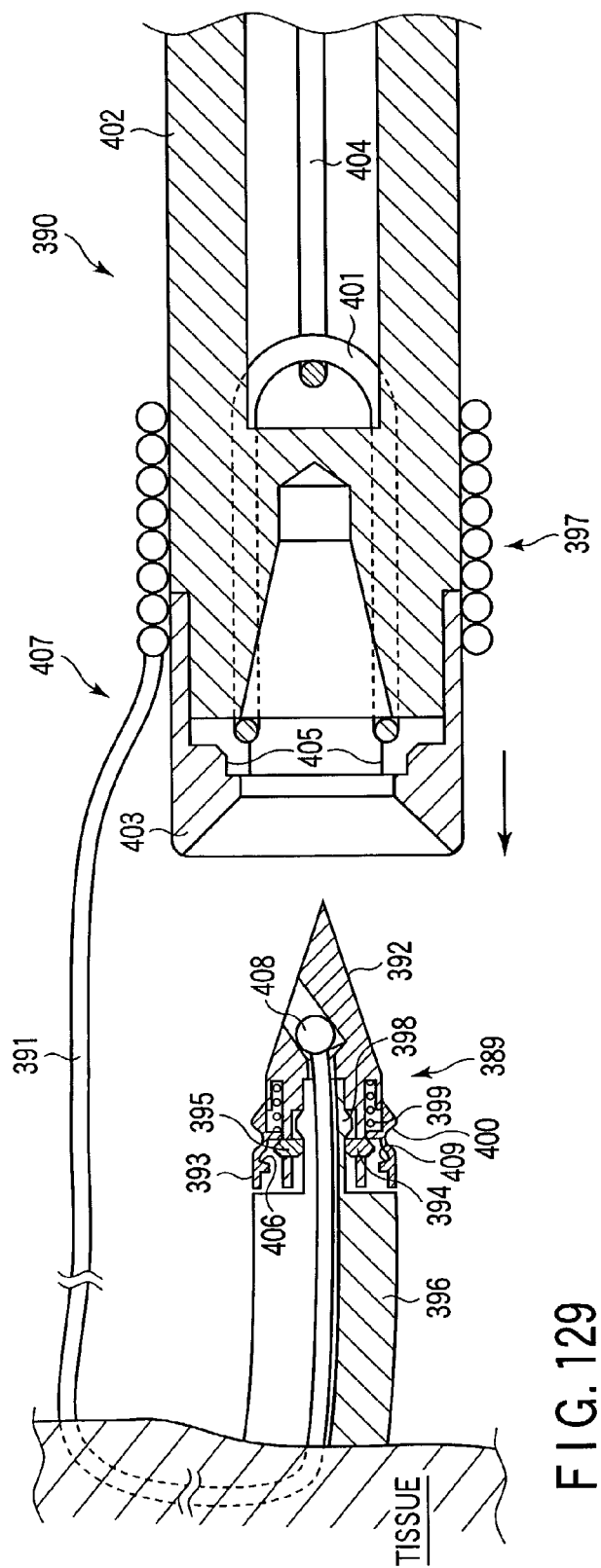
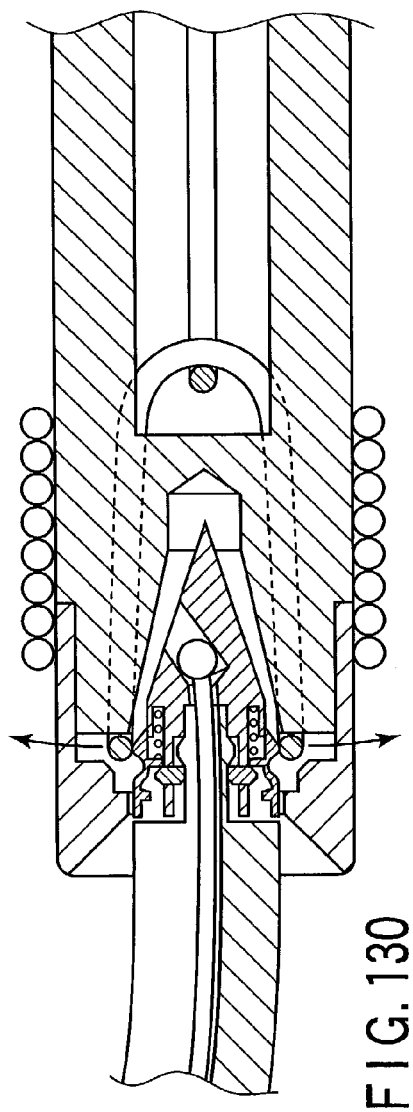
FIG. 129
FIG. 130

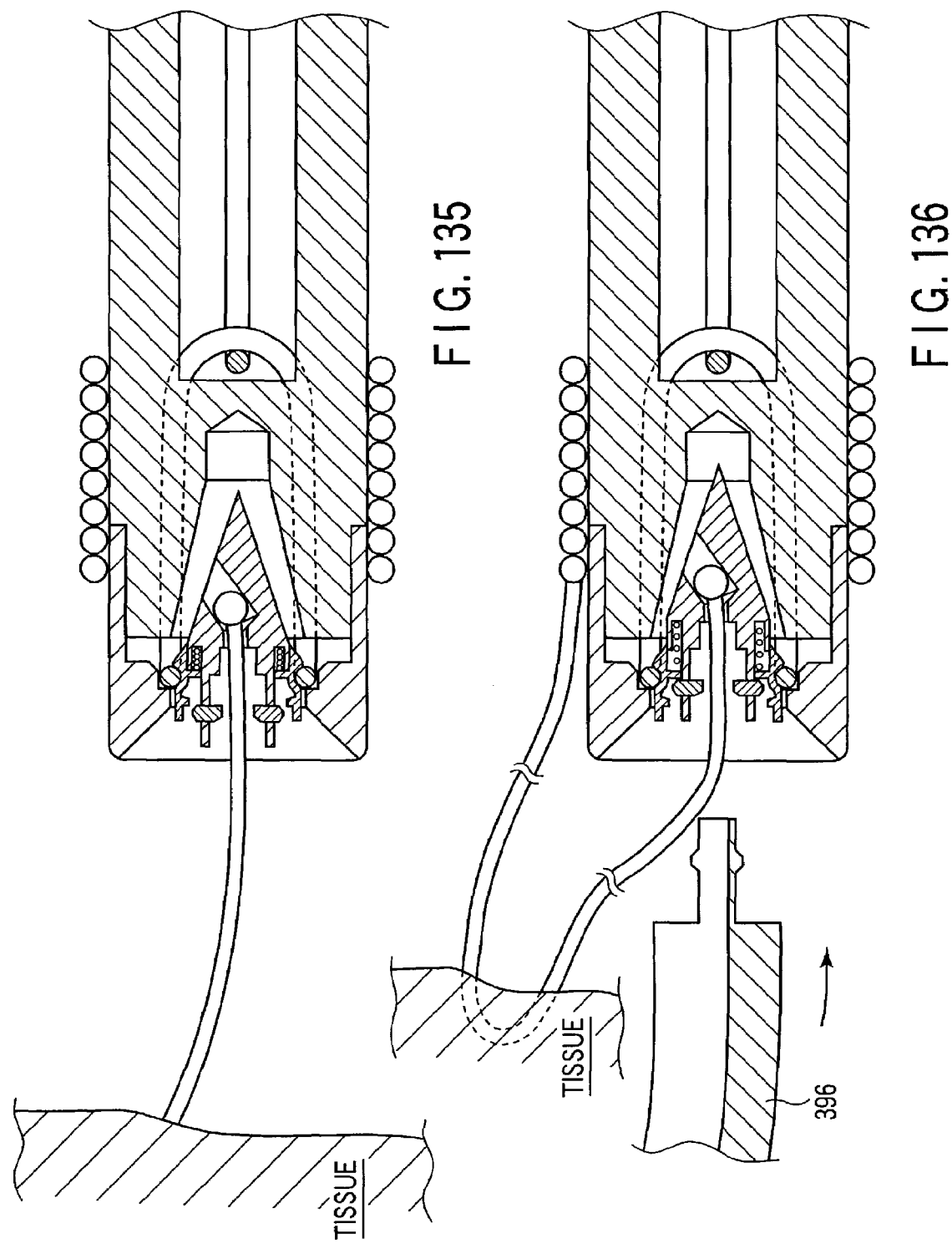

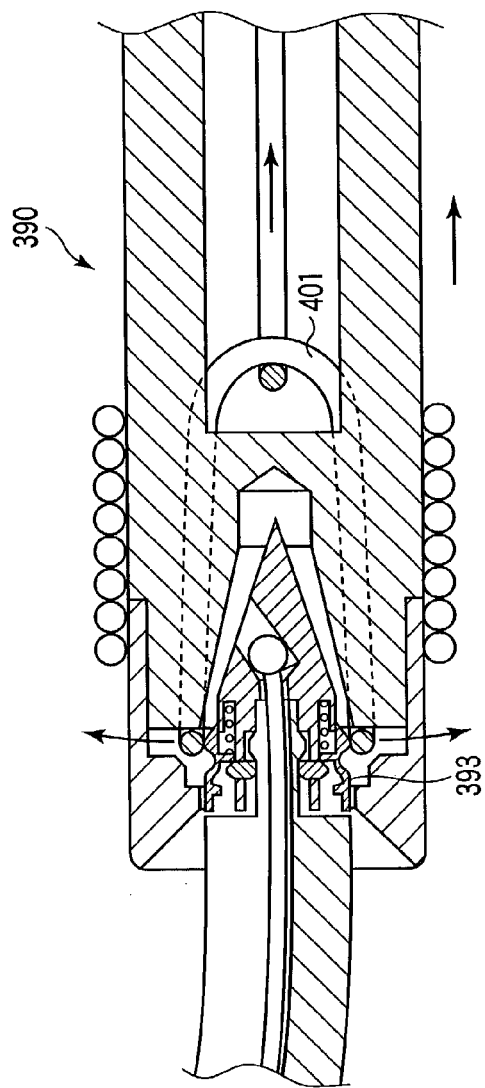
FIG. 140
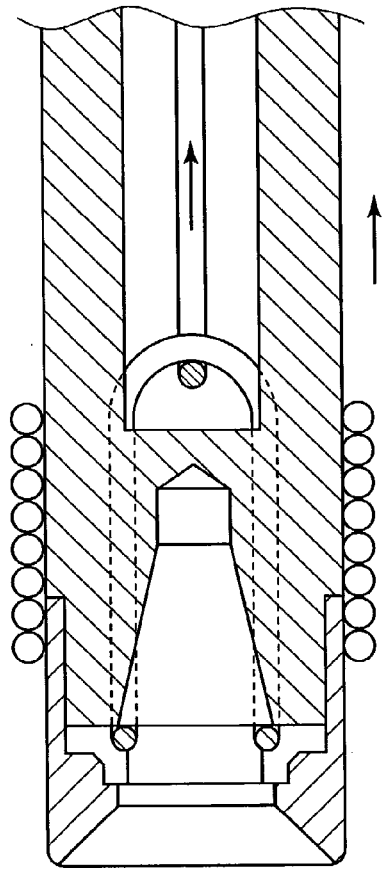
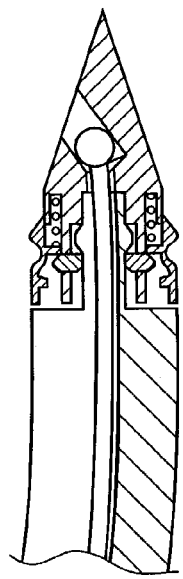
FIG. 141

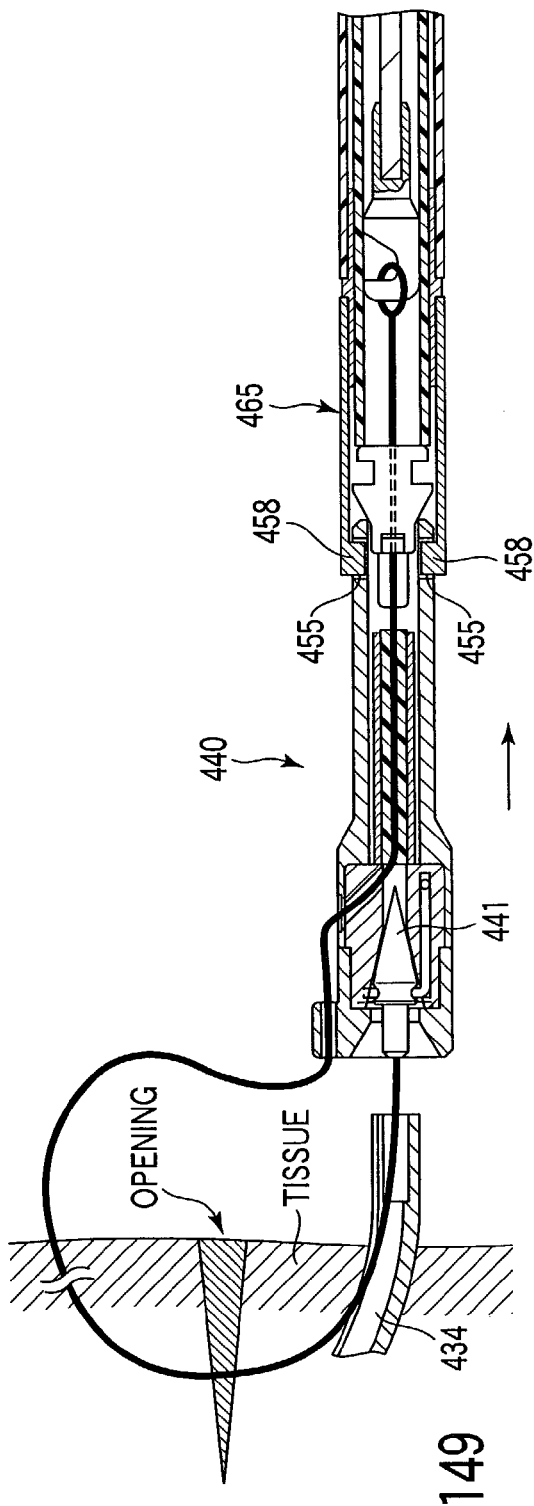
F I G. 149
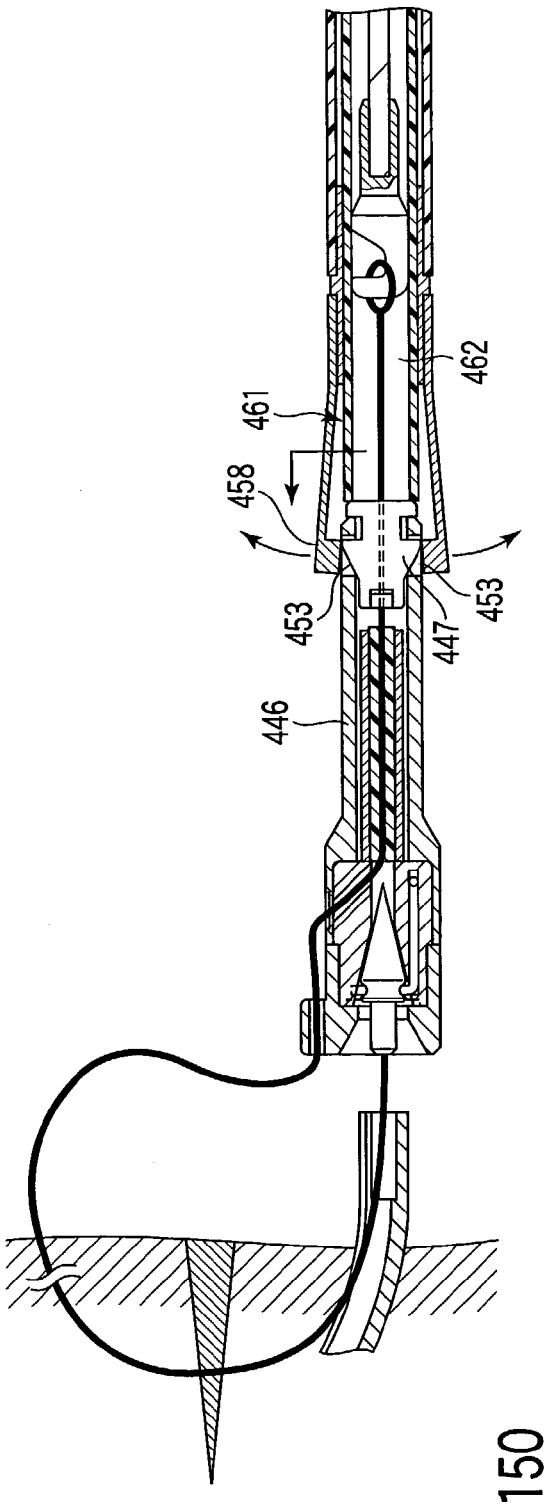
F I G. 150

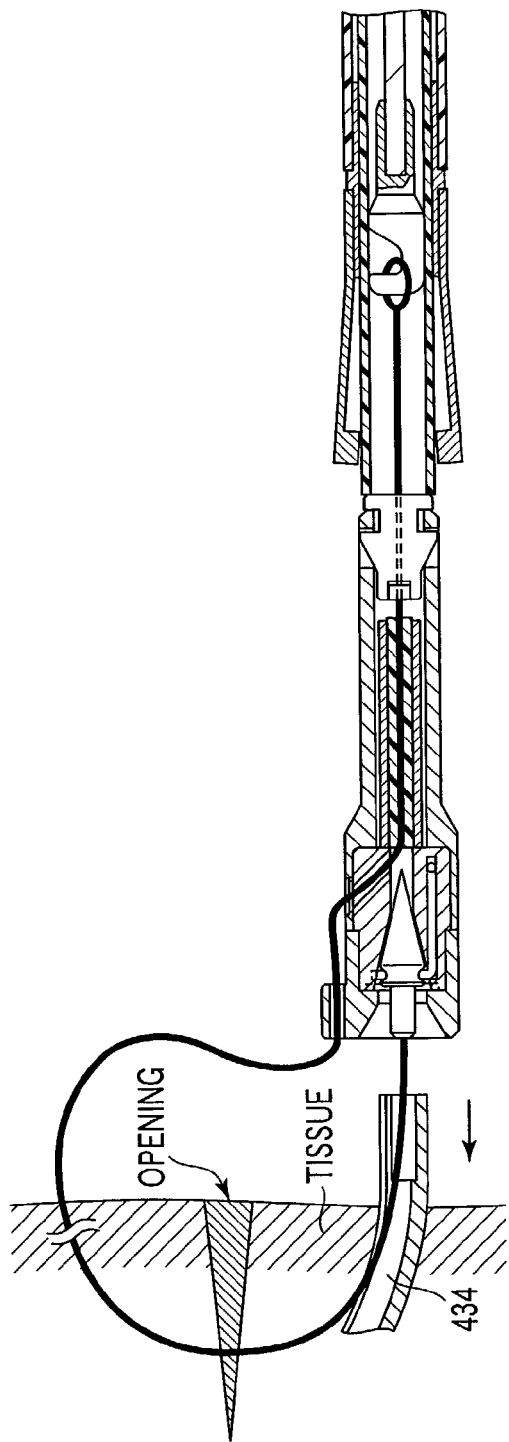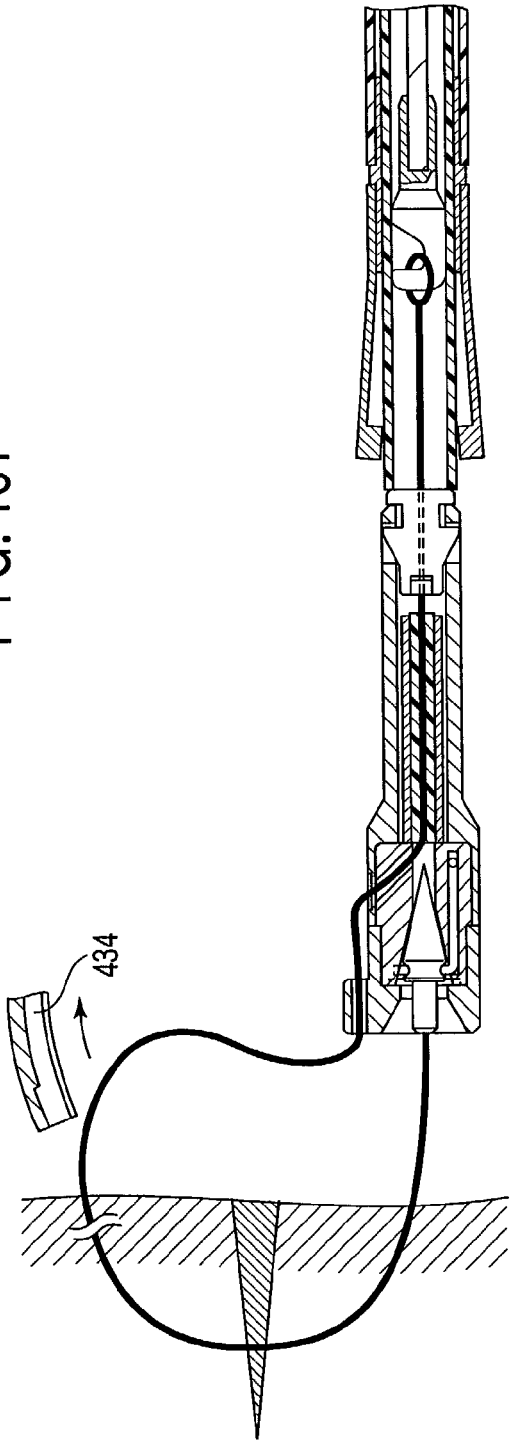

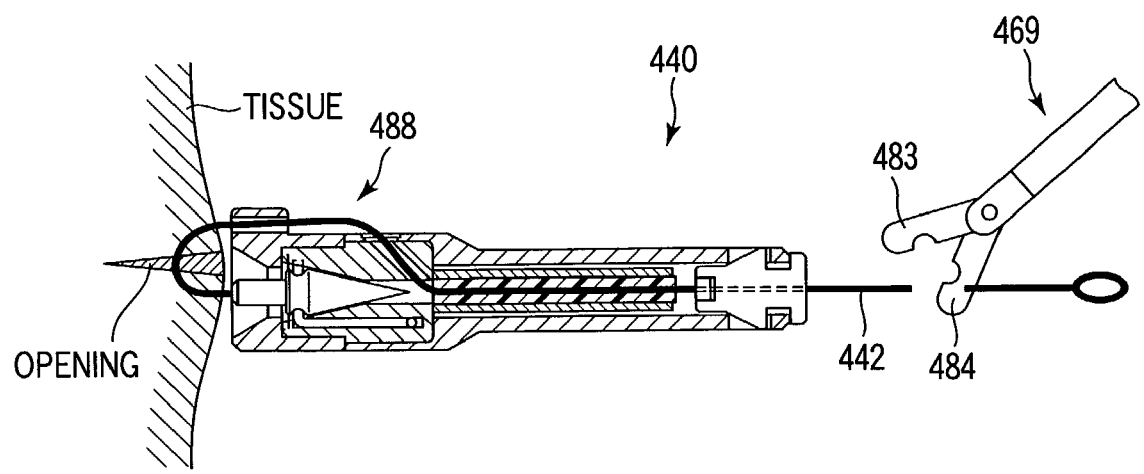
F I G. 157

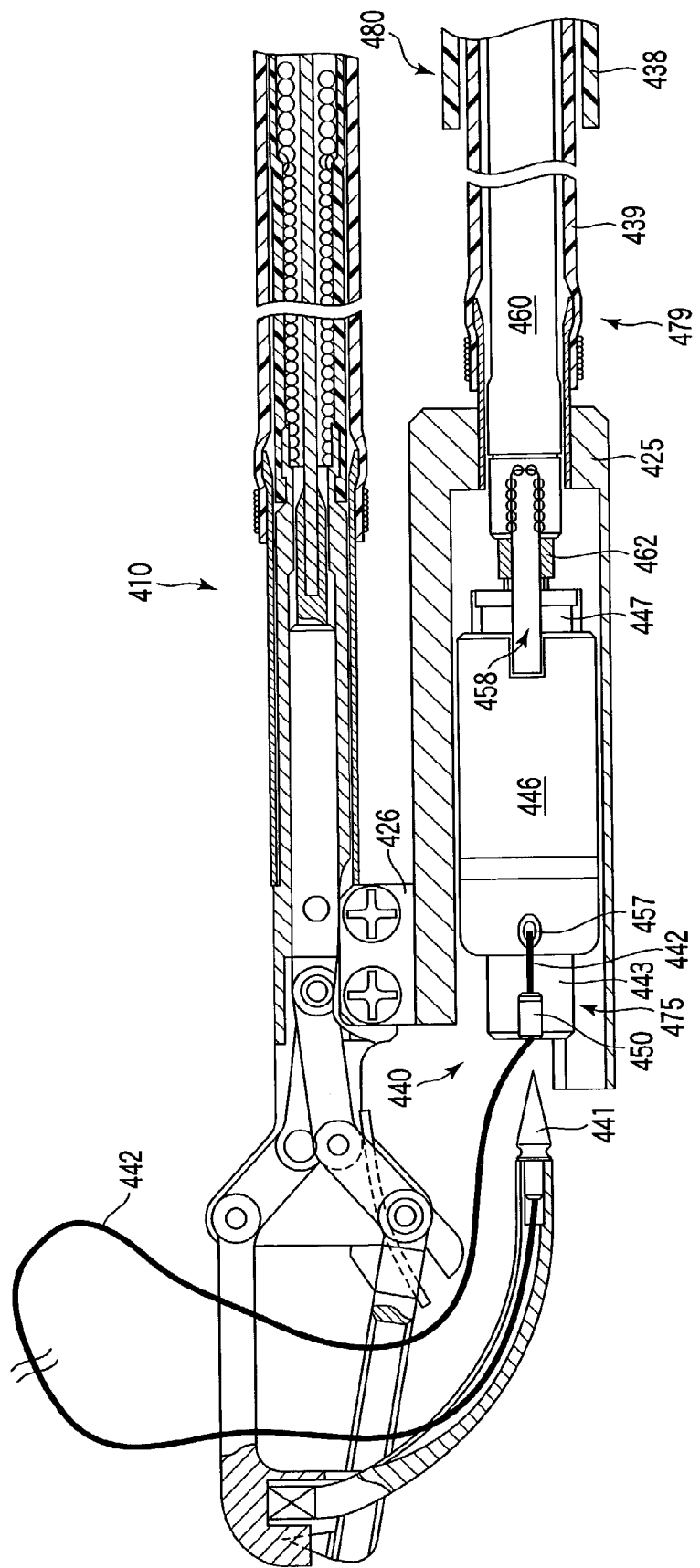
F I G. 164

ENDOSCOPIC SUTURING SYSTEM

CROSS-REFERENCE TO RELATED APPLICATIONS

This application claims the benefit of U.S. Provisional Application No. 60/352,728, filed Jan. 30, 2002; and No. 60/430,259, filed Dec. 2, 2002.

BACKGROUND OF THE INVENTION

The present invention relates to a treatment device which can be inserted into a body together with an endoscope. U.S. Pat. No. 5,171,258 (Symbiosis Co., Ltd.) discloses a medical instrument that is applicable to a surgical operation using a laparoscope. This medical instrument comprises a pair of posts for supporting a pair of devises in order to produce a large force required to grip a thick tissue. However, the posts and devises interfere with each other, whereby an angle that can be formed between the devises is restricted to an angle of about 90 degrees.

On the other hand, where the inside of a body is sutured by using an endoscope, it is required to puncture a needle through a tissue. Therefore, a treatment device is required to be a small size, nevertheless the treatment device being capable of moving a needle over a large angle, is required. Further, it is required to transmit a large force to the needle in order to securely puncture the tissue.

However, in the prior art, a treatment device for endoscope requiring a large opening/closing angle and transmission of a large force cannot be provided.

BRIEF SUMMARY OF THE INVENTION

The present invention has been made in view of the above described circumstance. It is an object of the present invention to provide an endoscopic treatment device comprising a structure for further increasing an opening/closing angle and further producing a large force.

According to an aspect of the present invention, there is provided a treatment device which is used to perform treatment in a body by being operated outside the body. This treatment device comprises a flexible member having a distal end portion that can be inserted into a body, a link mechanism which is arranged at the distal end portion of the flexible member and actuated by an operation outside the body, and a curved needle which is actuated by the link mechanism and can move in a direction to puncture a tissue and a direction to be removed from the tissue.

According to another aspect of the present invention, there is provided an endoscopic treatment device which is used together with an endoscope to perform treatment in a body by being operated outside the body. This endoscopic treatment device comprises a transmission member with a flexible structure which has a distal end portion inserted into a body and can be operated outside the body, a push rod coupled to the distal end portion of the transmission member, first and second connecting members coupled to the push rod, each of the first and second connecting members having a distal end portion and a proximal end portion rotatably coupled to the push rod, first and second arm members each having a distal end portion and a proximal end portion rotatably coupled to the distal end portion of a corresponding one of the first and second connecting members, a holding member which rotatably holds the distal end portions of the respective arm members at a predetermined interval therebetween, first and second actuating members which are integrally formed with the distal end portions of the arm members and can open/close when the transmission member actuates the first and second connecting members and the first and second arm members through the push rod, and a needle which is mounted on at least one of the first and second actuating members and is used to puncture a tissue.

According to still another aspect of the present invention, there is provided an endoscopic treatment device which includes recovery means for recovering the thread inserted into a tissue from a needle, wherein the recovery means has a lock member which detaches the needle from one of the first and second actuating members.

According to sill another aspect of the present invention, there is provided an endoscopic treatment device comprising recovery means which is used together with an endoscope to recover a thread inserted into a tissue to perform treatment in a body by being operated outside the body, wherein the recovery means has a needle lock member which can lock a needle, and a thread lock member which can lock a thread, thereby forming needle/thread fixing means which can clamp a tissue between the needle locked to the needle lock member and the thread lock member.

According to still another aspect of the present invention, there is provided an endoscopic treatment device comprising a restriction mechanism which is mounted on at least one of first and second actuating members which can open/close, and restricts a movement range of one actuating member.

According to still another aspect of the present invention, there is provided an endoscopic treatment device which is used together with an endoscope to perform treatment in a body by being operated outside the body. This endoscopic treatment device comprises a transmission member with a flexible structure which has a distal end portion inserted into a body and can be operated outside the body, a push rod coupled to the distal end portion of the transmission member, first and second connecting members coupled to the push rod, each of the first and second connecting members having a distal end portion and a proximal end portion rotatably coupled to the push rod, first and second arm members each having a distal end portion and a proximal end portion rotatably coupled to the distal end portion of a corresponding one of the first and second connecting members, a holding member which rotatably holds the distal end portions of the respective arm members at a predetermined interval therebetween, first and second actuating members which are integrally formed with the distal end portions of the arm members and can open/close when the transmission member actuates the first and second connecting members and the first and second arm members through the push rod, a third actuating member which is pivotally attached to the first actuating member, a third connecting member which is pivotally coupled to the holding member and the third actuating member and moves together with the first and second actuating members, and a needle which is mounted on at least one of the first and second actuating members and is used to puncture a tissue.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 13 is a view seen in a direction indicated by the arrow G of FIG. 7;

FIG. 20 is a view showing the insert assisting device according to a modified example when the endoscope and the suturing device are mounted;

FIG. 21 is a view showing a state in which the endoscope and the suturing device are protruded from the insert assisting device of FIG. 20;

FIG. 22 to FIG. 27 each show a suturing procedure using the suturing device, wherein FIG. 22 is a view showing a state in which a curved needle is proximal to a tissue;

FIG. 23 is a view showing a state in which the curved needle punctures a tissue;

FIG. 24 is a view showing a state in which the thread-catching-device hooks the suture thread;

FIG. 25 is a view showing a state in which the suture thread is retracted into a flexible tubular member together with the hook when the thread is hooked;

FIG. 26 is a view showing a state in which the thread-catching-device is pulled out from an instrument channel port;

FIG. 27 is a view showing a state in which the curved needle is removed from the tissue;

FIG. 31 is an illustrative view showing a state in which the suturing device is protruded in the endoscopic suturing system of FIG. 30;

FIG. 32 to FIG. 35 are views each showing a protect member in the second embodiment, wherein FIG. 32 is a view showing a state in which a movable portion is protruded;

FIG. 33 is a view showing a state in which a moving member disengages a lock member;

FIG. 34 is a view showing a state in which the movable portion is retracted;

FIG. 35 is a detailed view of the lock member;

FIG. 37 to FIG. 41 each show an endoscopic suturing system according to a fourth embodiment, wherein FIG. 37 is a view showing a suturing device used therefor;

FIG. 38 is a view showing a state in which a removable needle after punctured into a tissue is engaged with a needle thread fixing device;

FIG. 39 is a view showing a state in which an injury is closed by tying the suture thread;

FIG. 40 is a view showing a state in which a redundant portion of the suture thread is cut by a thread cutting device;

FIG. 41 is a sectional view taken along the line H-H of FIG. 37;

FIG. 46 is a view showing a suturing device for use in an endoscopic suturing system according to a sixth embodiment of the present invention;

FIG. 47 is a view showing a state in which a removable needle after punctured into a tissue is engaged with a needle fixing device;

FIG. 50 is a view showing a state in which a tissue is sutured while the tissue is pulled by a grasping forceps;

FIG. 51 is a view showing a state for use in an endoscopic suturing system according to a seventh embodiment of the present invention;

FIG. 52 is a view showing a state when a removable needle after punctured into a tissue is engaged with a needle thread fixing device;

FIG. 57 to FIG. 63 each show a suturing procedure using an endoscopic suturing system according to an eighth embodiment of the present invention, wherein FIG. 57 is a view showing a state in which the suturing device is proximal to a tissue to be sutured;

FIG. 58 is a view showing a state in which a removable needle after punctured into a tissue is engaged with a needle fixing device;

FIG. 59 is a view showing a state in which a needle holder is pulled out from a tissue;

FIG. 60 is a view showing a state in which the suturing device and endoscope are spaced from a tissue while the needle thread fixing device is left;

FIG. 61 is a view showing a state in which a tissue is tied with the suture thread;

FIG. 62 is a view showing a state in which the suture thread can be separated;

FIG. 63 is a view showing a state in which a redundant portion of the suture thread is cut by a thread cutting device;

FIG. 67 to FIG. 99 each show the 10th embodiment, wherein FIG. 67 is a sectional view taken along the line A-A of FIG. 68;

FIG. 68 is a view showing an outer appearance of a suturing device (a view taken in the direction of an arrow B in FIG. 67);

FIG. 69 is a view taken in the direction of an arrow C in FIG. 67 (with a partially sectional view);

FIG. 70 is a view taken in the direction of an arrow D in FIG. 69;

FIG. 71 is a sectional view taken along the line E-E of FIG. 69;

FIG. 72 is a sectional view taken along the line F-F of FIG. 69;

FIG. 73 is a sectional view taken along the line G-G of FIG. 69;

FIG. 74 is a view showing the details of the operating section of the suturing device;

FIG. 75 is a sectional view taken along the line H-H of FIG. 74;

FIG. 76 is a view showing an outer appearance of a pre-knot cartridge;

FIG. 77 to FIG. 80 are views for explaining how a removable needle is removed by using a needle-catching-device;

FIG. 81 to FIG. 85 are views showing how the removable needle is removed by using the needle-catching-device;

FIG. 86 and FIG. 87 are views showing a state wherein a cover is so mounted as to prevent a pre-knot of the pre-knot cartridge from coming off the needle-catching-device;

FIG. 88 is a view showing an outer appearance of a spring for locking the removable needle mounted in the needle-catching-device;

FIG. 89 is a view showing in detail how a pre-knot is formed;

FIG. 90 to FIG. 98 are views showing a suturing procedure;

FIG. 99 is a view showing a needle-catching-sheath as another modification of the needle-catching-sheath;

FIG. 100 to FIG. 111 each show the 11th embodiment, wherein FIG. 100 is view showing an outer appearance of a suturing device (a view taken in the direction of an arrow G in FIG. 102);

FIG. 101 is a partially sectional view of FIG. 100;

FIG. 102 is a sectional view taken along the line A-A of FIG. 100;

FIG. 103 is a view taken in the direction of an arrow B in FIG. 101;

FIG. 104 is a sectional view taken along the line C-C of FIG. 101;

FIG. 105 is a sectional view taken along the line D-D of FIG. 101;

FIG. 106 is a sectional view taken along the line E-E of FIG. 102;

FIG. 107 is a sectional view taken along the line F-F of FIG. 102;

FIG. 108 to FIG. 111 are views showing how the suturing device punctures the tissue;

FIG. 112 to FIG. 122 each show the 12th embodiment, wherein FIG. 112 is a view showing an outer appearance of a suturing device (a view taken in the direction of an arrow G in FIG. 114);

FIG. 113 is a partially sectional view of FIG. 112;

FIG. 114 is a sectional view taken along the line A-A of FIG. 112;

FIG. 115 is a view taken in the direction of an arrow B in FIG. 113;

FIG. 116 is a sectional view taken along the line C-C of FIG. 113;

FIG. 117 is a sectional view taken along the line E-E of FIG. 114;

FIG. 118 is a sectional view taken along the line F-F of FIG. 114;

FIG. 119 to FIG. 122 are views showing how the suturing device punctures the tissue;

FIG. 123 to FIG. 126B each show the 13th embodiment, wherein FIG. 123 to FIG. 126A are views showing how the suturing device punctures the tissue;

FIG. 126B is a sectional view of the suturing device;

FIG. 127 to FIG. 128B each show the 14th embodiment, wherein FIG. 127 is a view showing a method of fixing a scope and a suturing device;

FIG. 128B is a view showing an arrangement obtained by mounting a protecting member in the arrangement shown in FIG. 127;

FIG. 129 to FIG. 143 each show the 15th embodiment, wherein FIG. 129 to FIG. 141 are views showing a procedure for continuously suturing the tissue;

FIG. 142 and FIG. 143 are views showing how a continuous suturing operation is performed;

FIG. 144 to FIG. 163 each show the 16th embodiment, wherein FIG. 144 is a partially sectional view of a suturing device;

FIG. 145 is a sectional view taken along the line A-A of FIG. 144;

FIG. 146 is a partial sectional view of an end loop cartridge in FIG. 158;

FIG. 147 to FIG. 157 are views showing the operation of a suturing device when puncturing the tissue;

FIG. 158 is a view showing an outer appearance of the end loop cartridge;

FIG. 159 is a view showing an outer appearance of a lock tubular member;

FIG. 160 and FIG. 161 are views showing a seal structure and operating section formed on the proximal end side of the suturing device;

FIG. 162 is a sectional view of the distal end portion of a thread cutting forceps used to cut a suture thread;

FIG. 163 is a view showing another example of the structure of an outer sheath;

FIG. 164 is a view showing a state wherein the end loop cartridge is loaded in a suturing device;

FIG. 165 and FIG. 166 are views showing another form of a removable needle;

FIG. 167 is a view showing a state wherein the suturing device is mounted on an endoscope and the distal end of the suturing device is brought nearest to the distal end of the endoscope;

FIG. 168 is a view showing a state wherein the distal end of the suturing device is separated from the distal end of the endoscope;

Figure 169:
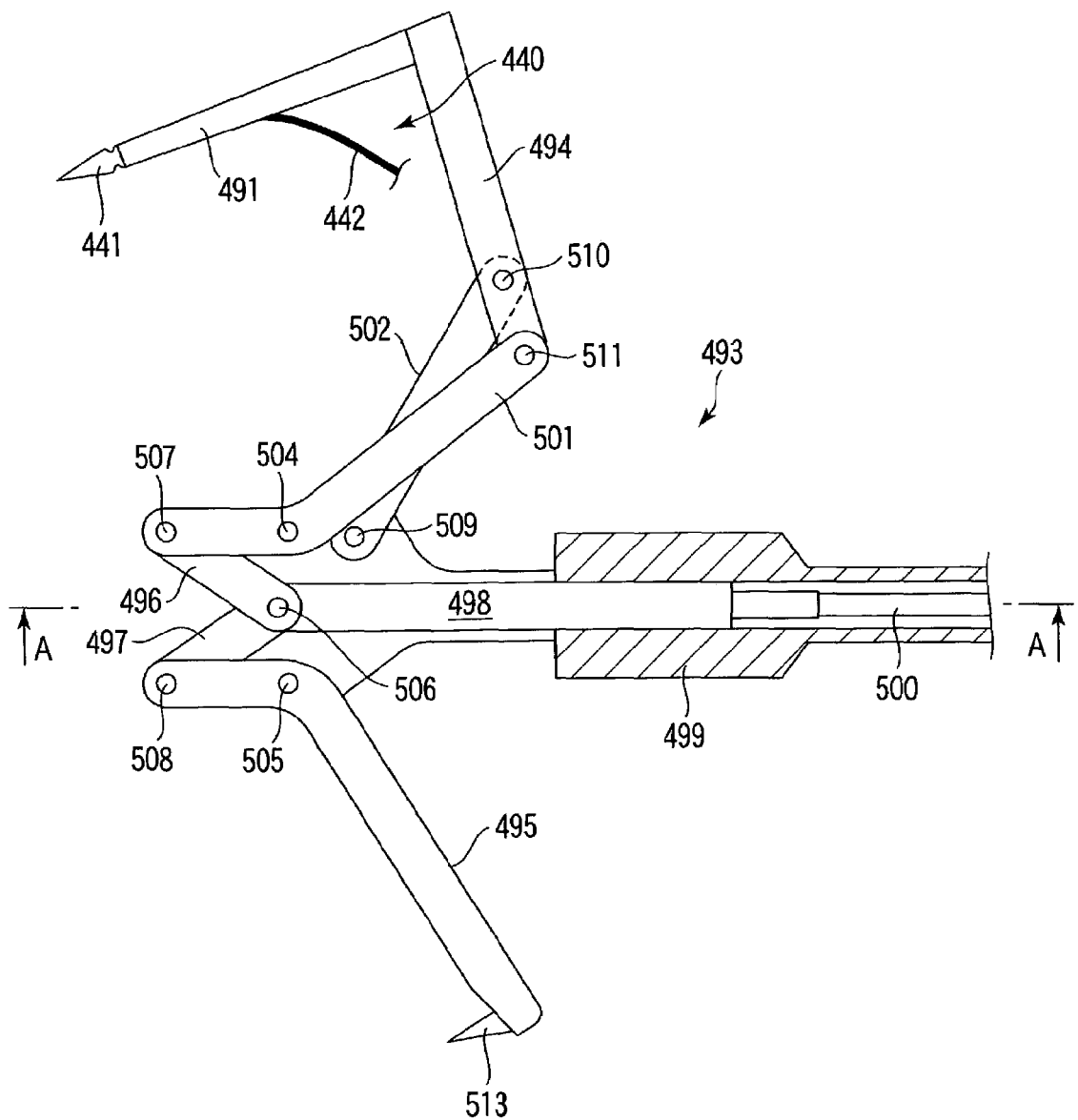
Figure 170:
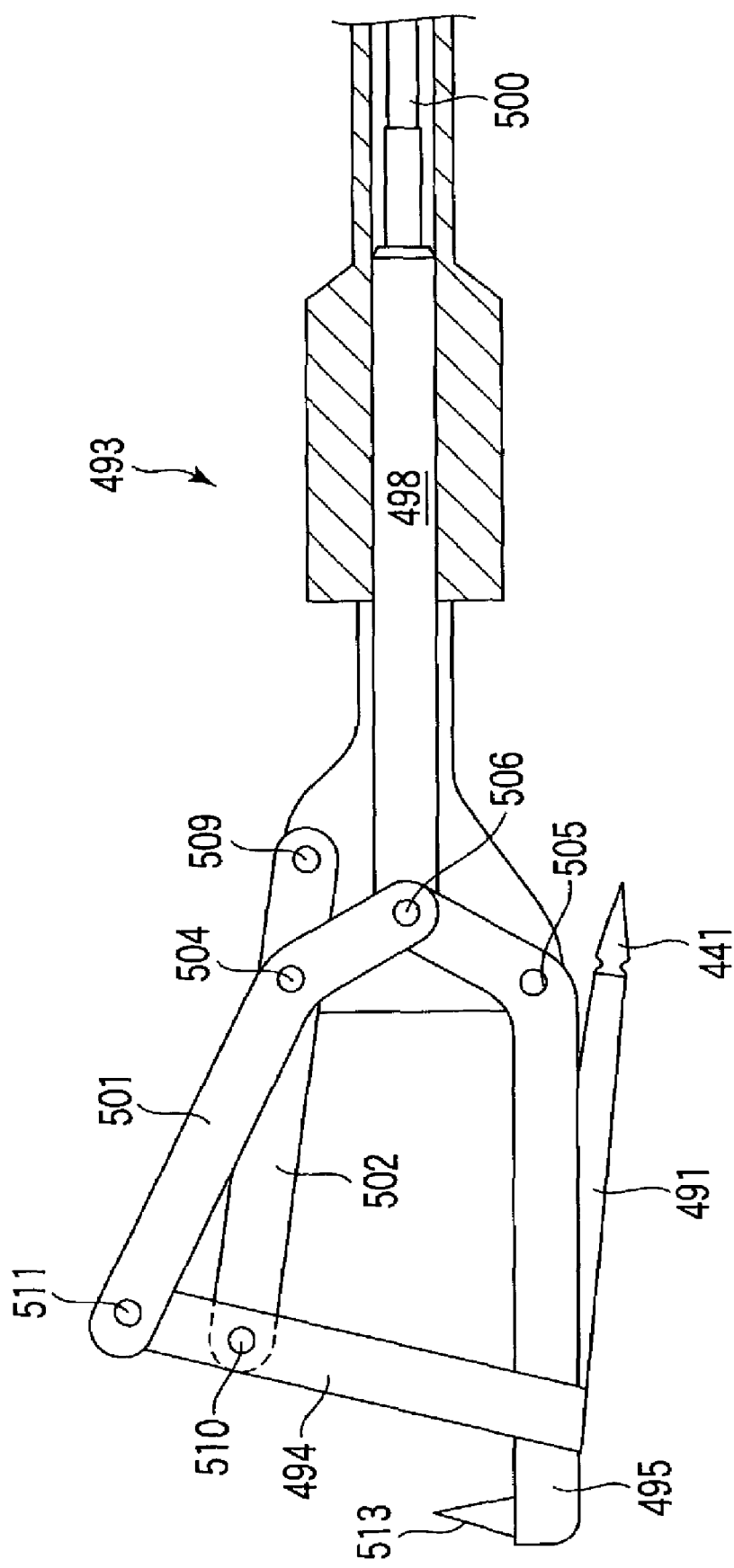
Figure 171:
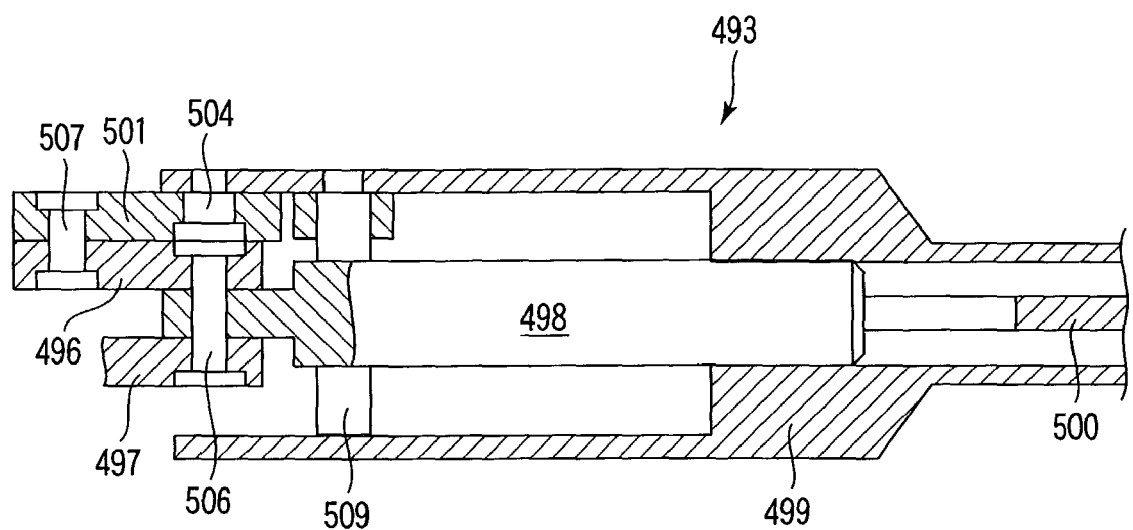
Figure 172:
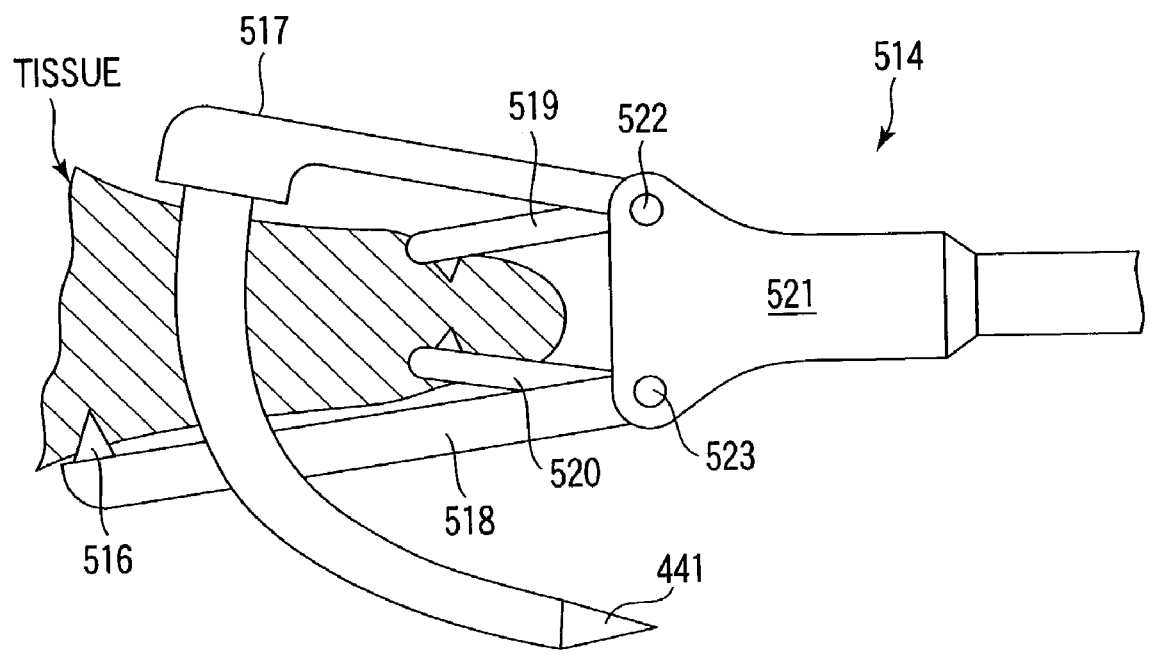
Figure 173:
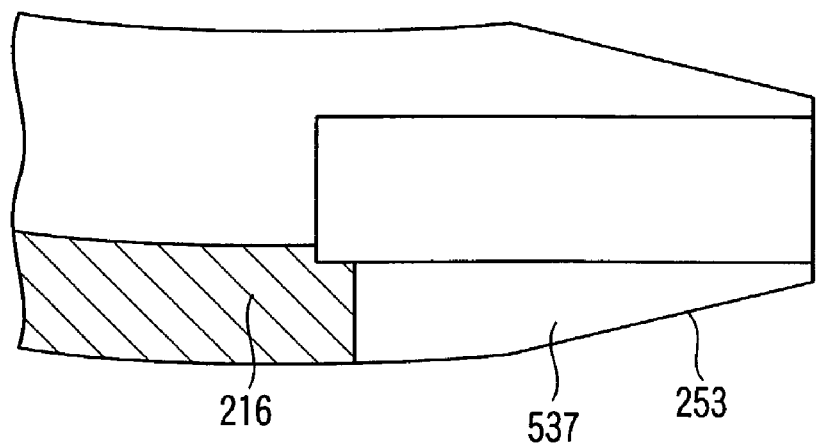
Figure 174:
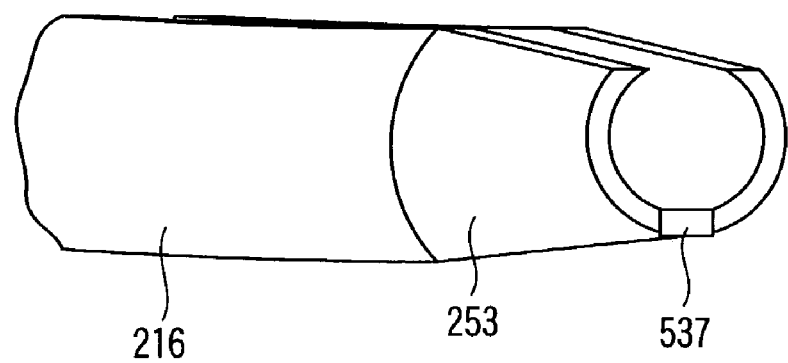
Figure 175:
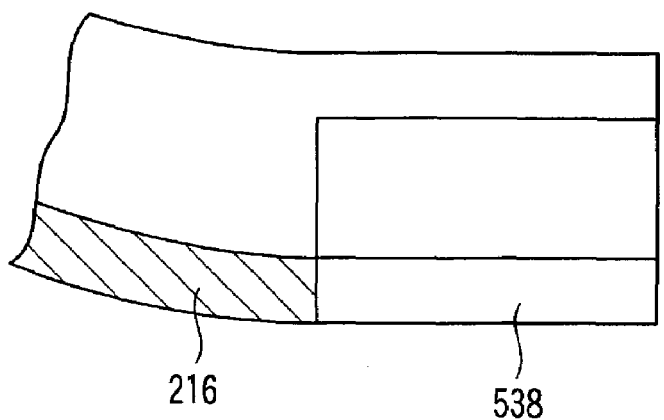
Figure 176:
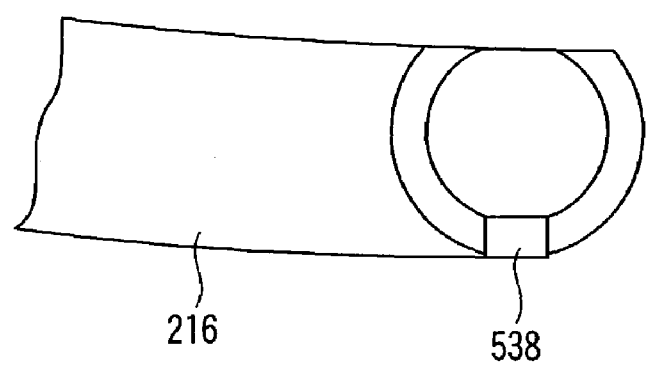
Figure 177:
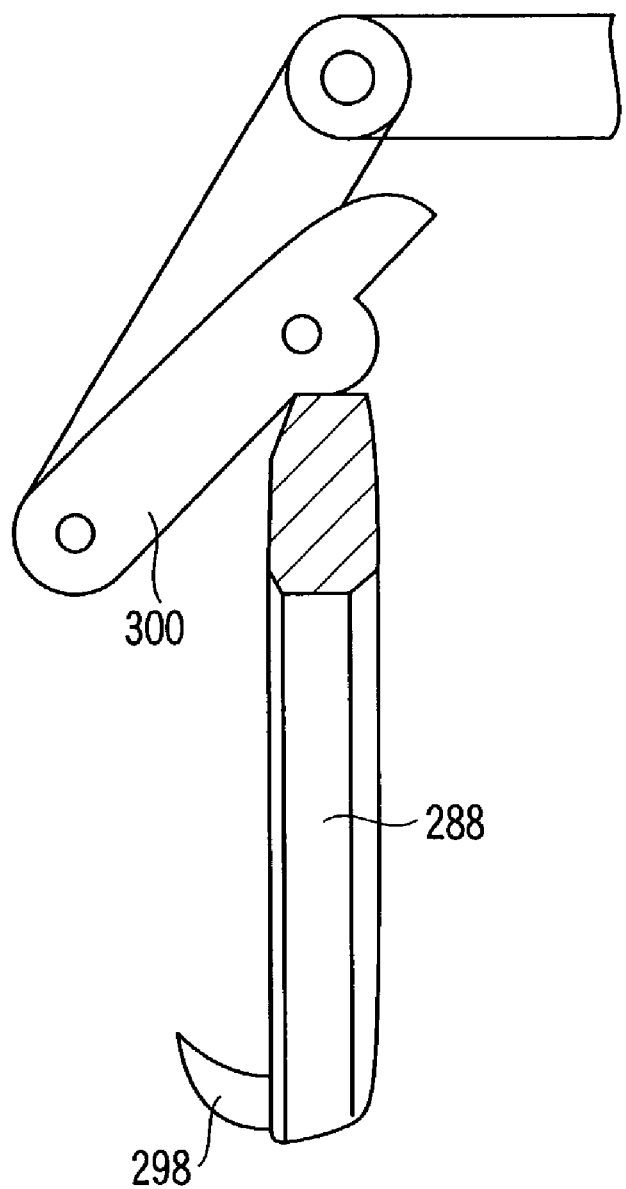
Figure 178:
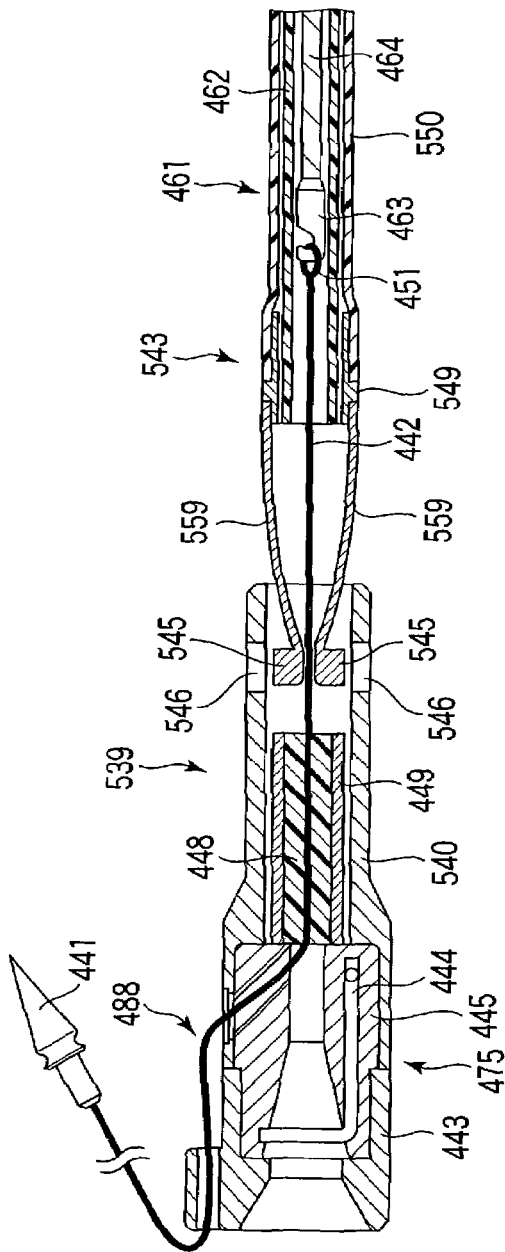
Figure 179:
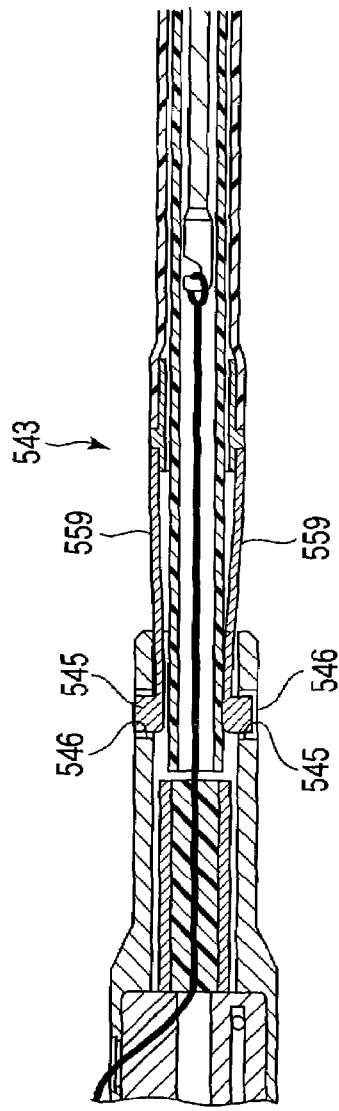
Figure 180:
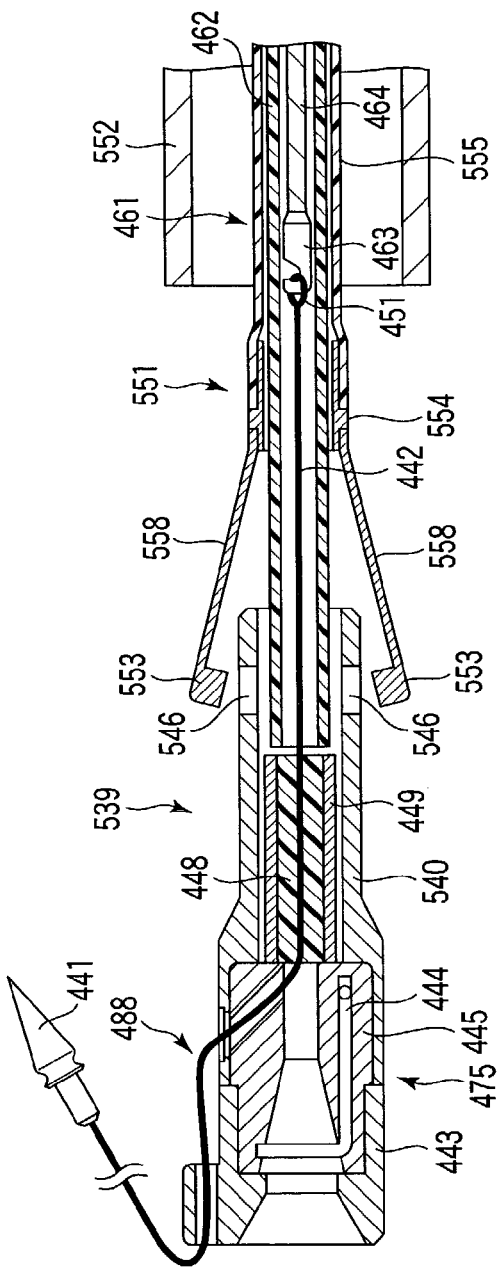
Figure 181:
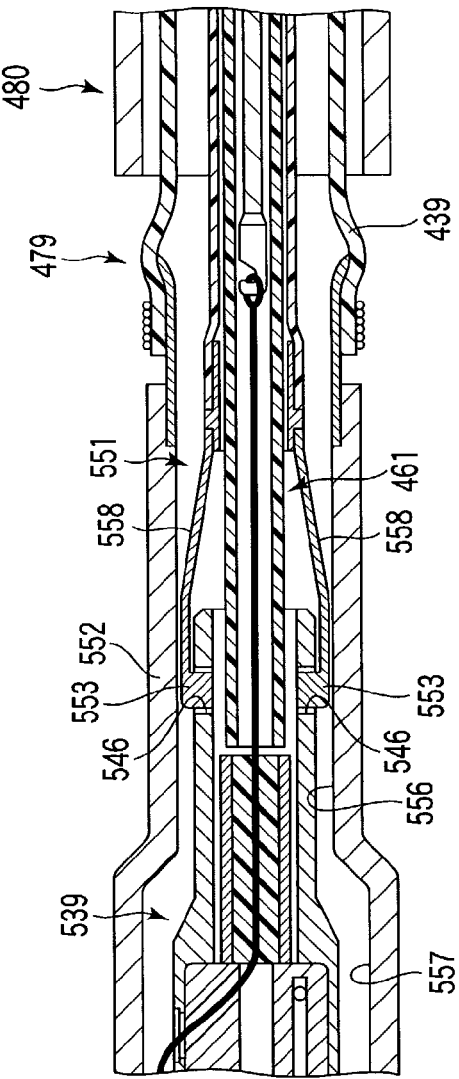

FIG. 169 to FIG. 171 each show the 17th embodiment, wherein FIG. 169 is a partial sectional view showing a state wherein the first and second actuating members of a suturing device are open;

FIG. 170 is a partially sectional view showing a state wherein the first and second actuating members of the suturing device are closed;

FIG. 171 is a sectional view taken along the line A-A of FIG. 169;

FIG. 172 is a view showing a state wherein the tissue is punctured with a suturing device according to the 18th embodiment;

FIG. 173 and FIG. 174 are views showing a modification of a needle holder which can applied to the 10th embodiment;

FIG. 175 and FIG. 176 are views showing another modification of the needle holder;

FIG. 177 is a view showing a fixing needle which can applied to the 10th embodiment and other embodiments;

FIG. 178 and FIG. 179 each show the 19th embodiment, wherein FIG. 178 is a view showing a state wherein an end loop cartridge is to be mounted in an engage tube, and FIG. 179 is a view showing a state wherein the end loop cartridge is mounted in the engage tube; and FIG. 180 and FIG. 181 each show the 20th embodiment, wherein FIG. 180 is a view showing a state wherein an end loop cartridge is to be mounted in an engage tube, and FIG. 181 is a view showing a state wherein the engage tube and a hood device are housed in a distal pipe.

DETAILED DESCRIPTION OF THE INVENTION

First Embodiment

FIG. 1 to FIG. 29 show an endoscopic suturing system according to a first embodiment of the present invention. In the respective systems described hereinafter, although the endoscopic suturing system is used, a gripping forceps, a scissors forceps, a hot biopsy forceps, or a rotational clipping device may be used instead of the suturing system.

Figure 1:
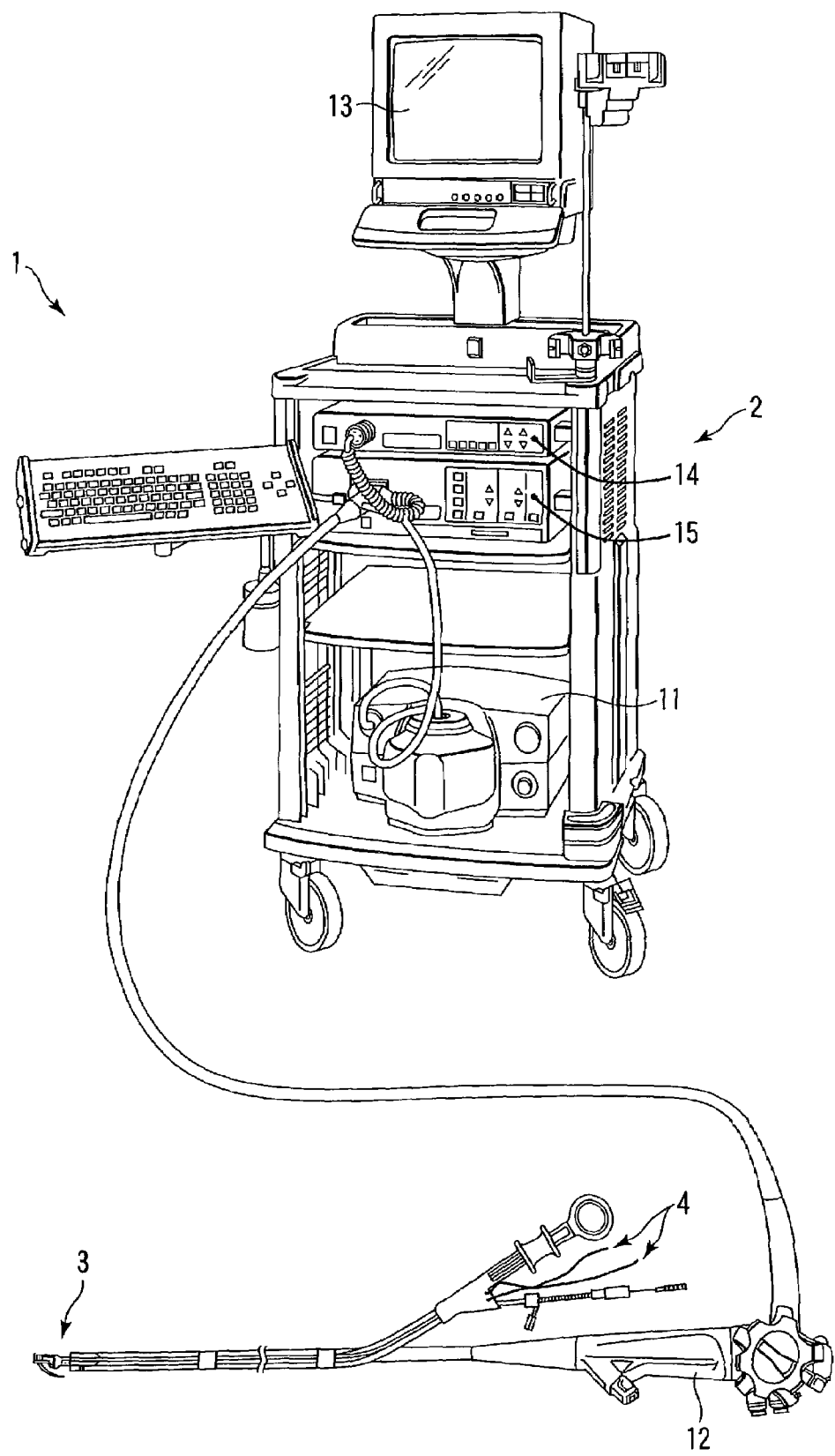
FIG. 1 is an illustrative view showing an entire configuration of an endoscopic suturing system according to a first embodiment of the present invention.
Figure 2:
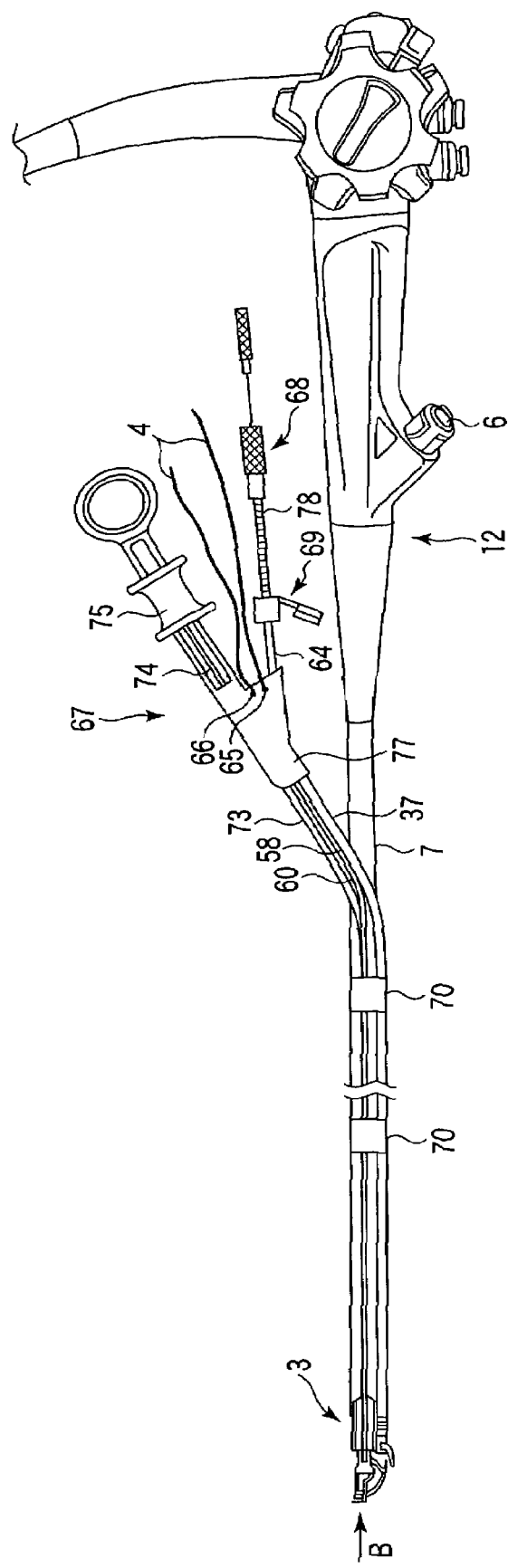
FIG. 2 is an enlarged view of an endoscope and a suturing device shown in FIG. 1.

As shown in FIG. 1, an endoscopic suturing system 1 according to the present embodiment comprises an endoscope system 2, a suturing device 3, and a suture thread 4. This suture thread 4 is preferably formed like a monofilament line or stranded wire by using a material such as nylon, polyester, silk, fluoroplastic or bioabsorbable resin. The endoscope system 2 comprises an endoscope 12, an image processing device 14, a light source device 15, an observation monitor 13, and a suction device 11 as in a generally used videoscope system. The endoscope 12 is connected to the light source device 15 via a universal code. Then, an image signal delivered from a CCD camera 10 (refer to FIG. 8) at its distal end portion is processed in the image processing device device 14, and the processed image is displayed on the monitor 13. As best shown in FIG. 2, although the endoscope 12 is used as having an instrument channel port 6, an endoscope of such type having two instrument channel ports may be used instead thereof.

Figure 8:
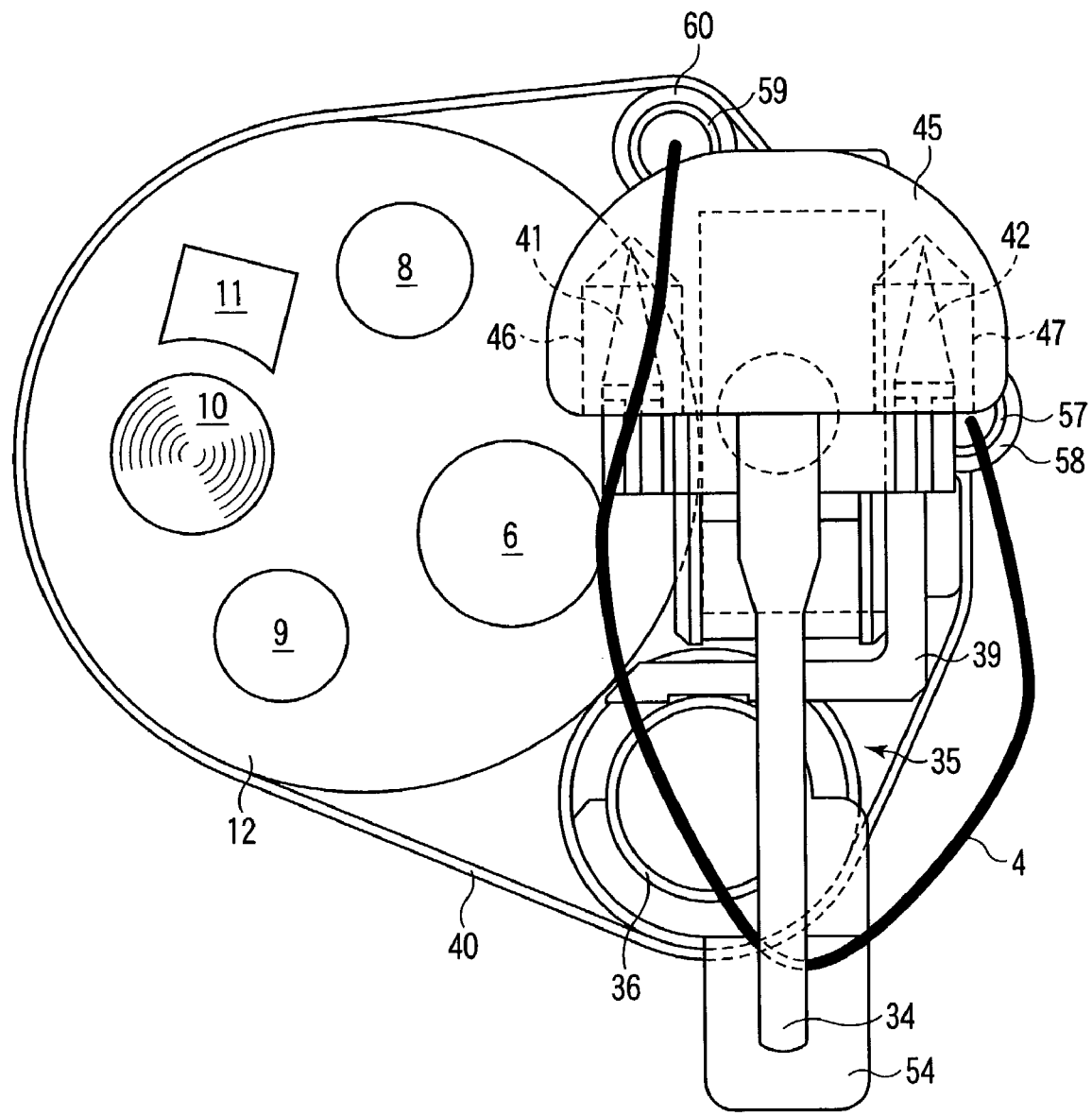
FIG. 8 is a view seen in a direction indicated by the arrow B of FIG. 4.

In addition, as shown in FIG. 8, the CCD camera 10, light guides 8 and 9, instrument channel port 6, and lens washing nozzle 11 for the CCD camera are arranged at a distal end portion of the endoscope 12. A fiberscope with its eyepiece lens may be used instead of the videoscope using the CCD. As shown in FIG. 8, although the suturing device 3 is removably fixed at a distal end of the endoscope 12 by a fixing member 40, the suturing device 3 and the endoscope 12 may be structured integrally with each other instead thereof.

As shown in FIG. 3 to FIG. 7, the suturing device 3 comprises a flexible tube 73 described later and a holding member 18 fixed at its distal end portion to hold a needle described later. This holding member 18 is formed of: two support plate portions 18a opposed to each other through a slit 31 (refer to FIG. 7); and a hole 19 (refer to FIG. 5) which communicates with the slit 33 between these support plate portions and an inner hole of the flexible tube 73. In this hole 19, a push rod 20 is disposed retractably in an axial direction.

At a distal end of this push rod 20, one end of each of first and second connecting members 22 and 23 is pivoted via a pin 21. The other end of each of the connecting members 22 and 23 is pivoted at a proximal end portion of each of first and second arm members 24 and 25 via pins 26 and 27, respectively. Further, a first actuating member 16 formed integrally with the first arm member 24 is rotatably linked with the support plate portion 18a via a pin 28. Similarly, a second actuating member 17 formed integrally with the second arm member 25 is rotatably linked with the support plate portion 18a via a pin 29.

Figure 7:
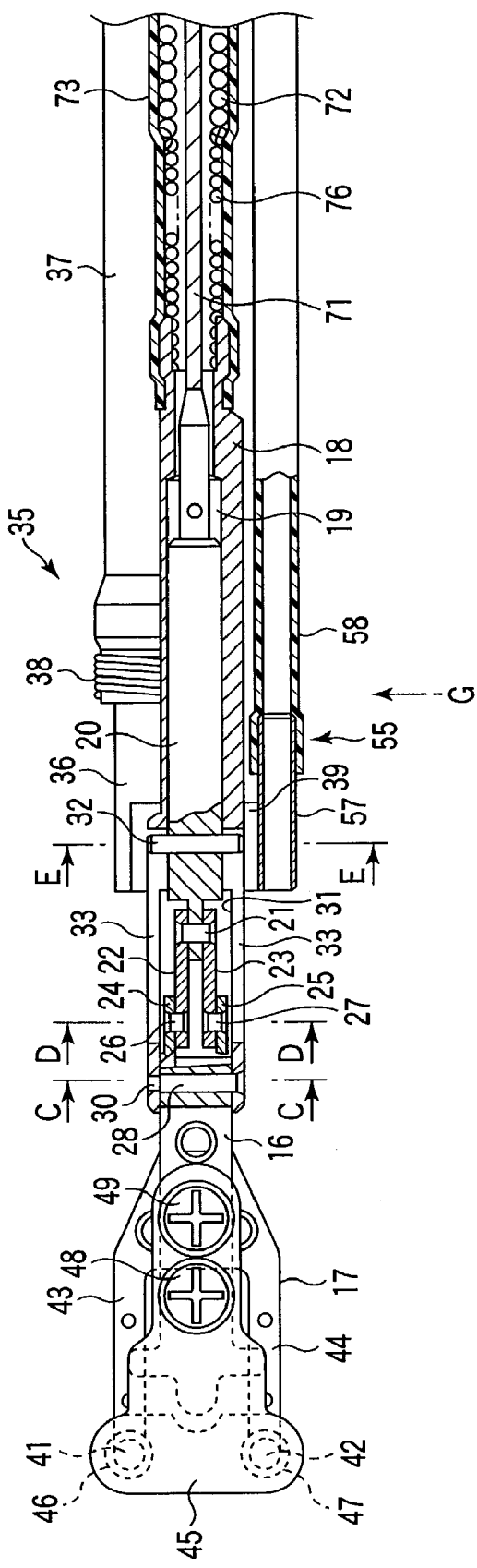
FIG. 7 is a sectional view taken along the line A-A of FIG. 5.

In FIG. 7, as is illustrated by the pin 28, the pins 28 and 29 each have an end portion formed by a reduced diameter portion 30. In this manner, the size of the slit 31 defined between the support plate portions 18a of the holding member 18 is maintained to be slightly larger than a sum of the thickness of the first actuating member 16 and the second actuating member 17. The first actuating member 16 and the second actuating member 17 can be moved in the slit 31 without generating a remarkable friction.

As shown in FIG. 7, the push rod 20 is linked with an elongated flexible transmission member 71. In addition, the holding member 18 is linked with coils 72 and 76 that form an axial hole. These coils 72 and 76 are linked with each other at their end faces opposed to each other by suitable means such as laser welding, blazing, soldering, adhering or the like. The coil 76 is formed of an element wire that is more smaller in diameter than the coil 72, whereby the suturing device 3 is formed more flexibly at its distal end side. These coils 72 and 76 are covered with the flexible tube 73 almost all over their full lengths, and is held so as to be in intimate contact with this flexible tube 73. The tube 73 restricts contraction in the axial direction of the coils 72 and 76, thereby increasing a force for opening and closing the first actuating member 16 and the second actuating member 17.

As shown in FIG. 2, frontal side end portions of the tube 73 and the coil 72 are fixed to an operating member main body 77 of an operating member 67 of the suturing device. In addition, a frontal side end portion of the transmission member 71 is inserted into the operating member main body 77, and is linked with a pipe 74 while it is inserted into the pipe 74 that is slidable relative to this operating member main body 77. This pipe 74 is connected to a movable member 75 by a link member (not shown). Therefore, when the movable member 75 is moved relative to the operating member main body 77, the first actuating member 16 and the second actuating member 17 can be opened/closed via the transmission member 71.

Figure 5:
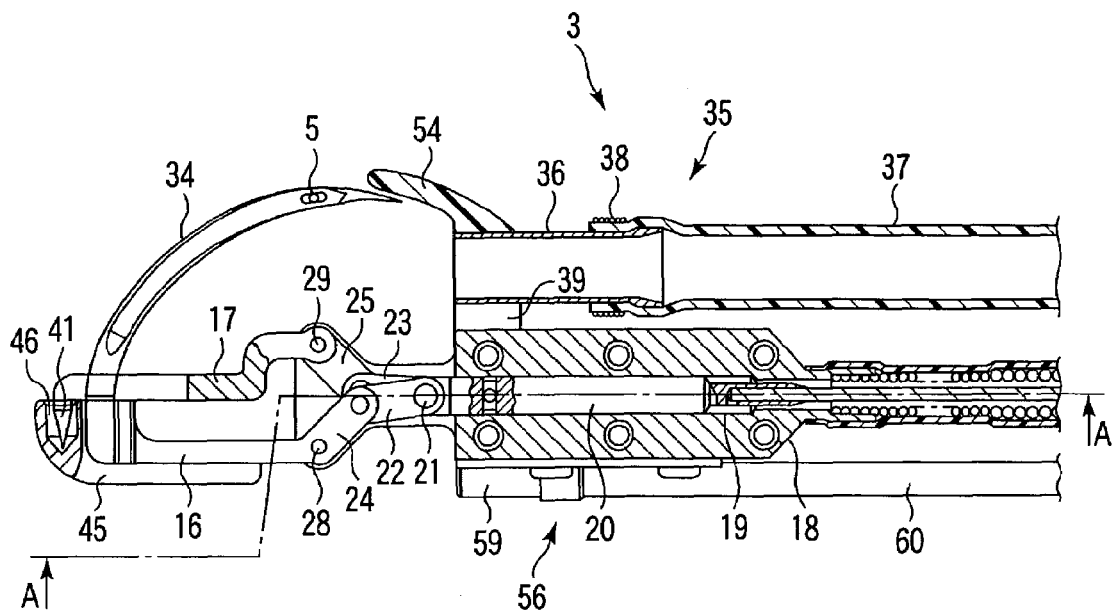
FIG. 5 is a sectional view showing an internal structure of the suturing device of FIG. 3.
Figure 6:
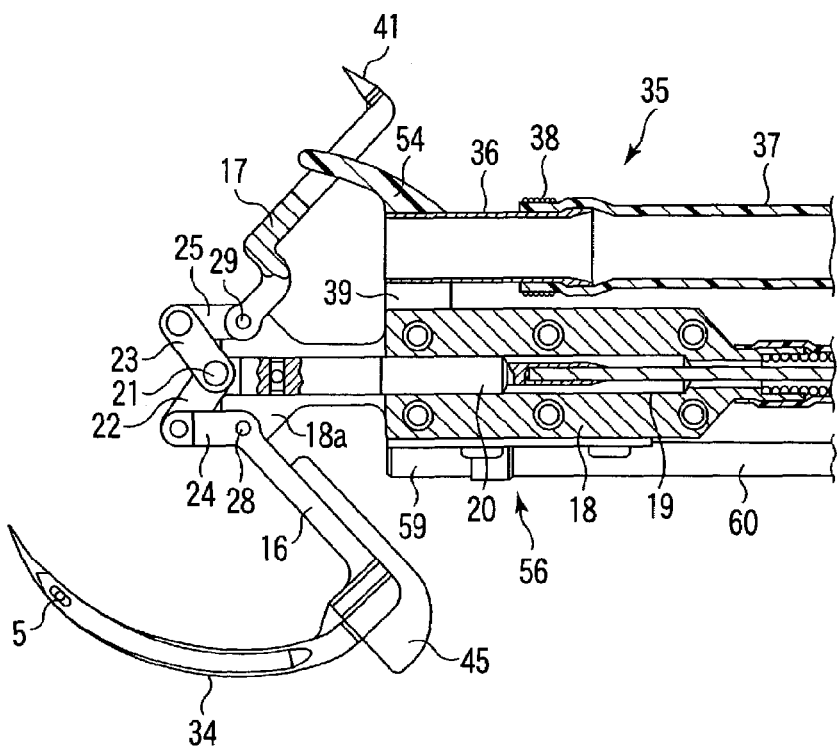
FIG. 6 is a sectional view showing an internal structure of the suturing device of FIG. 4.

As shown in FIG. 5 and FIG. 6, the first and second arm members 24 and 25 can pass through the pins 28 and 29, and can be opened up to an angle shown in FIG. 6. The length of these first and second arm members 24 and 25 each and the length of the first and second connecting members 22 and 23 each are properly set, whereby an angle between the first and second arm members 24 and 25 can be further increased or decreased, of course. Needless to say, these members can be opened/closed within the angle range of 95 degrees or more and less than 360 degrees.

Figure 3:
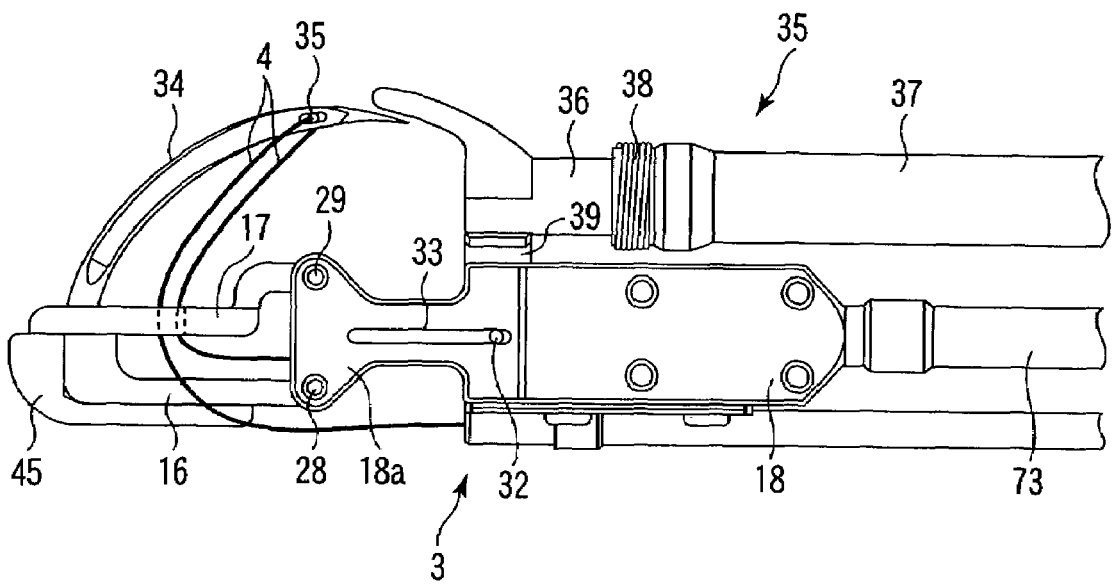
FIG. 3 is an illustrative view showing a state in which first and second actuating members of the suturing device are closed.
Figure 4:
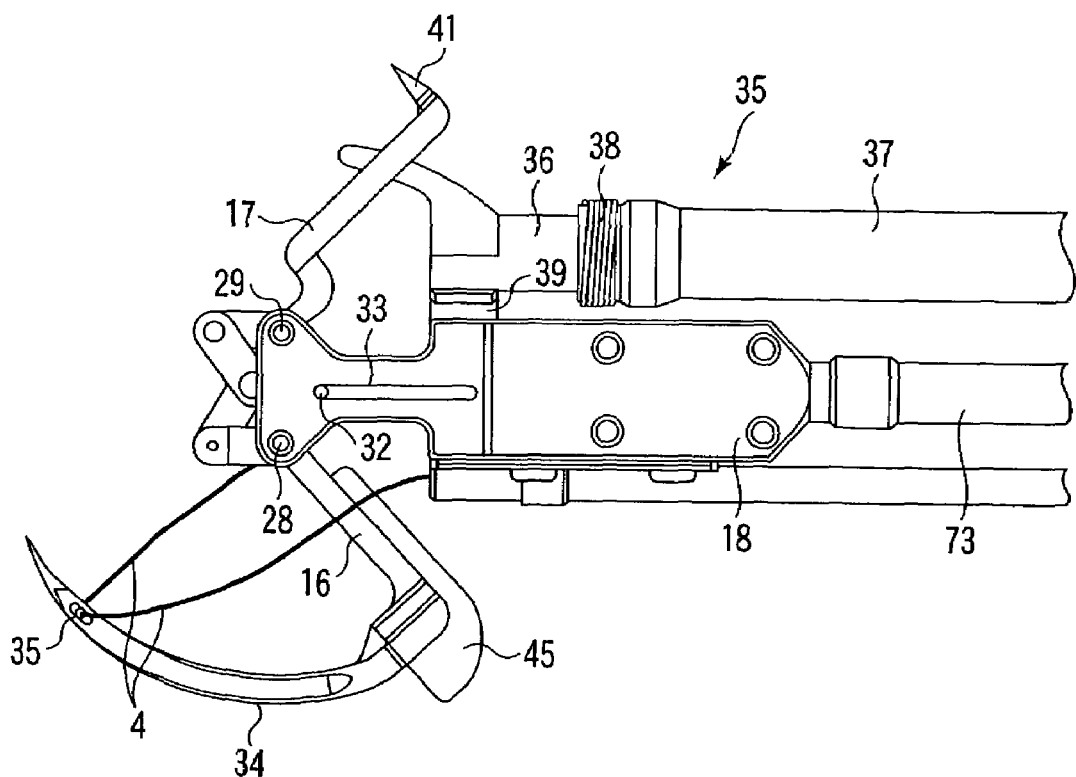
FIG. 4 is an illustrative view showing a state in which the first and second actuating members of the suturing device are opened.
Figure 11:
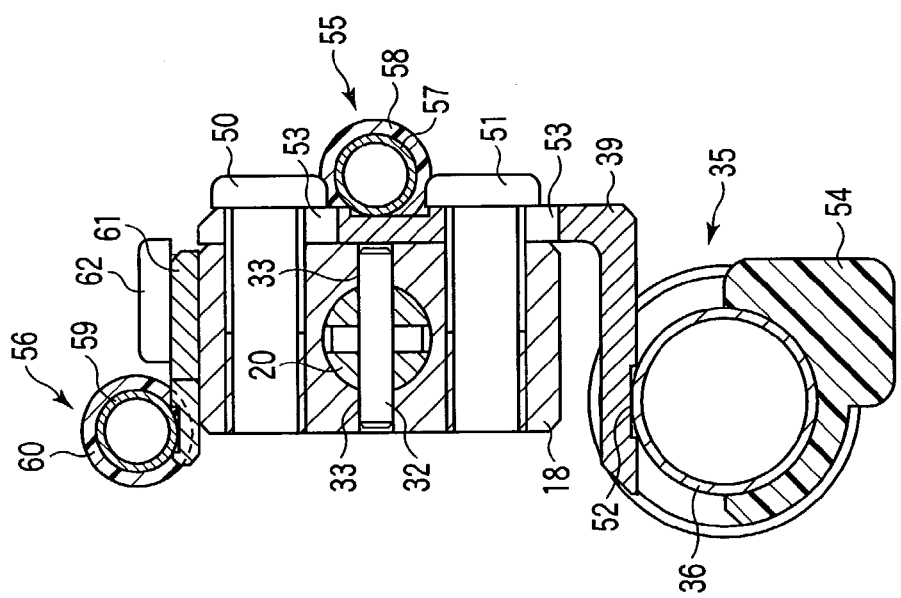
FIG. 11 is a sectional view taken along the line E-E of FIG. 7.

As shown in FIG. 7 and FIG. 11, a stopper pin 32 is fixed to the push rod 20. The stopper pin 32 is guided to the inside of a slit 33 that extends in a longitudinal direction formed at the holding member 18, as shown in FIG. 3, FIG. 4, and FIG. 7, and the movement in the opening direction of the first and second actuating members 16 and 17 can be restricted.

A curved needle 34 is fixed to a distal end of the first actuating member 16. Alternatively, this curved needle 34 may be detachably mounted on the first actuating member 16. A needle eye 5 into which a suture thread 4 can be inserted is formed at a distal end side of the curved needle 34. In addition, as shown in FIG. 8, the curved needle 34 is so small in thickness as to be better punctured into a tissue.

As shown in FIG. 5 to FIG. 8A, the second actuating member 17 has bifurcated fixing arms 43 and 44. Fixing needles 41 and 42 are fixed to distal ends of these fixing arms 43 and 44, respectively. In the present invention, although the fixing needles 41 and 42 are fixed integrally to the fixing arms 43 and 44, these needles may be removably mounted. On the other hand, as shown in FIG. 7, a protect member 45 having holes 46 and 47 formed thereat is fixed to the first actuating member 16 by screws 48 and 49. As shown in FIG. 5 and FIG. 6, this protect member 45 covers a needle tip of the fixing needles 41 and 42 each when the first and second actuating members 16 and 17 are closed. For example, this protect member prevents a tissue or the like from being caught by the fixing needles 41 and 42. Alternatively, the protect member 45 may have a structure in which a recess 254 is formed in a first actuating member 218 as in the 10th embodiment (see FIG. 68) (to be described later).

As shown in FIG. 5 and FIG. 11, a channel member 35 is fixed to the holding member 18 via an L shaped supporting member 39. This channel member 35 has: a pipe 36 formed of a comparatively hard member disposed at its distal end portion; and a tube 37 formed of a comparatively soft material tightened by a fixing thread 38 after pressed into this pipe. This fixing thread 38 is fixed to the tube 37 by an adhesive. This pipe 36 is inserted into a concave portion 52 (refer to FIG. 11) of the support member 39, and is fixed to this support member 39 by proper means such as brazing, soldering, or bonding. This support member 39 is formed of two elongated holes 53 through which screws 50 and 51 can pass, as shown in FIG. 11 and FIG. 13, whereby the support member 39 can be fixed to the holding member 18 by the screws 50 and 51 so as to make it possible to adjust a position relevant to the holding member 18.

Figures 8A, 9, 10:
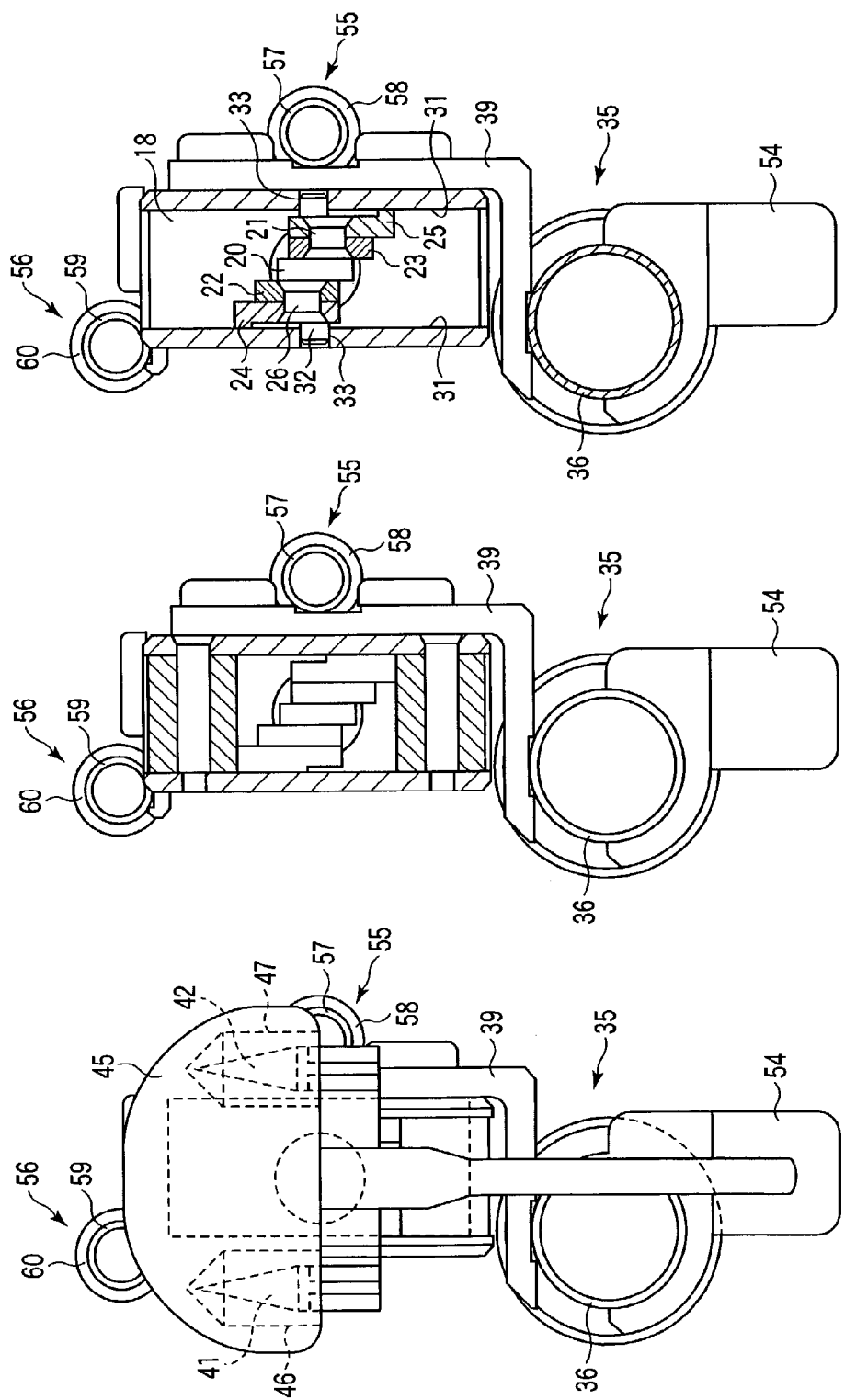
FIG. 8A is a view showing a suturing device when an endoscope is removed, the view being similar to FIG. 8.
FIG. 9 is a sectional view taken along the line C-C of FIG. 7.
FIG. 10 is a sectional view taken along the line D-D of FIG. 7.

In addition, as shown in FIG. 10 and FIG. 11, a protect member 54 is fixed to the pipe 36 by proper means such as brazing, soldering, or bonding. This protect member 54 covers a needle tip of the curved needle 34 when the first and second actuating members 16 and 17 are closed, and prevents the curved needle 34 from being caught by a tissue or the like. As shown in FIG. 11 and FIG. 13, a thread guide 55 having its axial hole through which the suture thread 4 can pass is mounted on the support member 39. This thread guide 55 is composed of: a pipe 57 formed of a relatively hard material; and a tube 58 formed of a relatively soft material. The pipe 57 is fixed to the tube 58 by proper means such as press-in or bonding, for example. In addition, the pipe 57 is fixed to the support member 39 by proper means such as brazing, soldering, or bonding.

Figure 12:
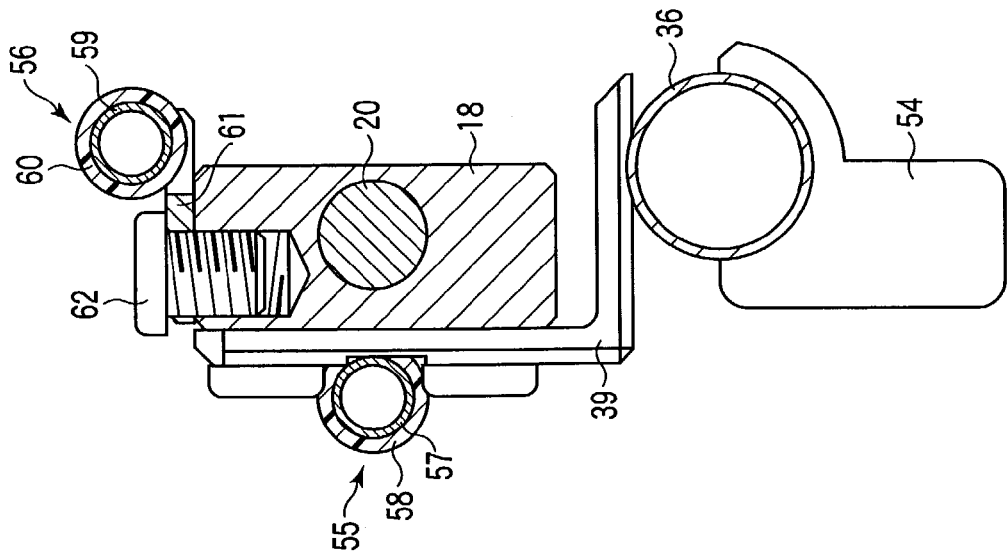
FIG. 12 is a sectional view taken along the line F-F of FIG. 13.

As shown in FIG. 11 to FIG. 13, like the thread guide 55, a thread guide 56 is fixed to the holding member 18 by screws 62 and 63. This thread guide 56 is composed of: a pipe 59 formed of a relatively hard material; a tube 60 formed of a relatively soft material; and a plate shaped support member 61. The support member 61 and the pipe 59 are fixed by appropriate means such as brazing, soldering, or bonding.

As shown in FIG. 2, the tube 37 communicates with a base 64 linked with the operating member main body 77 at its frontal side. A biopsy valve 69 is attached to the frontal side of this base 64. In addition, tubes 58 and 60 communicate with holes 65 and 66 formed at the operating member main body 77, respectively, at their frontal side.

In addition to the above described fixing member 40 (refer to FIG. 8), the suturing device 3 according to the present embodiment is fixed at several positions to an insert portion 7 of the endoscope 12 by another fixing member 70 as shown in FIG. 2. These fixing members 70 as well are removably formed, whereby the suturing device 3 can be removably mounted on the insert portion 7 of the endoscope 12. Of course, the suturing device 3 and the insert portion 7 are formed integrally with each other, whereby they are made removable from each other.

Figure 14:
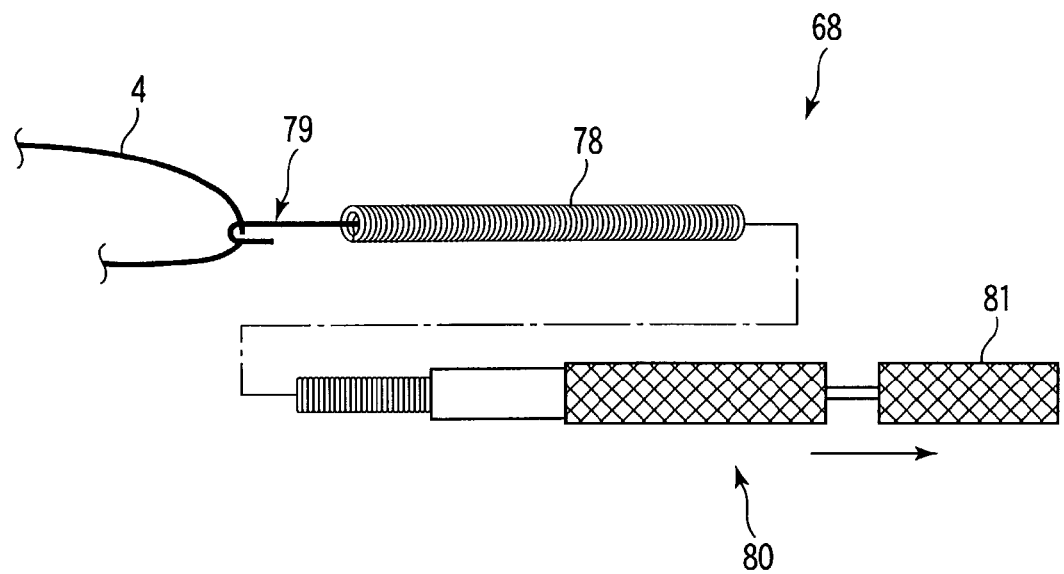
FIG. 14 is a view showing a hook of a thread-catching-device when a suture thread is hooked.
Figure 15:
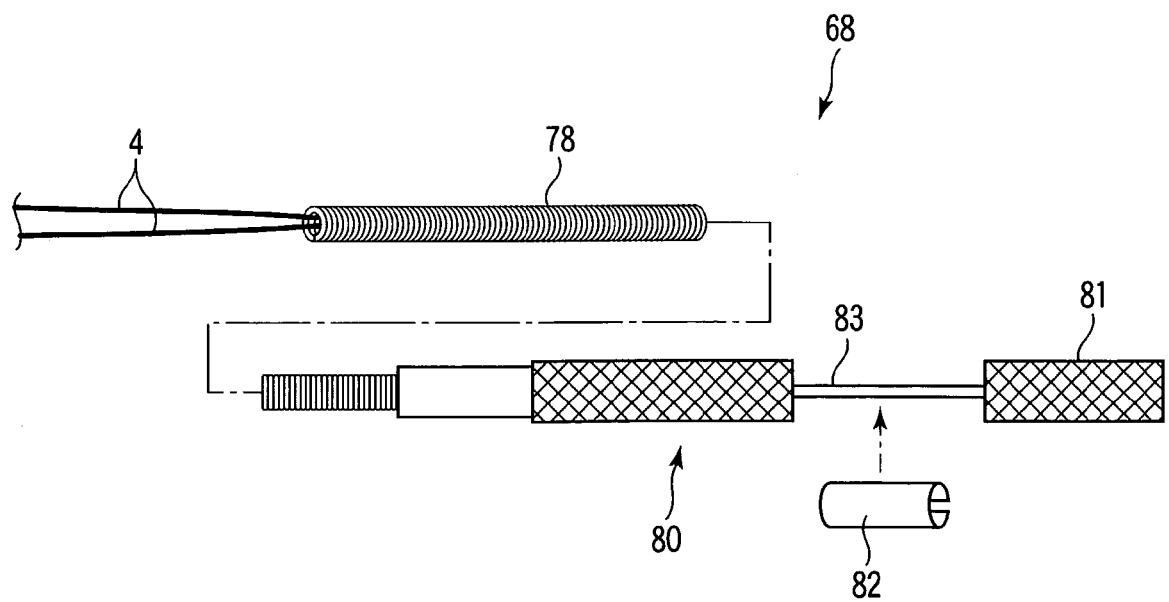
FIG. 15 is a view showing a hook of a thread-catching-device when the suture thread and hook are retracted into a sheath.
Figure 15A:
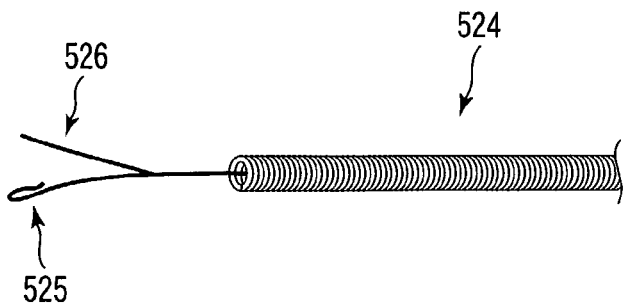
FIG. 15A is a view showing an outer appearance of another thread-catching-device.
Figure 15B:
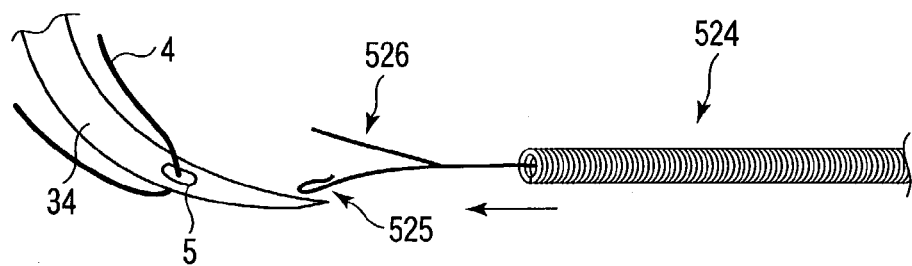
FIG. 15B and FIG. 15C are views showing how the thread-catching-device catches a thread by using a hook.
Figure 15C:
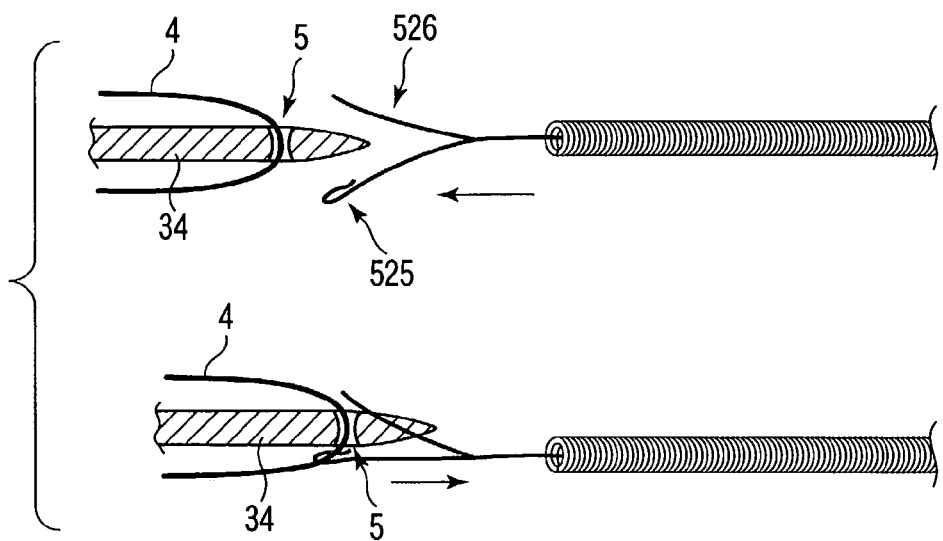

As shown in FIG. 2, FIG. 14, and FIG. 15, a thread-catching-device 68 for catching the suture thread 4 comprises: a hook 79 which is movable in an axial direction and rotatable within a flexible tubular member 78 formed of a coil or the like; and an operating member 80 of the thread-catching-device for operating the hook 79. The hook 79 advances and retracts a grip 81 disposed movably via a pipe 83, for example, whereby the hook can be housed in the flexible tubular member 78 or can be protruded therefrom. The suture thread 4 can slid on this hook 79 when it is hooked by the hook 79. In addition, a stopper 82 which inhibits advancing movement of the grip 81 is engaged in the pipe 83, for example, whereby the hook 79 can be locked so as not to come off the flexible tubular member 78. Such a thread-catching-device 68 is formed to have outer diameter capable of passing through the inside of the channel 35. Alternatively, a thread-catching-device 524 shown in FIG. 15A to FIG. 15C may be used. This thread-catching-device 524 has a hook 525 on which the suture thread 4 can slide as in the case with the thread-catching-device 68. In addition, a guide member 526 is so formed as to face the thread-catching-device 524. As shown in FIG. 15C, the curved needle 34 is caught between the guide member 526 and the hook 525 to facilitate catching the suture thread 4 by using the hook 525.

Figure 16:
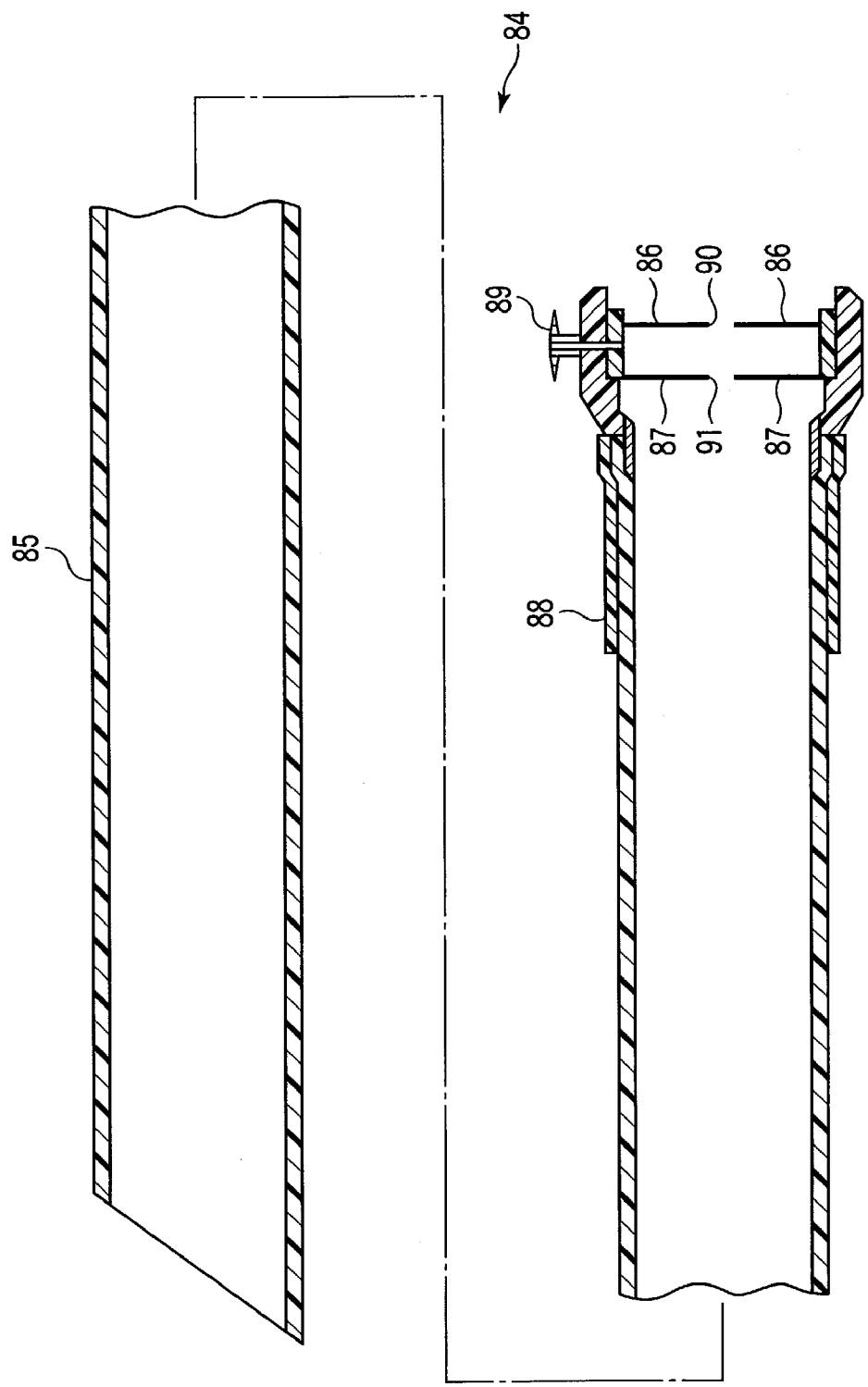
FIG. 16 is a schematic longitudinal cross section of an insert assisting device.

FIG. 16 shows an insert assisting device 84 for inserting the insert portion 7 that includes the suturing device 3 into a body.

The insert assisting device 84 according to the present embodiment comprises: a flexible tubular member 85 formed in a shape such that its distal end can be easily inserted into a body, for example, in a tapered shape; two valves 86 and 87 having circular holes 90 and 91 disposed respectively at the proximal end side of this flexible tubular member 85; and a base 89 which communicates with an axial hole of the flexible tubular member 85. This base 89 can be used to connect an aspirator (not shown) via a tube, for example, if an aspirating function is required. It is preferable that this base 89 be sealed with a cap (not shown) when it is not used.

Figure 19:
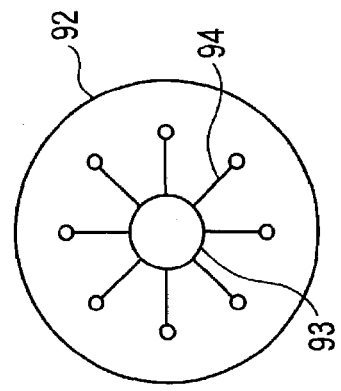
FIG. 19 is a view showing a modified example of a valve mounted on the insert assisting device.

As shown in FIG. 19, instead of the above described valves 86 and 87, a plurality of slits 94 are provided around a hole 93, thereby making it possible to use a valve 92 such that an object having its external diameter larger than the hole 93 can pass.

In addition, instead of the insert assisting device 84, an insert assisting device 95 shown in FIG. 20 and FIG. 21 may be used. This insert assisting device 95 comprises: a flexible tubular member 96; a flexible hood member 97 disposed frontally of the flexible tubular member 96; and a fixing member 98 for fixing this hood member so as to be almost sealed at the insert portion 7 that includes the suturing device 3. This insert assisting device 95 is useful to maintain air tightness in a body. After this insert assisting device 95 has been inserted into the body, an endoscope is pushed out in a direction indicated by the arrow in FIG. 21, whereby the suturing device 3 fixed to this endoscope can be protruded from the flexible tubular member 96.

Figure 42:
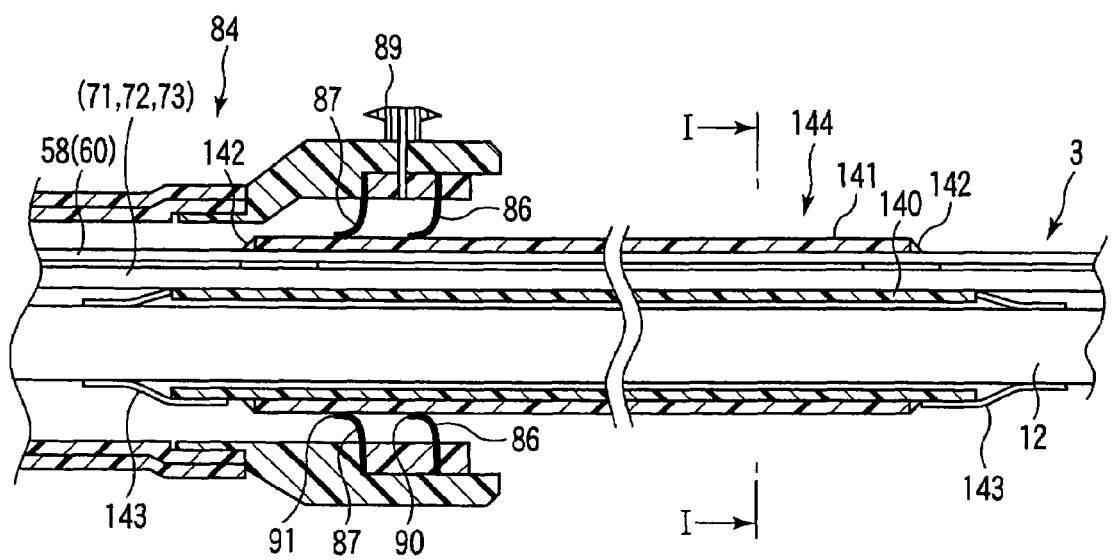
FIG. 42 is a sectional view showing a state in which sealing means is incorporated into the frontal side of the insert assisting device shown in FIG. 16.
Figure 43:
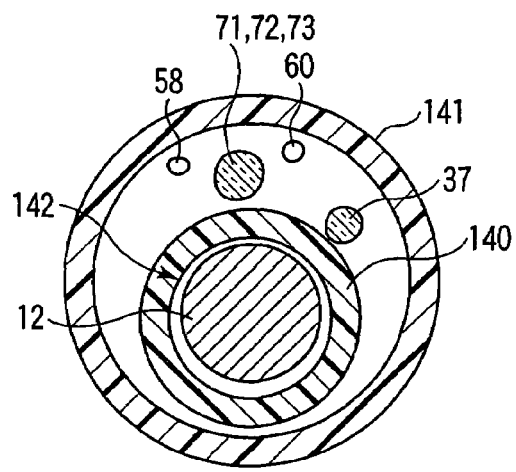
FIG. 43 is a sectional view taken along the line I-I of FIG. 42.

In addition, as shown in FIG. 42 and FIG. 43, sealing means 144 may be provided at the proximal end side of the suturing device 3 and the endoscope 12.

This sealing means 144 comprises: an inner tube 140 having its inner diameter through which the endoscope 12 can pass; and an outer tube 141 having its inner diameter larger than the inner tube 140, the outer tube having this inner tube inserted therethrough. The outer diameter of the outer tube 141 is slightly larger than the inner diameter of each of the holes 90 and 91 of the valves 86 and 87. Tubes 37, 58, 60, and 73 and the like are passed through a space formed between the inner tube 140 and the outer tube 141. A sealing member 142 is filled in a space between these tubes. At both ends of the inner tube 140, a space between the tube and the endoscope 12 is sealed by a tape 143. In this manner, a space between the insert assisting device 84 and the suturing device 3 and the endoscope 12 are securely sealed, and air is fed into a body, thereby preventing air leakage when the body is inflated.

Now, suturing procedures using the above described suturing system will be described here.

Figure 17:
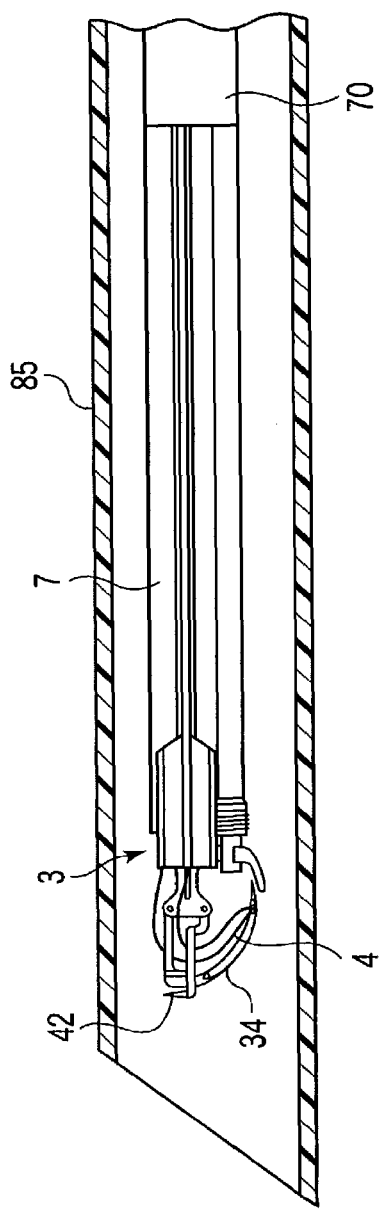
FIG. 17 is an illustrative view showing a state in which an endoscope having a suturing device mounted thereon is housed in an insert assisting device.

(1) The suturing device 3 and the endoscope 12 assembled in a state shown in FIG. 2 are inserted into the flexible tubular member 85 shown in FIG. 16, and are disposed until a state shown in FIG. 17 has been obtained. At this time, the suture thread 4 is inserted into the needle eye 5 of the curved needle 34, and each end portion passes through the thread guides 55 and 56 each. Then, the suture thread 4 is held so as to be pulled out of the suturing device 3 from the holes 65 and 66 of the operating member main body 77. In addition, the endoscope 12 is connected to the image processing device 14, the light source device 15 and the like (FIG. 1) via a universal code. Then, while the inside of the body is observed through the monitor 13, the flexible tubular member 85 having the suturing device 3 and the endoscope 12 housed therein is inserted into a required location in the body.

(2) The inside of the body is inflated by using an air feeding function such as an endoscope, thereby providing a space.

Figure 18:
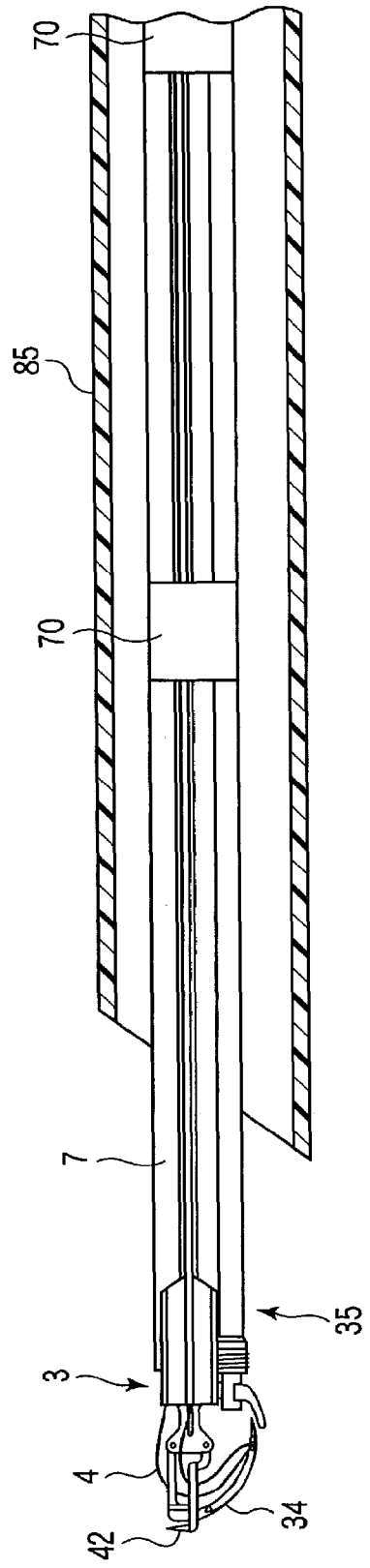
FIG. 18 is an illustrative view showing a state in which the endoscope having the suturing device mounted thereon is protruded from the insert assisting device.

(3) As shown in FIG. 18, the endoscope 12 is advanced, whereby the suturing device 3 is protruded from the flexible tubular member 85.

(4) The suturing device 3 is placed close to the suture site, the movable member 75 shown in FIG. 2 is pushed, and the second actuating members 16 and 17 are opened as shown in FIG. 4.

Figure 22:
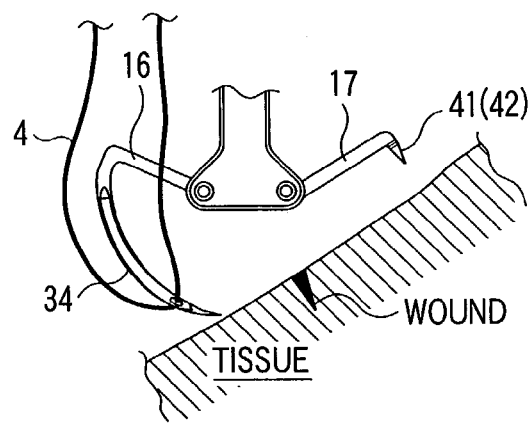
Figure 23:
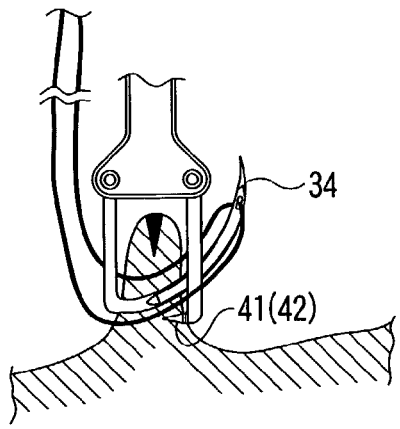

(5) As shown in FIG. 22, the movable member 75 is operated while the curved needle 34 and the fixing needles 41 and 42 are pushed against the suture site. As shown in FIG. 23, the first and second actuating members 16 and 17 are closed.

Figure 24:
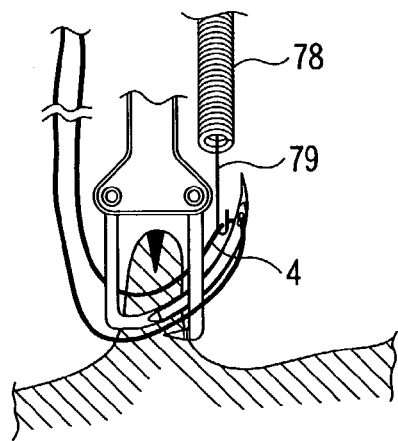
Figure 25:
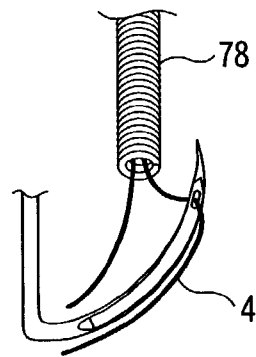

(6) As shown in FIG. 24, the suture thread 4 coming off a tissue is hooked by the hook 79 of the thread-catching-device 68 inserted via the biopsy valve 69. As shown in FIG. 25, the suture thread 4 is retracted into the flexible tubular 78 together with the hook 79.

Figure 26:
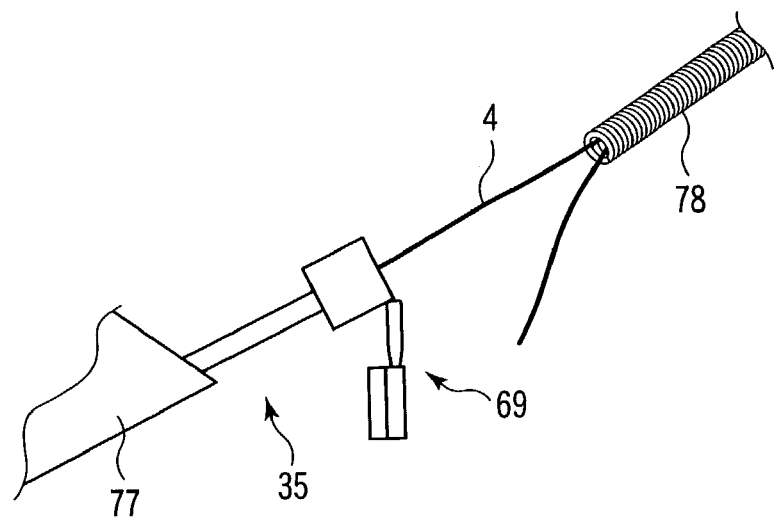

(7) As shown in FIG. 26, the thread-catching-device 68 is pulled out from the channel 35 to the outside of the body, and the suture thread 4 is pulled out from the biopsy valve 69. At this time, the suture thread 4 slides on the hook 79, whereby one end portion of the suture thread 4 moves from one of the thread guides 55 and 56 into the channel 35, and is pulled out from the channel 35 to the outside of the body together with the thread-catching-device 68. The other end portion of the suture thread 4 is held so as to be inserted through the other end of the thread guides 55 and 56 each.

Figure 27:
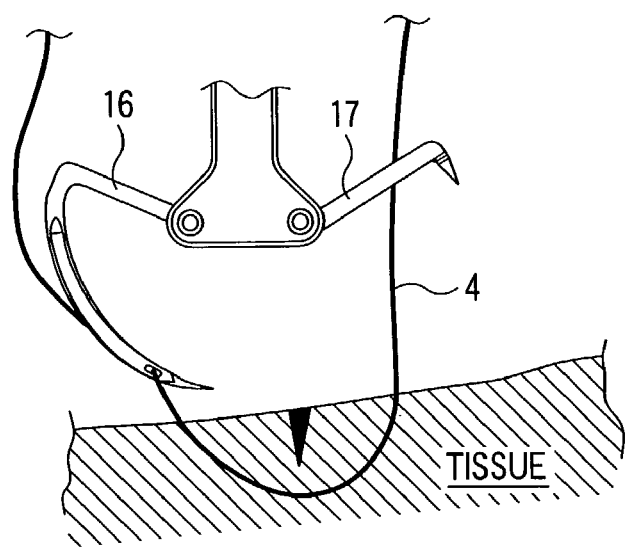

(8) As shown in FIG. 27, the movable member 75 is operated, the first and second actuating members 16 and 17 are opened, and the curved needle 34 and the fixing needles 41 and 42 are pulled out from a suture site.

Figure 28:
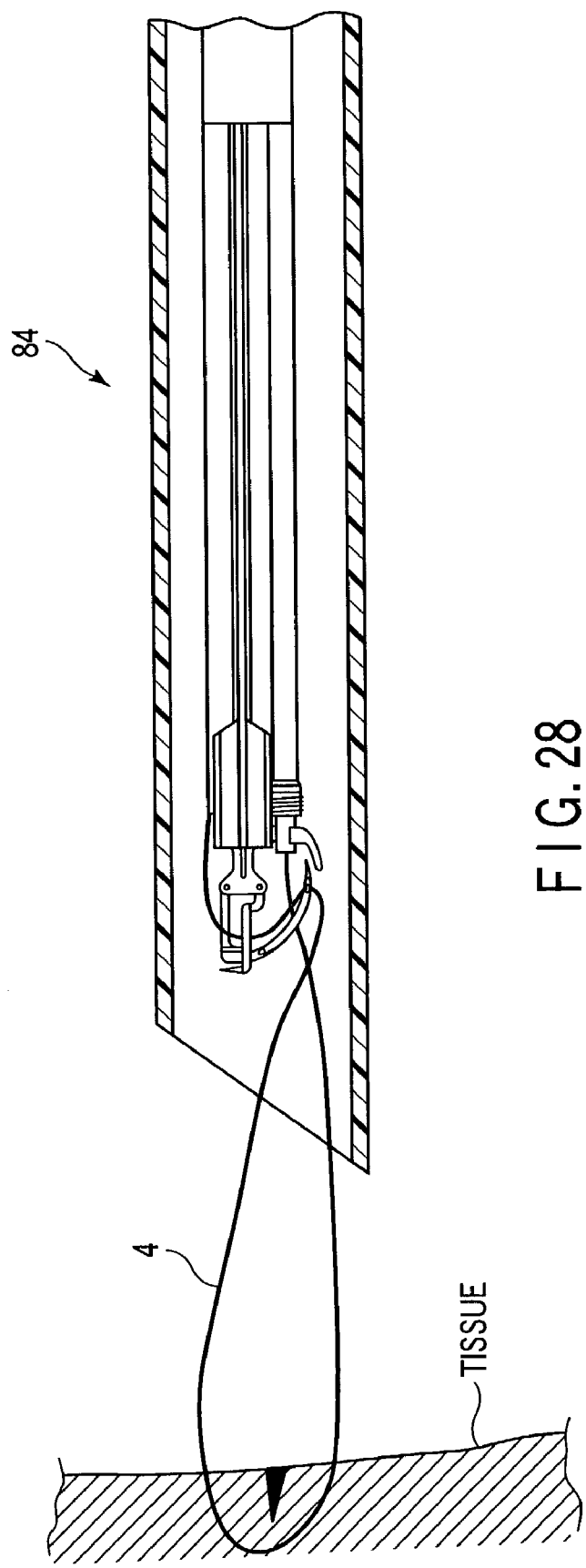
FIG. 28 is a view showing a state in which the suturing device is removed from the cavity together with the insert assisting device.

(9) As shown in FIG. 28, the suturing device 3 is retracted again into the flexible tubular member 85, and the suturing device 3 is pulled out from the inside of the cavity together with the flexible tubular member 85.

Figure 29:
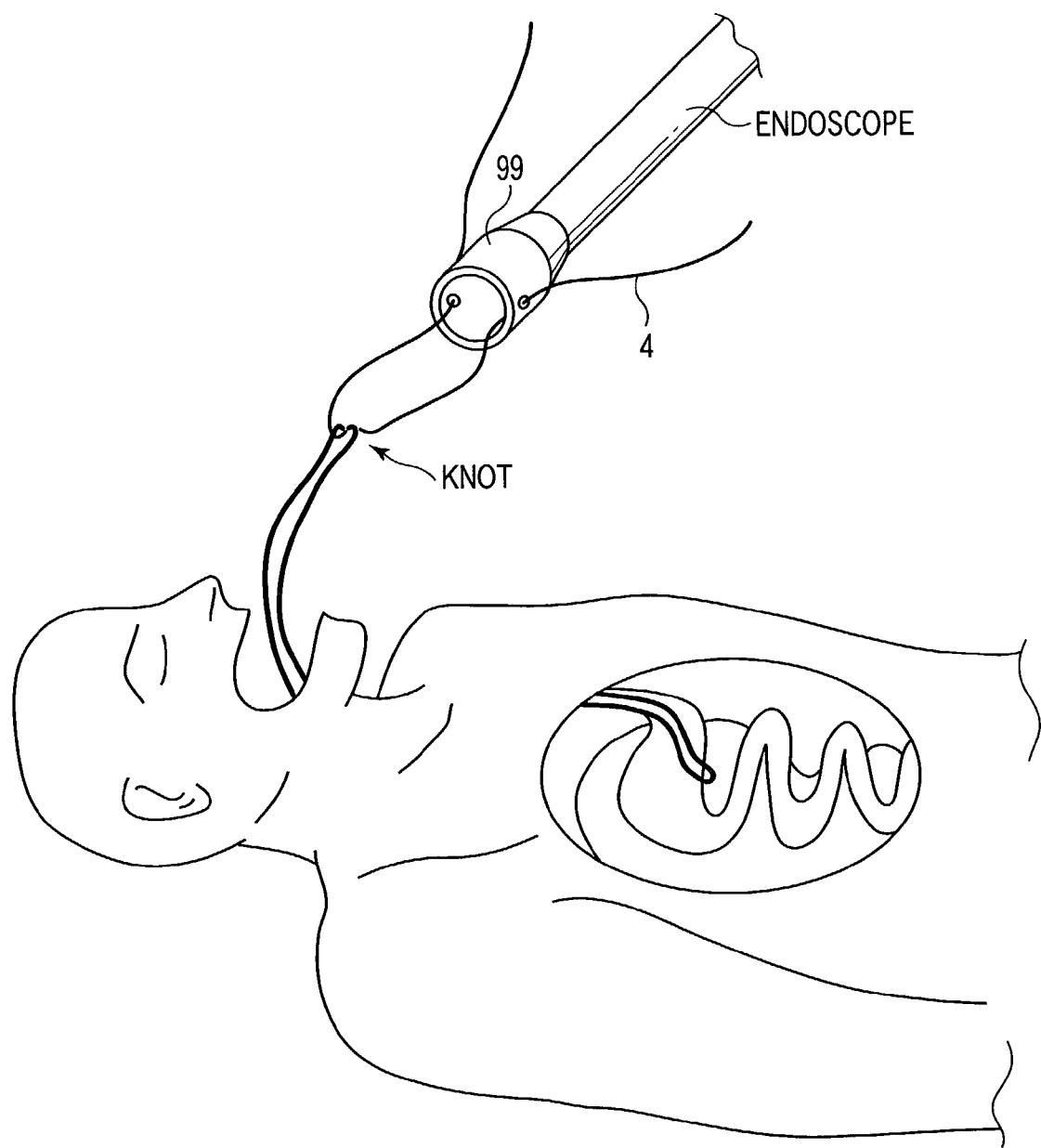
FIG. 29 is a view showing a state in which a knot is fed into a body by using a knot pusher.

(10) A knot is formed in the suture thread 4 at the outside of the body, and this knot is fed into the body several times by the knot pusher 99 as shown in FIG. 29. The knot pusher 99 shown in FIG. 29 has a hood shaped cylindrical member mounted on a distal end portion of the endoscope, and two holes are provided on a side face of this cylindrical member. Of course, any knot pusher is available for use without being limited to the shown knot pusher 99 as long as it has a structure or form such that a knot can be fed into the body. In addition, for example, a knot itself such as Grinch knot or Loaders knot may be formed movably. In this case, the knot can be fed into the body by using proper means.

(11) Lastly, an endoscope on which the suturing device 3 is not mounted is inserted into an endoscope, and a residual suture thread 4 is cut by using a scissors forceps or the like.

According to the endoscopic suturing system 1 of the present embodiment, the first and second actuating members 16 and 17 holding the curved needle 34 and the fixing needles 41 and 42 are formed integrally with the first and second arm members 24 and 25 that can be pass through the pins 28 and 29, whereby a large opening/closing angle can be formed between the first and second actuating members 16 and 17. In this manner, even in a size which is small for an endoscope, there can be formed a suturing device having one or a plurality of needles capable of moving all over a sufficiently large angle required for a suturing operation.

In addition, the coils 72 and 76 linked with the holding member 18 that rotatably supports the first and second actuating members 16 and 17 are restricted from expansion and contraction by the flexible tube 73. Thus, a large force can be transmitted via the coils 76 and 72. In this manner, a large force required for a suturing operation can be transmitted to needles 34, 41, and 42 via the coils 76 and 72 and the first and second actuating members 16 and 17.

Further, the suturing device 3 is fixed to the insert portion of the endoscope 12, thereby making it easily to do a suturing work by a flexible endoscope that has been very difficult in the prior art.

Furthermore, a minimal invasive suturing procedure can be carried out for a patient because no open surgical operation is required.

As described above with reference to each of the above embodiments, when the tissue is to be sutured, for example, a grasping forceps 152 is inserted into the body through the instrument channel port 6 of the endoscope 12, as shown in FIG. 50. While the tissue is pulled by this grasping forceps 152, the first and second actuating members 16 and 17 can be closed, and the tissue can be punctured with a curved needle 34. The subsequent procedure is the same as that described with reference each of the embodiments.

Second Embodiment

FIG. 30 to FIG. 35 each show an endoscopic suturing system according to a second embodiment of the present invention. A variety of endoscopes described hereinafter are basically similar to those according to the above described embodiment. Like elements are designated by like reference numerals. A detailed description thereof is omitted here.

Figure 30:
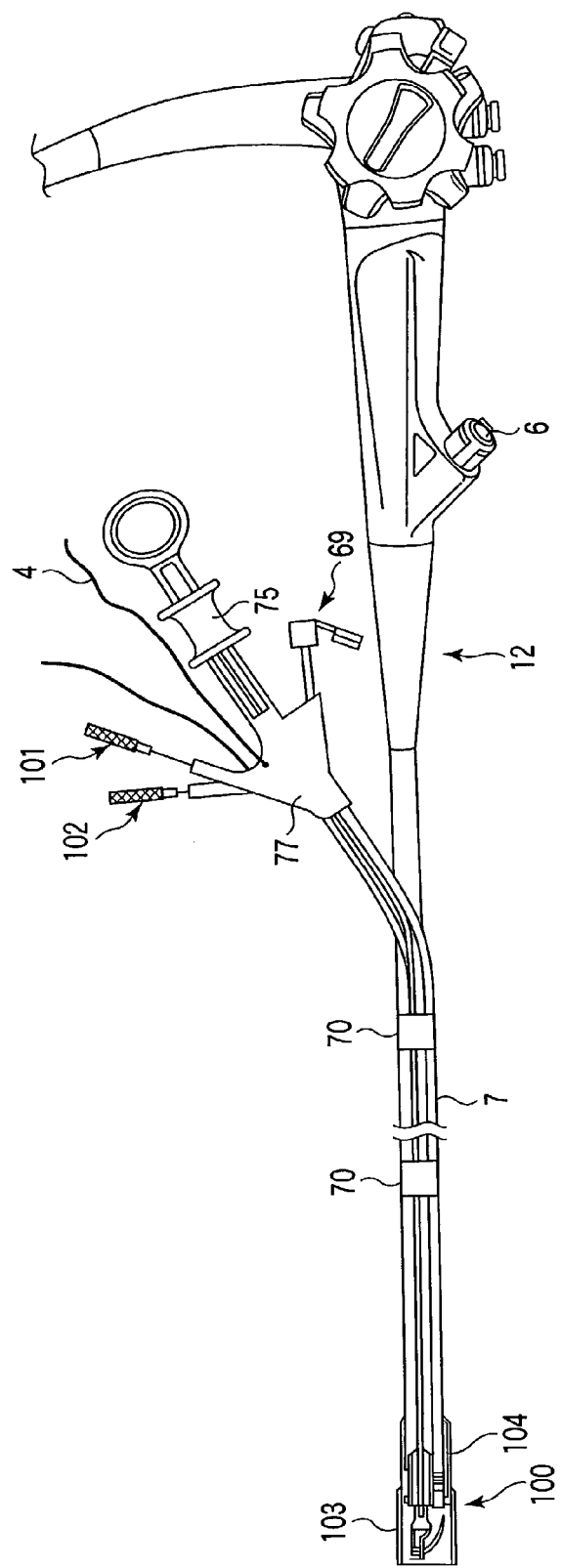
FIG. 30 is a view showing a state in which the suturing device is housed in a protect member, the figure being similar to FIG. 2 showing an endoscopic suturing system according to a second embodiment of the present invention.

As shown in FIG. 30 and FIG. 31, a system according to the present embodiment comprises a protect member 100 mounted at a distal end portion of the insert portion 7 of the endoscope 12, the protect member 100 covering the distal end portion of the suturing device 3. This protect member 100 comprises: a cylindrical fixing portion 104, for example, that can be removably fixed at a distal end of the insert portion 7; and a movable portion 103 slidably mounted on the outer periphery of this fixing portion 104. This movable portion 103 is preferably made of a transparent resin, e.g., polycarbonate, norbornene resin, cycloolefin-based resin, or polyethylene terephthalate.

Figure 32:
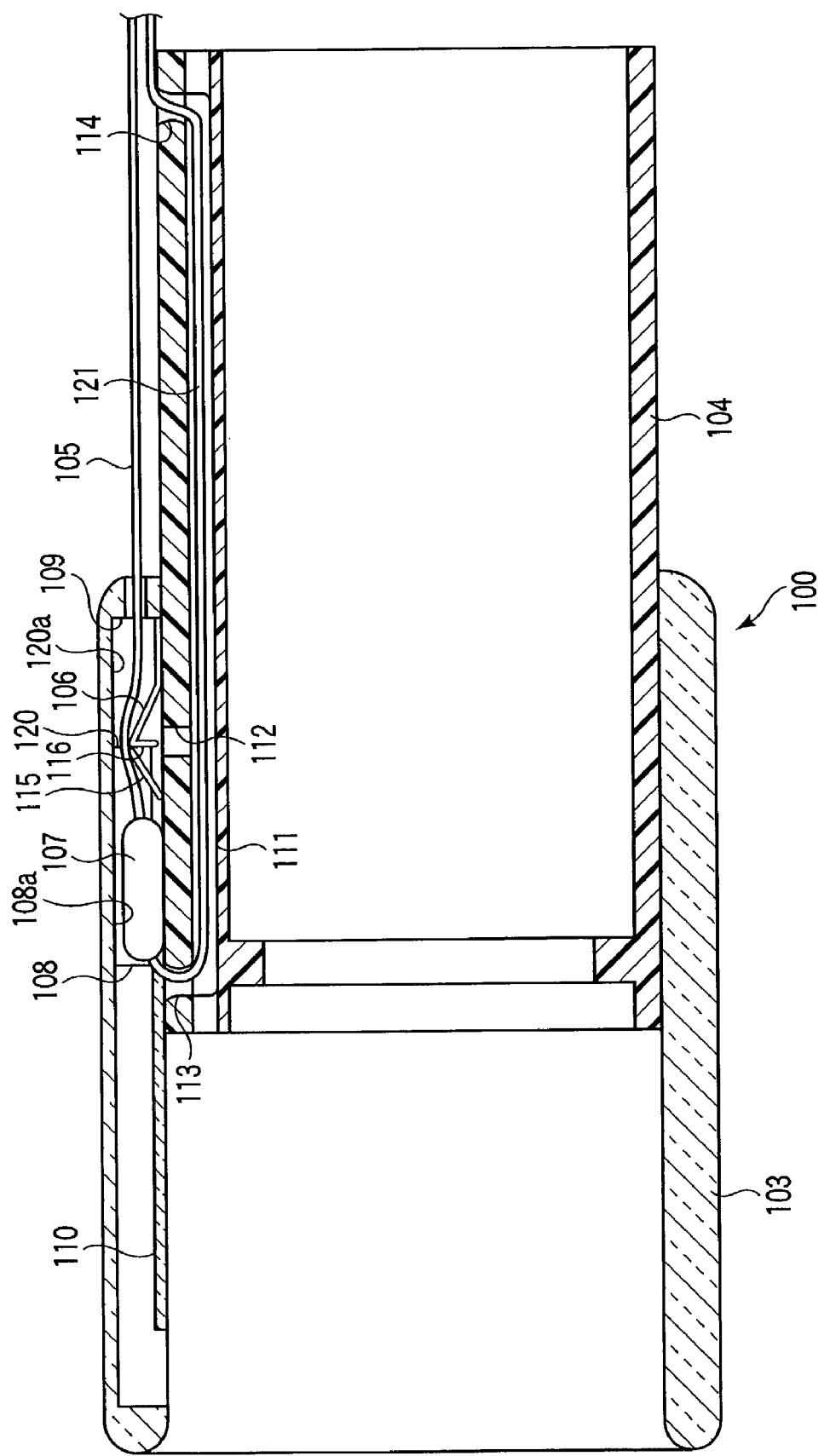
Figure 33:
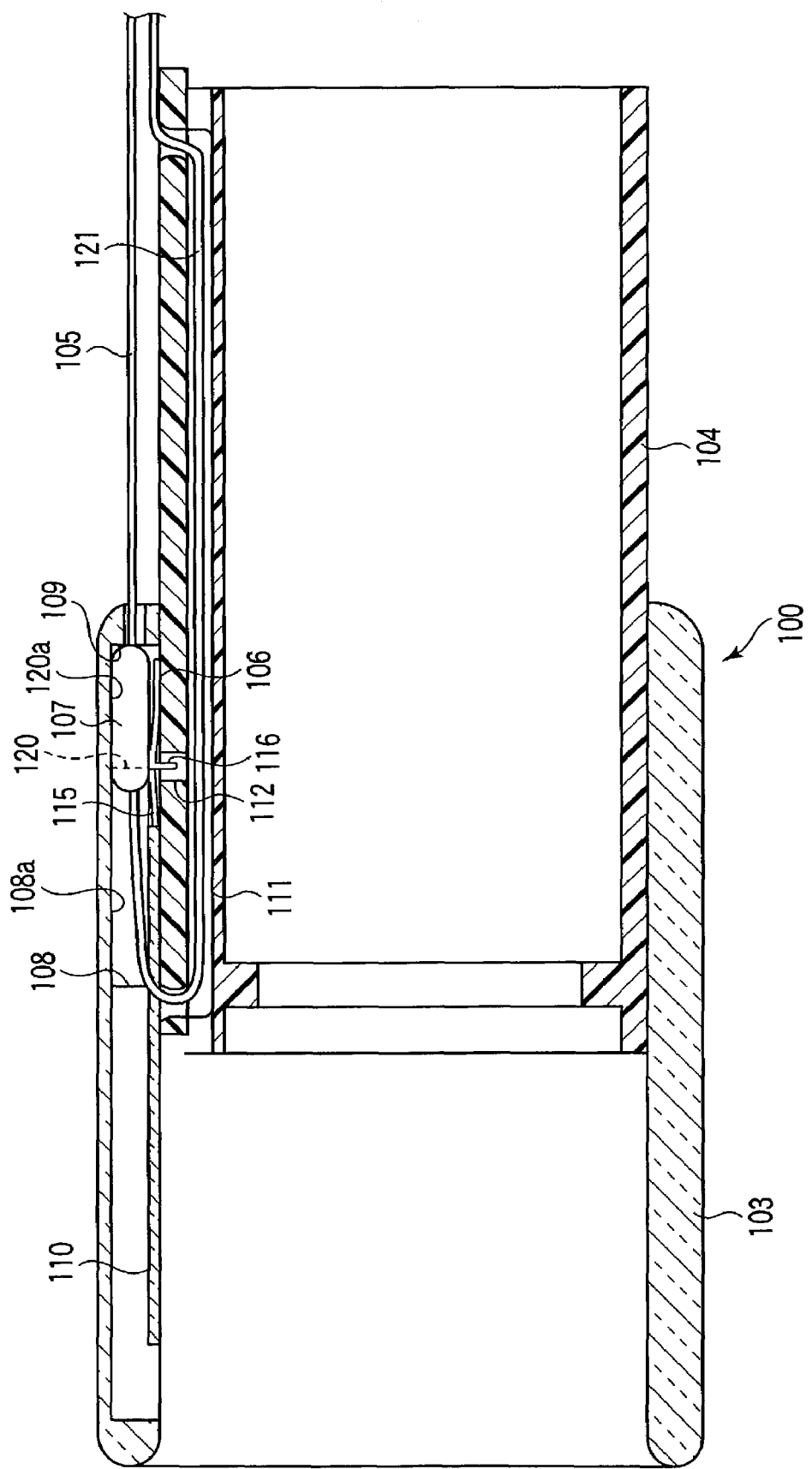
Figure 35:
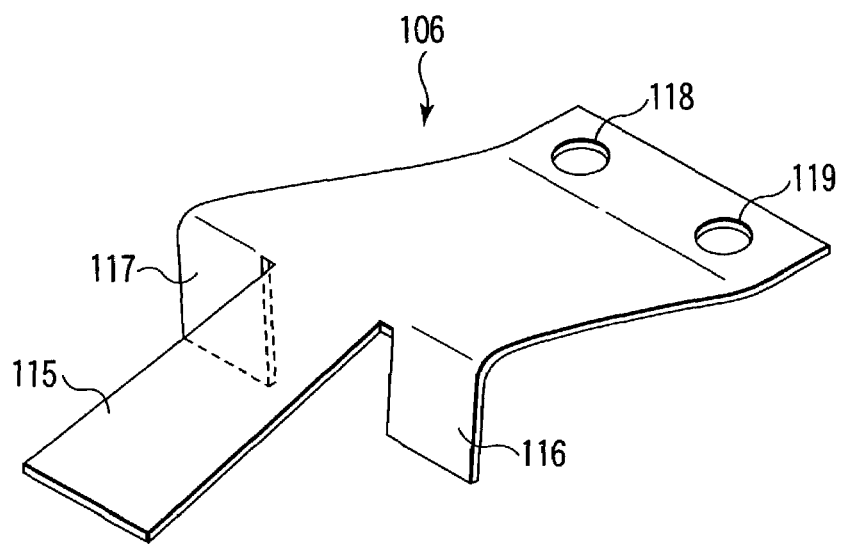

As shown in FIG. 32 to FIG. 34, at a wall portion of the fixing portion 104, there are formed an axial hole 111 and radial holes 113 and 114 having this axial hole communicating with a peripheral face at the proximal part of each end portion. In addition, at the outer periphery of the fixing portion 104, a lock member 106 shown in FIG. 35 is fixed with screws or the like inserted via mount holes 118 and 119, for example. This lock member 106 comprises engaging portions 116 and 117 which is disposed so as to be almost perpendicular relative to the outer periphery face of the fixing portion when fixed to the fixing portion 104, and an inclined portion 115 which descends gradually toward a distal end from a space between these engagingly fixing portions. The entirety of the lock member is formed of a resilient material such as metal or resin. At a position that corresponds to these engaging portions 116 and 117 each, an opening 112 is formed at the outer periphery face of the fixing section 104. In this manner, when the lock member is compressed against the outer periphery face of the fixing portion 104, the engaging portions 116 and 117 are housed in the opening 112, and the entirety of the lock member 106 is flattened.

On the other hand, the movable portion 103 has: a concave portion 120*a* defined at its distal end side on an engaging wall 120 which can be engaged with the engaging portions 116 and 117 of the lock member 106; and a concave portion 108*a* communicating with this concave portion 120*a*, the concave portion being limited at its distal end side on an engaging wall 108. The rear end side of these concave portions 108*a* and 120*a* each is defined by the engaging wall 109. In the concave portion 108*a*, there are housed an inclined portion 115 of the lock member 106; and a moving member 107 that controls engagement or disengagement between this lock member 106 and the engaging wall 120.

The moving member 107 according to the present embodiment is formed of a hard material, for example, in a substantially cylindrical shape or flat shape. It is preferable that its length be formed to be larger than the axial dimension of the concave portion 120*a* and be formed so as to be housed in the concave portion 108*a* without compressing the inclined portion 115 when the engaging portions 116 and 117 and the engaging wall 120 are engaged with each other. Transmission members 105 and 121 are extended, respectively, from an end portion of this moving member 107. The transmission member 105 is extended from the concave portion 120*a* via a small hole that passes through the engaging wall 109. The transmission member 121 is extended to the inner periphery side of the movable portion 103 from a slit 110 that communicates with the concave portion 108*a*, and further, is extended to the outer periphery of the fixing portion via a radial hole 113, an axial hole 111, and a radial hole 114 of the fixing portion 104. These transmission members 105 and 121 extend to the operating member main body 77 shown in FIG. 30 and FIG. 31 via a proper flexible tube (not shown), and is connected with operating member 101 and 102 of the protect member 100.

In this protect member 100, movement in the right side on paper of the movable portion 103 is restricted when an engagingly lock wall formed at the movable portion 103 as shown in FIG. 32 abuts against the engaging portions 116 and 117 of the lock member 106 fixed to the fixing portion 104. In this manner, as shown in FIG. 30, the needle fixed to the distal end portion of the suturing device is covered with the movable section 103, and is free of being exposed to the outside.

If the operating member 101 of the protect member 100 connected to the transmission member 105 is pulled in this state, the moving member 107 moves in the right direction, as shown in FIG. 33. At this time, the moving member 107 rolls over the inclined portion 115 of the lock member 106, and thus, the engaging portions 116 and 117 are housed in the opening 112, and are disengaged from the engaging wall 120. The movable portion 103 can move to the rear end side, i.e., to the right side shown in the figure. Further, when the operating member 101 of the protect member 100 is pulled, the moving member 107 abuts against the engaging wall 109, as shown in FIG. 34, and the movable portion 103 moves to the right side together with the moving member 107 and enters a state shown in FIG. 31. At this time, the lock member 106 abuts against the inner periphery face at both sides of the slit 110 formed at the movable portion 103. In contrast, if the operating member 102 of the protect member 100 connected to the frontal side of the transmission member 121 is pulled, the movable member 107 moves to the left side, and is engaged with the engaging wall 108. Then, the movable portion 103 moves to the left side together with the moving member 107. If the engaging wall 120 exceeds the opening 112, the lock member 106 returns to a state shown in FIG. 32 by its resilience. Then, the engaging portions 116 and 117 are protruded again from the outer periphery face of the fixing portion 104, whereby the movement in the left direction of the movable portion 103 can be restricted.

Now, the suturing procedure using the above described suturing system will be described here.

(1) The above described protect member 100 is mounted on the suturing device and endoscope assembled as in the above described embodiment, and then, the operation member 102 of the protect member 100 is pulled. In this manner, the moving portion 103 is protruded at its distal end side and comes into a state shown in FIG. 30. In this state, the moving portion is inserted into the body while the inside of the body is observed through the endoscope 12.

(2) After insertion into the body, the operating member 101 of the protect member 100 is pulled, and the moving portion 103 is retracted to enter a state shown in FIG. 31. In this manner, a distal end portion of the suturing device 3 is exposed so that a suturing operation can be carried out by using a procedure similar to that according to the first embodiment.

(3) After suturing has been completed, the moving portion 103 is protruded in a state shown in FIG. 30 by pulling the operating member 102 of the protect member 100. In this state, the suturing device and endoscope is removed from the body.

In the present embodiment, the moving portion 103 of the protect member 100 moves in an axial direction. Thus, the outer diameter of the device can be reduced in addition to advantageous effect of the first embodiment. Furthermore, operation can be simplified.

Third Embodiment

Figure 36:
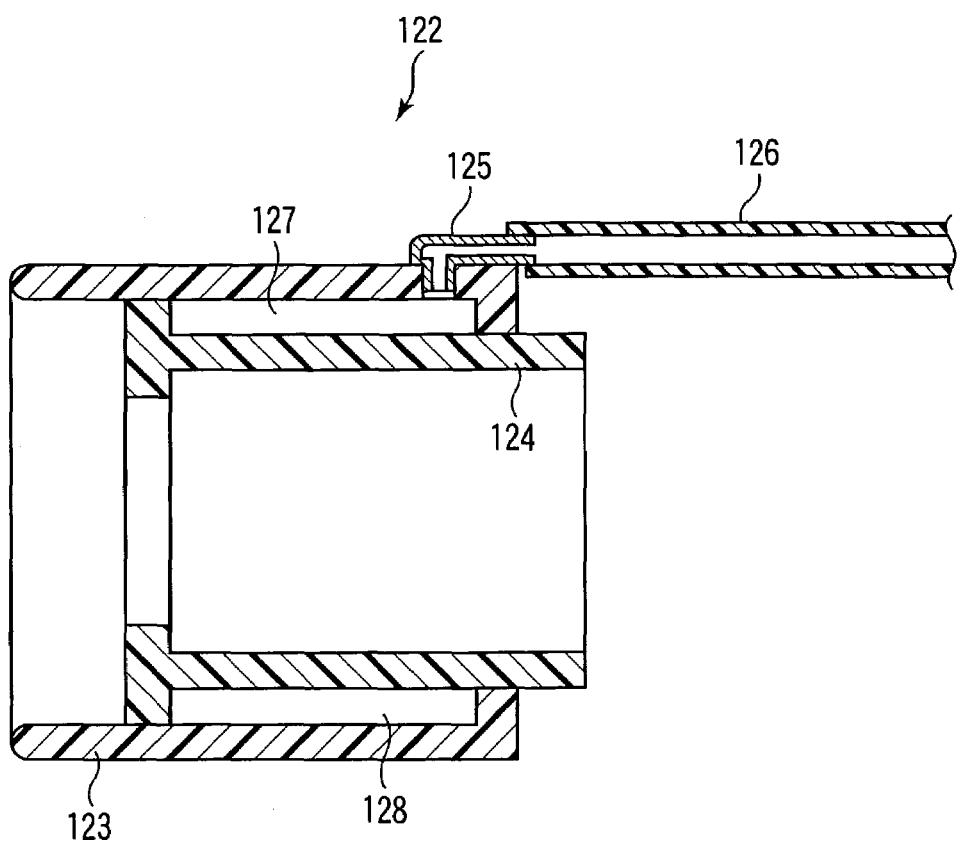
FIG. 36 is an illustrative view of the protect member using an endoscopic suturing system according to a third embodiment of the present invention.

FIG. 36 shows a protect member 122 used for an endoscopic suturing system according to a third embodiment of the present invention.

The protect member 122 according to the present embodiment comprises: a fixing portion 124 fixed to a distal end portion of an insert portion 7; and a movable portion 123 that can slide on this fixing portion 124. An externally sealed annular space 128 is formed between these fixing portion and movable portion. A base 125 communicating with the annular space 128 is mounted at the outer periphery of the movable portion 123, a fluid 127 can be poured into or discharged from the annular space 128. This fluid 27 may be liquid or gas.

In the present embodiment, at the protect member 122, for example, when the suitable fluid 127 such as physiological saline, water, or air is filled in a fluid pouring device (not shown) such as syringe, and this fluid is poured into the annular space 128, the movable portion 123 slides to the right side on paper. In contrast, the fluid 127 is discharged from the annular space 128 by setting a fluid pouring device 129 to a negative pressure, the movable portion 123 can slide to the left side.

Advantageous effect similar to each of the above described embodiments is provided by using this protect member 122.

Fourth Embodiment

FIG. 37 to FIG. 41 each show an endoscopic suturing system according to a fourth embodiment of the present invention.

Figure 37:
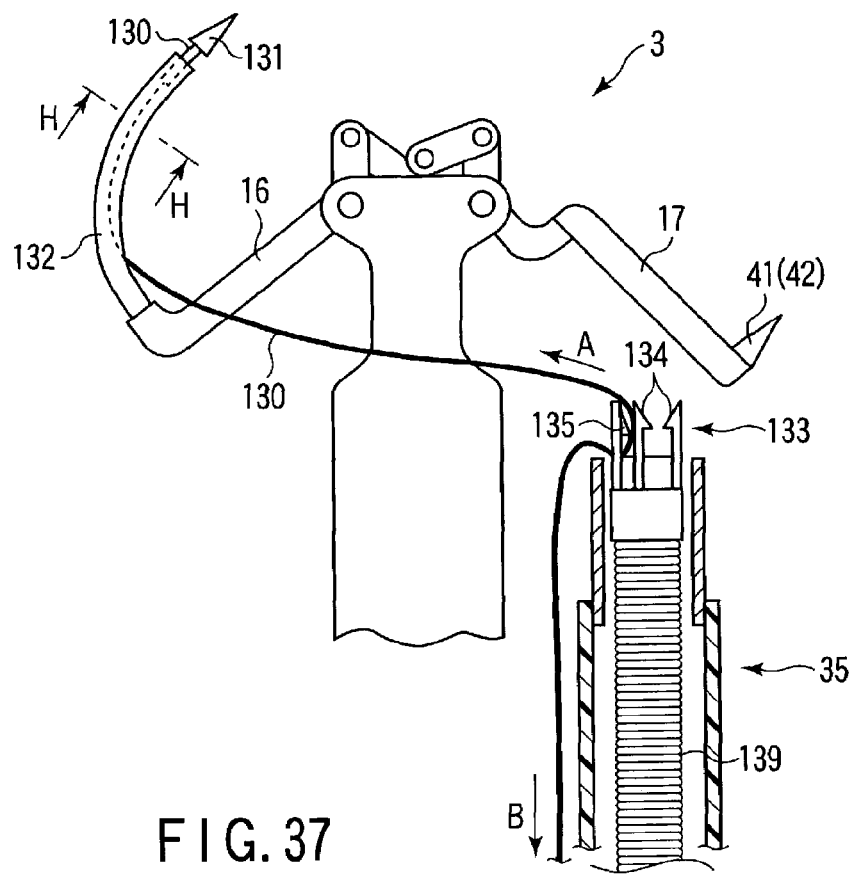
Figure 41:
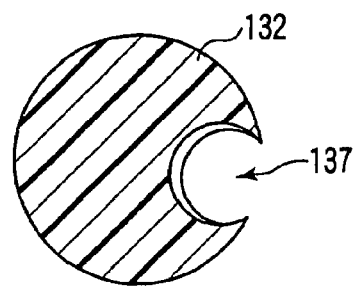

As shown in FIG. 37, in the present embodiment, a needle holder 132 is fixed to a first actuating member 16 of a suturing device 3, and a removable needle 131 is removably connected to a distal end of the needle holder 132. This removable needle 131 has a shaft portion 138, and one end of a suture thread 130 is fixed to a distal end of the shaft portion 138. The needle holder 132 has a groove 137 opened along almost all the full length at the inner periphery side, as shown in FIG. 41, and the suture thread 130 is removably extended inside of the groove 137.

On the other hand, the other end of this suture thread 130 extends to the frontal vicinity of the endoscope through thread lock means 135 formed at a needle thread fixing device 133. This thread lock means 135 is formed so that the suture thread 130 can be moved arbitrarily in a direction indicated by the arrow B, i.e., in a direction in which the suture thread is retracted. In contrast, the lock means 135 is formed so that the suture thread cannot be moved in a direction indicated by the arrow A, i.e., in a direction in which the suture thread is advanced.

Figure 38:
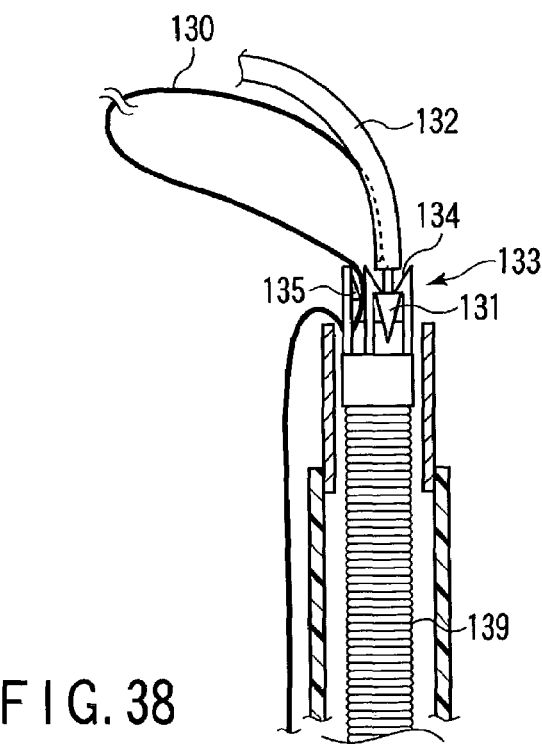

Further, as shown in FIG. 38, needle lock means 134 capable of engaging a removable needle 131 as well is formed at the needle thread fixing device 133. It is preferable that this needle lock means 134 be formed of a resilient member or the like. In the present embodiment, this needle thread fixing device 133 is removably mounted on a distal end of a needle fixing device main body 139. This needle thread fixing device main body 139 can be inserted into a body via a suitable channel 35. In addition, although the needle thread fixing device 133 is engaged by being pressed into the needle thread fixing device main body 139, the fixing device can be fixed to be grasped by a suitable device such as a grasping forceps, for example.

In this case, the removable needle 131 and needle thread fixing device 133 described above are at least partly made of a biocompatible metal such as stainless steel, pure titanium or titanium alloy, a biocompatible resin such as polyimide, poly (etheretherketone) (PEEK), polysulfon, liquid crystal polymer, or polyamide, a biocompatible ceramic material such as alumina, silicon nitride, or the like. As in the first embodiment, the suture thread 130 is formed like a monofilament line or stranded wire by using a material such as nylon, polyester, silk, fluoroplastic or bioabsorbable resin.

This endoscopic suturing system can be used as follows.

(1) The suturing device 3 is inserted into a body while its distal end portion is protected by the insert assisting devices 84 and 95 according to the first embodiment described above; a protect member 100 according to the second embodiment; or alternatively, a protect member 122 or the like according to the third embodiment. The inside of the body can be observed through the endoscope 12 as in the above described embodiment.

(2) During suturing, the first actuating member 16 and the second actuating member 17 are closed so as to press the removable needle 131 and the fixing needles 41 and 42 against a suture site, and the removable needle 131 is punctured into a tissue.

(3) As shown in FIG. 38, the removable needle 131 after punctured is protruded from the tissue. Thereafter, the removable needle 131 is inserted into the needle lock means 134 of the needle thread fixing device 133 by pushing out the needle fixing device main body 139 toward the front end side, and is latched thereby.

(4) When the first actuating member 16 and the second actuating member 17 are opened, the removable needle 131 is latched by the needle lock means 134. Thus, the removable needle 131 is removed from the needle holder 132, and the suture thread 130 is removed from the groove 137 of the needle holder 132. In this manner, as shown in FIG. 39, the suture thread 130 remains in the tissue while a portion between the needle thread fixing device 133 and thread lock means 135 forms a loop.

(5) As shown in FIG. 39, the needle thread fixing main body 139 is advanced toward the tissue while an end portion of the suture thread 130 disposed at the outside of the body is pulled frontally. In this manner, a loop of the suture thread 130 is contracted, and the tissue is tied until a state shown in FIG. 40 has been obtained.

(6) Lastly, a redundant suture thread 130 is cut by a thread cutting device 136. The needle thread fixing device 133 left in the body can be removed during thread removal.

According to the system of the present embodiment, in addition to advantages according to the above described first and second embodiments, there is no need for making a knot outside of the body, and feeding the knot into the body. This makes it possible to reduce an operation time, and further, facilitate procedures. In addition, the tied state of the tissue can be easily adjusted.

Fifth Embodiment

Figure 44:
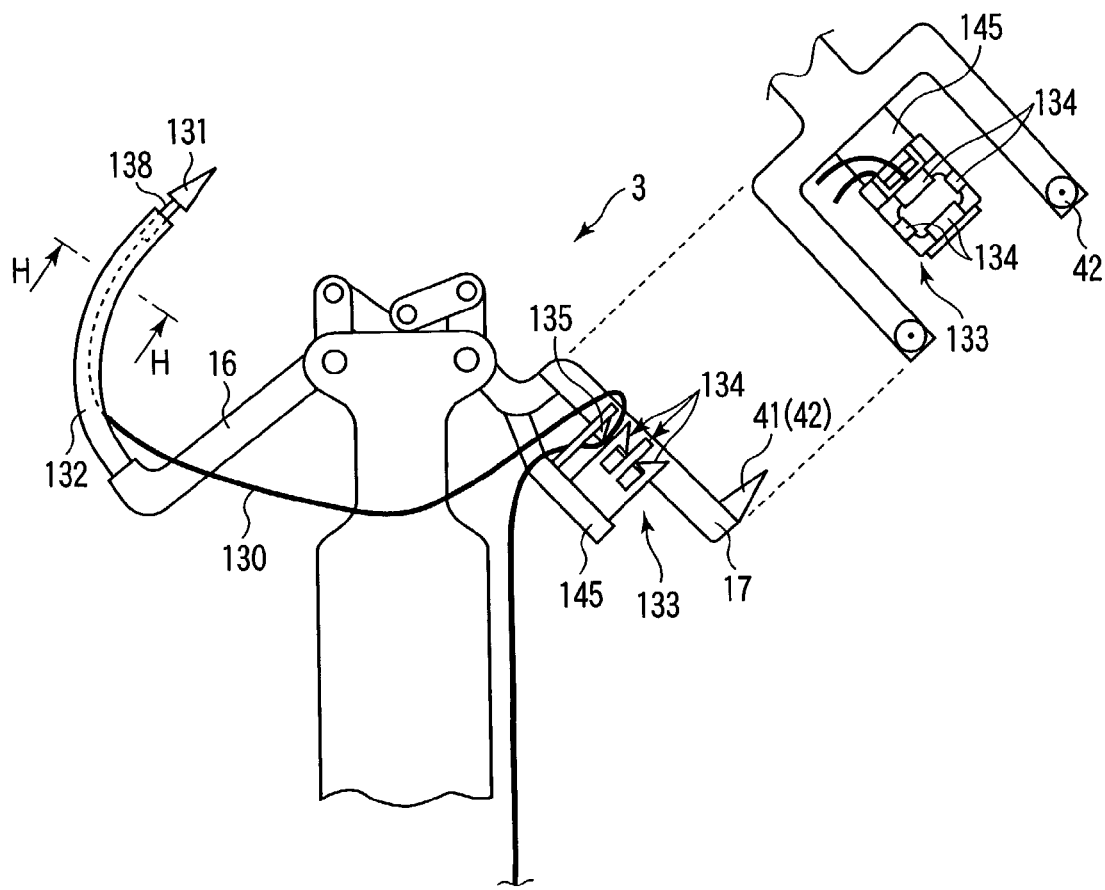
FIG. 44 is a view showing a suturing device for use in an endoscopic suturing system according to a fifth embodiment of the present invention.
Figure 45:
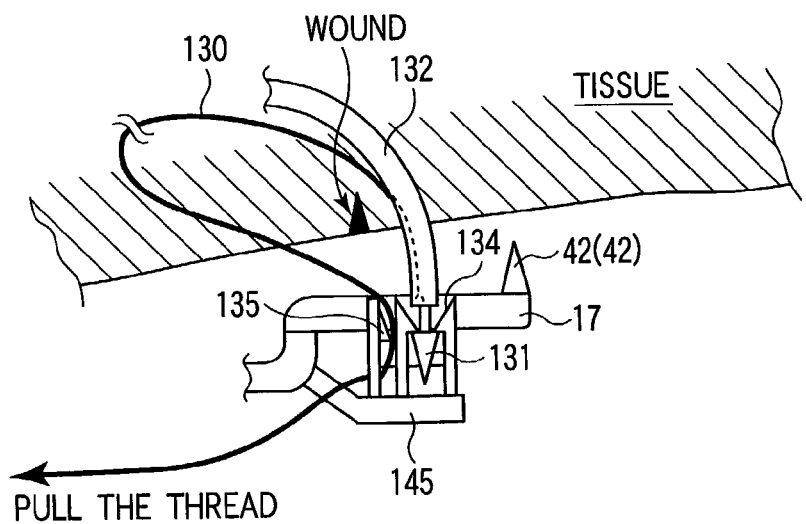
FIG. 45 is a view showing a state in which a removable needle after punctured into a tissue is engaged with a needle thread fixing device.

FIG. 44 and FIG. 45 each show a fifth embodiment of the present invention. This fifth embodiment is basically similar to the above-described fourth embodiment, and is different therefrom in the point below.

As shown in FIG. 44, the needle thread fixing device 133 according to the present embodiment is removable mounted on a holding member 145 formed at the second actuating member 17.

The needle thread fixing device 133 described above are at least partly made of a biocompatible metal such as stainless steel, pure titanium or titanium alloy, a biocompatible resin such as polyimide, poly(etheretherketone) (PEEK), polysulfon, liquid crystal polymer, or polyamide, a biocompatible ceramic material such as alumina, silicon nitride, or the like.

This endoscopic suturing system can be used as follows.

(1) When the suturing device 3 is inserted into a body, its distal end portion is particularly protected by the insert assisting devices 84 and 95, protect member 100, protect member 122 or the like according to the above described embodiment, for example. The needle thread fixing device 133 is mounted on the second actuating member 17, thus making it unnecessary to use a thread fixing device main body 139 or an ordinary grasping forceps and the like, for example.

(2) During suturing, as in the fourth embodiment, the first actuating member 16 and the second actuating member 17 are closed so as to press the removable needle 131 and fixing needles 41 and 42 against a suture site, and the removable needle 131 is punctured into a tissue.

(3) As shown in FIG. 45, the removable needle 131 protruded from a tissue after punctured is inserted into the needle lock means 134 of the needle thread fixing device 133 held at the holding member 145, and is engaged therewith.

(4) When the proximal end side of the suture thread 130 is pulled, the tissue is tied because one end of the suture thread 130 is fixed to the removable needle 131, and the groove 137 of the needle holder 132 is opened at the inner periphery side.

(5) When the first actuating member 16 and the second actuating member 17 are opened, the removable needle 131 is engaged with the needle lock means 134. Thus, the removable needle 131 and the needle thread fixing device 133 are removed from the holding member 145 to enter a state shown in FIG. 40.

(6) Lastly, a redundant suture thread 130 is cut by the thread cutting device 136.

In the present invention, advantages similar to those according to the fourth embodiment are obtained. Further, in the present embodiment, there is no need for holding the needle thread fixing device 133 solely, and thus, the suturing operation is further facilitated.

Sixth Embodiment

FIG. 46 to FIG. 49 each show a sixth embodiment. The sixth embodiment as well is basically similar to the fourth embodiment, and is different therefrom in the point below.

As shown in FIG. 46, in the present embodiment, four engagingly lock members 146 for holding at least one loop formed in advance at the suture thread 130 made of the same material as that in the first embodiment are provided at the second actuating member 17. These engagingly lock members 146 are formed of a resilient element in a claw shape, and is fixed so that two of these lock members are opposed to the remaining two members at a site opposed to the first actuating member 16. A part of the suture thread 130 is hooked by these engagingly lock members 146, and two large loops 148, for example, are formed. The removable needle 131 can pass through the inside of these large loops 148. Further, at least one loop 149 for forming a knot described later is formed at the periphery of the suture thread 130 that forms the large loop 148 and a knot like a pre-knot 232 shown in, for example, FIG. 89 (to be described later) is formed.

A needle fixing device 150 comprises: needle fixing means 147 capable of being engaged with the removable needle 131; and a tubular member 151 to which this needle fixing mans is fixed. This needle fixing device 150 is formed so that the device can be inserted into a suitable channel 35. Alternatively, the needle fixing device 150 may be fixed onto the suturing device 3. In this case, a position at which the needle fixing device 150 corresponds to a position at which the removable needle 131 can be engaged with the needle fixing means 147.

This endoscopic suturing system can be used as follows.

(1) When the suturing device 3 is inserted into a body, as in the above described embodiment, the device is protected by the above described insert assisting devices 84 and 95, protect member 100, a protect member 122 or the like, for example.

(2) When the removable needle 131 is punctured into a tissue, the first actuating member 16 and the second actuating member 17 are closed so as to press the removable needle 131 and the fixing needles 41 and 42 against a suture site.

(3) As shown in FIG. 47, the removable needle 131 after punctured is protruded from the tissue. Thereafter, the tubular member 151 is pushed out toward the front end side, the removable needle 131 is inserted into the needle lock means 147 of the needle thread fixing device 150 held on the tubular member 151, and is latched thereby.

Figure 48:
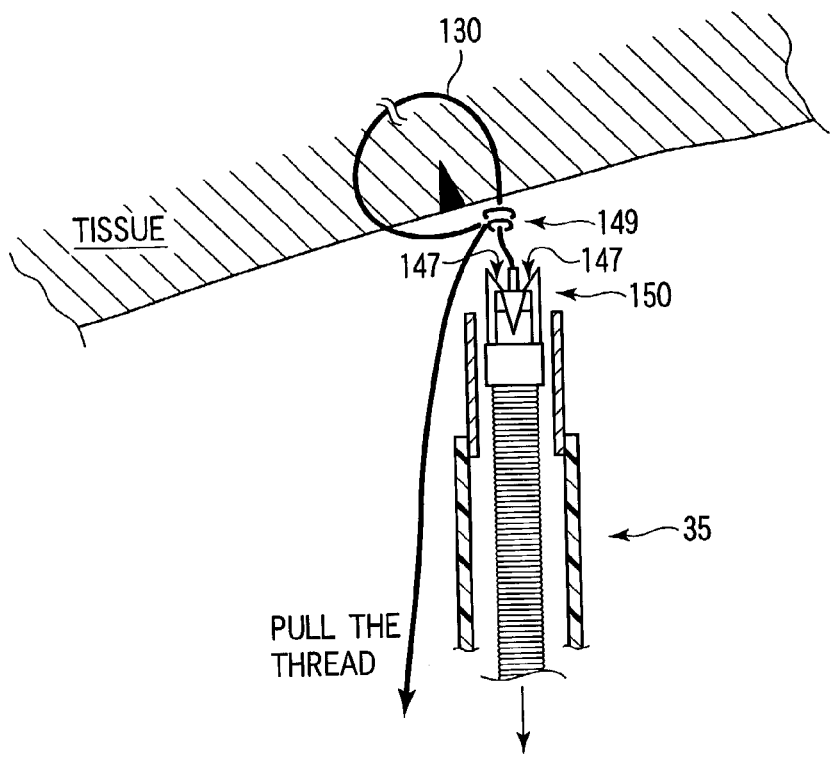
FIG. 48 is a view showing a state in which a knot is formed by a loop removed from an engagingly lock member when the first and second actuating members are opened.

(4) As shown in FIG. 48, when the first actuating member 16 and the second actuating member 17 are opened, the removable needle 131 is engaged with the needle engagingly lock means 147. Thus, the removable needle 131 is removed from the needle holder 132, and a large loop 148 is removed from the engagingly lock member 146. In this manner, a small loop 149 forms a knot on a suture thread 130 in corporation with the large loop.

Figure 49:
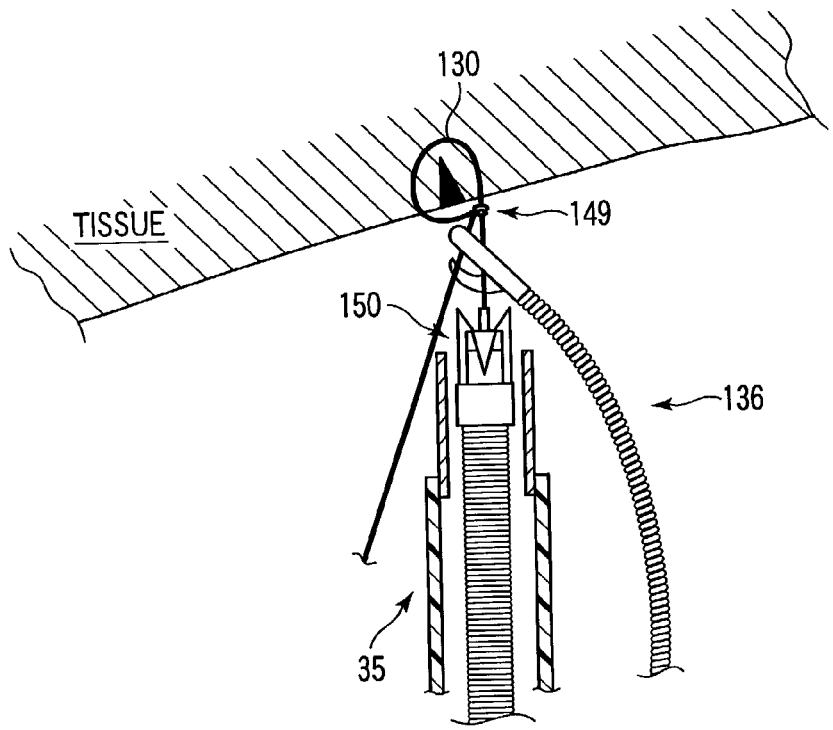
FIG. 49 is a view showing a state in which a redundant portion of the suture thread is cut by a thread cutting device.

(5) Then, as shown in FIG. 49, the proximal end side of the suture thread 130 and the needle fixing device 150 are pulled, the knot 149 is tied, and an injury is sutured.

(6) Lastly, as shown in FIG. 49, a redundant suture thread 130 is cut by a thread cutting device 136.

This system according to the sixth embodiment provides advantages that are similar to those according to the above described fourth embodiment. In addition, there is no need for keeping any member except the suture thread 130 in the body.

As has been described with respect to each of the above described embodiments, when a tissue is sutured, a grasping forceps 152, for example, can be inserted into a body through the instrument channel port 6 of the endoscope 12 as shown in FIG. 50. While the tissue is pulled by this grasping forceps 152, the first and second actuating members 16 and 17 are closed, thereby making it possible to puncture the removable needle 131 into the tissue. The subsequent procedure is similar to that described with respect to the respective embodiments.

Seventh Embodiment

FIG. 51 to FIG. 56 each show a seventh embodiment of the present invention. In this system, a structure of the suturing device 3 is different from that according to the above described fourth embodiment. Further, a needle thread fixing device 153 is disposed instead of the needle thread fixing device 133 in the above described embodiment.

Figure 54:
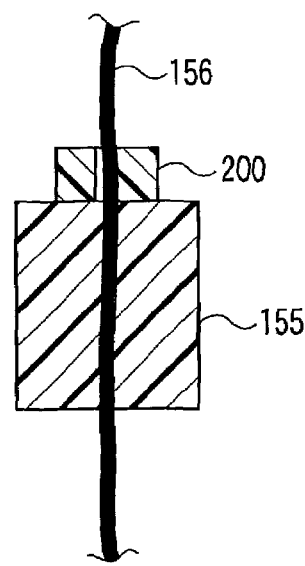
FIG. 54 is a view showing a structure by thread lock means.

As shown in FIG. 51, the needle thread fixing device 153 comprises thread lock means 155 and needle lock means 154. This thread lock means 155 is composed of a resilient tubular member having its small axial hole, and the suture thread 156 is inserted into this axial hole so as to be pressed into the hole. In this manner, the thread lock means 155 can engagingly lock the suture thread 156 at an arbitrary position. This thread lock means 155 can be formed of a silicon tube or the like, for example. On the other hand, in the case where sufficient strength cannot be obtained by a silicon tube which is easily broken after ligation, for example, a reinforce member 200 such as a PTFE resin based tube may be disposed coaxially of the thread lock means 155, as shown in FIG. 54.

Figure 54A:
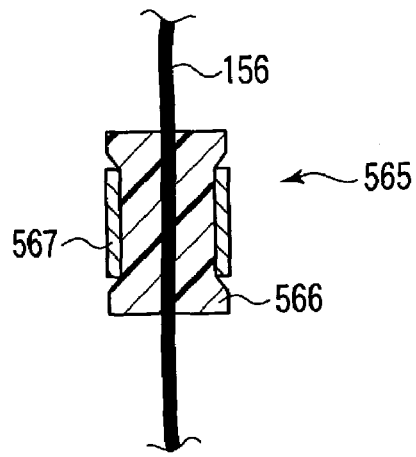
FIG. 54A to FIG. 54D are views showing various modifications of the lock means.
Figure 54B:
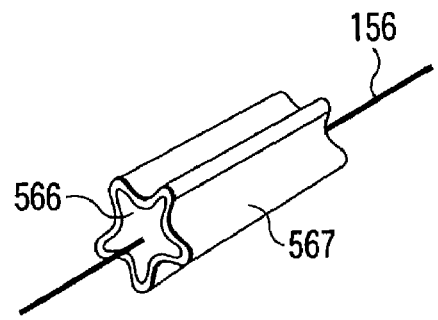
Figure 54C:
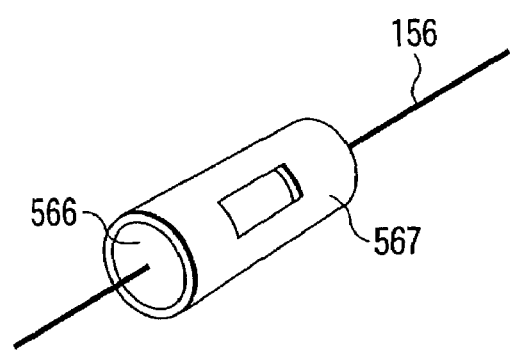
Figure 54D:
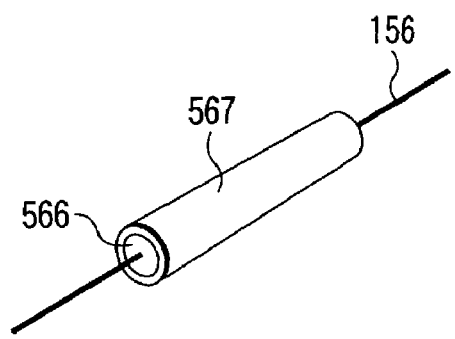
Figure 55:
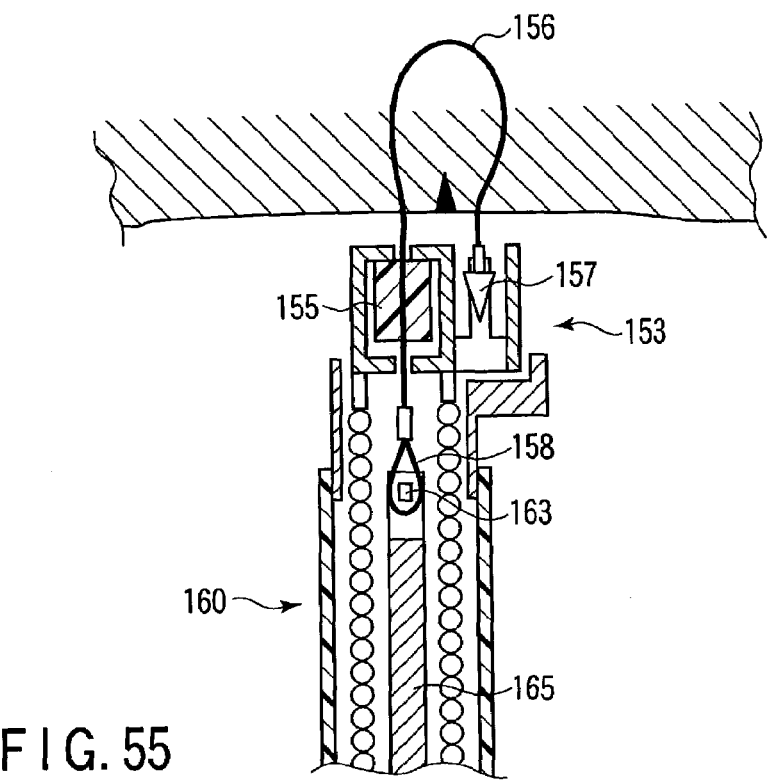
FIG. 55 is a view showing a state in which a needle holder is removed from a tissue.

In addition, the thread lock means 155 may be modified into a thread lock means 565 as shown in FIG. 54A. The thread lock means 565 is comprised of an elastic member 566 and tubular member 567. The tubular member 567 is arranged on the outer surface of the elastic member 566 and has at least one recess formed by an outer force to increase the sliding resistance between the thread 156 and the elastic member 566. This makes it possible to increase the tying force in a suturing operation. FIG. 54B to FIG. 54D show arrangements in which the tubular member 567 are deformed in different manners. FIG. 54B shows an arrangement in which a plurality of recesses are formed in the tubular member 567 in the longitudinal direction. FIG. 54C shows an arrangement in which a recess is formed in a direction perpendicular to the longitudinal direction of the tubular member 567. FIG. 54D shows an arrangement in which the tubular member 567 is swaged to uniformly and radially apply a pressure to the elastic member 566.

For the suture thread 156, a loop portion 158 is formed at the proximal end of the suture thread 156. This loop portion 158 is removably engaged with an engaging portion 163. This engaging portion 163 is fixed to a transmission member 165, and is arranged retractably in a coil 164. The proximal end portion of the transmission member 165 is linked with an operating member (not shown) which is operable at the outside of the body. This operating member is advanced or retracted, whereby the engaging portion 163 can be advanced or retracted along the coil 164. In addition, a channel 160 through which the coil 164 is inserted has a flexible tubular member 162 and a receiving portion 161 fixed to a distal end thereof. A needle thread fixing device 153 is held via this receiving portion 161.

Figure 53:
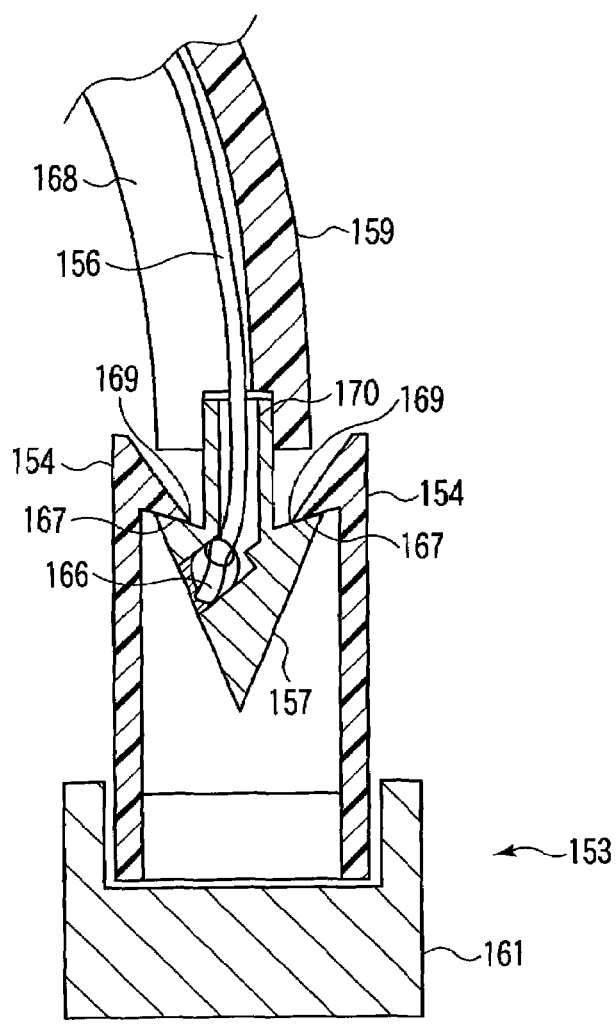
FIG. 53 is a sectional view taken along the line J-J of FIG. 52.

As shown in FIG. 53, an inclined portion 167 is formed at needle lock means 154. In addition, an inclined portion 169 is formed similarly at a removable needle 157 as well. Thus, the needle lock means 154 and the removable needle 157 are hardly removed from each other while they are engaged with each other via these inclined portions 167 and 169. In addition, in the present embodiment, there is provided a through hole 170 opened on a tapered face at a distal end through an axial portion of the removable needle 157. This through hole 170 is formed to have a stepped structure. As shown in FIG. 53, for example, a knot 166 formed at the other end of the suture thread 156 is housed in this through hole 170, and this knot 166 can be engaged at a stepped portion so as not to move to the other end side. For this suture thread 156, this knot 166 can be fixed to the removable needle 157 by a suitable bonding agent. In addition, a groove 168 similar to that shown in FIG. 41 is formed at a needle holder 159 that holds this removable needle 157, a groove 168 similar to that shown in FIG. 41 is formed, and a suture thread 156 can be removed from the needle holder 159.

The removable needle 157 and needle thread fixing device 153 described above are at least partly made of a biocompatible metal such as stainless steel, pure titanium or titanium alloy, a biocompatible resin such as polyimide, poly(etheretherketone) (PEEK), polysulfon, liquid crystal polymer, or polyamide, a biocompatible ceramic material such as alumina, silicon nitride, or the like. As in the first embodiment, the suture thread 156 is formed like a monofilament line or stranded wire by using a material such as nylon, polyester, silk, fluoroplastic or bioabsorbable resin.

This endoscope suture system can be used as follows.

(1) When the suturing device 3 is inserted into a body, the suturing device 3 is inserted while its distal end portion is particularly protected as in the above described embodiment.

(2) The first actuating member 16 and the second actuating member 17 are closed so as to press the removable needle 157 and the fixing needles 41 and 42 against a suture site, and the removable needle 157 is punctured into a tissue. Of course, this operation can be observed through the endoscope 12.

(3) As shown in FIG. 52, the needle 157 protrudes from a tissue. Then, the coil 164 is pushed out to the forward side, the removable needle 157 is inserted into needle lock means 154 of the needle thread fixing device 153, and is latched therewith.

(4) When the first actuating member 16 and the second actuating member 17 are opened, the removable needle 157 is engaged with the needle lock means 154. Thus, the removable needle 157 is removed from the needle holder 159 to enter a state shown in FIG. 55.

Figure 56:
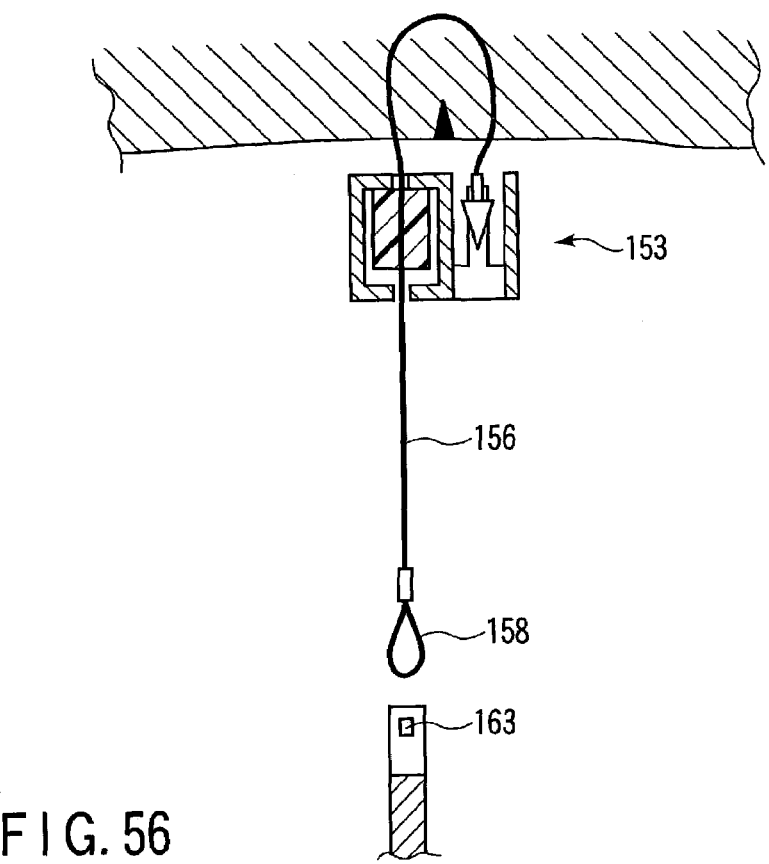
FIG. 56 is a view showing a state in which a tissue is tied.

(5) A transmission member 165 is pulled to the proximal end side by an operating member (not shown), and a tissue is tied until a state shown in FIG. 56 has been obtained. Then, a distal end portion of the transmission member 165 is protruded from the coil 164, and the loop portion 158 is removed from the engaging portion 163.

(6) Lastly, a redundant thread 156 is cut by a thread cutting device 136.

This system according to the seventh embodiment as well provides advantages similar to those according to the above described fourth embodiment. Further, in the present embodiment, a length of the suture thread 156 may be short. Thus, a suturing operation is further facilitated.

Eighth Embodiment

Embodiment

FIG. 57 to FIG. 63 each show an endoscopic suturing system according to an eighth embodiment of the present invention.

Figure 57:
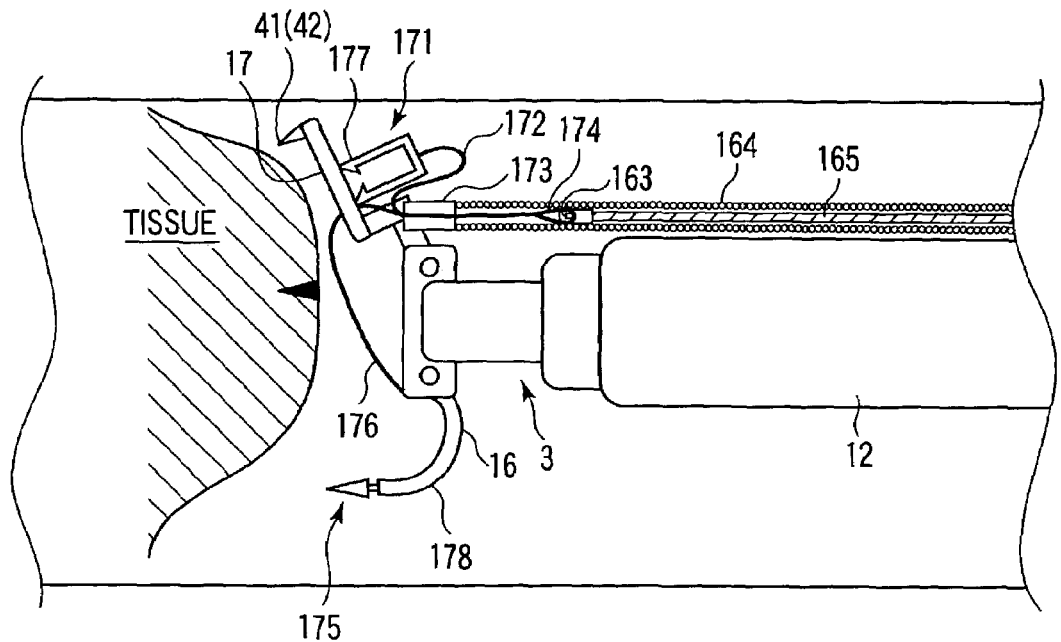

As shown in FIG. 57, a needle thread fixing device 171 is removably attached to a second actuating member 17 instead of the holding member 145 according to the fifth embodiment (refer to FIG. 44). Needle fixing means 177 is formed at the needle thread fixing device 171. One end of a suture thread 172 is fixed to this needle thread fixing device 171. In addition, the other end of this suture thread is extended into a coil 164 via thread lock means 173 similar to that according to the seventh embodiment, and a loop section 174 is formed.

A needle holder 178 that holds the removable needle 175 at its distal end portion is fixed to a first actuating member 16. One end of the other suture thread 176 is fixed to this removable needle 175, the other end of this suture thread as well is extended in the coil 164 via thread lock means 173, and a loop portion 174 is formed. These loop portions 174 are engaged with an engaging portion 163 of a transmission member 165 as in the seventh embodiment.

A suturing operation using this endoscope system is carried out as follows.

(1) As in the above described embodiments each, the suturing device 3 is inserted into a body while its distal end portion is particularly protected by the insert assisting devices 84 and 95, protecting member 100, protect member 122 or the like.

Figure 58:
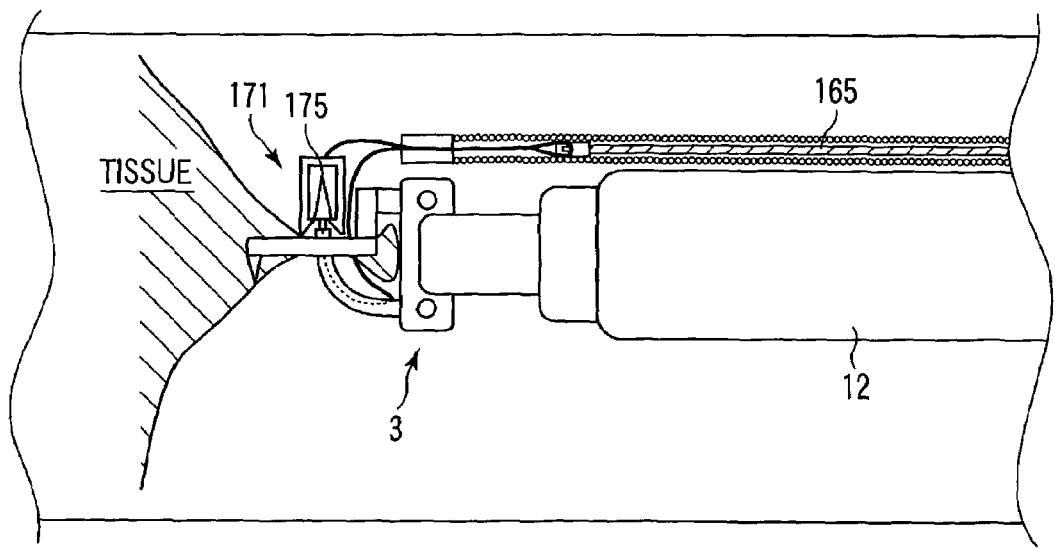

(2) As shown in FIG. 58, the first and second actuating members 16 and 17 are closed so as to press the removable needle 175 and the fixing arms 41 and 42 against a suture site, and the removable needle 175 is punctured into a tissue.

(3) As shown in FIG. 58, the removable needle 175 after punctured is inserted into needle fixing means 177 of the needle thread fixing device 171 held at a predetermined position, and is engaged therewith.

(4) As shown in FIG. 59, when the first and second actuating members 16 and 17 are opened, the needle fixing device 171 is removed from the second actuating member 17 while the removable needle 175 is engaged with the needle fixing device 171.

Figure 61:
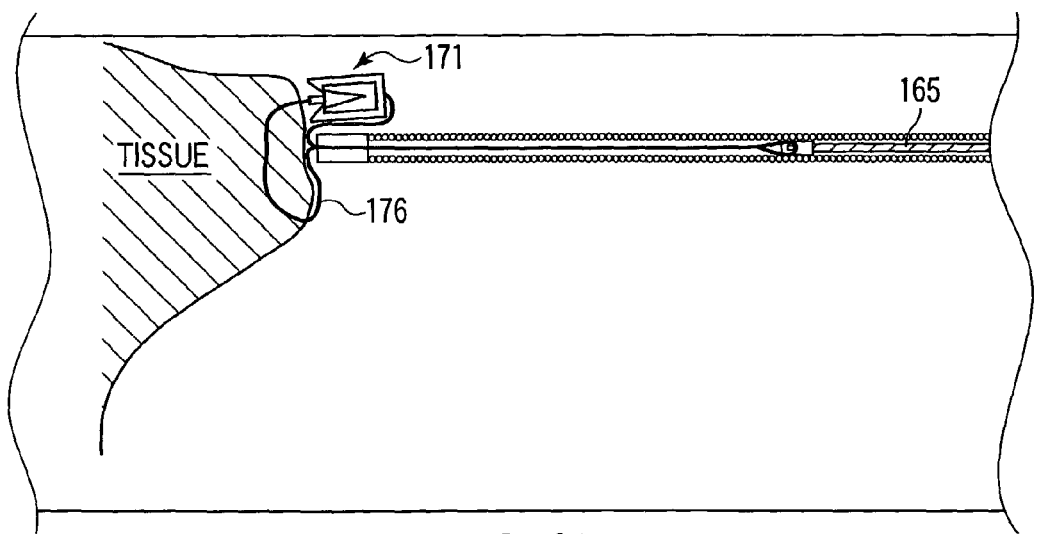
Figure 62:
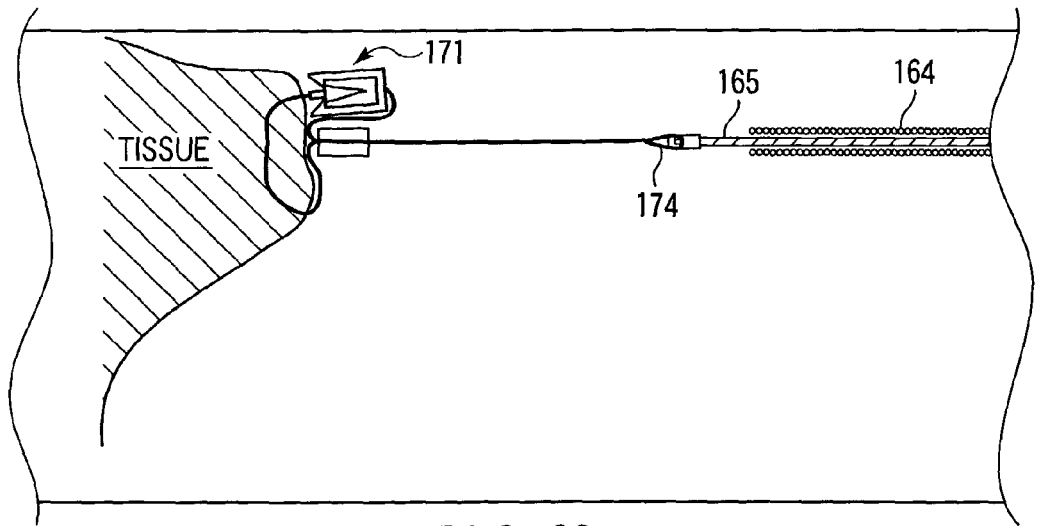

(5) The transmission member 165 is pulled by an operating member (not shown) in a state shown in FIG. 60, a tissue is tied by the suture thread 176 until a state shown in FIG. 61 has been obtained. Then, as shown in FIG. 62, a distal end portion of the transmission member 165 is pushed out from the coil 164. The loop portion 174 is removed from the engaging portion 163 of the transmission member. Only the loop portion 174 of one suture thread can be pulled if necessary.

The removable needle 157 and needle thread fixing device 171 described above are at least partly made of a biocompatible metal such as stainless steel, pure titanium or titanium alloy, a biocompatible resin such as polyimide, poly(etheretherketone) (PEEK), polysulfon, liquid crystal polymer, or polyamide, a biocompatible ceramic material such as alumina, silicon nitride, or the like. As in the first embodiment, the suture thread 172 is formed like a monofilament line or stranded wire by using a material such as nylon, polyester, silk, fluoroplastic or bioabsorbable resin.

Figure 63:
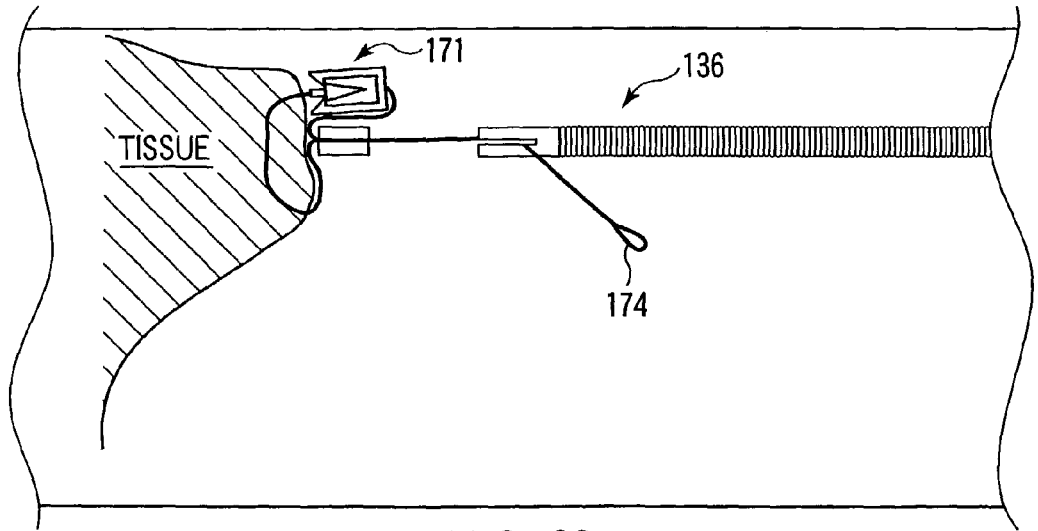

(6) Lastly, as shown in FIG. 63, redundant suture threads 172 and 176 are cut by the thread cutting device 136.

This system according to the eighth embodiment as well provides advantages similar to the above described fourth embodiment. Further, in the present embodiment as well, a length of the suture threads 172 and 176 each may be short. Thus, a suturing operation is further facilitated.

Ninth Embodiment

Figure 64:
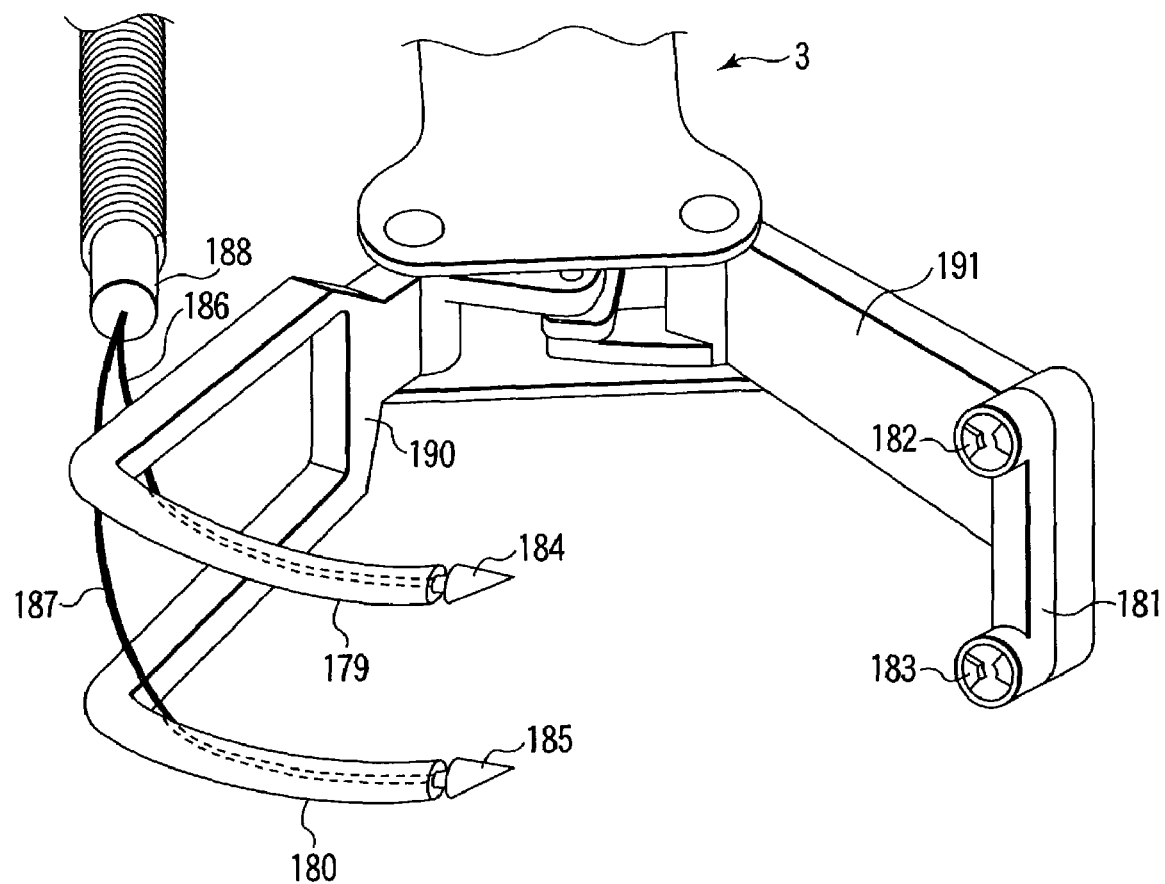
FIG. 64 is a view showing a suturing device for use in an endoscopic suturing system according to a ninth embodiment of the present invention.
Figure 65:
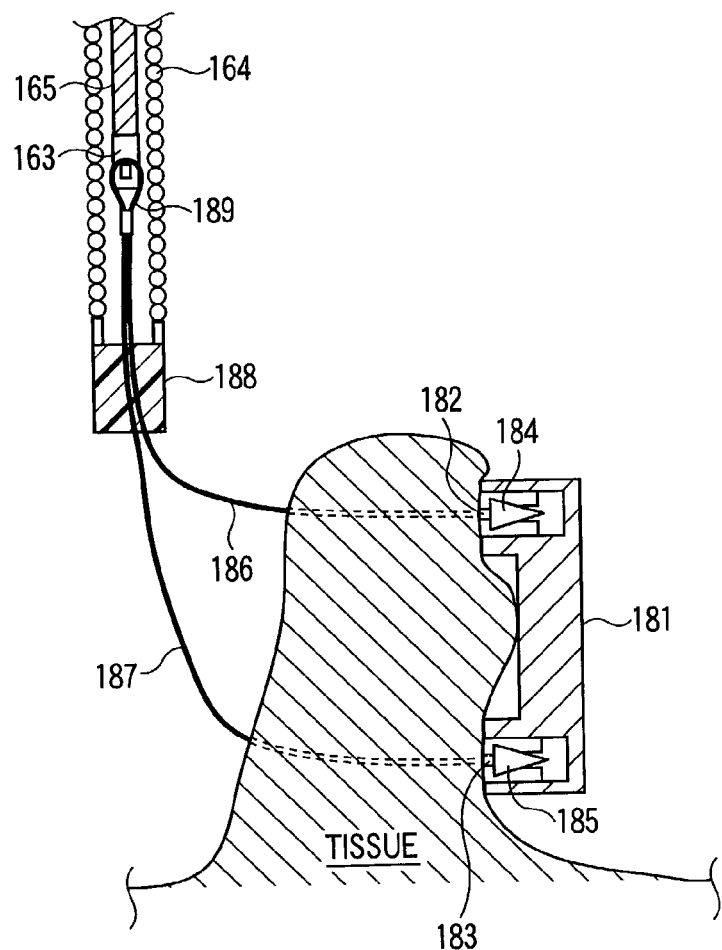
FIG. 65 is a view showing a state in which a removable needle after punctured into a tissue is engaged with a needle fixing device.
Figure 66:
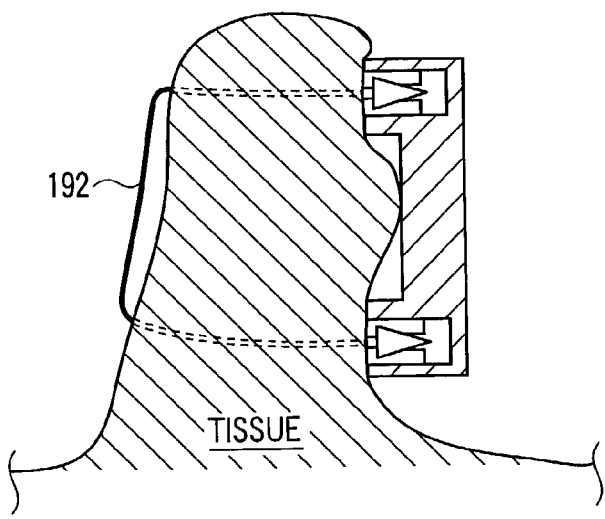
FIG. 66 is a view showing a tissue when the tissue is sutured.
Figure 67:
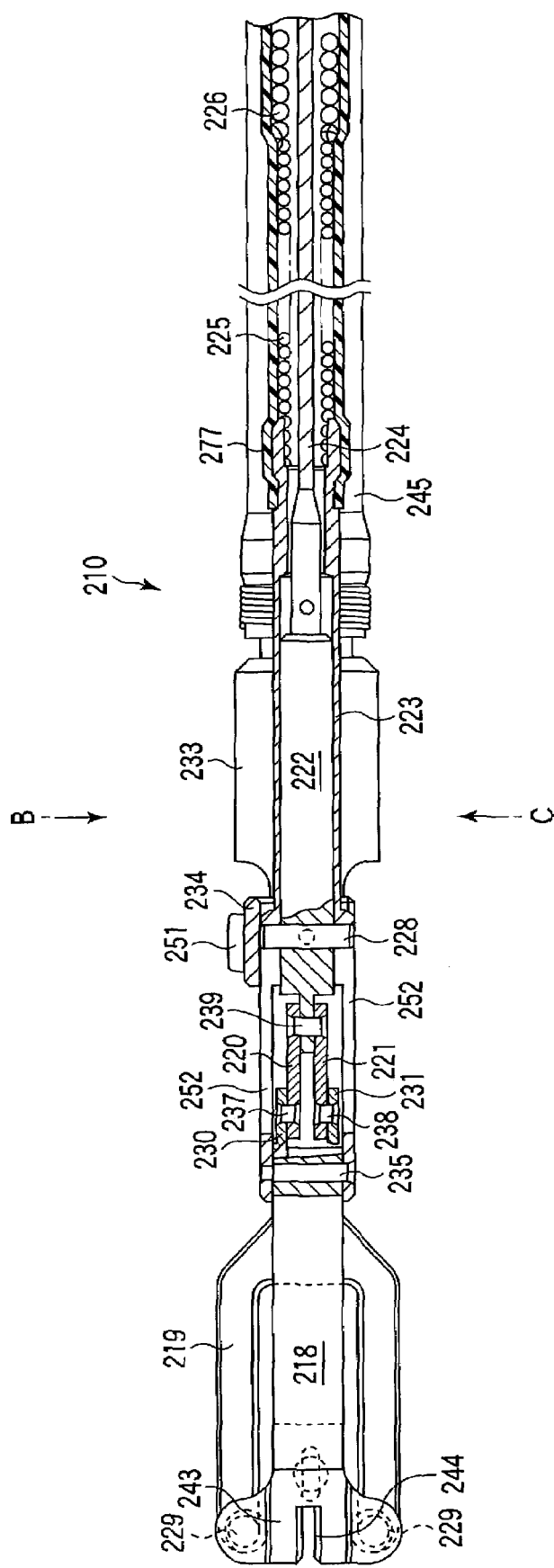
Figure 73:
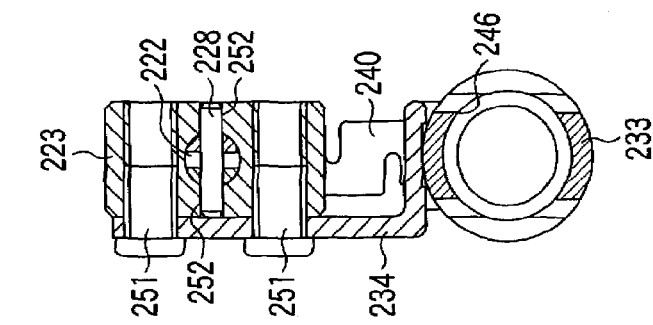
Figure 72:
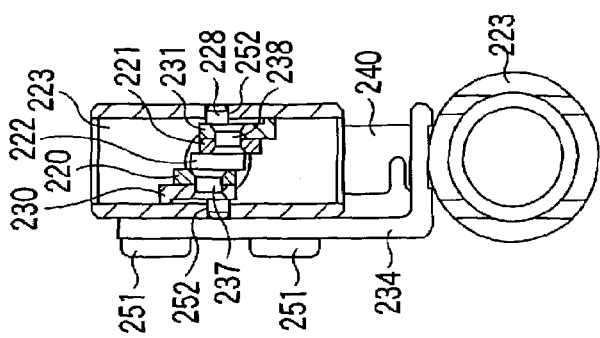
Figure 71:
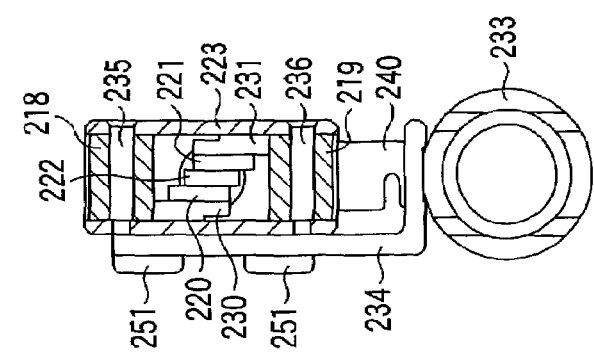
Figure 70:
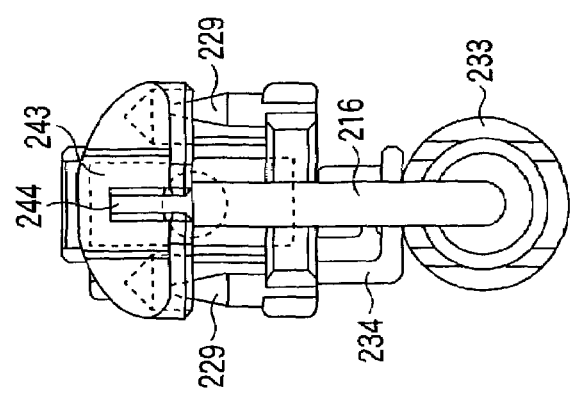

FIG. 64 to FIG. 66 each show an endoscopic suturing system according to a ninth embodiment of the present invention. The ninth embodiment is different from the eighth embodiment in the point below.

As shown in FIG. 64, in the present embodiment, a first actuating member 190 is disposed at needle holders 179 and 180 each mounting removable needles 184 and 185 each. A groove opened inwardly is extended at these needle holders 179 and 180 each, as shown in FIG. 41. In addition, one of the suture threads 186 and 187 each is fixed to the two removable needles 184 and 185 each in a manner similar to the seventh embodiment.

A needle fixing device 181 is removably mounted on the second actuating member 191. Needle lock means 182 and 182 for engaging the removable needles 184 and 185 are formed at the needle fixing device 181.

As shown in FIG. 65, the other ends of the suture threads 186 and 187 are extended into the coil 164 via thread lock means 188 similar to the thread lock means 155 according to the seventh embodiment, and a loop portion 189 is formed. This loop portion 189 as well is engaged with the engaging portion 163 of the transmission member 165 as in the seventh embodiment.

The removable needles 184 and 185 and needle thread fixing device 181 described above are at least partly made of a biocompatible metal such as stainless steel, pure titanium or titanium alloy, a biocompatible resin such as polyimide, poly(etheretherketone) (PEEK), polysulfon, liquid crystal polymer, or polyamide, a biocompatible ceramic material such as alumina, silicon nitride, or the like. As in the first embodiment, the suture threads 186 and 187 are formed like a monofilament line or stranded wire by using a material such as nylon, polyester, silk, fluoroplastic or bioabsorbable resin.

A suturing operation using this endoscope system is carried out as follows.

(1) As in the above described embodiments each, the suturing device 3 is inserted into a body while its distal end portion is protected by the insert assisting devices 84 and 95, protect member 100, protect member 122 or the like as in the above described embodiments each.

(2) The first and second actuating members 190 and 191 are closed so as to press the needle lock means 182 and 183 and the removable needles 184 and 185 against a suture site, and the removable needles 184 and 185 are punctured into a tissue.

(3) As shown in FIG. 65, the removable needles 184 and 185 after punctured is inserted into the needle lock means 182 and 183 of the needle fixing device 181 held at a predetermined position, and is engaged therewith.

(4) When the first and second actuating members 190 and 191 are opened, the removable needles 184 and 185 are engaged with the needle fixing device 181. Thus, the removable needle 184 and 185 are removed from the needle holders 179 and 180. In addition, the needle fixing device 181 as well is removed from the second actuating member 191. In this manner, a state shown in FIG. 65 is obtained.

(5) Then, as in the seventh embodiment, thread lock means 188 is pushed against a tissue, an engaging portion 163 is pulled via the transmission member 165, and the tissue is tied. Then, the engaging portion 163 is pushed out from the coil 164, and the loop portion 189 is removed.

(6) Lastly, redundant suture threads 186 and 187 are cut by the thread cutting device 136 as in the fourth embodiment.

On the other hand, as shown in FIG. 66, the tying force may be adjusted with a length of one suture thread 192 instead of the two suture threads 186 and 187. In this case, measures such as thread lock means 188, the engaging portion 163, the coil 164, the transmission member 165, the loop portion 189 and the like become unnecessary.

This system according to the ninth embodiment as well provides advantages similar to the above described fourth embodiment. Further, in the present embodiment, the two suture threads 186 and 187 can be sutured at the same time by the two removable needles 184 and 185.

10th Embodiment

FIG. 67 to FIG. 99 show the 10th embodiment.

(Arrangement)

The 10th embodiment differs from the first to third embodiments in the following points.

Figure 76:
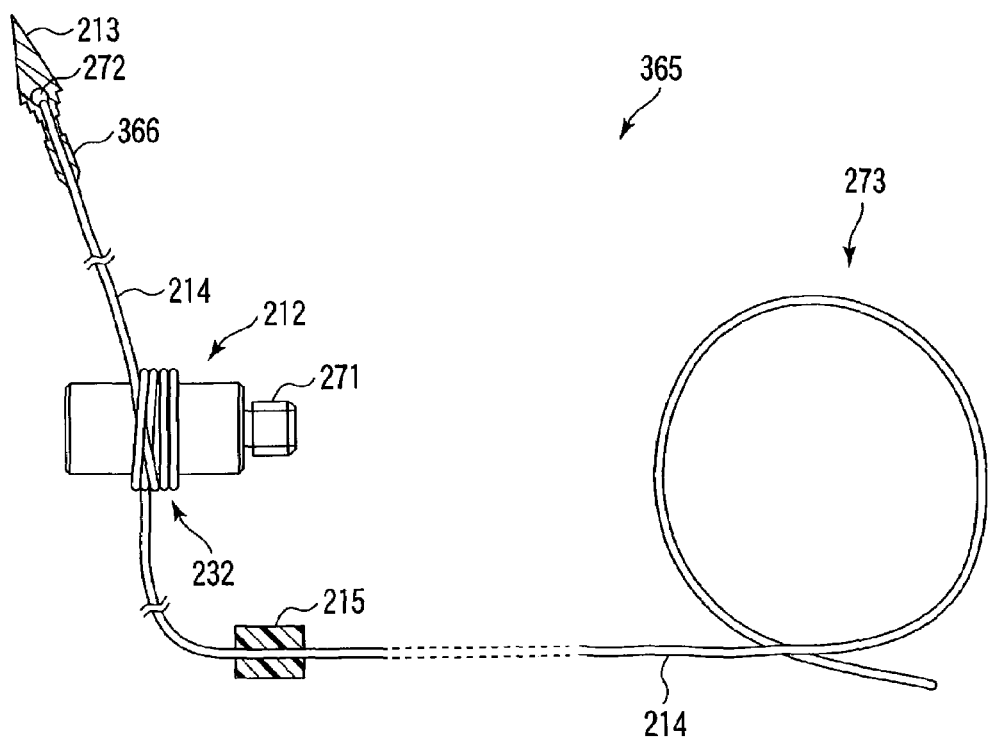
Figure 77:
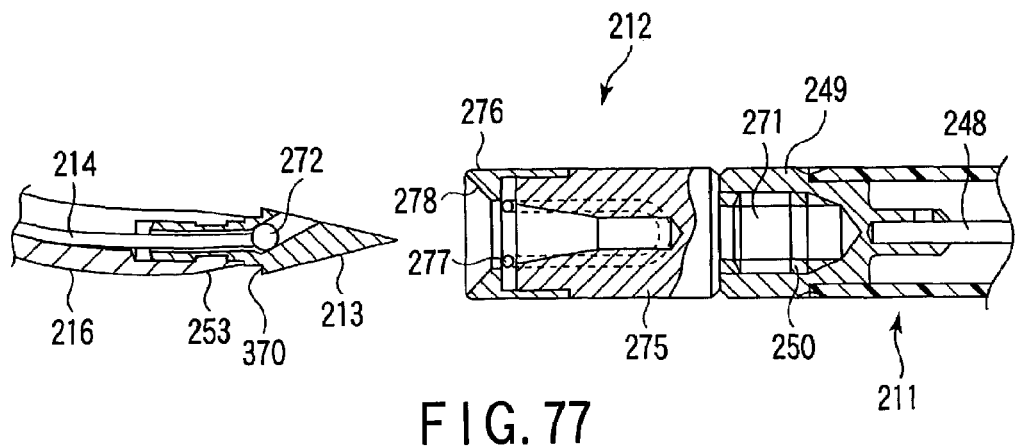
Figure 86:
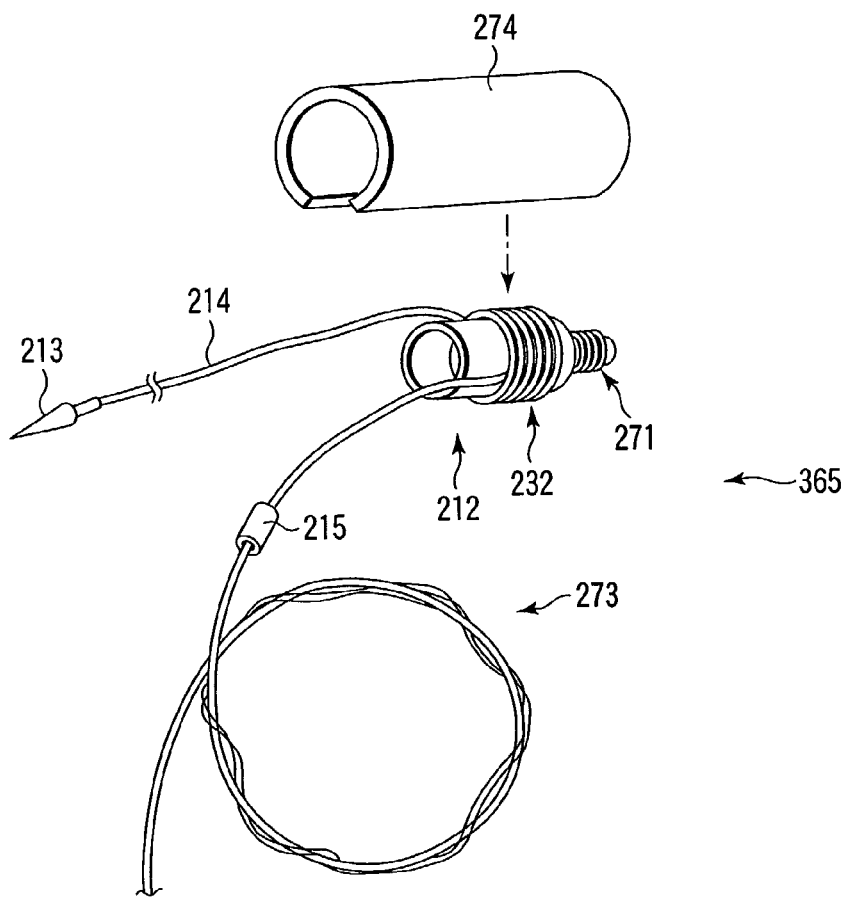
Figure 87:
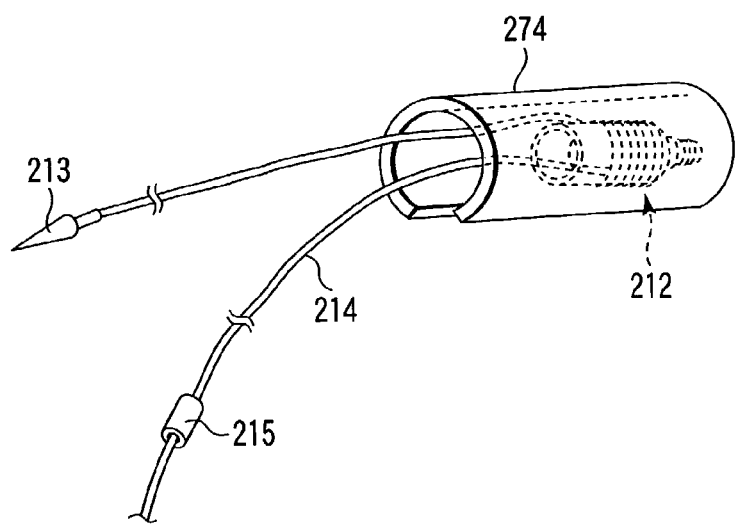
Figure 89:
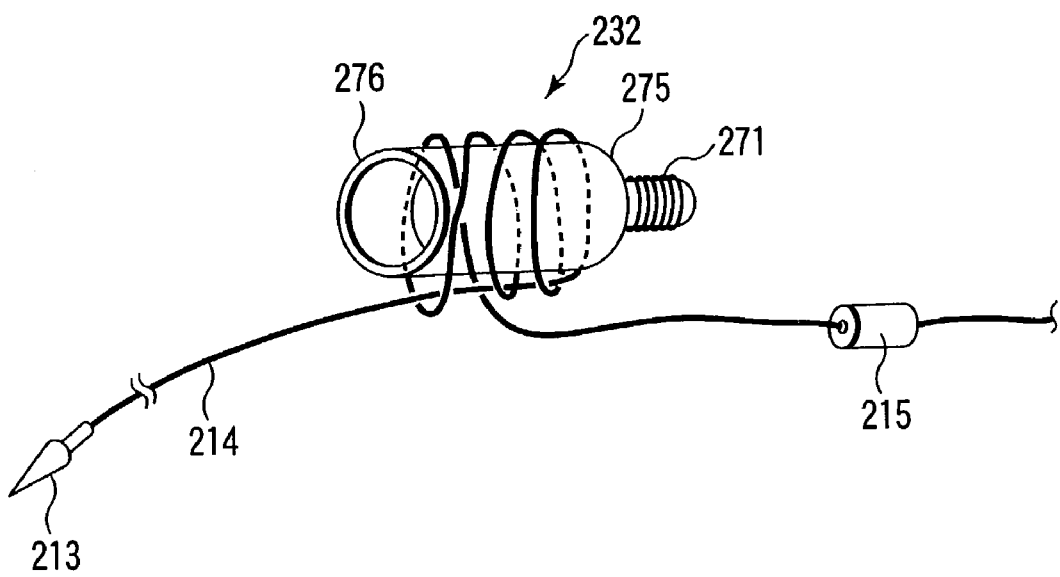

The embodiment uses a pre-knot cartridge 365 like the one shown in FIG. 76, FIG. 86, and FIG. 87. This pre-knot cartridge 365 is comprised of a removable needle 213, suture thread 214, needle-catching-device 212, flexible tubular member 215, and the like. The suture thread 214 is inserted into a hole 366 of the removable needle 213 and has a stopper 272 at its distal end face so as not to come off the removable needle 213. In this embodiment, an end face of a thread is rounded by heat. To fix the thread to the removal needle more firmly, a peripheral portion of the stopper 272 may be coated with an adhesive or the hole 366 may be caulked. Before the end face of the thread is rounded by heat, a knot may be formed at the end face of the thread and thermally molded by a mold which can be divided into two parts and forms a spherical surface. In addition, as shown in FIG. 69, FIG. 76, and FIG. 89, a pre-knot 232 is formed in the suture thread 214 on the surface of the needle-catching-device 212. The pre-knot 232 is preferably tied in the form of a Roeder knot as shown in FIG. 89, which can slide. The suture thread 214 is also slidably inserted into the flexible tubular member 215. The suture thread 214 is formed into a loop 273 on the proximal end side. As shown in FIG. 86 and FIG. 87, the pre-knot 232 is pressed by a cover 274 so as not to come off the needle-catching-device 212 before the use of the pre-knot cartridge 365.

As shown in FIG. 69, a needle-catching-sheath 211 is comprised of a distal tip 249, a flexible tubular member 247, a flexible rod 248 inserted into the inner hole of the flexible tubular member 247, and the like. A female screw 250 is formed on the distal tip 249. The flexible rod 248 is fixed to the other end of the distal tip 249. The flexible rod 248 prevents the expansion of the flexible tubular member 247 upon application of a force.

Figure 99:
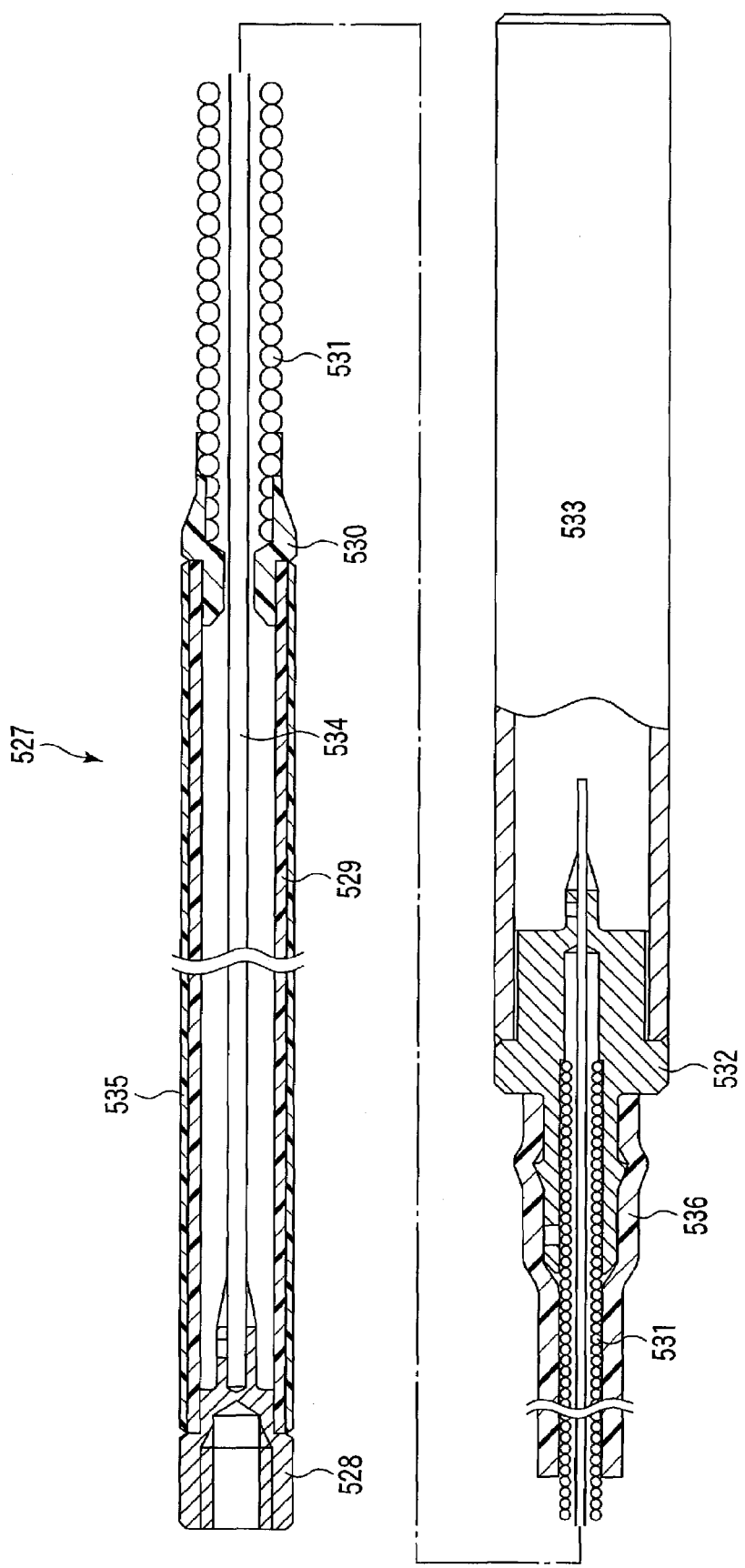
Figure 100:
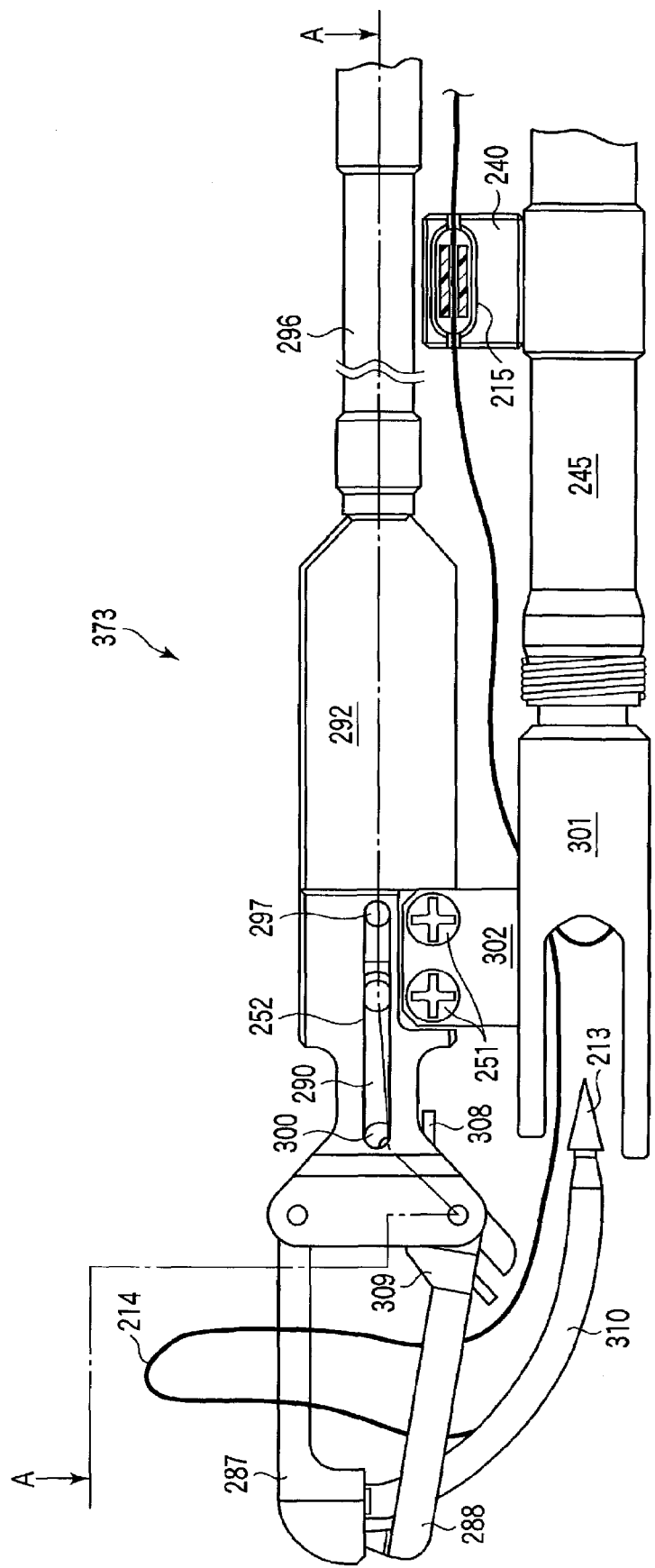

In place of the needle-catching-sheath 211, a needle-catching-sheath 527 like the one shown in FIG. 99 may be used. The needle-catching-sheath 527 is comprised of a distal tip 528, a flexible tubular member 529 (made of, for example, a flat coil), a connecting member 530 which connects the flexible tubular member 529 to the flexible tubular member 531, a connecting member 532 connected to a handle 533 on the proximal end side of the flexible tubular member 531, a buckling preventing means 536 that partly covers the flexible tubular member 531 and connecting member 532 by thermal contraction, a stylet 534 for preventing the elongation of the flexible tubular member 529 and flexible tubular member 531 having both ends connected to the distal tip 528 and connecting member 532, a flexible tubular body 535 (e.g., a tube made of fluoroplastic) fitted on the outer surface of the flexible tubular member 529 by thermal contraction, and the like.

Figure 94:
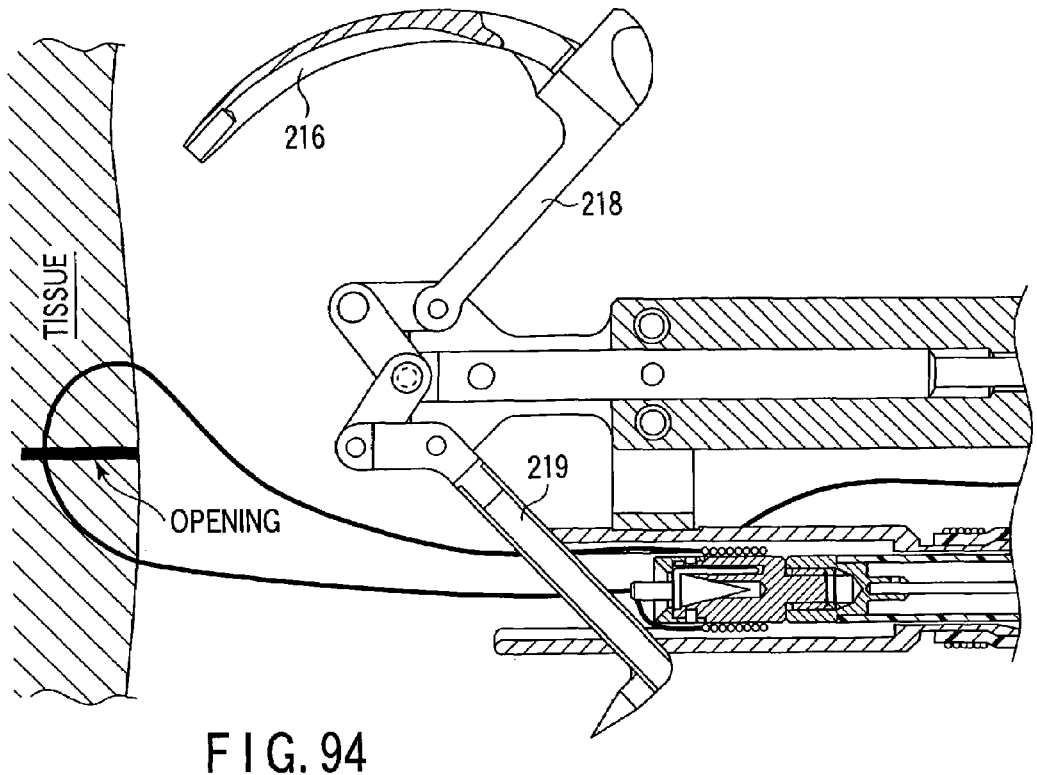
Figure 95:
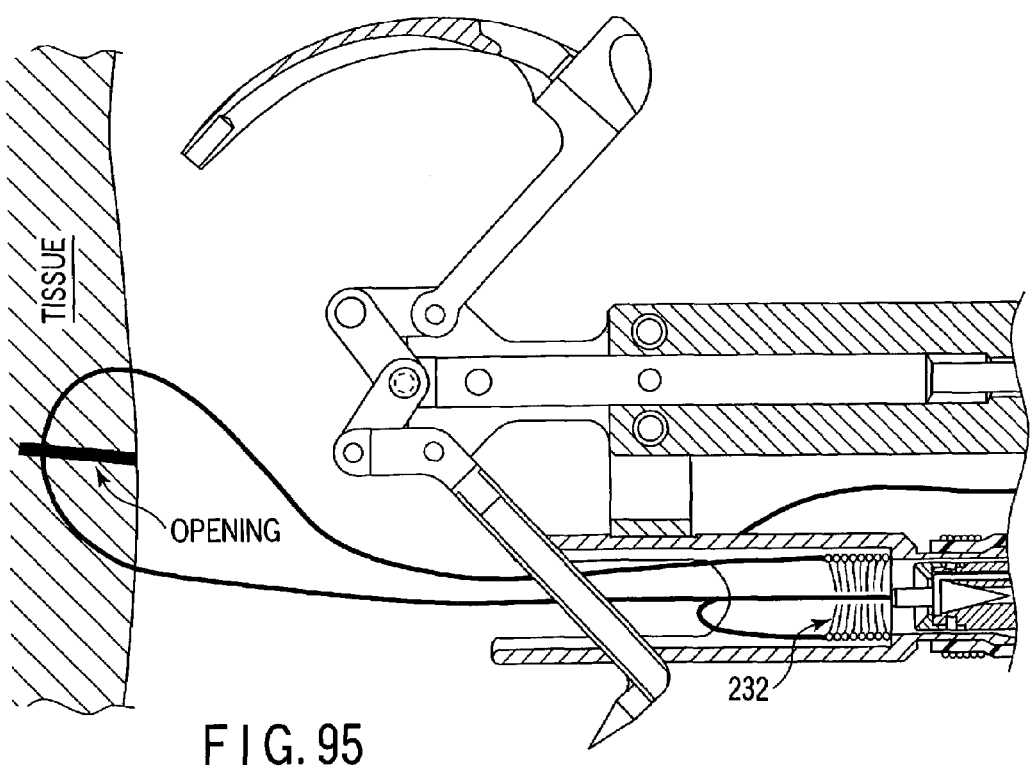

Unlike the needle-catching-sheath 211, the needle-catching-sheath 527 has the flexible tubular body 535. Even if, therefore, a suturing operation to be described later (FIG. 90 to FIG. 98) is performed after the pre-knot 232 is placed on the flexible tubular body 535, the thread is not caught between windings forming the flexible tubular member 529. In addition, since the flexible tubular body 535 allows the thread to slide more smoothly than a coil, it facilitates removing the pre-knot 232 from the needle-catching-sheath as shown in FIG. 94 and FIG. 95.

As shown in FIG. 69, a channel member 367 is comprised of a distal pipe 233, a tube. 245 fixed to the distal pipe 233, and the like, and fixed to a holding member 223 through a support member 234. Holes 368 and 369 having different diameters are formed in the distal pipe 233. The diameter of the hole 369 is designed to be slightly larger than the outer diameters of the needle-catching-sheath 211 and needle-catching-device 212 and smaller than the outer diameter of the pre-knot 232. The needle-catching-sheath 211 is inserted into the distal pipe 233 through the inner hole of the channel member 367 having almost the same diameter as that of the hole 369. The needle-catching-sheath 211 as a constituent element of the pre-knot cartridge 365 is detachably connected to the distal end of the needle-catching-sheath 211 with screws. The needle-catching-device 212 is detachably connected to the distal tip 249 with screws and loaded into the hole 368. The removable needle 213 of the pre-knot cartridge 365 is detachably fixed to a needle holder 216, as shown in FIG. 69. The suture thread 214 is placed in a groove 217 formed in the needle holder 216.

As shown in FIG. 173 and FIG. 174, a slit 537 may be formed in the needle holder 216. The formation of such a slit gives elasticity to the fitting portion between the needle holder 216 and the removable needle 213, thereby forming a press-fitting structure that prevents the removable needle 213 from easily coming off the needle holder 216. As shown in FIG. 69 to FIGS. 77 and 80, the needle-catching-device 212 is comprised of a needle-catching-body 275, inserting member 276, and spring 277.

Figure 78:
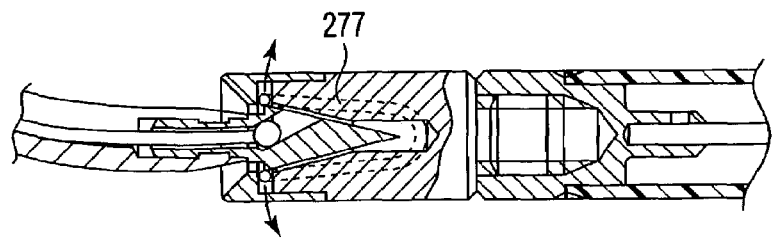
Figure 79:
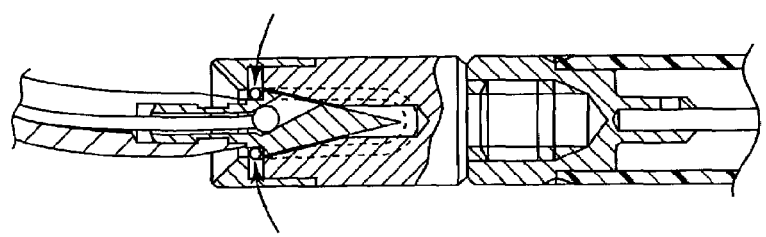
Figure 80:
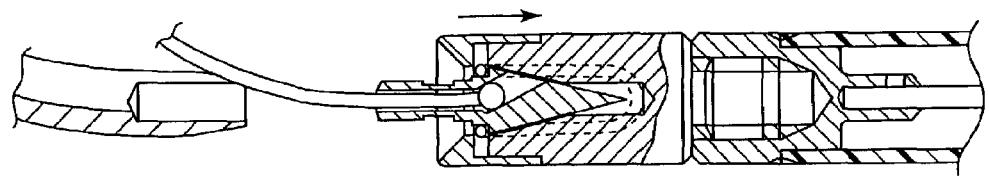
Figure 88:
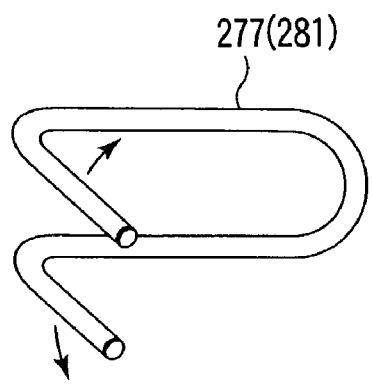

As shown in FIG. 78, when the needle-catching-sheath 211 is moved to the left on the drawing surface, the removable needle 213 is inserted into an infundibular recess part 278 of the inserting member 276 and spreads the spring 277 (see FIG. 88). When the needle-catching-sheath 211 is further moved, the spring 277 returns to its original shape and comes into contact with a contact face 370 formed on the removable needle 213, as shown in FIG. 79. This makes it possible to lock the removable needle 213 to the needle-catching-device 212, as shown in FIG. 80.

The needle holder 216 has a taper 253 to reduce the resistance produced when it punctures the tissue.

Figure 74:
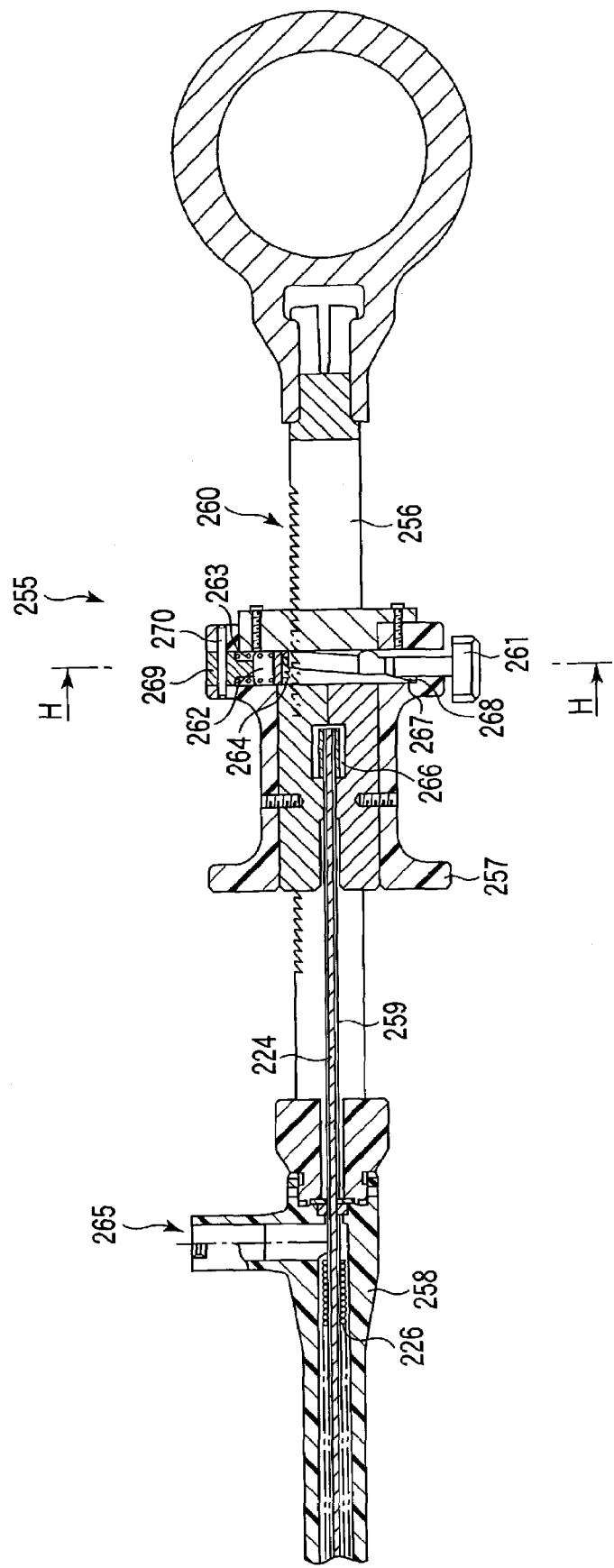
Figure 75:
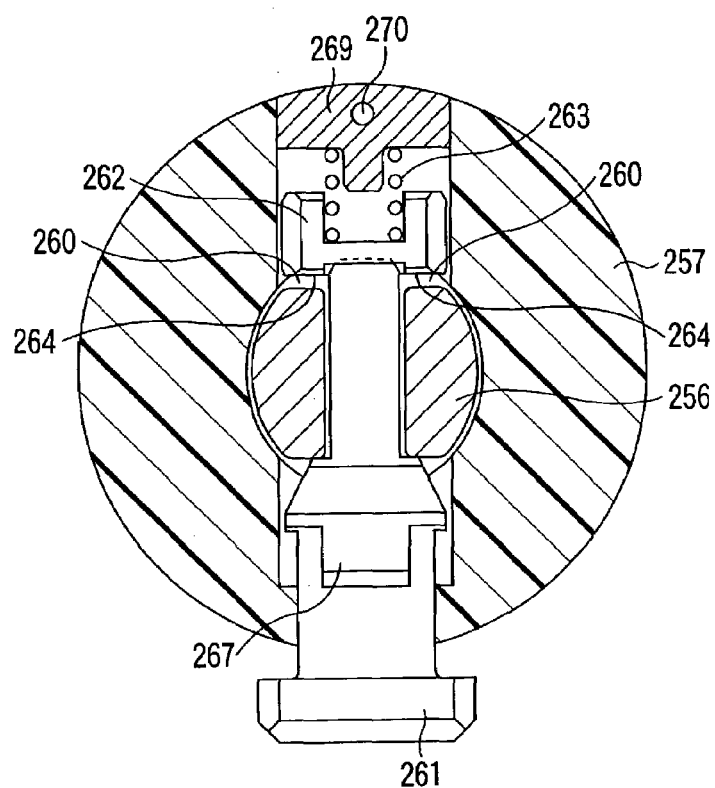

As shown in FIG. 74 and FIG. 75, an operating section 255 of the suturing device is arranged on the proximal end side of flexible tubular members 225 and 226 and transmission member 224. The operating section 255 incorporates a ratchet mechanism. When a button 261 is pressed as shown in FIG. 74, the ratchet mechanism is released to allow a slider 257 to be freely pushed and pulled. When the button 261 is slid to the right side on the drawing surface, a stopper 267 formed on the button 261 is unlocked from an engage part 268 formed on the slider 257, and an engage part 262 that has been biased by a spring 263 is pressed downward. As a consequence, the engage part 262 engages with a burr member 260 formed in an operating section body 256. The slider 257 can move only to the right. This inhibits first and second active members 218 and 219 from moving in a direction to open.

On the other hand, as shown in FIG. 69, the flexible tubular member 215 of the pre-knot cartridge 365 is pressed into a recess 241 of a holder 240 fixed to the tube 245. In this case, since the flexible tubular member 215 is formed from a flexible resin member such as a silicone member, the suture thread 214 can slide with respect to the flexible tubular member 215 even while the flexible tubular member 215 is pressed in the recess 241.

The structures of the needle-catching-device 212, removable needle 213, and needle holder 216 in this embodiment may be changed into those shown in FIG. 81 to FIG. 85.

Figure 81:
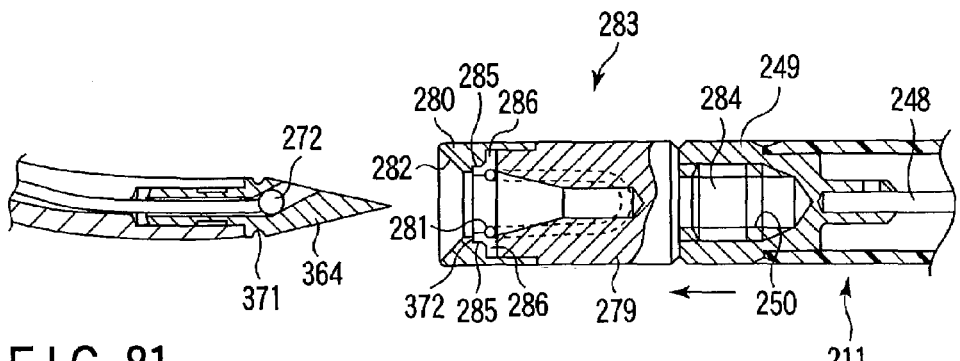
Figure 82:
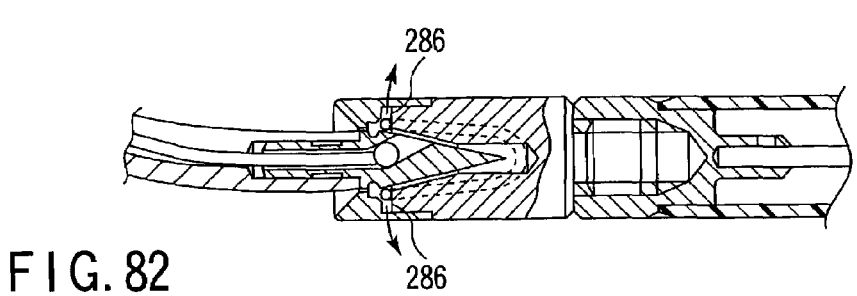
Figure 83:
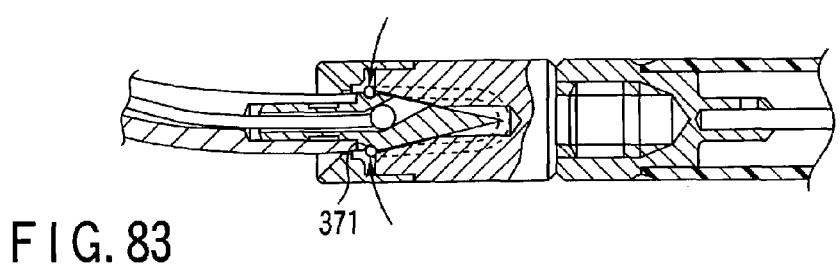
Figure 84:
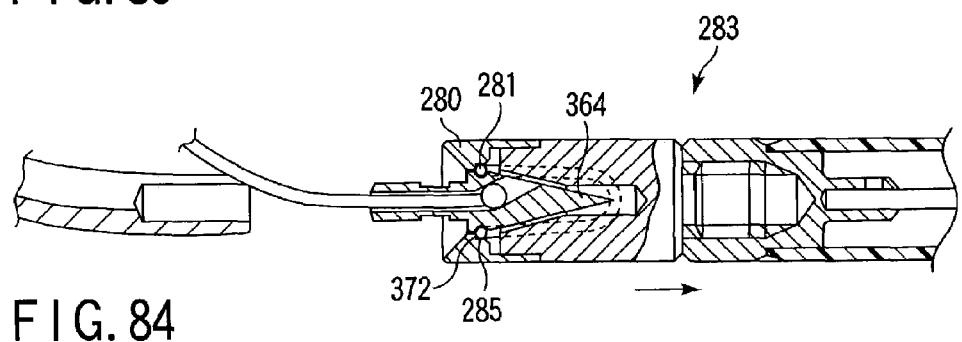
Figure 85:
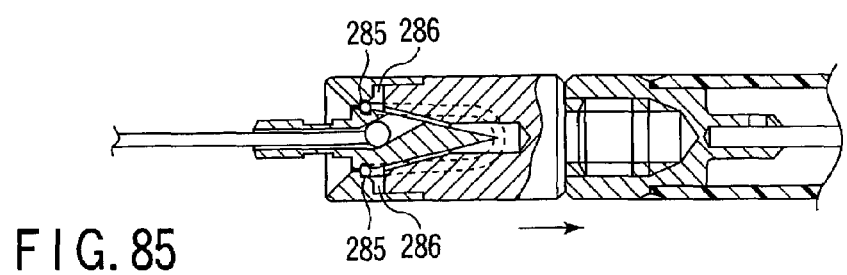

As shown in FIG. 81 and FIG. 88, a needle-catching-device 283 is comprised of a needle-catching-body 279, inserting member 280, spring 281, and the like. As shown in FIG. 81, when the needle-catching-device 283 is moved to the left on the drawing surface, a removable needle 364 is inserted into an infundibular recess part 282 of the inserting member 280 and spreads the spring 281 (see FIG. 88). When the needle-catching-device 283 is further moved, the spring 281 returns to its original shape, as shown in FIG. 83. As a consequence, the spring 281 engages with a recess 371 formed in at least part of the removable needle 364. When the needle-catching-device 283 is moved to the right on the drawing surface thereafter as shown in FIG. 84, the spring 281 including the removable needle 364 moves until it comes into contact with a contact face 372 formed on the inserting member 280. As a result, the movement of the spring 281 in a direction to spread is restricted by the wall of an engage part 285 formed on the inserting member 280, and hence the removable needle 364 can be locked to the needle-catching-device 283.

The removable needle 364 has the recess part 371 to reduce the resistance produced when it punctures the tissue. As shown in FIG. 175 and FIG. 176, a slit 538 may be formed in the needle holder 216 without the taper 253 to form a press-fitting structure in which the fitting between the removable needle 364 and the needle holder 216 is not easily released.

(Function)

A suturing procedure will be described with reference to FIG. 90 to FIG. 97.

(1) A suturing device 210 protected by the insert assisting devices 84 and 95 in the first embodiment, the protect member 100 in the second embodiment, or the protect member 122 in the third embodiment is inserted into the body.

Figure 90:
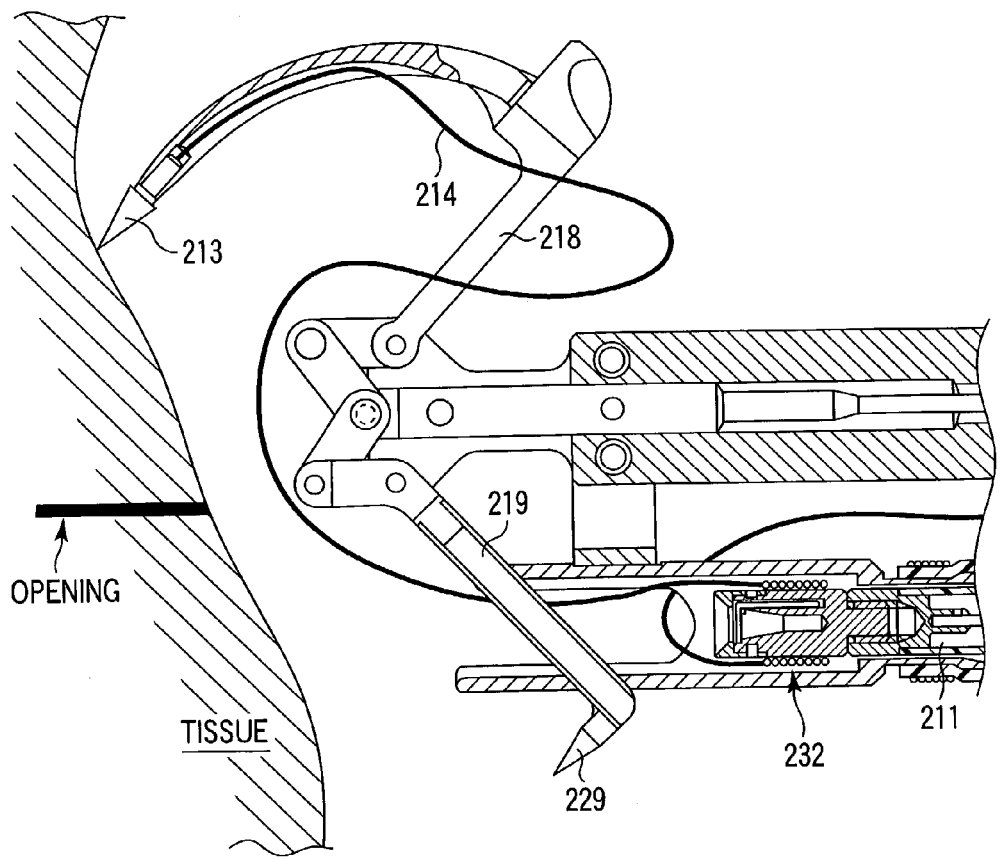
Figure 91:
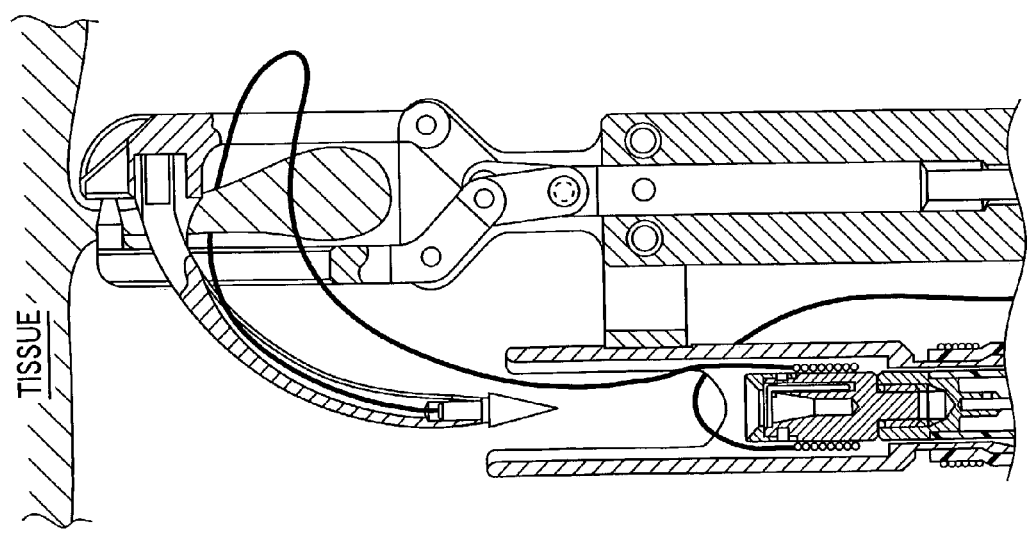

(2) As shown in FIG. 90 and FIG. 91, the removable needle 213 and two fixing needles 229 are so pressed against the region to be sutured as to close the first and second active members 218 and 219, and the tissue is punctured with the removable needle 213.

Figure 92:
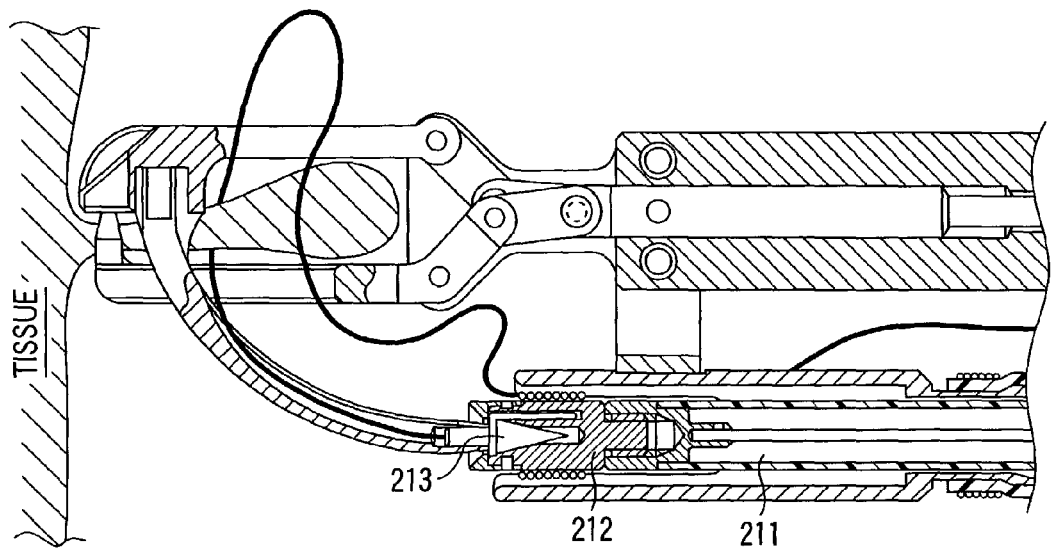

(3) As shown in FIG. 92, after puncturing, the needle-catching-sheath 211 is pushed into the removable needle 213, and the needle-catching-device 212 is engaged with the removable needle 213.

Figure 93:
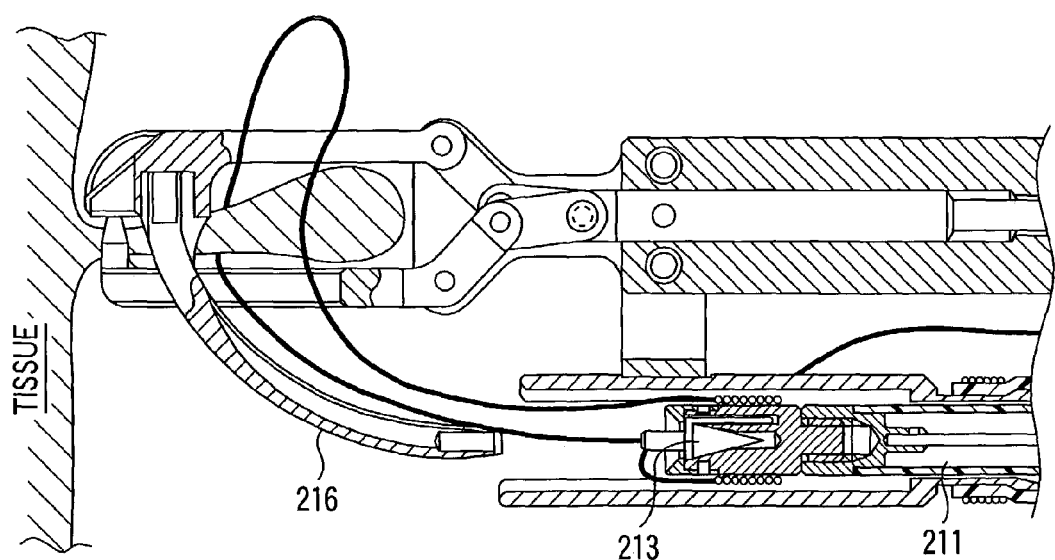

(4) As shown in FIG. 93, the needle-catching-sheath 211 is pulled, and the removable needle 213 is withdrawn from the needle holder 216.

(5) As shown in FIG. 94, the first and second active members 218 and 219 are opened to withdraw the needle holder 216 from the tissue.

(6) As shown in FIG. 95, the needle-catching-sheath 211 is further pulled to remove the pre-knot 232 from the needle-catching-device 212.

Figure 96:
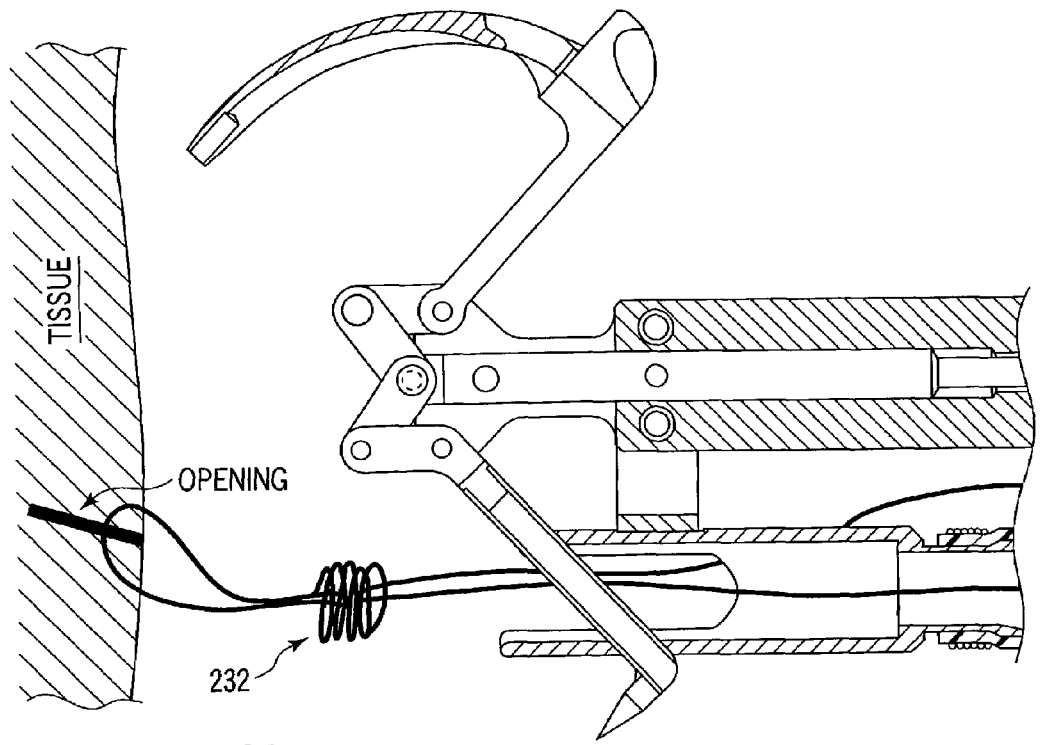
Figure 97:
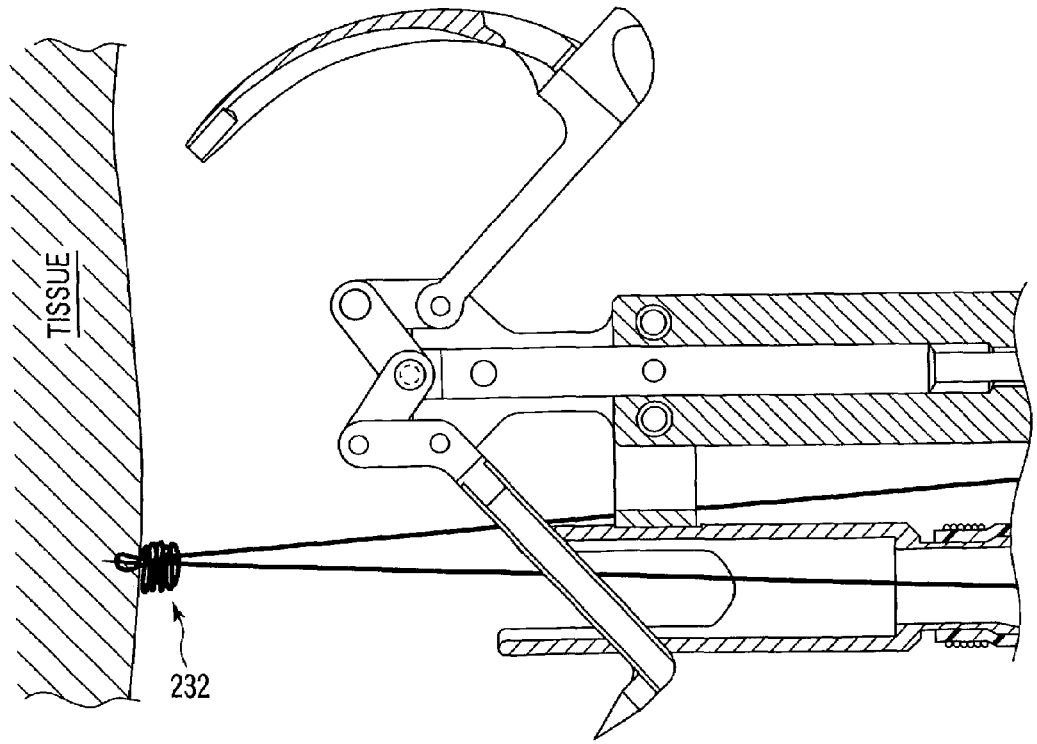

(7) As shown in FIG. 96 and FIG. 97, the needle-catching-sheath 211 is further pulled to move the pre-knot 232 to the opening portion of the tissue, and the opening portion is sutured.

Figure 98:
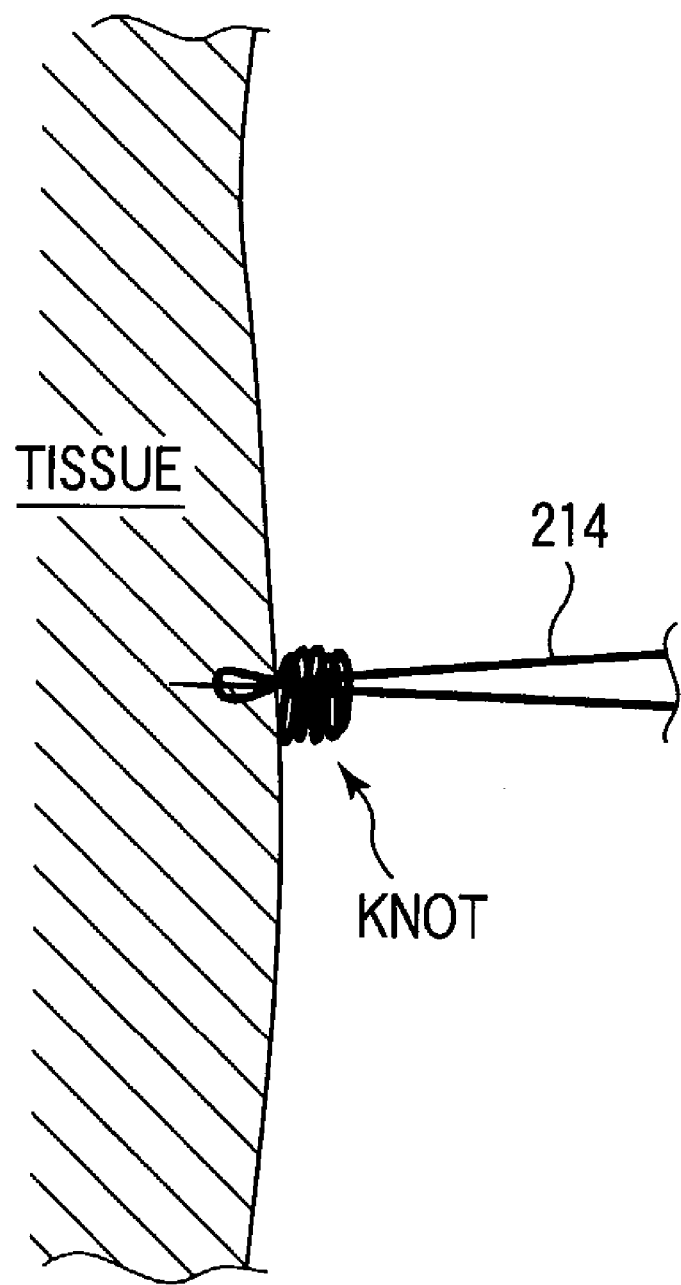

(8) As shown in FIG. 98, a redundant portion of the thread is cut by using a thread cutting device 136 or the like.

(Effects)

In addition to the advantages of the first and second embodiments described above, according to this embodiment, since there is no need to make a knot outside the body and feed it into the body, the manual operation time can be shortened, and the procedure is further facilitated. In addition, there is no need to indwell any member other than the suture thread in the body.

11th Embodiment

FIG. 100 to FIG. 111 show the 11th embodiment.

(Arrangement)

The 11th embodiment differs from the 10th embodiment in the following points.

Figure 101:
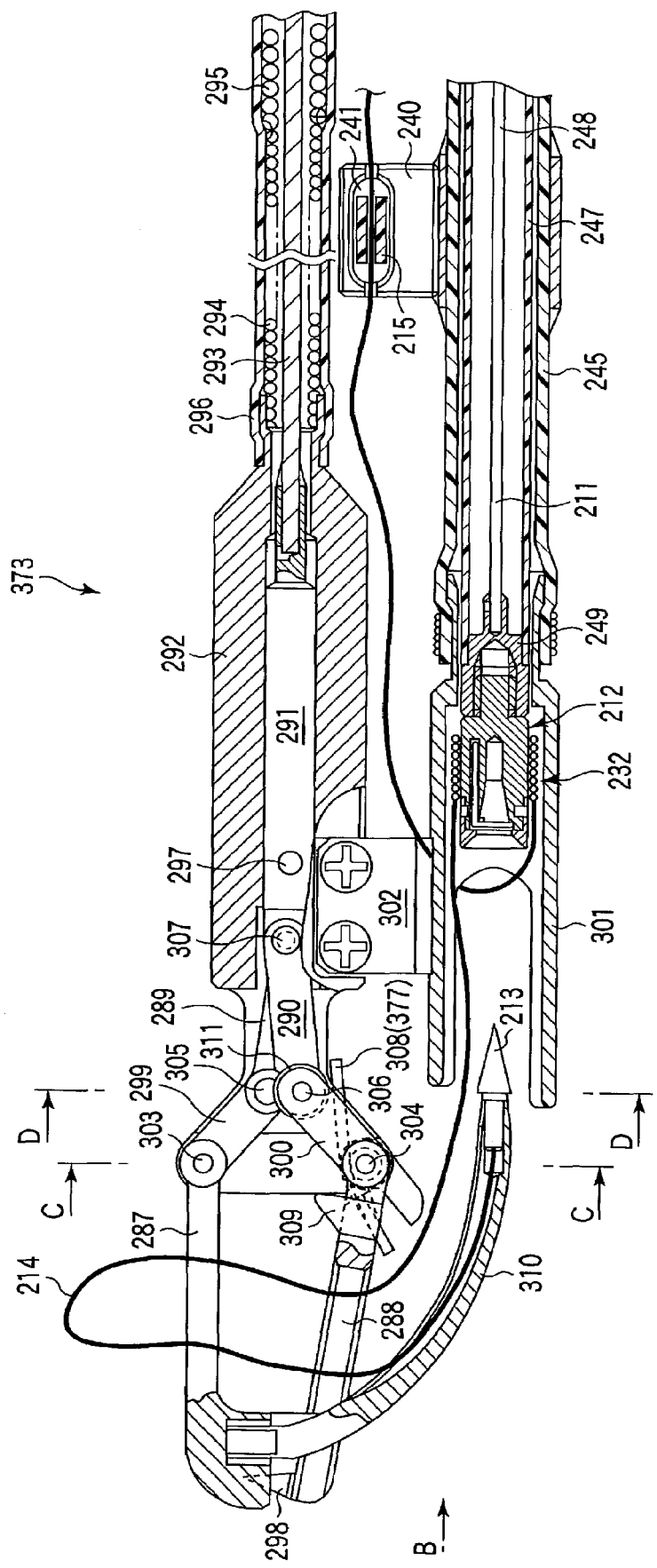
Figure 108:
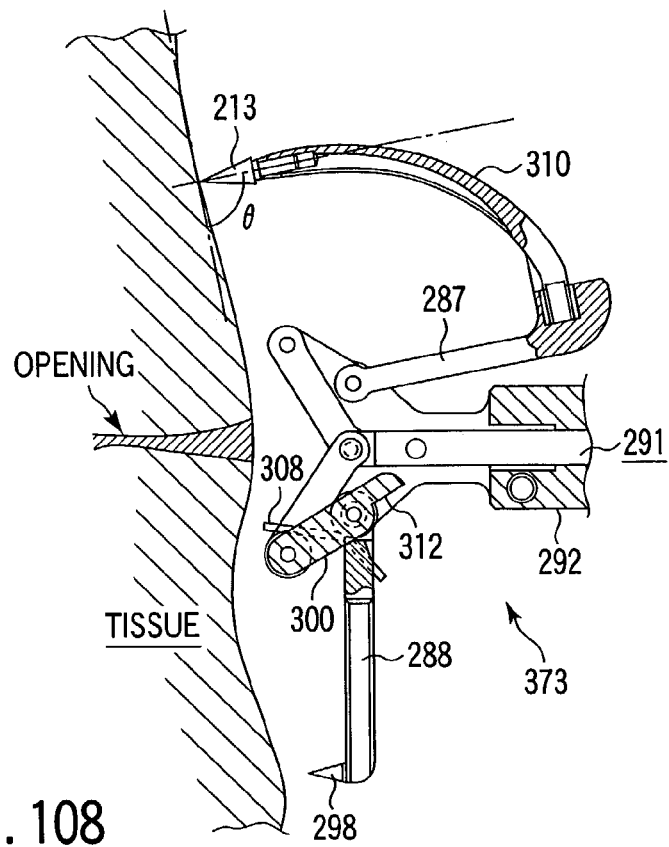

As shown in FIG. 101, the interval between pins 303 and 304 of a suturing device 373 of the 11th embodiment is larger than that between the pins 235 and 236 in the 10th embodiment. In addition, the interval between the pin 303 and a pin 305, the interval between the pin 304 and a pin 306, the interval between the pin 305 and a pin 307, and the interval between the pin 306 and the pin 307 are larger than those in the 10th embodiment. As shown in FIG. 108, this arrangement allows a first actuating member 287 to make a larger rotational movement than the first active member 218 (see FIG. 90) in the 10th embodiment, and also can increase the puncturing force acting on a removable needle 213 fixed to a needle holding member 310.

Figure 102:
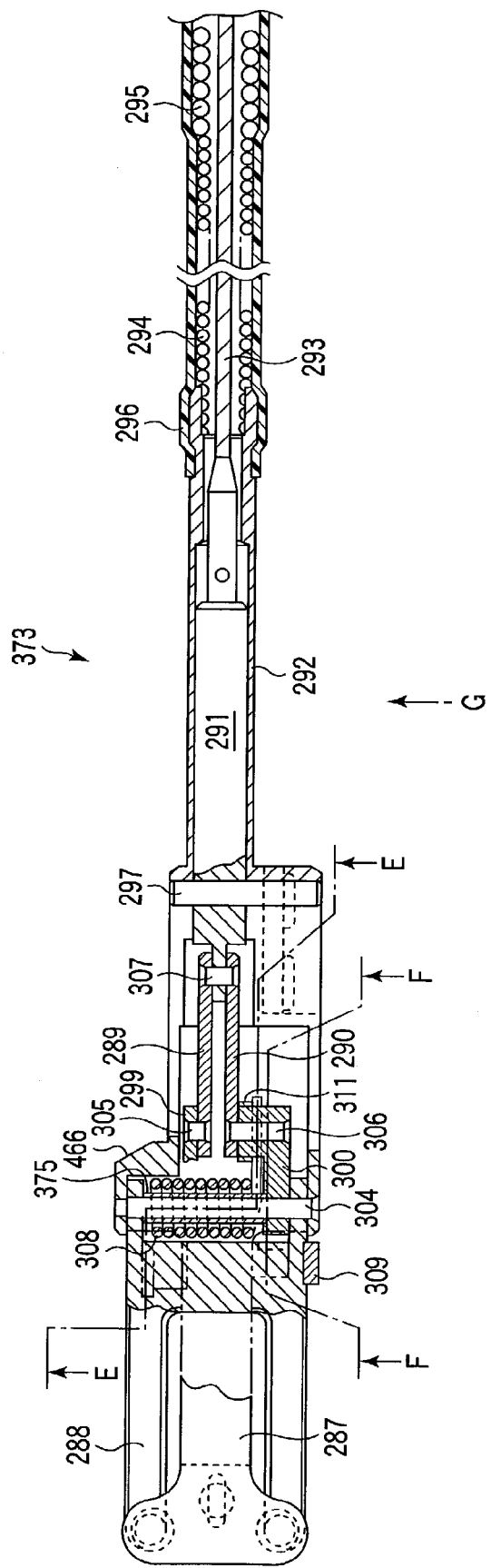
Figure 106:
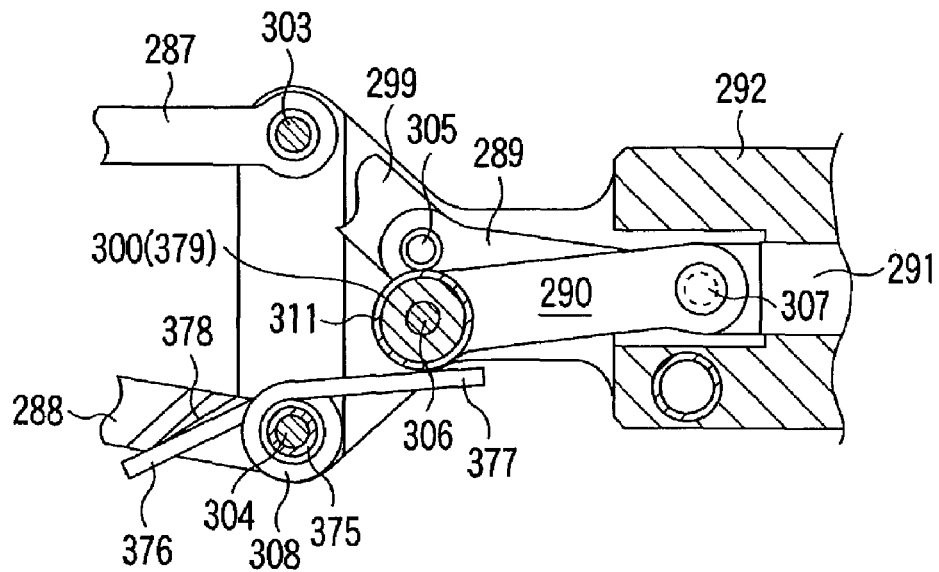
Figure 107:
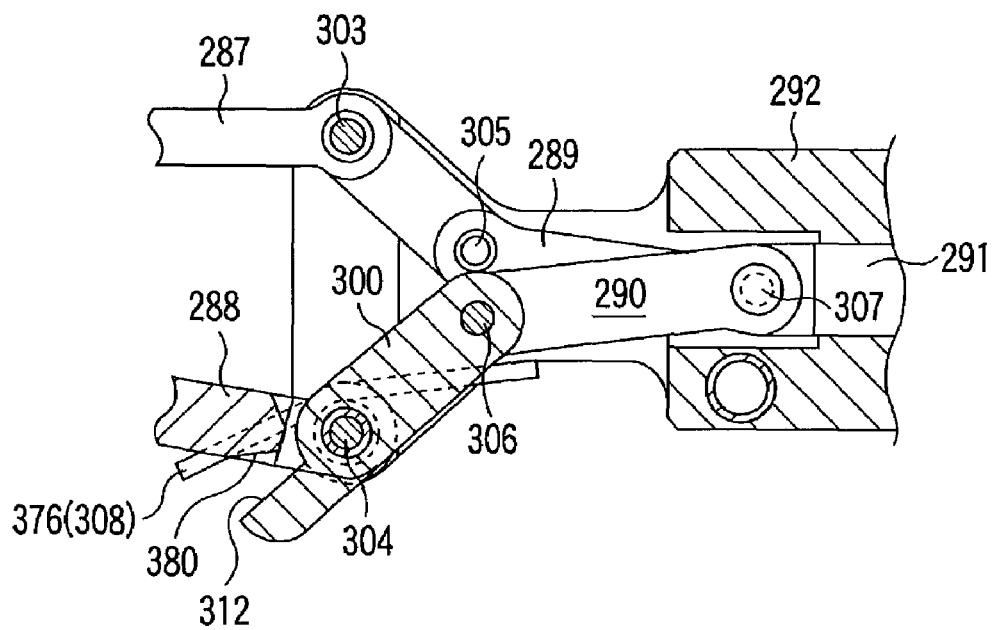

As shown in FIG. 102 and FIG. 106, a second active member 288 can rotate about the pin 304. A pipe 375 is rotatably fitted on part of the pin 304, and a spring 308 is arranged around them. An arm member 376 of the spring 308 is in contact with a contact face 378 formed on the second active member 288. As shown in FIG. 107, a force charging member 300 is connected, through the pin 306, to a second connecting member 290 which is connected to a rod 291 to be rotatable about the pin 307. This force charging member 300 can pivot about the pin 304. The other arm member 377 of the spring 308 is so arranged as to come into contact with a ring member 311 pivotally mounted on a cylinder part 379 of the force charging member 300 formed on the axis of the pin 306. In this case, the ring member 311 is arranged to reduce the resistance of the arm member 377. Obviously, however, this ring member 311 can be omitted. As in the 10th embodiment, two fixing needles 298 are mounted on a U-shaped end portion of the second active member 288. As shown in FIG. 177, these fixing needles 298 may be needles in the form of eagle's claw with its distal end curving inward. When the tissue is punctured with a fixing needle having such a form, the needle does not easily slip off from the tissue. Such a modification of the fixing needle can also be applied to other embodiments.

As shown in FIG. 101, a stopper 309 is fixed to the second active member 288 to prevent the second active member 288 from further rotating clockwise from the state shown in FIG. 101.

Since a pre-knot cartridge 365, a needle-catching-sheath 211, and an operating section 255 in addition to the removable needle 213, which are other constituent members, are the same as those in the 10th embodiment, a description thereof will be omitted. In addition, this embodiment may use the arrangement of the removable needle 364 and needle-catching-device 283 in described in the 10th embodiment.

(Function)

The operation of the suturing device 373 in a case wherein the tissue to be sutured is punctured will be described with reference FIG. 108 to FIG. 111.

(1) When the rod 291 is pushed to the left on the drawing surface as shown in FIG. 108 by operating the operating section 255 (not shown), the first active member 287 can be opened to the position shown in FIG. 108. At this time, since no external force is applied to the second active member 288 in a direction to open, the second active member 288 is opened by the spring 308 to only the position shown in FIG. 108. When the removable needle 213 is inserted into the tissue at an angle θ where 45 degrees<θ<110 degrees (preferably, 90 degrees), the tissue is punctured deep. This makes it possible to reliably suture the tissue.

Figure 109:
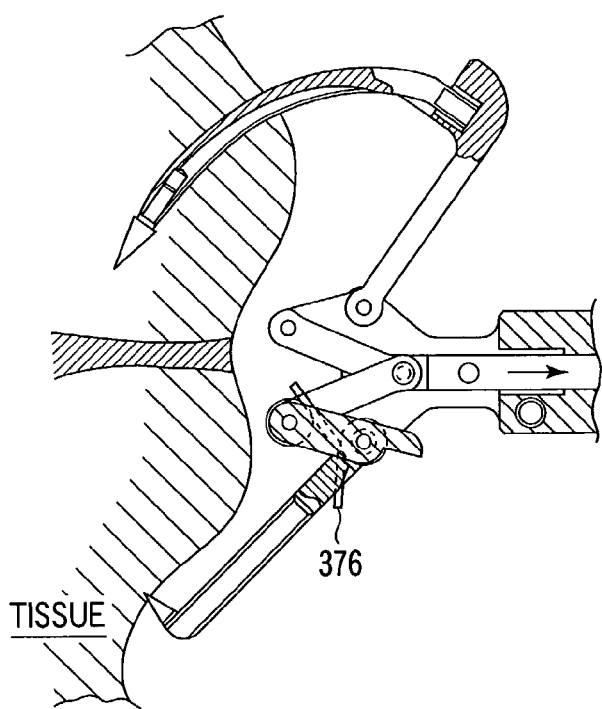

(2) As shown in FIG. 109, when the second actuating member 219 is moved to the right on the drawing surface, the tissue is punctured with the removable needle 213 and two fixing needles 229. At this time, the counterclockwise force acting on the second active member 288 is equal to the biasing force of the spring 308.

Figure 110:
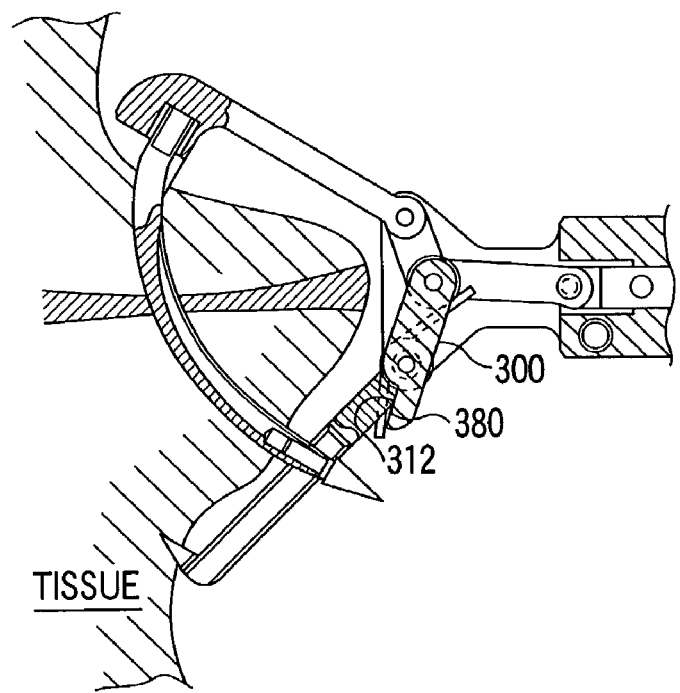
Figure 111:
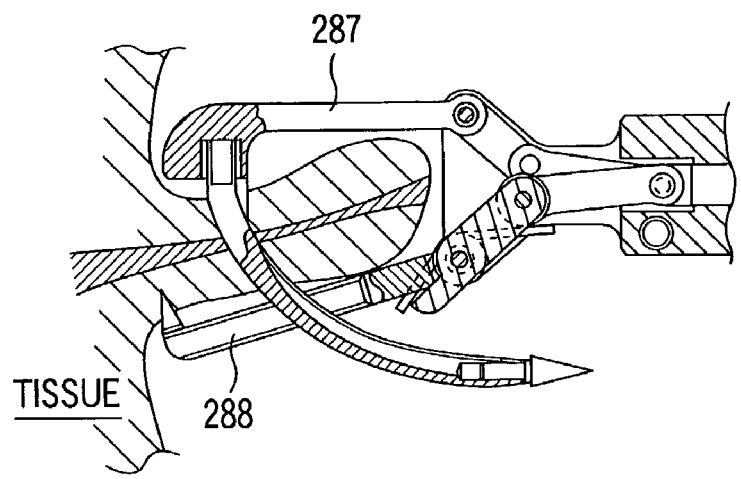
Figure 112:
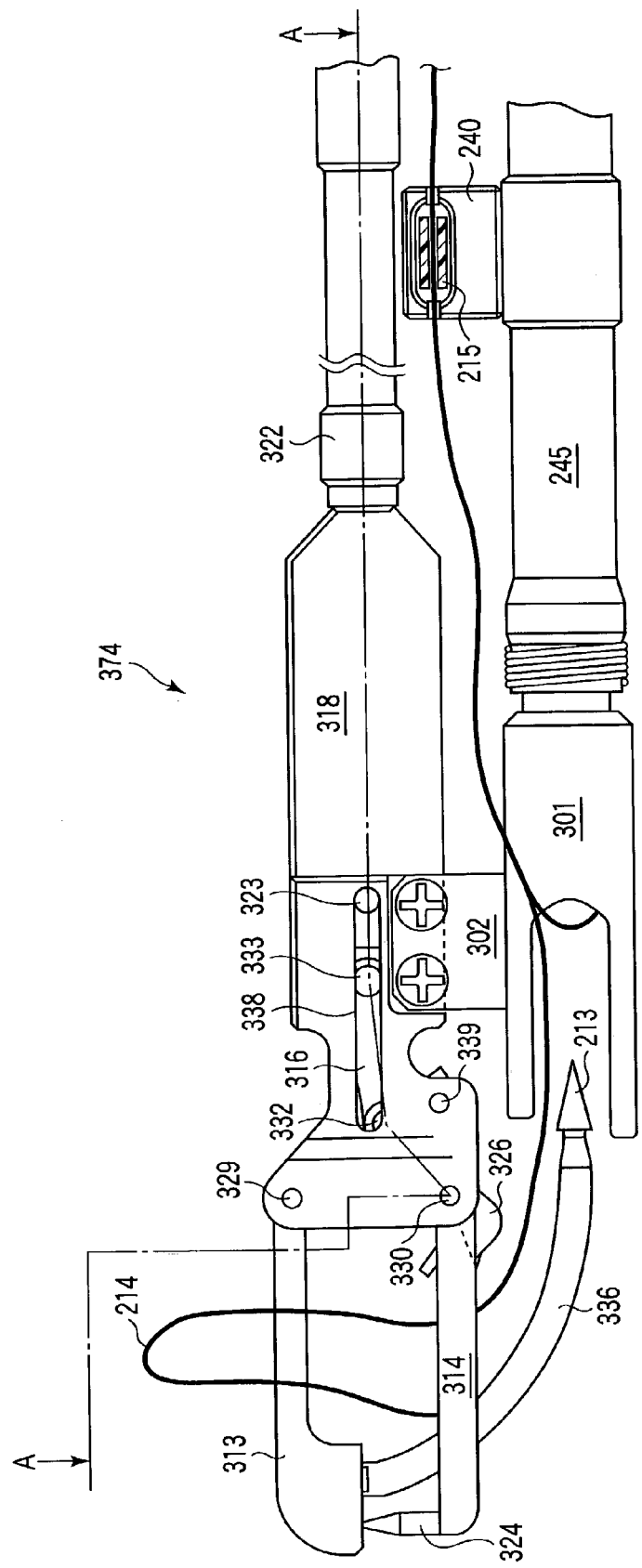

(3) As shown in FIG. 110 and FIG. 111, when the rod 291 is further moved to the right on the surface drawing, a contact face 312 of the force charging member 300 engages with a contact face 380 of the second active member 288. As a consequence, in addition to the biasing force, the force of the force charging member 300 acts on the second active member 288. This makes it possible to reliably rotate the second active member 288 clockwise. As shown in FIG. 111, to completely close the first active member 287 even when a large portion of the tissue is caught, the position where the contact face 312 engages with the contact face 380 is set in a direction in which the second active member 288 opens. In other words, while no tissue is caught, the second active member 288 is in contact with the first active member 287 with only the force of the spring 308. At this time, the contact face 312 is not in contact with the contact face 380. This makes it possible to match the axis of the removable needle 213 in FIG. 101 with that of the needle-catching-device 212 to a certain extent. Therefore, the needle-catching-device 212 can easily recover the removable needle 213. Since a suturing procedure is the same as that in the 10th embodiment (see FIG. 90 to FIG. 98), a description thereof will be omitted.

(Effects)

In addition to the effects of the 10th embodiment, the tissue can be punctured deeper, and the removable needle 213 can be easily recovered.

12th Embodiment

FIG. 112 to FIG. 122 show the 12th embodiment.

(Arrangement)

The 12th embodiment differs from the 10th embodiment in the following points.

As shown in FIG. 113, the interval between pins 329 and 330 of a suturing device 374 of the 12th embodiment is larger than that between the pins 235 and 236 in the 10th embodiment. In addition, the interval between the pin 329 and a pin 331, the interval between the pin 330 and a pin 332, the interval between the pin 331 and a pin 333, and the interval between the pin 332 and the pin 333 are also larger than those in the 10th embodiment. As in the 11th embodiment, this arrangement allows a first active member 313 to make a larger rotational movement, and also can increase the puncturing force acting on a removable needle 213 fixed to a needle holding member 336.

Figure 114:
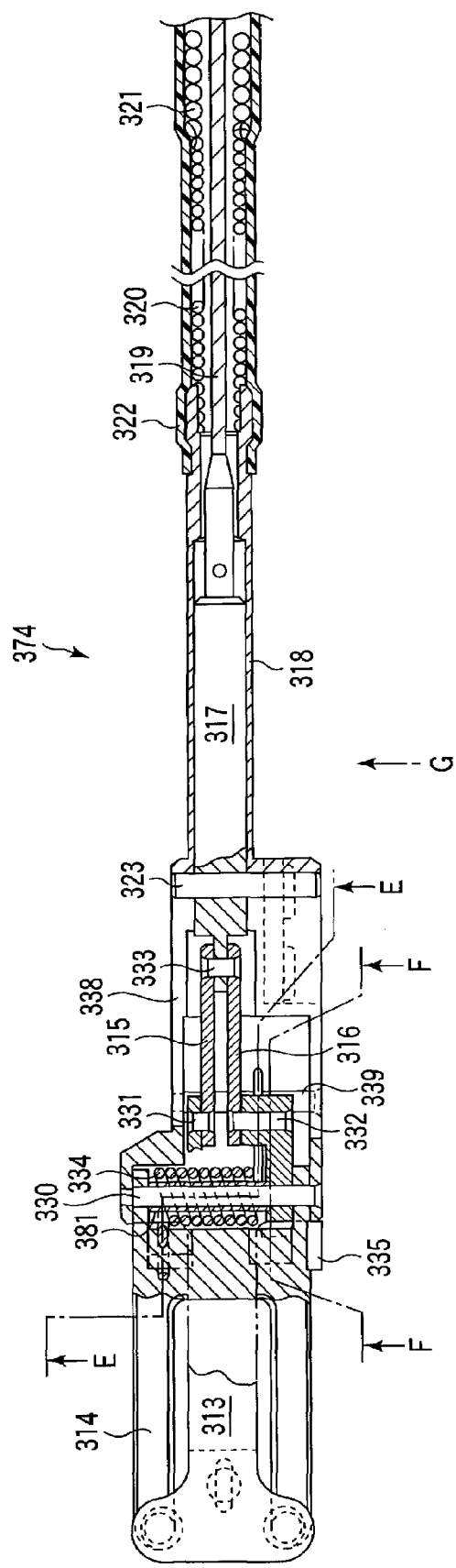
Figure 115:
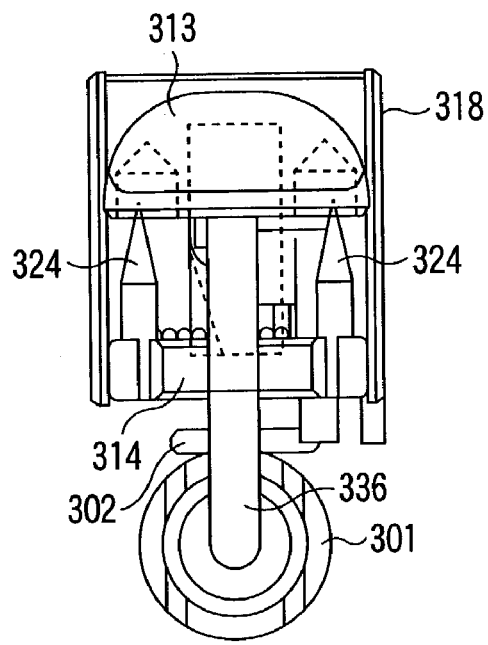
Figure 116:
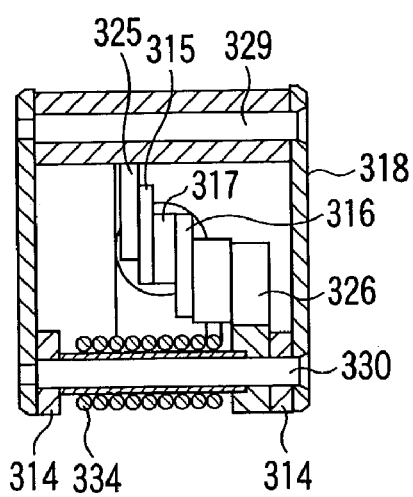
Figure 117:
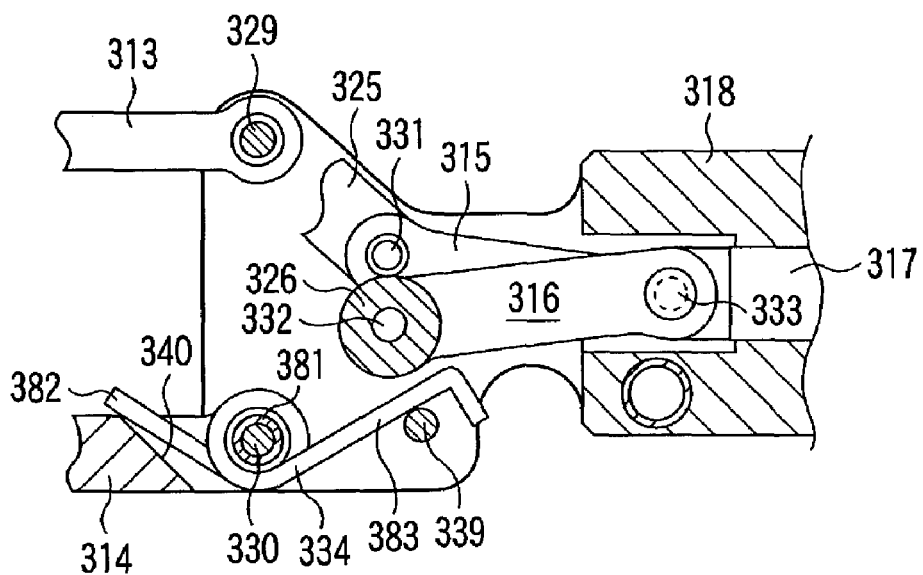
Figure 118:
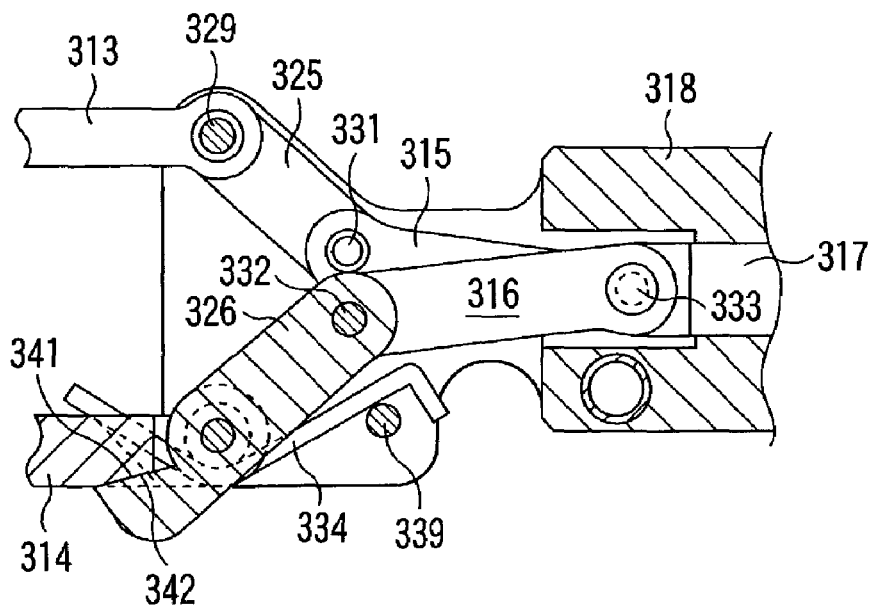

As shown in FIG. 114 and FIG. 117, a second active member 314 can rotate about the pin 330. A pipe 381 is rotatably fitted on part of the pin 330, and a spring 334 is arranged around them. An arm member 382 of the spring 334 is in contact with a contact face 340 formed on the second active member 314. As shown in FIG. 118, a force charging member 326 is connected, through the pin 332, to a second connecting member 316 which is connected to a rod 317 to be rotatable about the pin 333. A first arm member 325 can pivot about the pin 329. The other arm member 383 of the spring 334 engages with a pin 339 fixed to a holding member 318. In addition, as in the 10th embodiment, two fixing needles 324 are mounted on a U-shaped end portion of the second active member 314.

Figure 119:
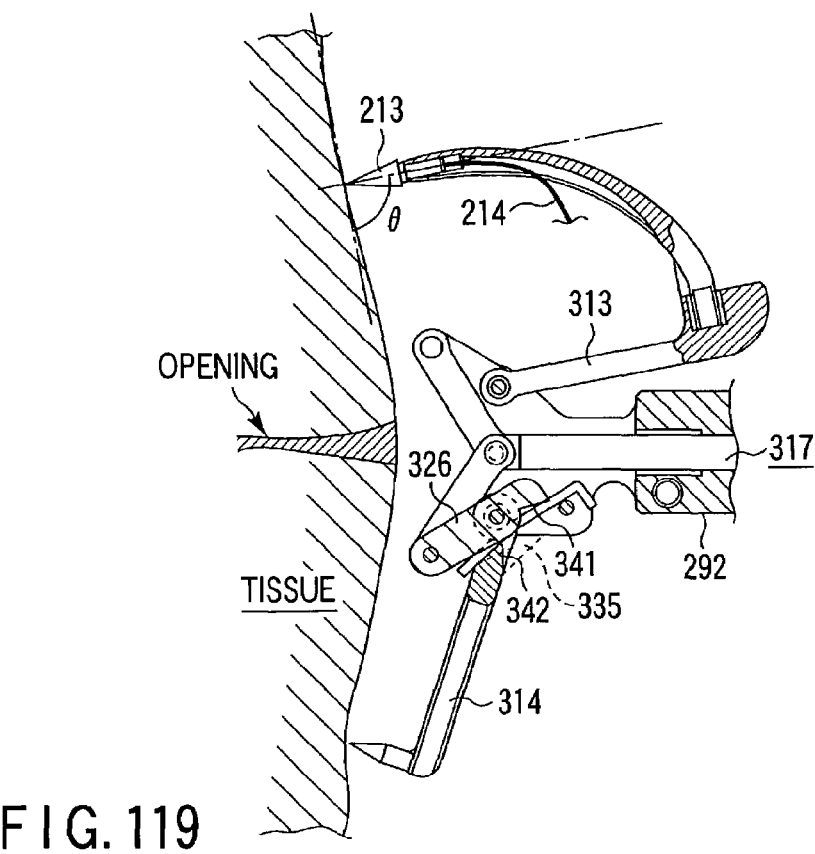

As shown in FIG. 113 and FIG. 119, a stopper 335 is fixed to the second active member 314 to prevent the second active member 314 from further rotating counterclockwise from the state shown in FIG. 119.

Since a pre-knot cartridge 365 containing the removable needle 213, a needle-catching-sheath 211, and an operating section 255, which are other constituent members, are the same as those in the 10th embodiment, a description thereof will be omitted. In addition, this embodiment may use the arrangement of the removable needle 364 and needle-catching-device 283 in described in the 10th embodiment.

(Function)

The operation of the suturing device 374 in a case wherein the tissue to be sutured is punctured will be described with reference to FIG. 119 to FIG. 122.

(1) When the rod 317 is pushed to the left on the drawing surface as shown in FIG. 119 by operating the operating section 255 (not shown), the first active member 313 can be opened to the position shown in FIG. 119. At this time, although a counterclockwise force is biased against the second active member 314, the member is opened by the spring 335 to only the position shown in FIG. 119. Note, however, that this device is designed to reduce the biasing force of the spring 334 in the state shown in FIG. 119. When the removable needle 213 is inserted into the tissue at an angle θ where 45 degrees<θ<110 degrees (preferably, 90 degrees) as in the 11th embodiment, the tissue is punctured deep. This makes it possible to reliably suture the tissue.

Figure 120:
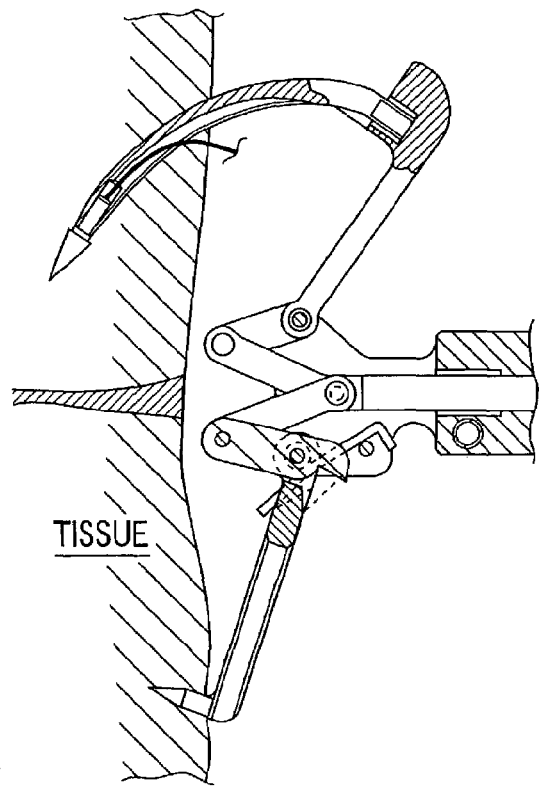

(2) As shown in FIG. 120, when the rod 317 is moved to the right on the drawing surface, the tissue is punctured with the removable needle 213 and two fixing needles 229. At this time, since the second active member 314 is biased counterclockwise, the member does not rotate.

Figure 121:
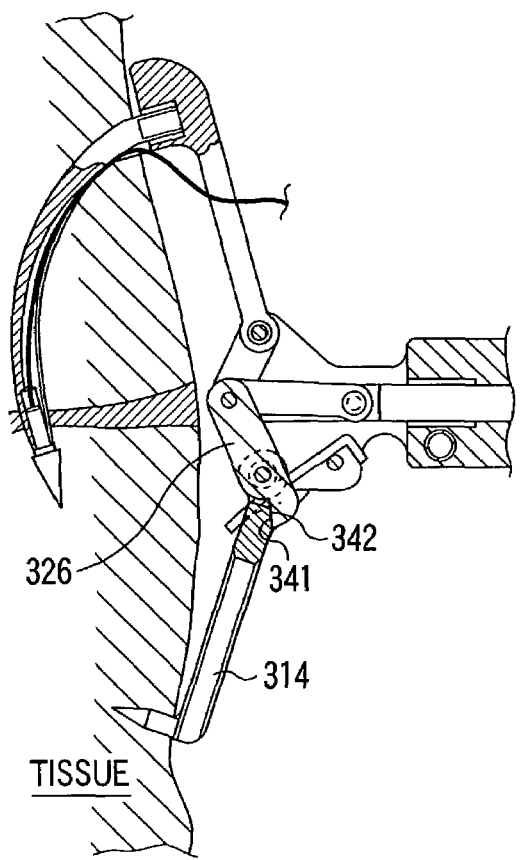
Figure 122:
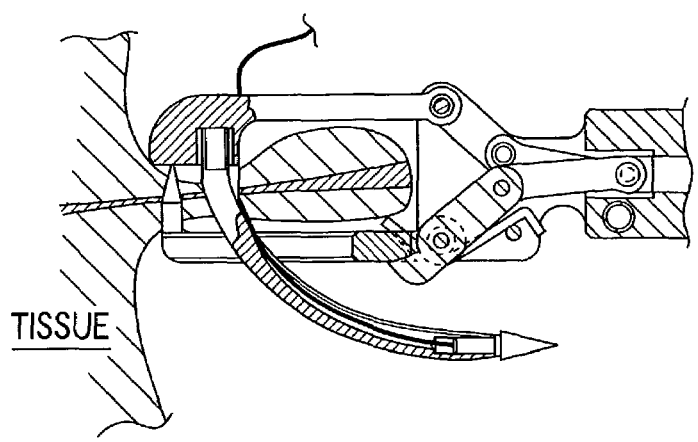

(3) As shown in FIG. 121 and FIG. 122, when the rod 317 is further moved to the right on the surface drawing, a contact face 341 of the force charging member 326 engages with a contact face 342 of the second active member 314. As a consequence, the second active member 314 rotates in a clockwise direction. Since a suturing procedure is the same as that in the 10th embodiment (see FIG. 90 to FIG. 98), a description thereof will be omitted.

(Effects)

In addition to the effects of the 10th embodiment, the tissue can be punctured deeper.

13th Embodiment

FIG. 123 to FIG. 126B show the 13th embodiment.

(Arrangement)

In the 13th embodiment, the arrangement of the 12th embodiment is modified as follows.

The spring 334 and pin 339 are removed. A stopper 384 is fixed to a second active member 349. As shown in FIG. 126B, a holding member 353, a first active member 348, and the second active member 349 are partly thinned.

(Function)

The operation of a suturing device 385 in a case wherein the tissue to be sutured is punctured will be described with reference FIG. 123 to FIG. 126A.

Figure 123:
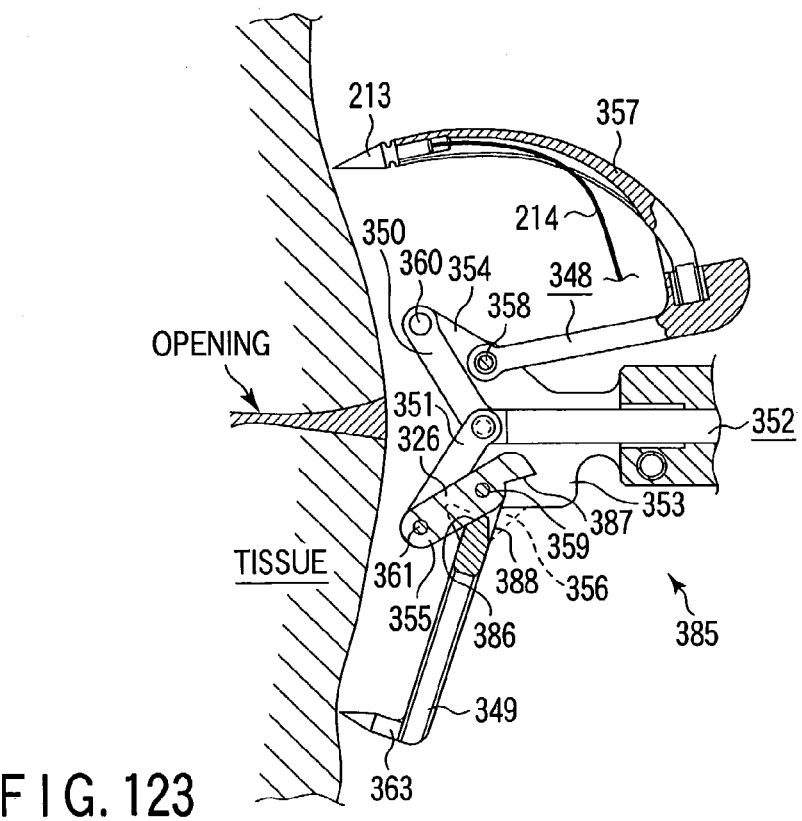

(1) When a rod 352 is pushed to the left on the drawing surface as shown in FIG. 123 by operating an operating section 255 (not shown) as in the 12th embodiment, a needle holder 357 can be opened to the position shown in FIG. 123. At this time, the second active member 349 opens to the position shown in FIG. 123 because a transmission member 355 interferes with a contact face 386 of the second active member 349.

Figure 124:
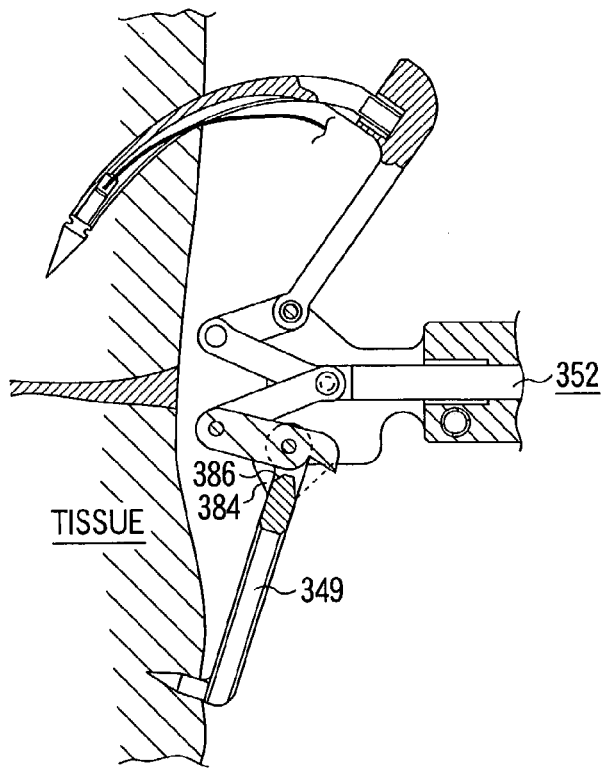

(2) As shown in FIG. 124, when the rod 352 is moved to the right on the drawing surface, the tissue is punctured with the removable needle 213 and two fixing needles 363. At this time, as shown in FIG. 124, the second active member 349 is pressed against the tissue and is biased counterclockwise by the resultant reaction force.

Figure 125:
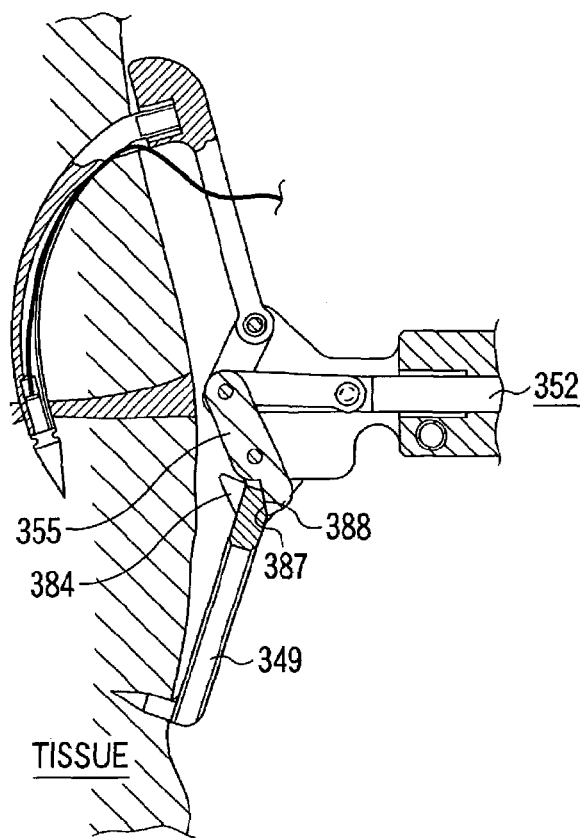
Figure 126A:
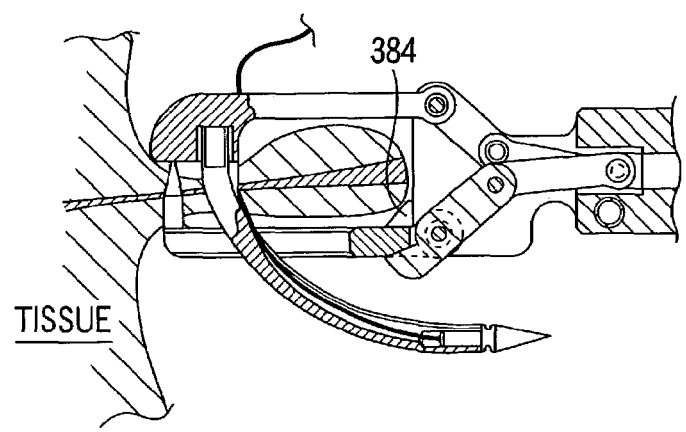
Figure 126B:
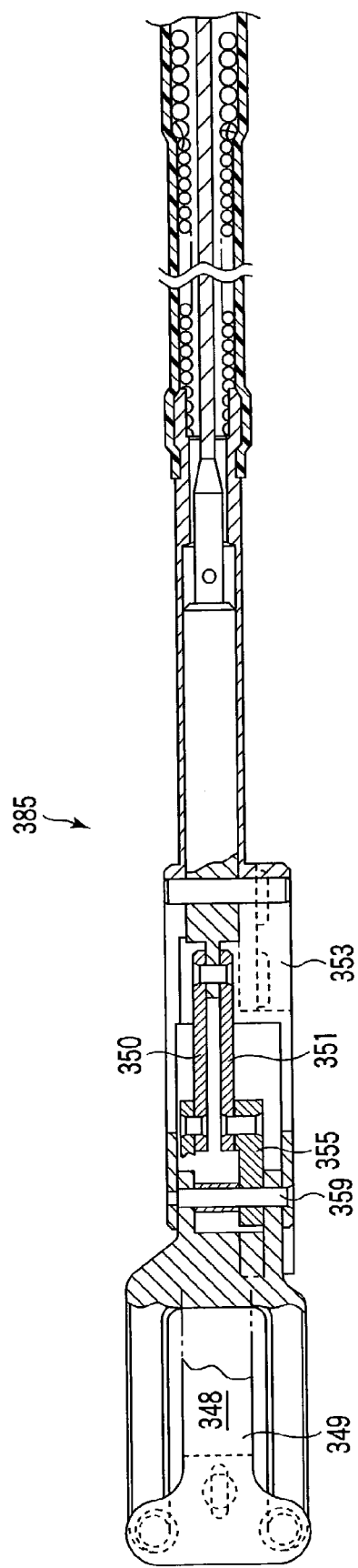

(3) As shown in FIG. 125 and FIG. 126A, when the rod 352 is further moved to the right on the surface of the drawing, a contact face 387 of the transmission member 355 engages with a contact face 388 of the second active member 349. As a consequence, the second active member 349 rotates clockwise. Since a suturing procedure is the same as that in the 10th embodiment (see FIG. 90 to FIG. 98), a description thereof will be omitted.

(Effects)

In addition to the effects of the 10th embodiment, the tissue can be punctured deeper. Furthermore, the suturing device can be thinner than the devices of the 11th and 12th embodiments. This improves the field of view.

14th Embodiment

Figure 127:
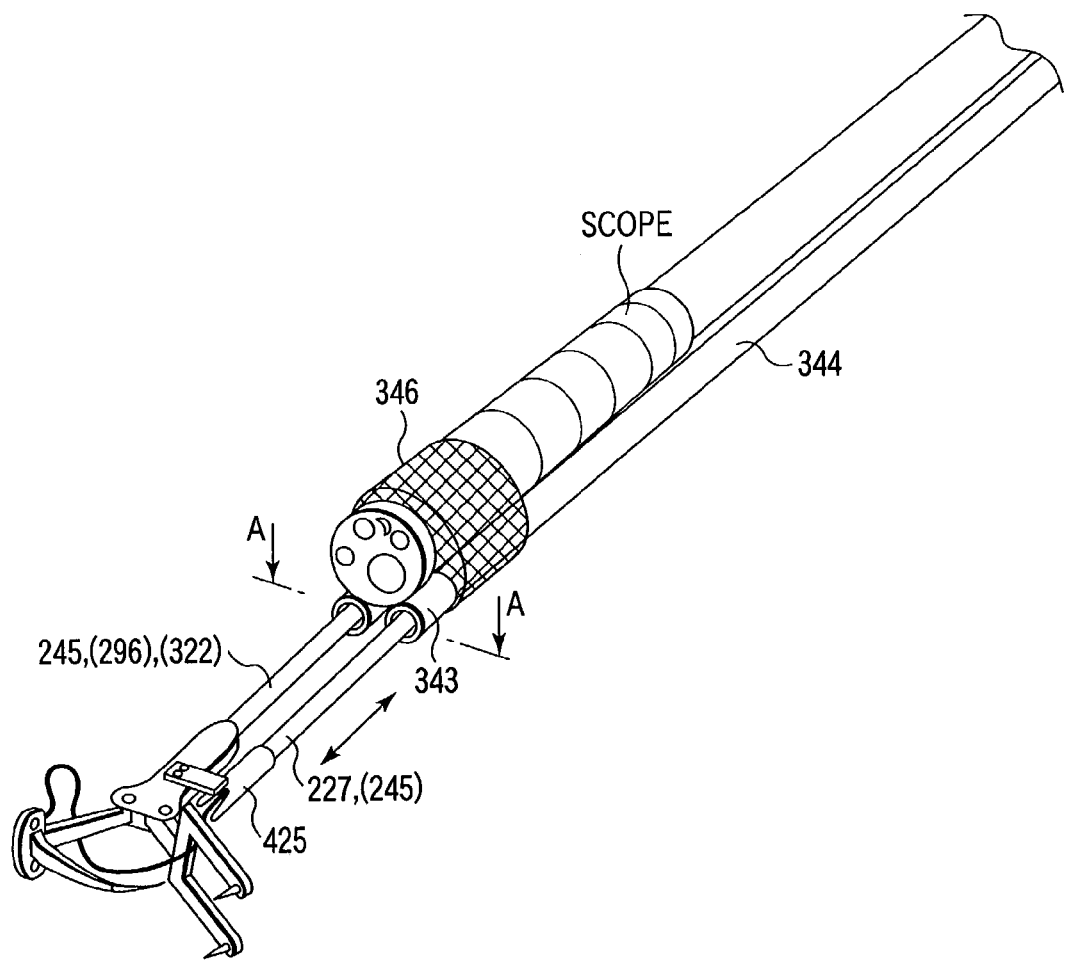
Figure 128A:
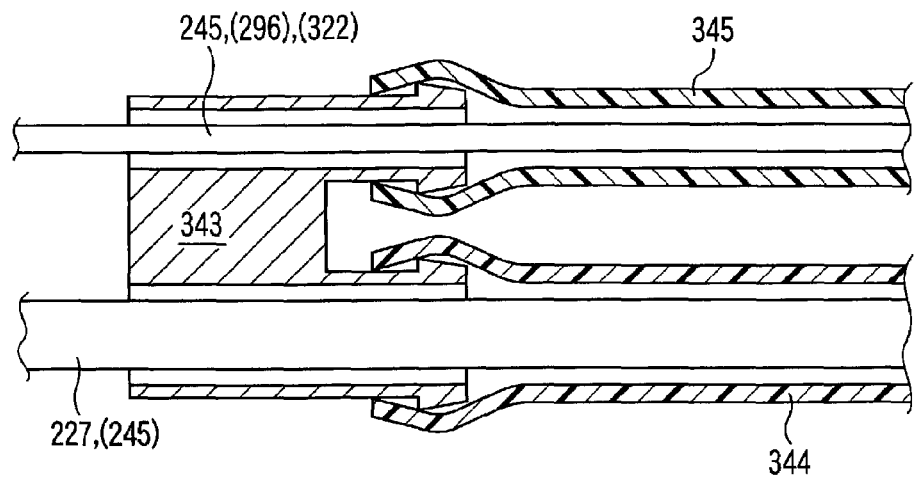
FIG. 128A is a sectional view of a tube holder.
Figure 128B:
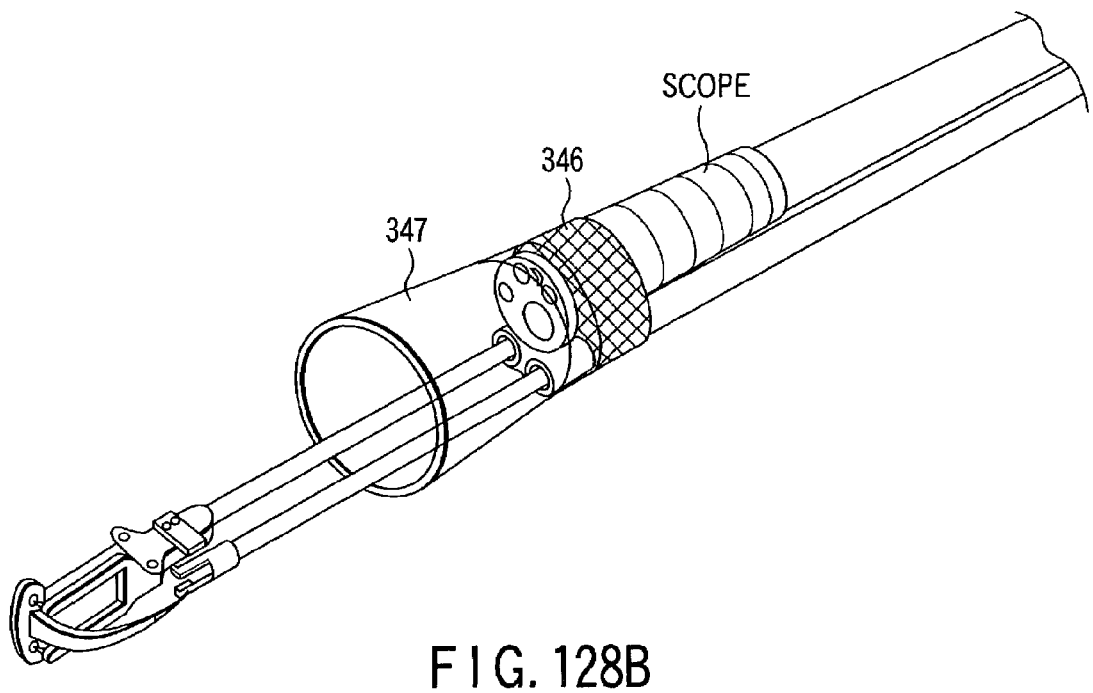

FIG. 127 to FIG. 128B show the 14th embodiment.

(Arrangement)

In the 14th embodiment, the suturing device of the first embodiment or another embodiment is designed to extend and retract from an endoscope as shown in FIG. 127.

The tubes 245 and 227 described in the first embodiment and the like are retractably inserted in the inner holes of a tube holding member 343 and tubes 345 and 344. Valves for hermetic sealing are arranged on the proximal end side of the tubes 344 and 345 to allow the tubes 245 and 227 to extend and retract while keeping the airtightness in the tubes 344 and 345. The tube holding member 343 is fixed near the distal end of the endoscope with a fixing member 346. The fixing member 346 may be an adhesive tape, press-fitting scheme, or the like.

In addition, as shown in FIG. 128B, a protect member 347 may be fixed to the tube holding member 343 and inserted into the body without using the insertion assisting tool 84 shown in FIG. 16 or the like.

(Function)

The suturing device is made to extend/retract with respect to the endoscope and approach a region to be sutured by pushing and pulling the proximal end portions of the tubes 245 and 227 with respect to the tubes 344 and 345.

(Effects)

The suturing device can be easily made to approach a region to be sutured.

After the suturing device is made to approach the region, the region can be sutured deeper by pressing the device against the tissue.

15th Embodiment

FIG. 129 to FIG. 143 show the 15th embodiment.

(Arrangement)

The 15th embodiment is configured to continuously suture the tissue by using the suturing device exemplified by the fourth to 14th embodiments.

As shown in FIG. 129, in the 15th embodiment, each of the needle holders 216, 336, and 357 in the fourth to 13th embodiments are modified into a needle holder 396. Likewise, the pre-knot cartridge 365 is modified into a pre-knot cartridge 407, and each of the needle-catching-devices 212 and 283 is modified into a needle-catching-device 390. The pre-knot cartridge 407 is comprised of a removable needle 389, thread 391, pre-knot 397, and the like. The removable needle 389 is comprised of a needle 392, slide member 393, spring 399, lock members 394 and 395, and the like. As in the case of the removable needle 213 in the 10th embodiment, the thread 391 is fixed to the needle 392 with a stopper 408 formed on the thread. The slide member 393 and needle 392 are slidably fitted together. The slide member 393 is biased to the left on the drawing surface by the spring 399. The needle 392 is engaged with the needle holder 396 by the lock member 394, 395. In the state shown in FIG. 129, the removable needle 389 does not come off the needle holder 396. The needle-catching-device 390 is comprised of a tip member 402, inserting member 403, spring 401, release member 404, and the like. Although not shown, the proximal end portion of the tip member 402 is connected to a flexible member like the needle-catching-sheath 211. As shown in FIG. 129, the spring 401 is connected to the release member 404 and can be moved to the right on the drawing surface. An operating section (not shown) is attached to the proximal end portion of the release member 404 to allow the release member 404 to extend and retract.

The pre-knot 397 is wound around the needle-catching-device 390.

(Function)

A continuous suturing procedure will be described below.

(1) As shown in FIG. 129, the removable needle 389 is inserted into the tissue.

Figure 131:
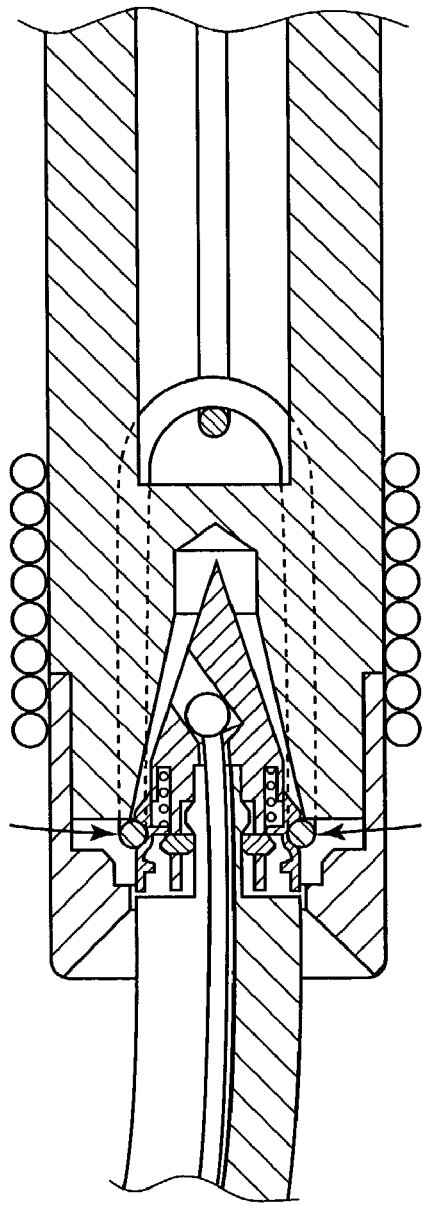

(2) When the needle-catching-device 390 is moved to the left on the drawing surface as shown in FIG. 130, the spring 401 spreads as shown in FIG. 130 and engages with a recess 400 of the slide member 383 as shown in FIG. 131.

Figure 132:
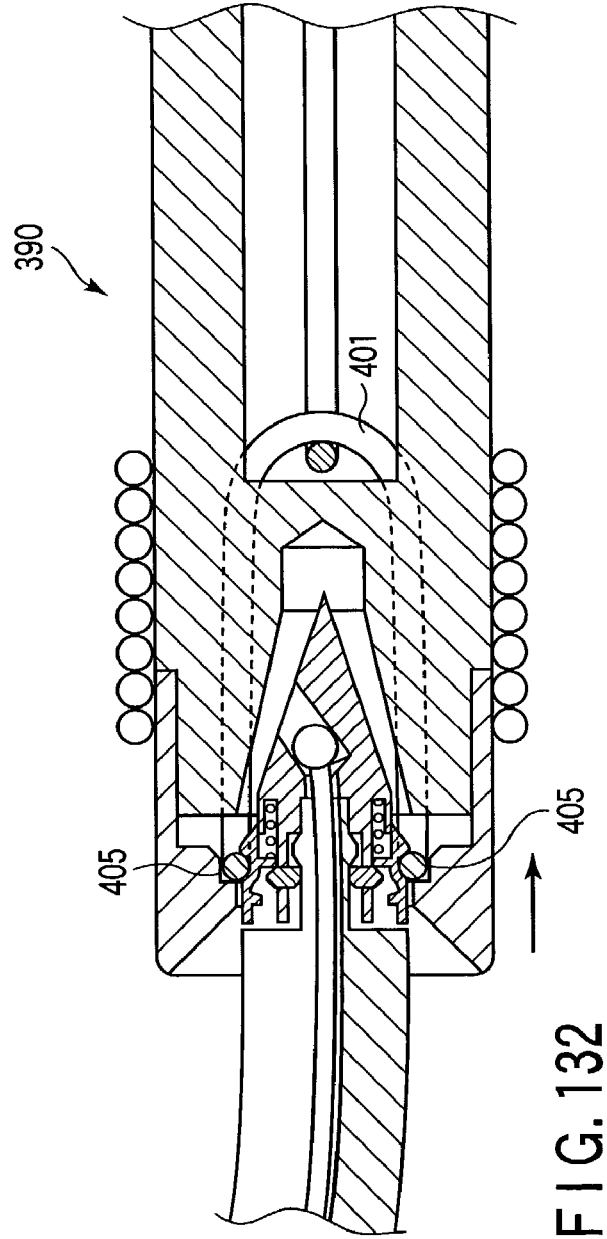

(3) When the needle-catching-device 390 is moved to the right on the drawing surface as shown in FIG. 132, the spring 401 moves to the left on the drawing surface. As a result, an engage part 405 restricts the spreading of the spring 401.

Figure 133:
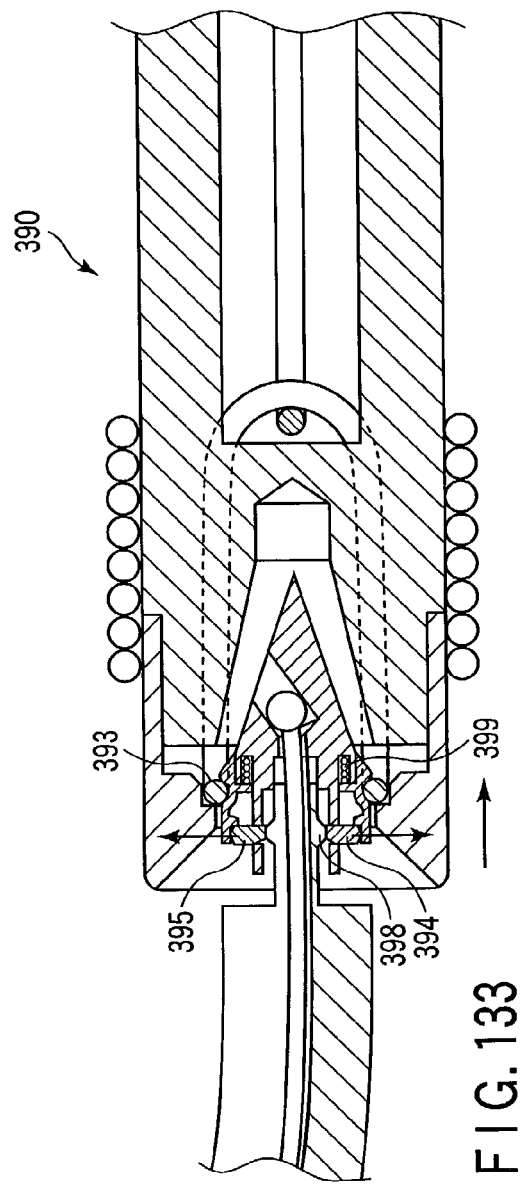
Figure 134:
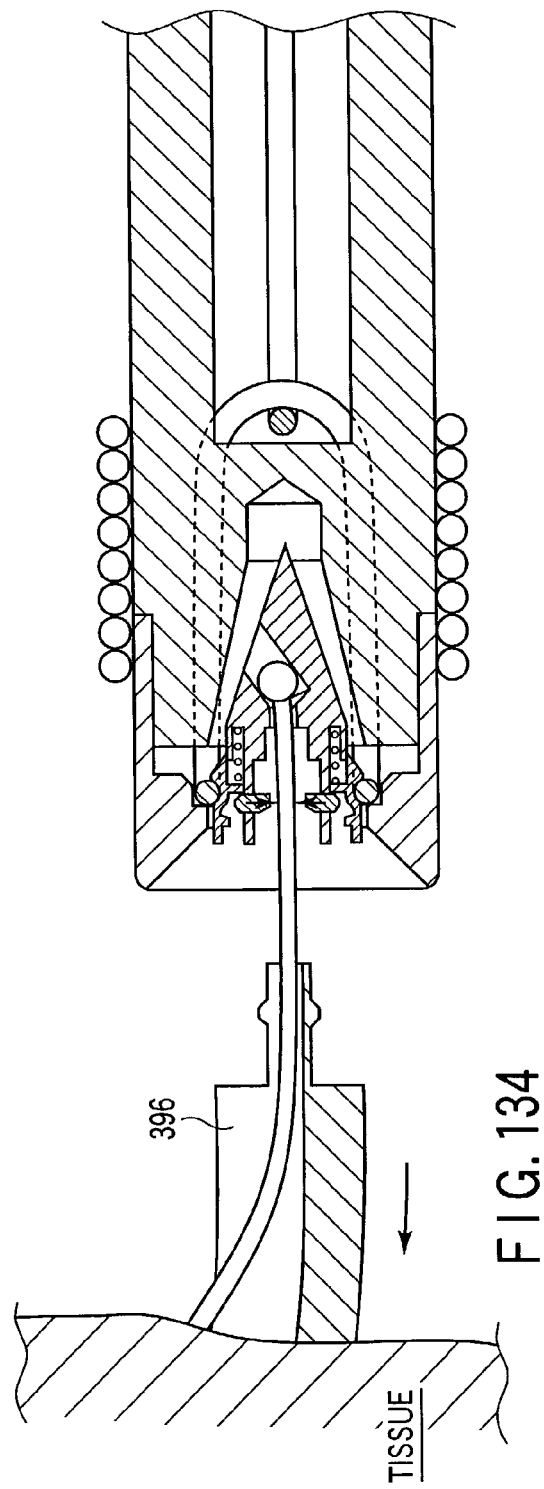

(4) When the needle-catching-device 390 is moved to the right on the drawing surface as shown in FIG. 133, the spring 399 that has biased the slide member 393 to the left on the drawing surface, is compressed to move the slide member 393 to the right on the surface drawing. At this time, the lock members 394 and 395 are released from the restriction in the vertical direction on the drawing surface, and can move as shown in FIG. 133. In this manner, as shown in FIG. 134, the removable needle 389 is removed from the needle holder 396.

(5) The needle holder 396 is pulled out from the tissue as shown in FIG. 135, and is then returned to the illustrated position shown in FIG. 136.

Figure 137:
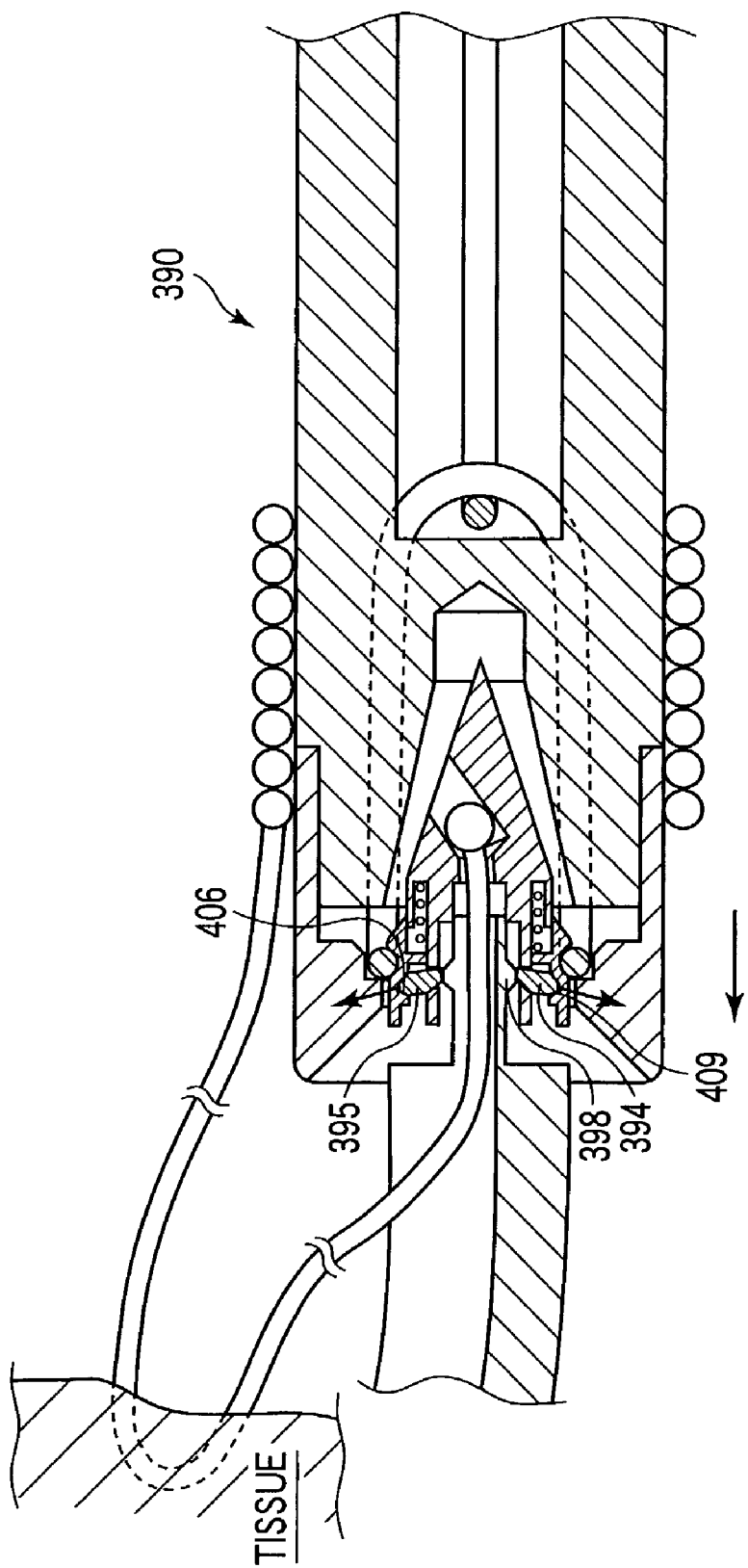
Figure 138:
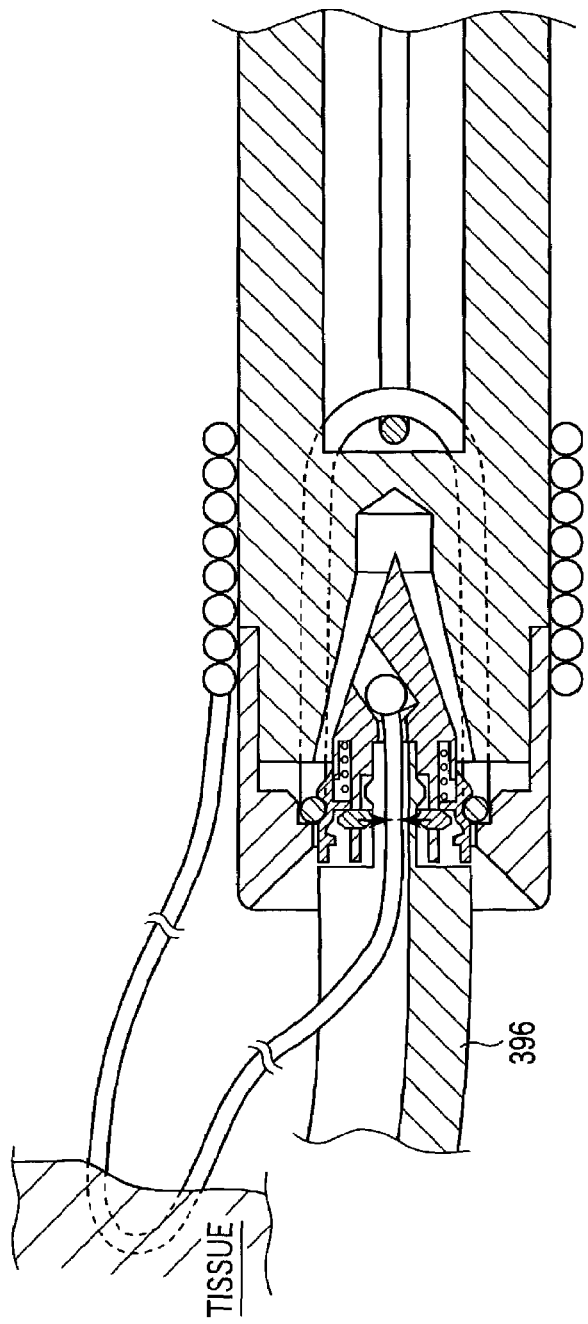

(6) When the needle-catching-device 390 is moved to the left on the drawing surface as shown in FIG. 137, the lock members 394 and 395 move on the engage member 398. At this time, the lock members 394 and 395 partly enter recesses 406 and 409 formed in the slide member 393, and hence can move on the engage member 398. In this manner, as shown in FIG. 138, the removable needle 389 can be mounted in the needle holder 396 again.

Figure 139:
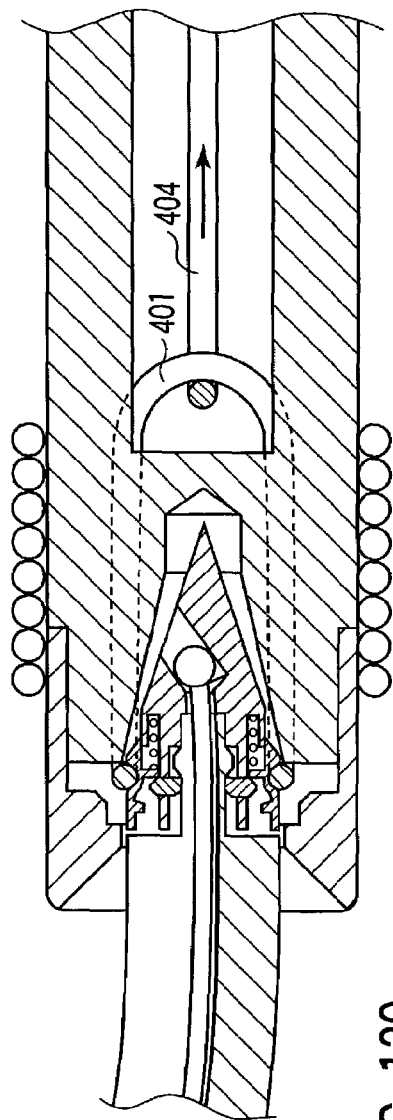
Figure 142:
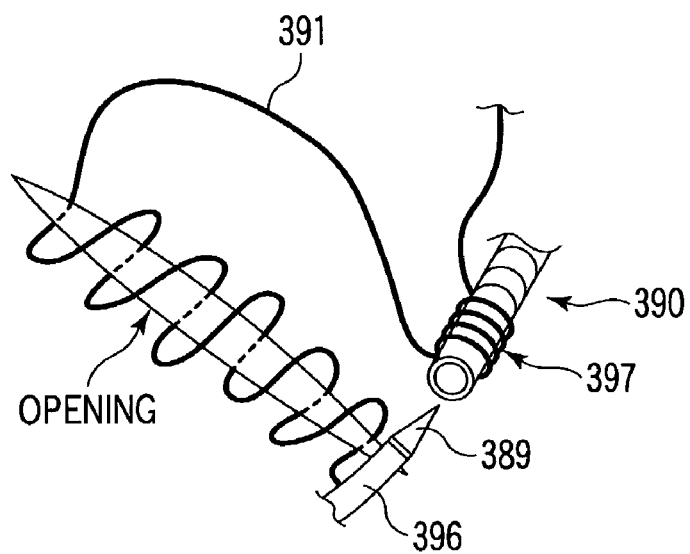
Figure 143:
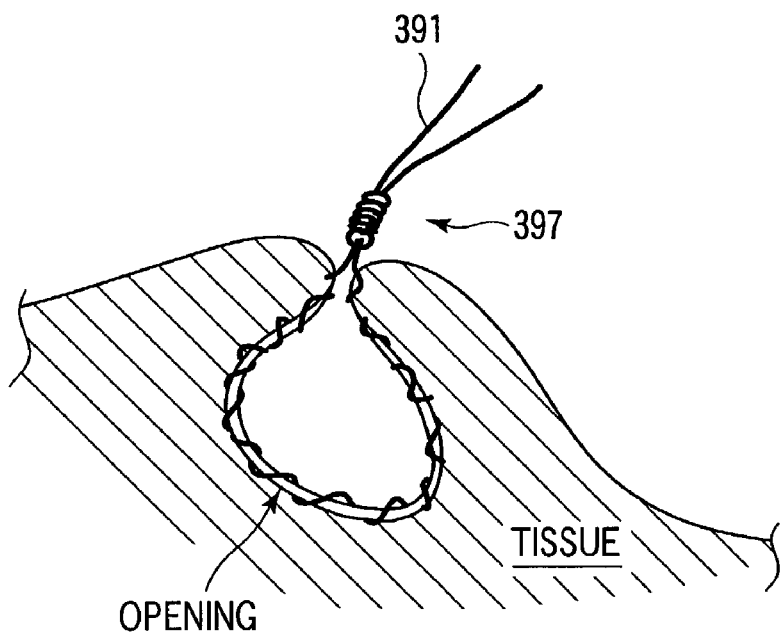

(7) As shown in FIG. 139, the release member 404 is moved to the right on the drawing surface by operating the operating section (not shown) to return the spring 401 to the illustrated position in FIG. 139. When the needle-catching-device 390 is moved to the right on the drawing surface while this state is kept, the spring 401 spreads and comes off the slide member 393, as shown in FIG. 140 and FIG. 141.

(8) The tissue is continuously sutured by repeating the above operation. When the tissue is completely sutured, a continuous suturing operation like that shown in FIG. 142 and FIG. 143 can be done by making a knot like the one shown in FIG. 94 to FIG. 98.

(Effects)

In addition to the effects of the fourth to 14th embodiments, the tissue can be continuously sutured.

16th Embodiment

FIG. 144 to FIG. 163 show the 16th embodiment.

(Arrangement)

The 16th embodiment differs from the 11th embodiment in the following points.

Since the length of a spring 432 is decreased as compared with that in the 11th embodiment shown in FIG. 102, a projection member 466 formed on the distal end of a holding member 292, which interferes with the field of view of an endoscope, is omitted. This improves the field of view in a suturing operation (see FIG. 145).

Figure 146:
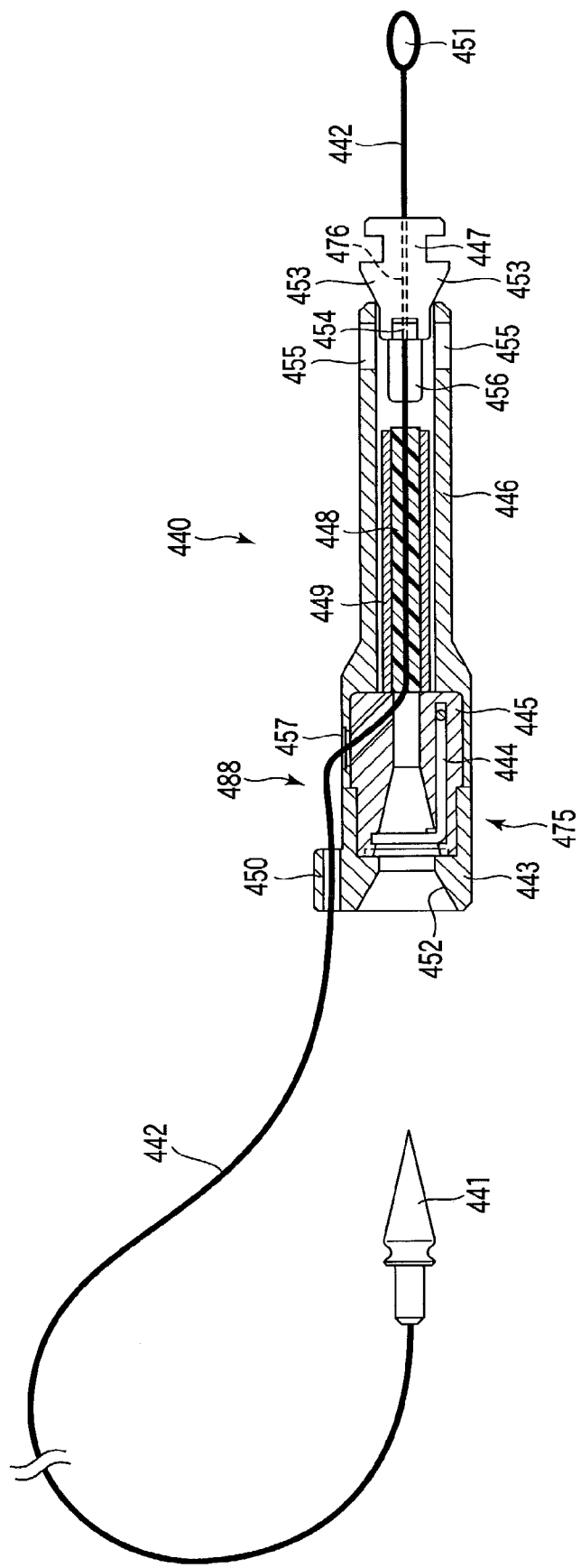
Figure 158:
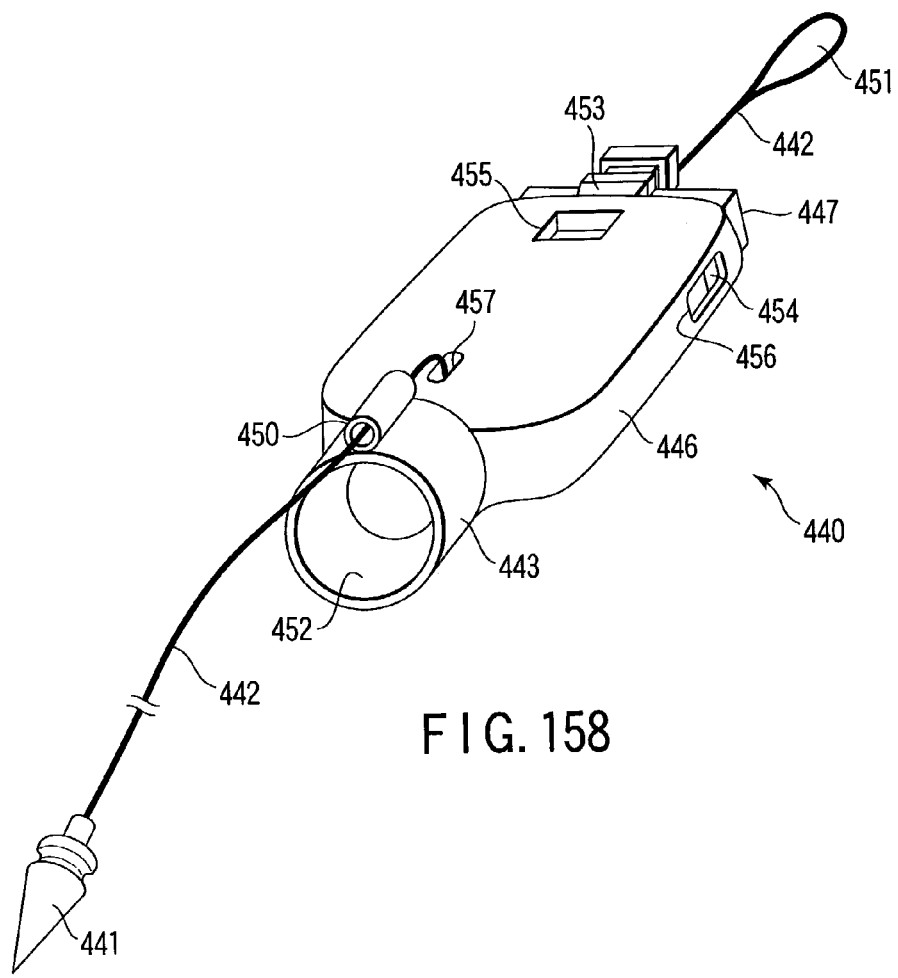

In this embodiment, a suturing operation is performed by using an end loop cartridge 440 shown in FIG. 146 and FIG. 158 in place of the pre-knot cartridge 365 in the 11th embodiment. The end loop cartridge 440 is comprised of a removable needle 441, suture thread 442, needle lock mechanism 475, casing member 446, releasing member 447, elastic member 448, rigid member 449, and the like.

Figure 165:
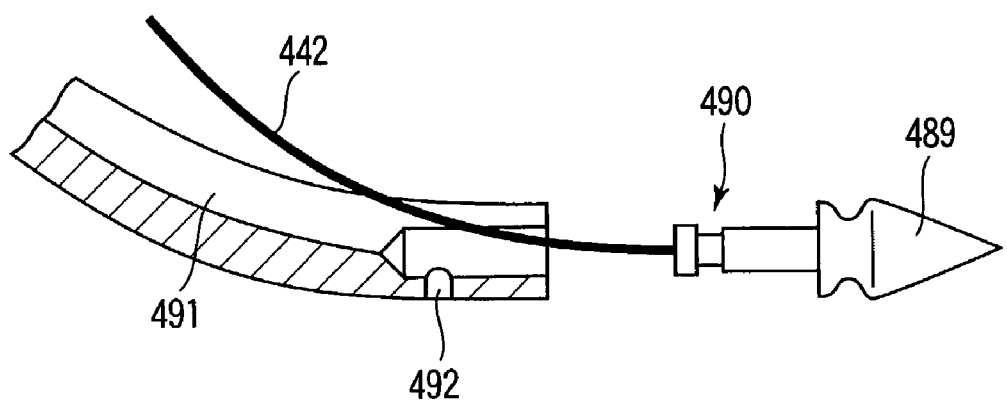
Figure 166:
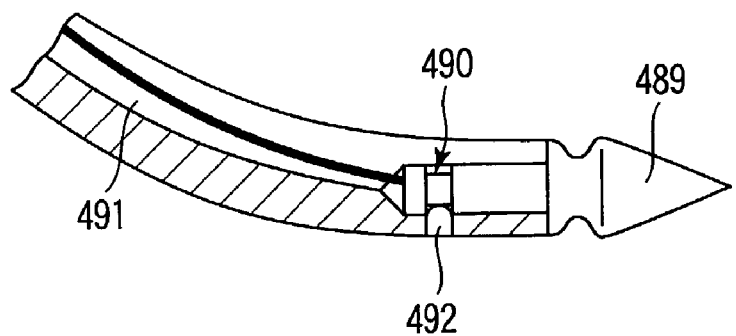
Figure 167:
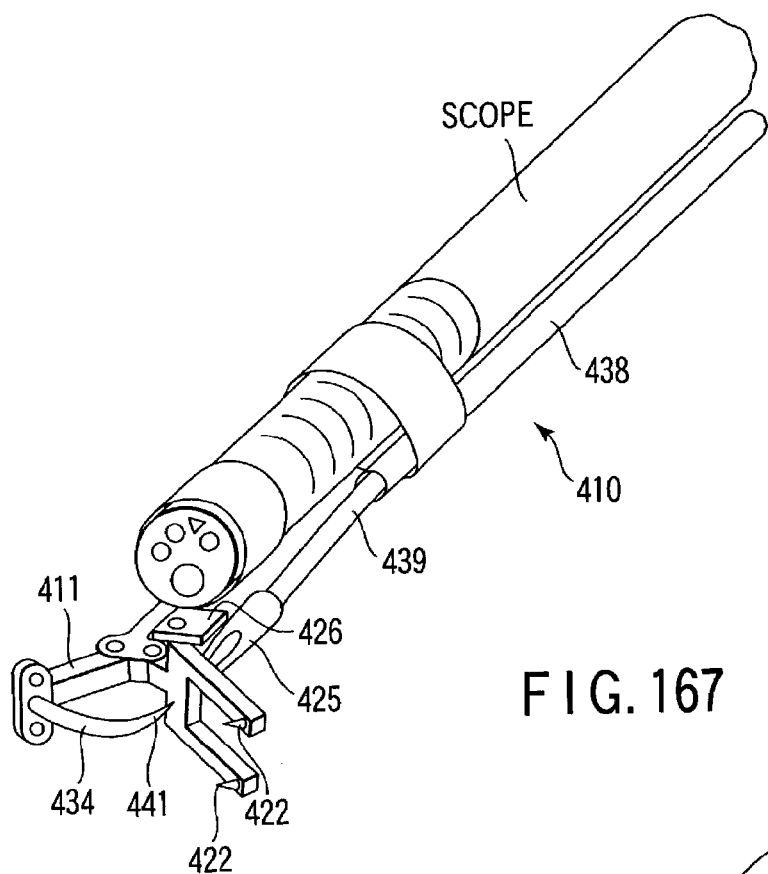
Figure 168:
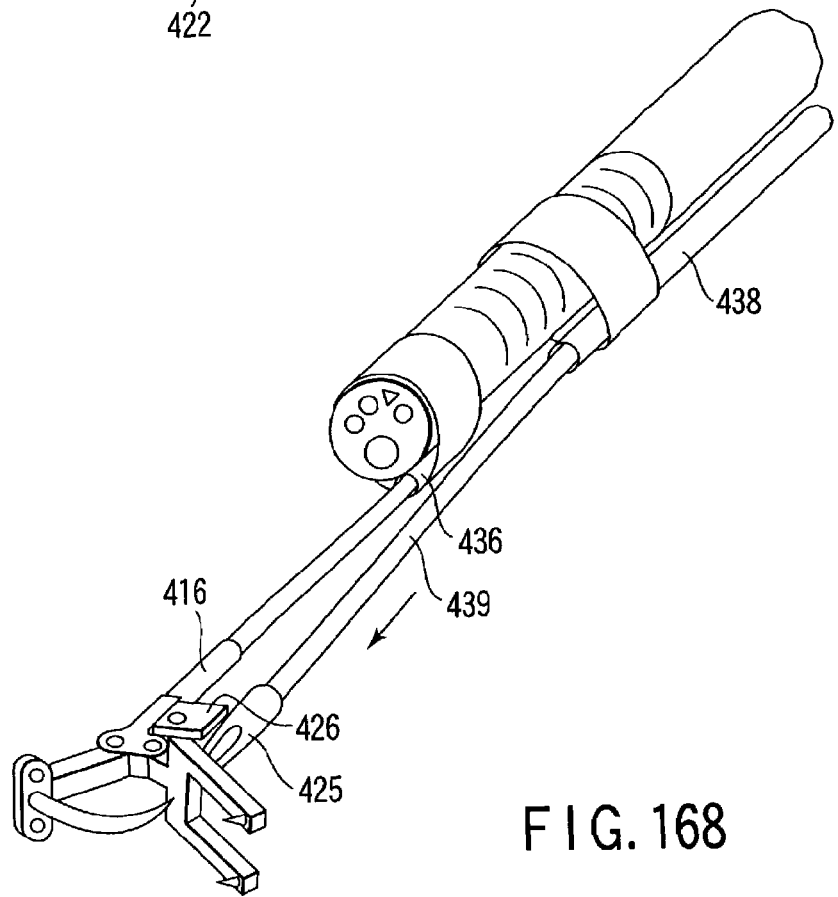

Referring to FIG. 146 and FIG. 158, the suture thread 442 fixed to the removable needle 441 is pressed into the elastic member 448 arranged in the casing member 446 through holes 450 and 457 formed in the needle lock mechanism 475. This thread further extends through a hole 476 formed in the releasing member 447 to form a loop 451 on the proximal end side. To increase the sliding resistance between the elastic member 448 and the suture thread 442, the rigid member 449 is tightly attached to the elastic member 448 by swaging, caulking, or the like. A lock member 454 formed on the releasing member 447 engages with a hole 456 formed in the casing member 446 to prevent the releasing member 447 from coming off the casing member 446. The removable needle 441 is detachably forced into a needle holding member 434. In this case, the removable needle 441 and needle holding member 434 may be designed such that a removable needle 489 having a groove 490 is fitted in the needle holding member 434 having an elastically deformable stopper 492 as shown in FIG. 165 and FIG. 166 to prevent the removable needle 489 from easily coming off a needle holding member 491. Alternatively, as shown in FIG. 175 and FIG. 176, a slit like the one shown in FIG. 175 and FIG. 176 may be formed in the needle holder to prevent the removable needle 441 from easily coming off the holder.

The casing member 446 is fitted in a distal pipe 425.

Figure 147:
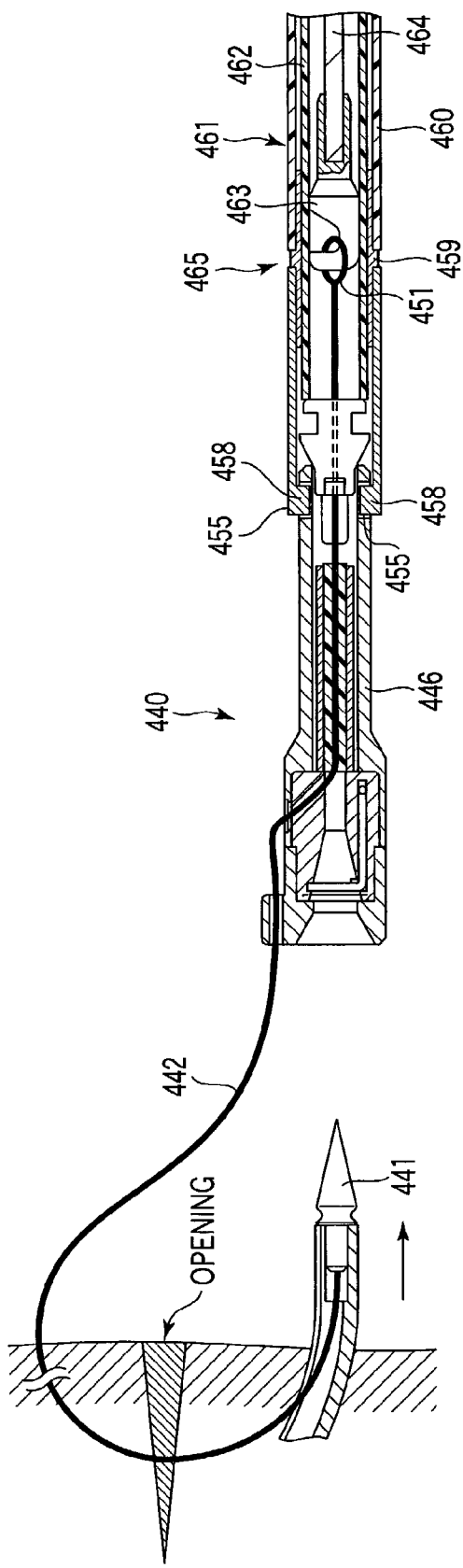
Figure 159:
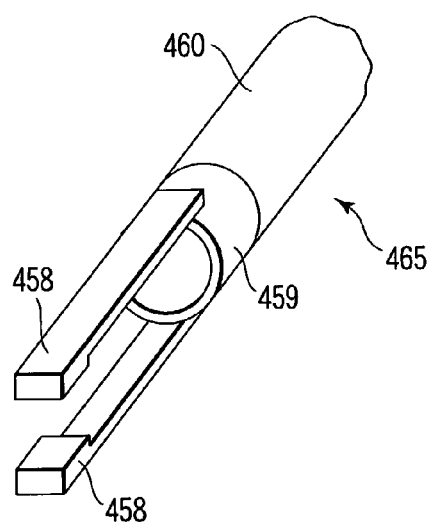

As shown in FIG. 147 and FIG. 159, an engage tube 465 comprised of two engage members 458, a pipe 459 which fixes the proximal end portions of the engage members, a tube 460 coupled to the pipe 459, and the like is designed to allow a hook device 461 to freely extend and retract. The hook device 461 is comprised of a flexible coil 462, a hook 463, a transmission member 464 fixed to the hook 463, and an operating section (not shown). The hook 463 can be made to extend and retract by operating the operating section. A seal structure made of an O-ring and the like is formed on the proximal end side of the engage tube 465 to ensure airtightness between itself and the hook device 461.

Figure 144:
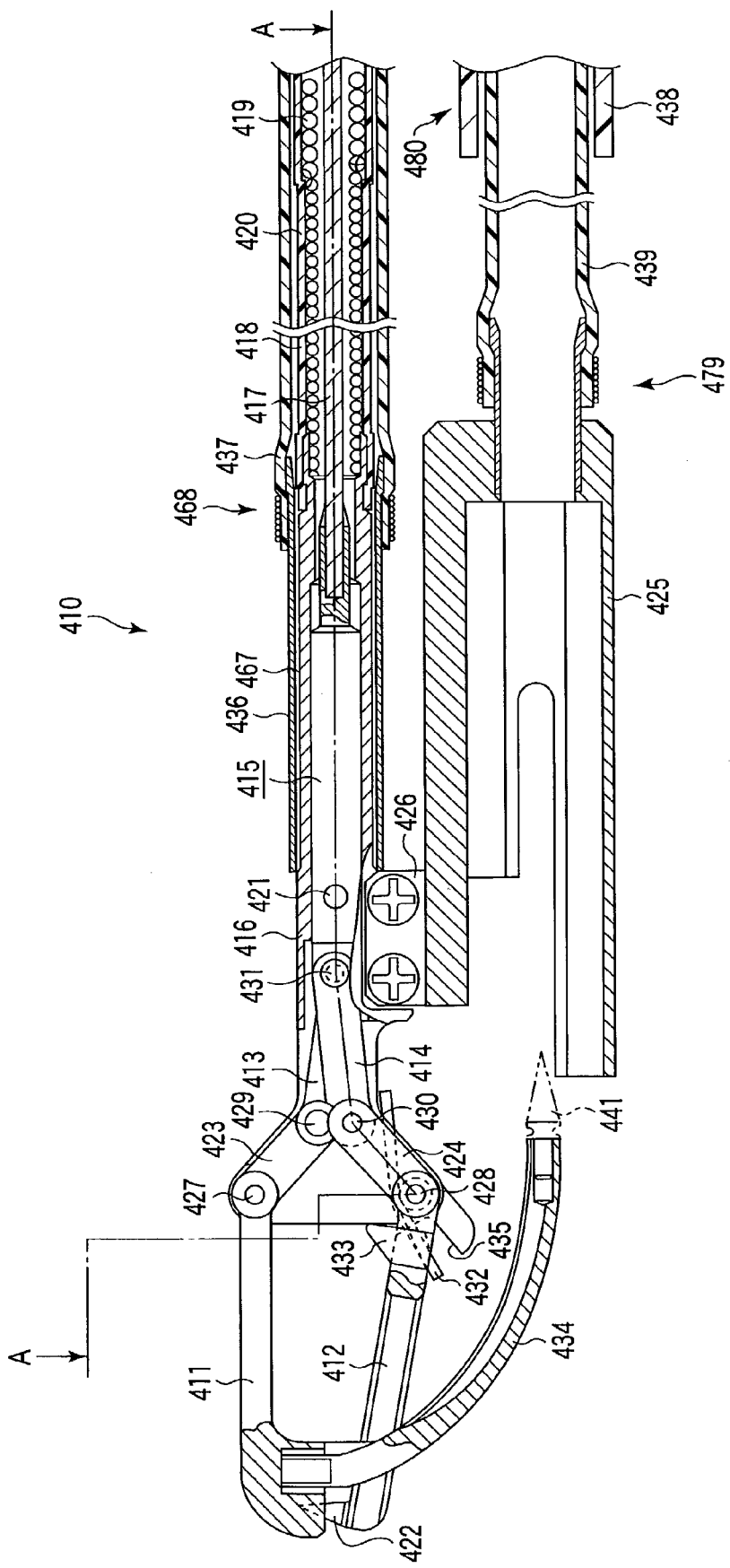
Figure 145:
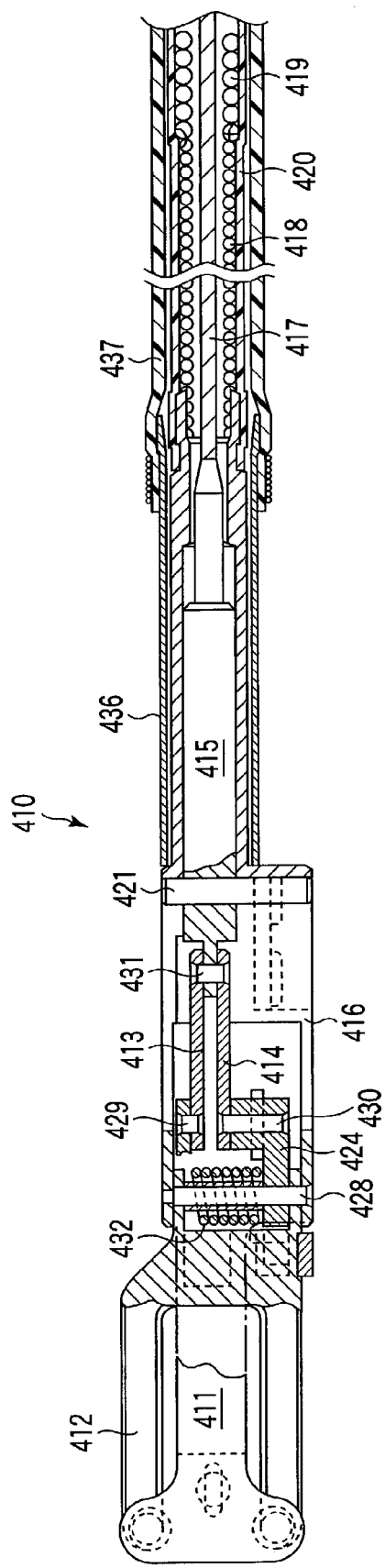
Figure 160:
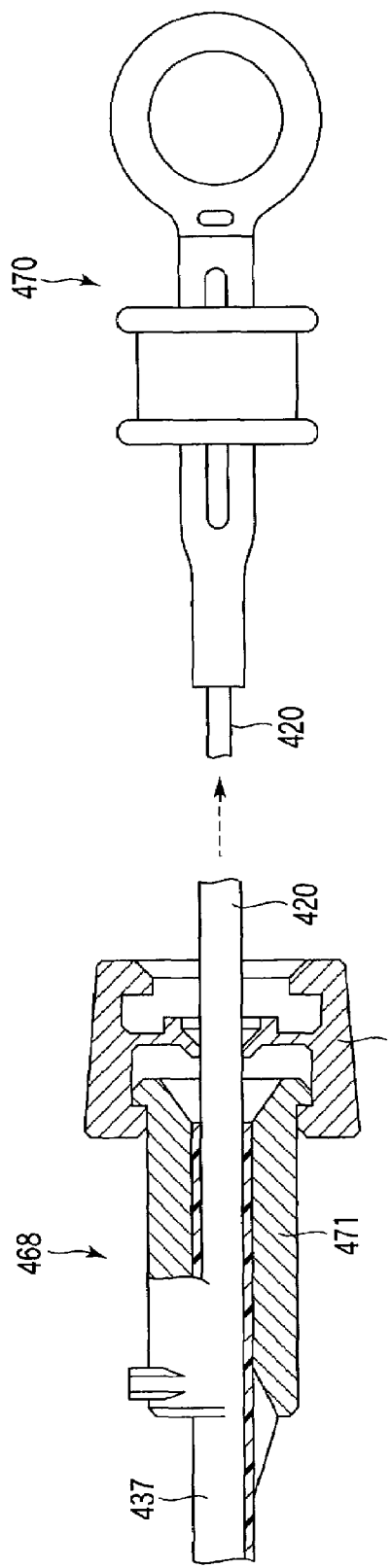
Figure 161:
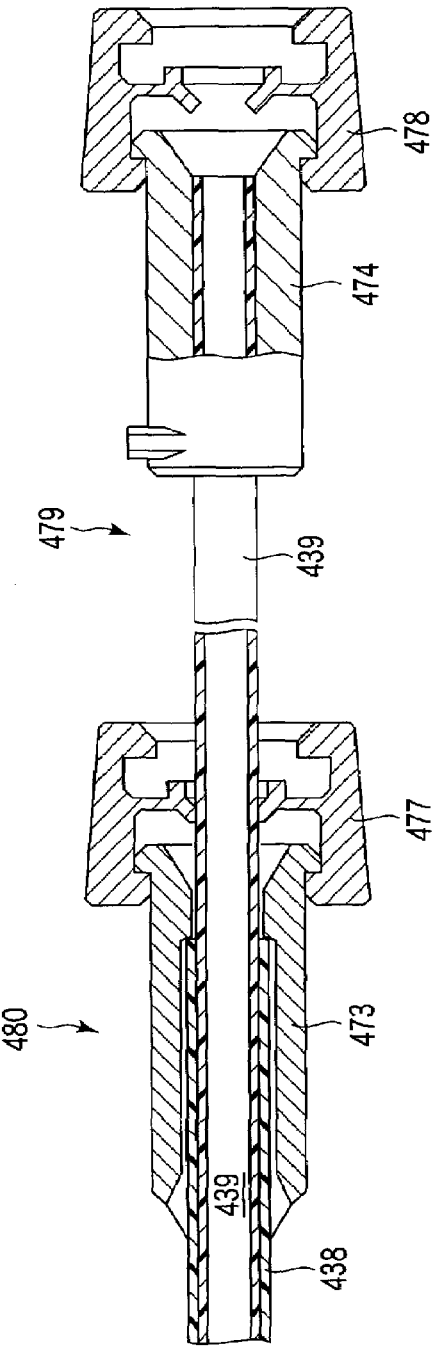

As shown in FIG. 144, a holding member 416 has a cylinder part 467 and is retractably arranged in an outer sheath 468. In addition, as shown in FIG. 144 and FIG. 160, the outer sheath 468 is comprised of a guide pipe 436, guide tube 437, port 471, seal member 472, and the like. With this arrangement, a tube 420 of a suturing device 410 can keep airtightness inside the outer sheath 468. An inner sheath 479 shown in FIG. 144 and FIG. 161 is comprised of a tube 439 and port 474 coupled to the distal pipe 425, and a seal member 478, and the like, and is inserted into an outer sheath 480 having a larger inner diameter. In this case, the outer sheath 480 is comprised of a guide tube 438, port 473, seal member 477, and the like. With this structure, airtightness in the outer sheath 480 is maintained by the seal member 477. The engage tube 465 in which the hook device 461 shown in FIG. 147 is inserted is inserted into the inner sheath 479 through the seal member 478. At this time, the airtightness between the tube 460 and the seal member 478 is also maintained.

Figure 163:
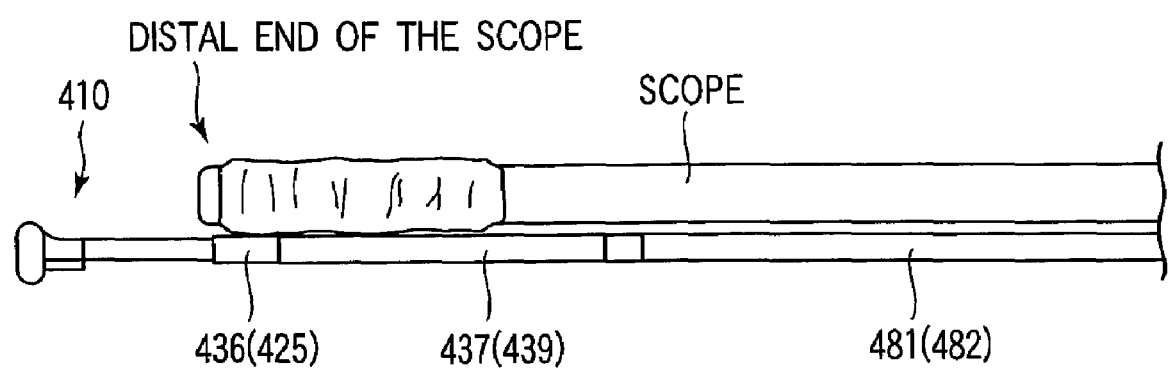

Referring to FIG. 144, the outer sheath 468 and inner sheath 479 are respectively formed from the flexible tubular members 437 and 439. As shown in FIG. 163, however, portions of these members which do not reach the curved portion of the distal end portion of the endoscope when the suturing device 410 is mounted in the endoscope may be modified into hard tubes 481 and 482 (e.g., tubes in which thin wires are embedded in a lattice form) which hardly extend and contract. This makes it possible to apply a large force to members inserted into the outer sheath 468 and inner sheath 479 without interfering with the bending operation of the endoscope.

The engage tube 465 in which the hook device 461 is inserted as shown in FIG. 147 extends through the seal member 478 shown in FIG. 161 and comes off the distal pipe shown in FIG. 144. By operating the operating section (not shown) of the hook device 461 coming off the distal pipe, the loop 451 of the end loop cartridge 440 is hung on the hook 463 and the hook 463 is pulled in, as shown in FIG. 147. As shown in FIG. 147, FIG. 158, and FIG. 157, the lock member 458 of the engage tube 465 is engaged with a hole 455 of the end loop cartridge 440, and is then loaded into the distal pipe shown in FIG. 144. FIG. 164 shows the loaded state.

The structure in which the removable needle 441 is locked to the needle lock mechanism 475 is the same as that shown in FIG. 81 to FIG. 85.

(Function)

A suturing procedure will be described below with reference to FIG. 147 to FIG. 157. For the sake of easy understanding of operation, an illustration of the suturing device 410 is omitted from FIG. 147 to FIG. 157. In reality, therefore, a suturing operation is performed while the end loop cartridge 440 is loaded as shown in FIG. 164.

(1) The operating section of the suturing device 410 (not shown) is operated to puncture the tissue with the removable needle 441 as shown in FIG. 147.

Figure 148:
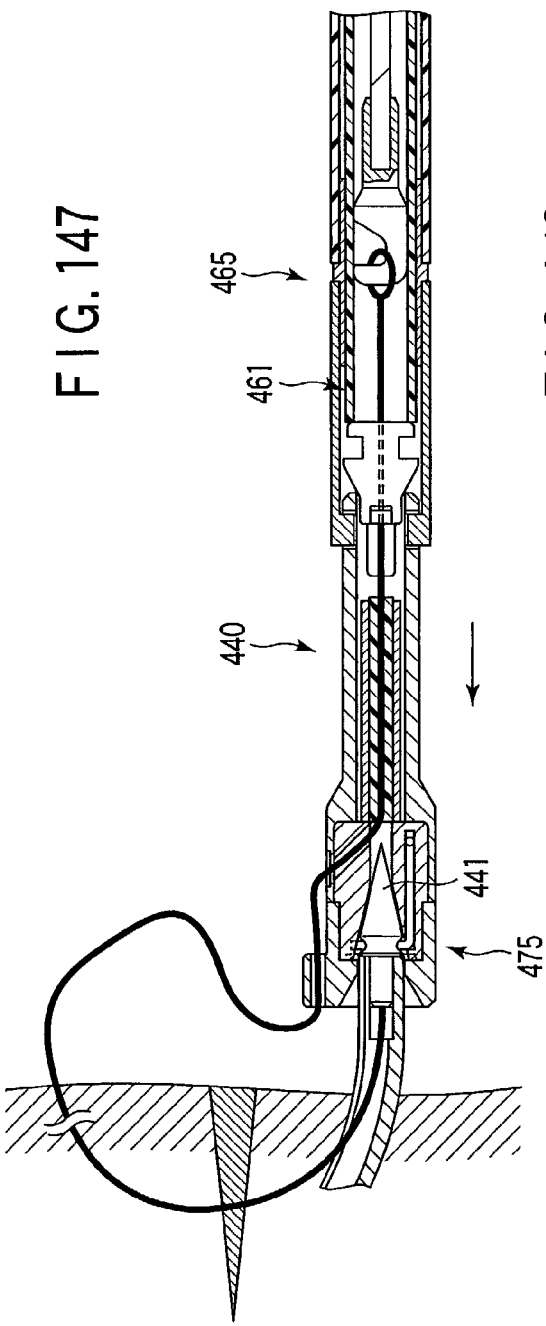

(2) As shown in FIG. 148, the hook device 461 and engage tube 465 are pushed into the end loop cartridge 440 to make the removable needle 441 engage with the needle lock mechanism 475 of the end loop cartridge 440.

(3) As shown in FIG. 149, when the hook device 461 and engage tube 465 are moved to the right on the drawing surface, the removable needle 441 is unlocked from the needle holding member 434. At this time, since the lock member 458 is engaged with a needle-catching-body 445 of the end loop cartridge 440, the removable needle 441 can be reliably unlocked from the needle holding member 434.

(4) As shown in FIG. 150, when the hook device 461 is pushed to the left side on the drawing surface, the releasing member 447 is pushed into the casing member 446, and an inclined portion 453 is engaged with the hole 455. At this time, since the lock member 458 moves on the inclined portion 453, the member is unlocked from the hole 455 (see FIG. 151). In addition, since the casing member 446 elastically deforms, the releasing member 447 can engage with the hole 455.

(5) As shown in FIG. 152, the needle holding member 434 is pulled off from the tissue.

Figure 153:
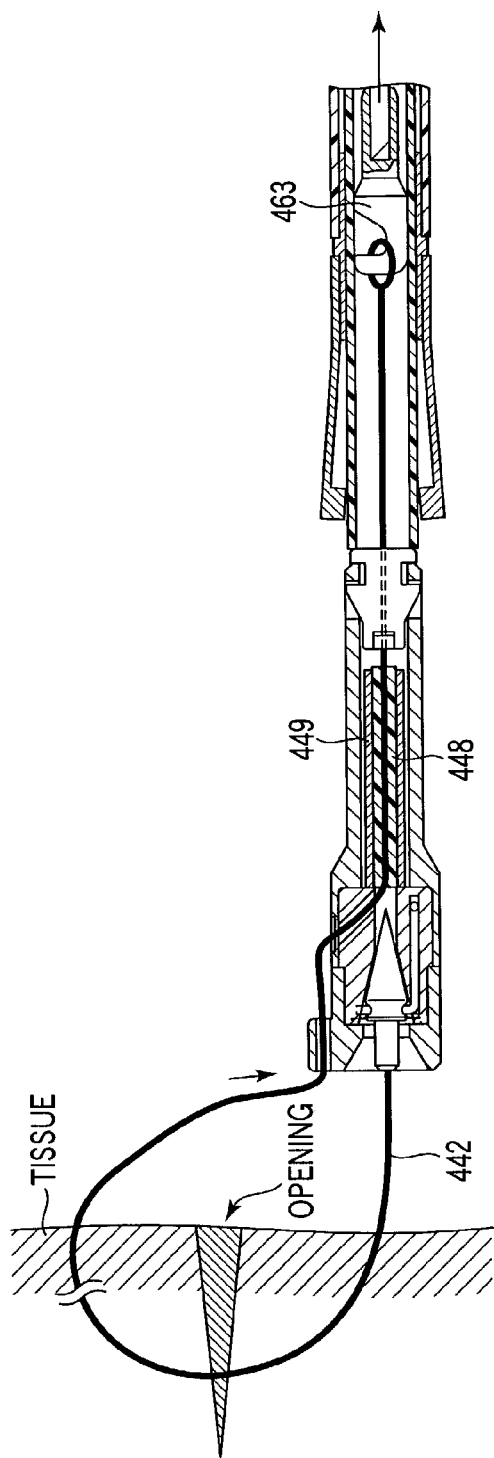
Figure 154:
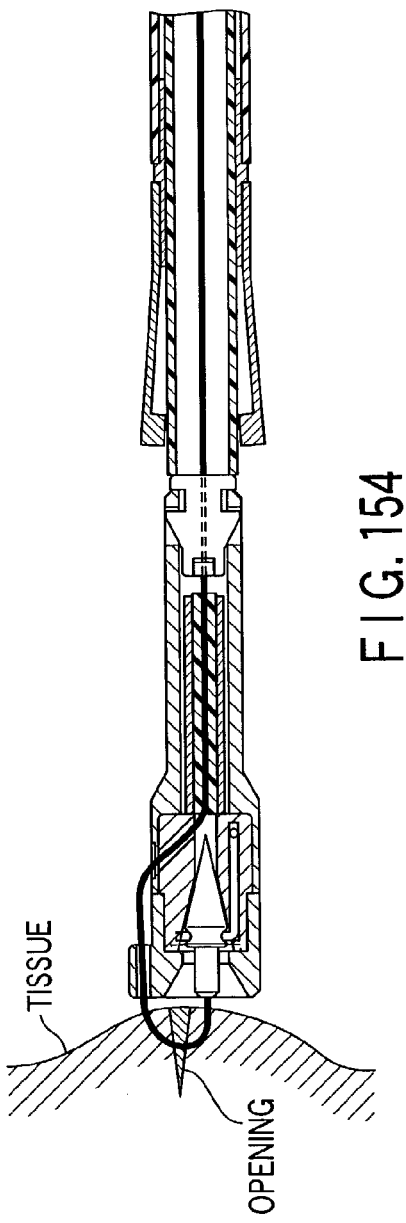

(6) As shown in FIG. 153 and FIG. 154, the hook 463 is pulled to fasten the suture thread 442. At this time, the sliding friction between the suture thread 442 and the elastic member 448 prevents the sutured region from loosening.

Figure 155:
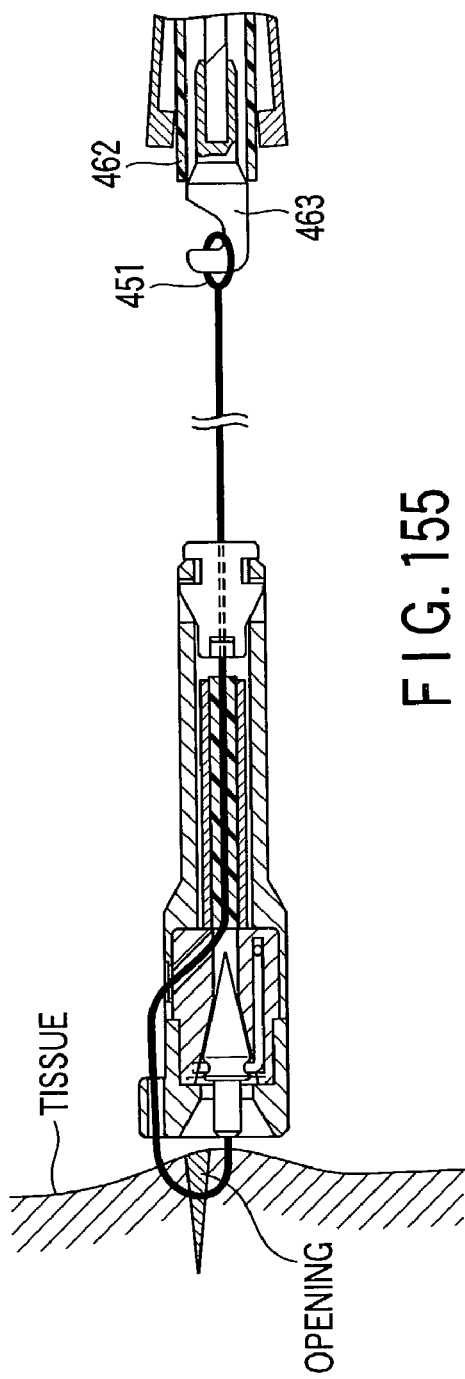
Figure 156:
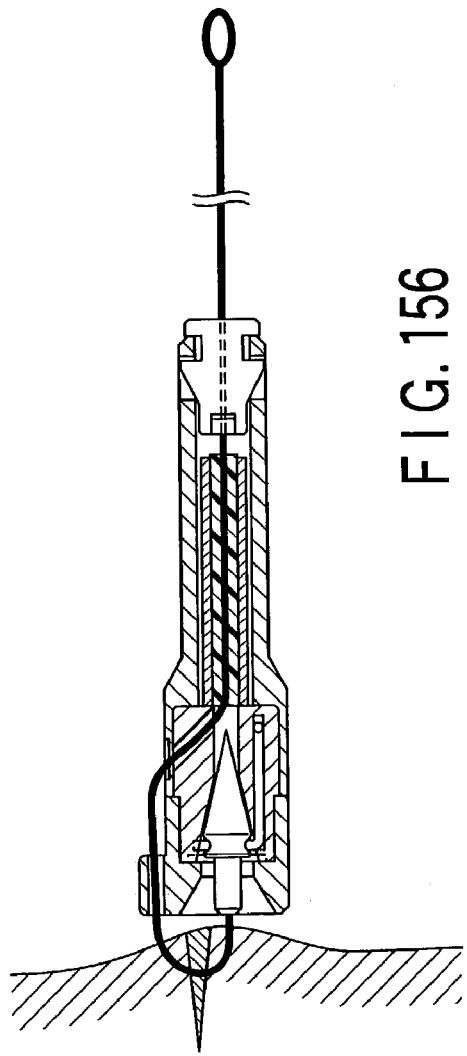

(7) As shown in FIG. 155 and FIG. 156, the hook 463 is pulled out from the coil 462, and the loop 451 is unfastened from the hook 463.

Figure 162:
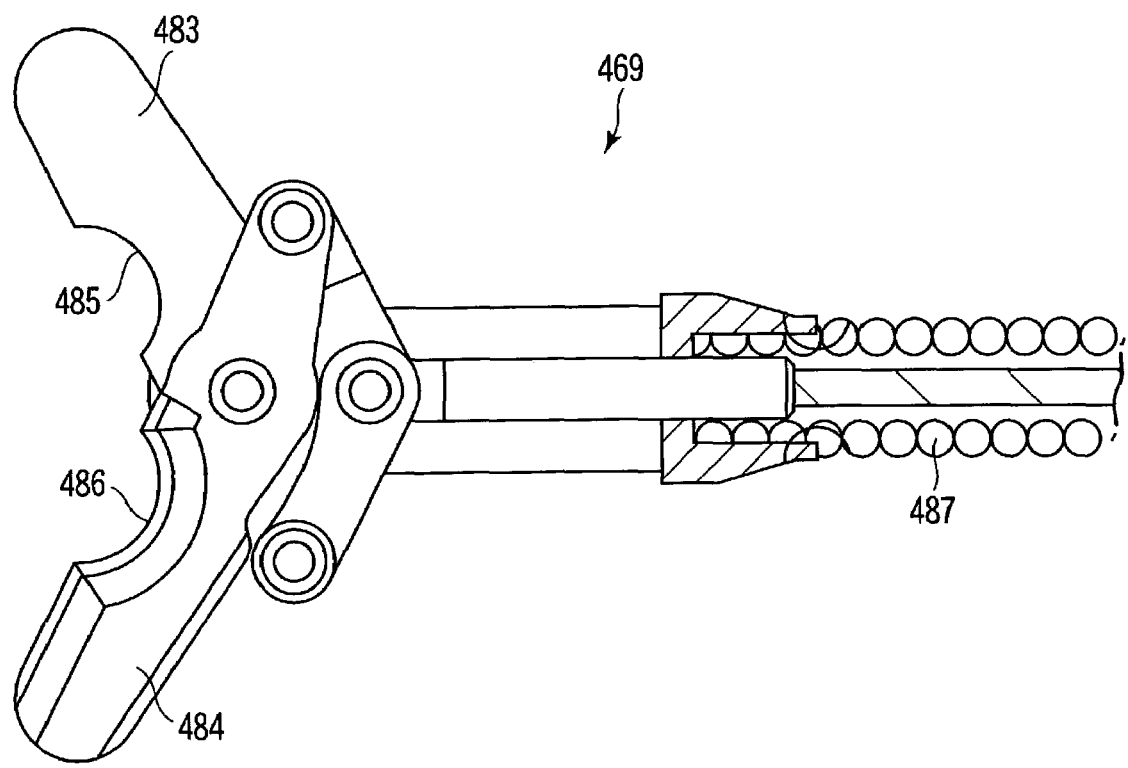

(8) As shown in FIG. 157, a redundant portion of the suture thread 442 is cut by using a thread cutting forceps 469. In this case, as shown in FIG. 162, the thread cutting forceps 469 is designed to cut the thread by opening/closing scissors members 483 and 484 having sharp cutting blades. In addition, the thread cutting forceps 469 has recess parts 485 and 486 to prevent the thread from escaping from the blades when it is cut. Furthermore, a rotatable sheath 487 allows the thread cutting forceps 469 to rotate about the axis, and hence the direction of the scissors members 483 and 484 can be freely changed. Since the suture thread 442 is exposed in a space 488 as shown in FIG. 157, when the operator wants to remove the end loop cartridge 440 after a suturing operation, he/she can easily remove the end loop cartridge 440 from the tissue by cutting this portion of the suture thread 442.

(Effects)

In addition to the effects of the 10th embodiment, the end loop cartridge 440 can be easily removed from the sutured region. In addition, this device allows an easy approach to a region to be sutured. Furthermore, after an approach to the tissue, the tissue can be sutured deep by pressing the suturing device against the tissue.

17th Embodiment

FIG. 169 to FIG. 171 show the 17th embodiment.

(Arrangement)

The 17th embodiment differs from the 16th embodiment in the following points.

As shown in FIG. 169 to FIG. 171, a third actuating member 494 is pivotally coupled to a first actuating member 501 and third connecting member 502 by using pins 511 and 510, respectively. The first actuating member 501 is pivotally coupled to a holding member 499 with a pin 504 serving as a holding shaft, and is also coupled to a first connecting member 496 with a pin 507. The third connecting member 502 is pivotally coupled to the holding member 499 with a pin 509. A second actuating member 495 is pivotally coupled to the holding member 499 with a pin 505 serving as a holding shaft, and is also pivotally coupled to a second connecting member 497 with a pin 508. The first and second connecting members 496 and 497 are pivotally coupled to a push rod 498 with a pin 506. As shown in FIG. 169 and FIG. 170, the first and second actuating members 501 and 495 can be opened/closed by pushing and pulling the rod 498. With this operation, the third actuating member 494 is moved by the first and third actuating member 501 and 502. Other arrangements are the same as those in the 16th embodiment, and hence a description thereof will be omitted.

(Function)

A suturing operation is performed in the same manner as in the sixth embodiment shown in FIG. 147 to FIG. 157. In FIG. 169 and FIG. 170, the end loop cartridge 440, the distal pipe, and the like are omitted.

(Effects)

In addition to the 16th embodiment, the locus of the distal end of a removable needle 441 can be made a one different from a circular locus around the pin 504. This makes it possible to puncture the tissue deeper.

The stroke of the push rod 498 which is required to open/close the third and second actuating members 494 and 495 can be reduced.

18th Embodiment

FIG. 172 shows the 18th embodiment.

(Arrangement)

The 18th embodiment differs from the 16th embodiment in the following points.

As shown in FIG. 172, this embodiment has first and second catching members 519 and 520 pivotable about pins 522 and 523. Needle-like members are formed on the distal ends of the first and second catching members 519 and 520 to prevent them from sliding on the tissue when they catch it. In addition, the first and second catching members 519 and 520 can operate independently of the opening/closing operation of first and second actuating members 517 and 518 owing to a link structure (not shown). Other arrangements are the same as those in the 16th embodiment, and hence a description thereof will be omitted.

(Function)

A suturing operation is performed in the same manner as in the 16th embodiment shown in FIG. 147 to FIG. 157. Note, however, that the tissue is caught by using the first and second catching members 519 and 520 before the tissue is punctured with a removable needle 441, and the tissue is punctured with the removable needle 441 after the tissue is pulled up.

(Effects)

In addition to the effects of the 16th embodiment, since the tissue can be punctured with the removable needle 441 while the tissue is pulled up by the first and second catching members 519 and 502, the tissue can be punctured deeper.

19th Embodiment

FIG. 178 and FIG. 179 show the 19th embodiment.

(Arrangement)

The 19th embodiment differs from the 16th embodiment in the following points.

As shown in FIG. 178 and FIG. 179, the end loop cartridge 440 is modified into an end loop cartridge 539, and the engage tube 465 is modified into an engage tube 543.

The end loop cartridge 539 is comprised of a removable needle 441 similar to the one in the 16th embodiment, a suture thread 442, a needle lock mechanism 475, an elastic member 448, a rigid member 449, a casing member 540, and the like. The engage tube 543 is comprised of two lock members 545, a pipe 549 that fixes the proximal end portions of these lock members, a tube 550 coupled to the pipe 549, and the like, and is designed to allow a hook device 461 to be retractably arranged inside.

As shown in FIG. 178, after a loop 451 of the end loop cartridge is hung on a hook 463 of the hook device and the loop 451 and suture thread 442 are partly pulled into the hook device 461, two lock members 545 of the engage tube 465 are positioned to holes 546 formed in the casing member 540. Thereafter, as shown in FIG. 179, the hook device 461 is moved to the left on the drawing surface to push the lock members 545 upward in the vertical direction on the drawing surface so as to make it engage with the hole 546. With this operation, the engage tube 543 and end loop cartridge 539 can integrally engage with each other. In addition, the lock members 545 have elastic arms 559.

(Function)

A suturing procedure is almost the same as that in the 16th embodiment shown in FIG. 147 to FIG. 157 except for the following point.

The operation of disengaging the end loop cartridge 440 from the engage tube 465, which is shown in FIG. 149 and FIG. 150, is modified into the operation shown in FIG. 178 and FIG. 179. In this case, the lock members 545 is unlocked from the hook device 461 by moving the hook device 461 to the right on the drawing surface, and the lock members 545 comes off the hole 546 owing to the elasticity properties of the arms 559.

Other operations are the same as those in the 16th embodiment, and hence a description thereof will be omitted.

(Effect)

In addition to the effects of the 16th embodiment, the attachment/detachment of the end loop cartridge 539 and engage tube 543 is facilitated.

20th Embodiment

FIG. 180 and FIG. 181 show the 20th embodiment.

As shown in FIG. 180 and FIG. 181, the end loop cartridge 440 is modified into an end loop cartridge 539, the engage tube 465 is modified into an engage tube 551, and the distal pipe 425 is modified into a distal pipe 552.

The end loop cartridge 539 is comprised of a removable needle 441 similar to the one in the 16th embodiment, a suture thread 442, a needle lock mechanism 475, an elastic member 448, a rigid member 449, a casing member 540, and the like. The engage tube 551 is comprised of two lock members 553, a pipe 554 which fixes the proximal end portions of these lock members, a tube 555 coupled to the pipe 554, and the like, and is designed to allow a hook device 461 to be retractably arranged inside.

As shown in FIG. 180, after a loop 451 of the end loop cartridge is hung on a hook 463 of the hook device and the loop 451 and suture thread 442 are partly pulled into the hook device 461, two lock members 553 of the engage tube 551 are positioned to holes 546 formed in the casing member 540. Thereafter, as shown in FIG. 181, the engage tube 551 and hook device 461 are moved to the left on the drawing surface to house the end loop cartridge 539, engage tube 551, and hook device 461 in the distal pipe 552. At this time, when the outer surfaces of the lock members 553 come into contact with the inner surface of hole 556 formed in the distal pipe 552, arms 558 elastically deform. As a result, the lock members 553 engage with the holes 546. With this operation, the engage tube 551 and end loop cartridge 539 integrally engage with each other.

A hole 557 larger in diameter than the hole 556 is formed in the distal pipe 552. In this case, since the distal end portion of the end loop cartridge 539 partly becomes large, the large-diameter hole 557 is formed. Obviously, however, if the maximum outer diameter of the end loop cartridge 539 is made smaller than the diameter of the hole 556, such a large-diameter hole 557 need not be formed.

(Function)

A suturing procedure is almost the same as that in the 16th embodiment shown in FIG. 147 to FIG. 157 except for the following point.

The operation of disengaging the end loop cartridge 440 from the engage tube 466 shown in FIG. 149 and FIG. 150 is modified into the operation of disengaging the distal pipe 552 from the hole 556 shown in FIG. 180 and FIG. 181. In this case, the engage tube 551 and hook device 461 are moved to the left on the drawing surface.

Other operations are the same as those in the 16th embodiment, and hence a description thereof will be omitted.

(Effects)

In addition to the effects of the 16th embodiment, the attachment/detachment of the end loop cartridge 539 and engage tube 543 is facilitated.

The present invention has been described in conjunction with the preferred embodiments shown in various drawings. Obviously, however, other similar embodiments can be used to realize the same functions as those of the present invention, the above embodiments can be modified, or other embodiments can be added without departing from the spirit and scope of the invention. The present invention is not therefore limited to any single embodiment.

For example, it is obvious that each treatment device described above can be used together with a rigid endoscope, trocar, or the like as well as flexible endoscopes. When each treatment device is to be used together with an endoscope, each treatment device can be inserted into the body through a proper lumen extending into the endoscope instead of being arranged outside the endoscope as described above.

What is claimed is:

1. A treatment device for use with at least a flexible endoscope, the treatment device being used to perform treatment in a body by being operated outside the body, comprising:

a flexible member configured to be detachably fixed to an outside of an insert section of the endoscope, the flexible member having a distal end portion which is capable of being inserted into the body with the insert section of the endoscope, the flexible member further including a coil of which contraction in an axial direction is restricted and which forms an axial hole;

a transmission member with a flexible structure which is movably arranged in the coil in the axial direction and capable of being operated outside the body;

a link mechanism which is arranged at the distal end portion of the flexible member and actuated by an operation outside the body through the transmission member, the link mechanism including:

first and second connecting members coupled to a push rod through the transmission member, each of the first and second connecting members having a distal end portion and a proximal end portion rotatably coupled to the transmission member;

first and second arm members each having a distal end portion and a proximal end portion rotatably coupled to the distal end portion of a corresponding one of the first and second connecting members;

a holding member which holds the distal end portions of the first and second arm members; and first and second actuating members which are integrally formed with the distal end portions of the first and second arm members and are able to open/close when the transmission member actuates the first and second connecting members and the first and second arm members through the push rod;

a curved needle which is mounted on one of the first and second actuating members and is able to move in a direction to puncture a tissue and a direction to be removed from the tissue; and at least one tissue fixing means which is arranged at the other one of the first and second actuating members, wherein the tissue fixing means has a needle shape, wherein the distal end portions of the first and second arm members are rotatably held by the holding member at a predetermined interval therebetween to enable the proximal end portions of the first and second arm members to pass between the distal end portions of the first and second arm members, the thereby the curved needle and the tissue fixing means are allowed to move between a position where distal end portions of the curved needle and the tissue fixing means face in the same direction, and a position where the distal end portions of the curved needle and the tissue fixing means face in respective positions substantially perpendicular to each other, through a position where the distal end portions of the curved needle and the tissue fixing means face each other.

2. A device according to claim 1, wherein the flexible member has an axis and is so held as to be movable with respect to the insert section in an axial direction of the insert section.

3. The device according to claim 1, further comprising:
an outer tube in which the flexible member is insertable and is configured to be fixed detachably outside the endoscope,
wherein the device is configured to move forward and backward in an axial direction of the endoscope via the outer tube.

4. The device according to claim 3, further comprising a tube holding member having at least one lumen which communicates with a lumen of the outer tube, wherein the endoscope is configured to be detachably fixed via the tube holding member.

5. An endoscopic treatment device which is used together with at least a flexible endoscope to perform treatment in a body by being operated outside the body, comprising:
a flexible member configured to be detachably fixed to an outside of an insert section of the endoscope, the flexible member having a distal end portion which is capable of being inserted into the body with the insert section of the endoscope, the flexible member further including a coil of which contraction in an axial direction is restricted and which forms an axial hole;
a transmission member with a flexible structure which is movably arranged in the coil in the axial direction, has a distal end portion inserted into a body and is capable of being operated outside the body;
a push rod coupled to the distal end portion of the transmission member;
first and second slender connecting members coupled to the push rod, each of the first and second slender connecting members having a distal end portion and a proximal end portion rotatably coupled to the push rod;
first and second slender arm members each having a distal end portion and a proximal end portion rotatably coupled to the distal end portion of a corresponding one of the first and second slender connecting members;
a holding member which rotatably holds the distal end portions of the first and second slender arm members at a predetermined interval therebetween to enable the proximal end portions of the first and second slender arm members to pass between the distal end portions of the first and second slender arm members;
first and second actuating members which are integrally formed with the distal end portions of the first and second slender arm members and are able to open/close when the transmission member actuates the first and second slender connecting members and the first and second slender arm members through the push rod; and
a needle which is mounted on at least one of the first and second actuating members and is used to puncture a tissue;
wherein each of the first and second slender arm members is shorter than each of the first and second slender connecting members, and wherein the proximal end portions of the first and second slender arm members are capable of moving from a position where they substantially overlap each other to a position where they are substantially parallel to each other through a position where they pass between the distal end portions of the first and second arm members that are held by the holding member.

6. A device according to claim 5, wherein at least one of the first and second actuating members has at least one tissue fixing means.

7. A device according to claim 5, wherein the needle is a curved needle.

8. A device according to claim 5, further comprising protective means for protecting a tissue from the needle.

9. A device according to claim 5, further comprising a suture thread attached to the needle, and recovery means for recovering the thread inserted in the tissue from the needle.

10. A device according to claim 5, wherein the treatment device can be inserted into the body along a guide member having an axis and is so held as to be movable with respect to the guide member in an axial direction of the guide member.

11. The device according to claim 5, wherein the endoscopic treatment device is configured to be integrally fixed outside the endoscope.

12. The device according to claim 5, further comprising:
an elongated tube in which the transmission member is insertable; and
an outer tube in which the elongated tube is insertable, wherein the outer tube is configured to be fixed detachably outside the endoscope, and the endoscopic treatment device is configured to move forward and backward in an axial direction of the endoscope.

13. The device according to claim 12, further comprising a tube holding member having at least one lumen which communicates with a lumen of the outer tube, wherein the endoscope is configured to be detachably fixed via the tube holding member.

14. The device according to claim 5, wherein when the first and second arm members open completely, the distal end of the needle is substantially parallel to an axis of the endoscopic treatment device.

15. The device according to claim 5, wherein when the first and second arm members are closed completely, a distal end of the needle is substantially parallel to an axis of the endoscopic treatment device even when a tissue is sandwiched between the first and second arm members.

16. The device according to claim 5, wherein the interval at which the holding member holds the distal end portion of the first and second arm members is larger than each length of the first and second arm members, thereby the distal end portion of the first and second connecting members being configured to pass between the distal end portion of the first and second arm members.

17. An endoscopic treatment device which is used together with at least a flexible endoscope to perform treatment in a body by being operated outside the body, comprising:

a flexible member configured to be detachably fixed to an outside of an insert section of the endoscope, the flexible member having a distal end portion which is capable of being inserted into the body with the insert section of the endoscope, the flexible member further including a coil of which contraction in an axial direction is restricted and which forms an axial hole;

a transmission member with a flexible structure which is movably arranged in the coil in the axial direction, has a distal end portion inserted into a body and is capable of being operated outside the body;

a push rod coupled to the distal end portion of the transmission member;

first and second slender connecting members coupled to the push rod, each of the first and second slender connecting members having a distal end portion and a proximal end portion rotatably coupled to the push rod;

first and second slender arm members each having a distal end portion and a proximal end portion rotatably coupled to the distal end portion of a corresponding one of the first and second slender connecting members;

a holding member which rotatably holds the distal end portions of the first and second slender arm members at a predetermined interval therebetween to enable the proximal end portions of the first and second slender arm members to pass between the distal end portions of the first and second slender arm members;

first and second actuating members which are integrally formed with the distal end portions of the first and second slender arm members and are able to open/close when the transmission member actuates the first and second slender connecting members and the first and second slender arm members through the push rod; and a needle which is mounted on at least one of the first and second actuating members and is used to puncture a tissue;

wherein the treatment device is fixed through the flexible member to an outside of the endoscope, can be inserted into the body together with the endoscope along a guide member having an axis, and is so held as to be movable with respect to the guide member in an axial direction of the guide member.

* * * * *